(12) United States Patent
Zhao et al.

(10) Patent No.: US 11,919,918 B2
(45) Date of Patent: *Mar. 5, 2024

(54) P2X3 ANDOR P2X2/3 RECEPTOR ANTAGONIST, PHARMACEUTICAL COMPOSITION COMPRISING SAME, AND USE THEREOF

(71) Applicant: BEIJING TIDE PHARMACEUTICAL CO., LTD., Beijing (CN)

(72) Inventors: Yanping Zhao, Beijing (CN); Hongjun Wang, Beijing (CN); Gong Li, Beijing (CN); Xiang Li, Beijing (CN); Yuanyuan Jiang, Beijing (CN); Kai Liu, Beijing (CN); Yeming Wang, Beijing (CN); Liying Zhou, Beijing (CN); Yanan Liu, Beijing (CN); Ning Shao, Beijing (CN); Fengping Xiao, Beijing (CN)

(73) Assignee: BEIJING TIDE PHARMACEUTICAL CO., LTD., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/826,711

(22) Filed: May 27, 2022

(65) Prior Publication Data

US 2022/0389039 A1    Dec. 8, 2022

Related U.S. Application Data

(62) Division of application No. 16/760,911, filed as application No. PCT/CN2018/112829 on Oct. 31, 2018, now Pat. No. 11,414,444.

(30) Foreign Application Priority Data

Nov. 1, 2017    (WO) ............... PCT/CN2017/108884

(51) Int. Cl.
```
A61K 31/506    (2006.01)
C07F 9/6568    (2006.01)
C07D 401/12    (2006.01)
C07D 401/14    (2006.01)
C07D 405/14    (2006.01)
C07D 413/14    (2006.01)
C07D 417/14    (2006.01)
C07D 487/04    (2006.01)
C07D 498/18    (2006.01)
```

(52) U.S. Cl.
CPC ........ *C07F 9/65685* (2013.01); *A61K 31/506* (2013.01); *C07D 401/12* (2013.01); *C07D 401/14* (2013.01); *C07D 405/14* (2013.01); *C07D 413/14* (2013.01); *C07D 417/14* (2013.01); *C07D 487/04* (2013.01); *C07D 498/18* (2013.01)

(58) Field of Classification Search
CPC .................................................... A61K 31/506
See application file for complete search history.

(56) References Cited

U.S. PATENT DOCUMENTS

| | | | |
|---|---|---|---|
| 2022/0177447 A1* | 6/2022 | Zhao | A61P 13/00 |
| 2022/0204475 A1* | 6/2022 | Cheng | A61K 31/506 |
| 2022/0211703 A1* | 7/2022 | Zhao | A61P 11/14 |
| 2022/0249478 A1* | 8/2022 | Zhao | A61P 15/00 |

FOREIGN PATENT DOCUMENTS

| | | |
|---|---|---|
| CN | 1930135 | 3/2007 |
| JP | 2009506998 | 2/2009 |
| WO | 2005095359 | 10/2005 |
| WO | 2007025900 | 3/2007 |
| WO | 2017165255 | 9/2017 |

OTHER PUBLICATIONS

Gever JR, Soto R, Henningsen RA, Martin RS, Hackos DH, Panicker S, Rubas W, Oglesby IB, Dillon MP, Milla ME, Burnstock G. AF-353, a novel, potent and orally bioavailable P2X3/P2X2/3 receptor antagonist. British journal of pharmacology. Jul. 2010;160(6):1387-98.

Bölcskei H, Farkas B. P2X3 and P2X2/3 receptor antagonists. Pharmaceutical patent analyst. Jan. 2014;3(1):53-64.

Database Reaxys, Database accession No. 789806, 801184, 816407 (XRN), XP055781752 (D1a); & Kompis et al. Eur. J. Med. Chem. 1977, 12, 531-536; & Kompis et al. Chemischer Informationsdienst 1978, 9, XP055683200.

Database Registry, Database accession No. 1823256-69-4, Dec. 6, 2015, XP055781930.

Kompis et al. "2, 4-Diamino-5-(Pyridylmethyl)-Pyrimidine Als Potentielle Chemotherapeutica." Chemischer Informationsdienst, vol. 9, No. (14), Apr. 4, 1978 (Apr. 4, 1978), ISSN: 1522-2667, see pp. 94-95, particularly see abstract 237.

(Continued)

*Primary Examiner* — Laura L Stockton
(74) *Attorney, Agent, or Firm* — Robin L. Teskin; Baker, Donelson, Bearman, Caldwell & Berkowitz PC

(57) ABSTRACT

A P2X3 and/or P2X2/3 receptor antagonist of formula (I), a pharmaceutical composition comprising the same, and a use thereof in preparing a drug for preventing or treating a disease mediated by the P2X3 and/or P2X2/3 receptor antagonist.

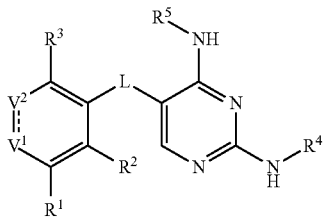

Formula (I)

20 Claims, No Drawings

(56) References Cited

OTHER PUBLICATIONS

International Search Report of Int'l Appl. No. PCT/CN2018/112829, dated Feb. 13, 2019.
Seiler P, Bischoff O, Wagner R. Partition coefficients of 5-(substituted benzyl)-2, 4-diaminopyrimidines. Arzneimittel- forschung. Jan. 1, 1982;32(7):711-4.
Chemical Abstracts Service (CAS) email regarding compounds in Seiler et al. reference, Nov. 5, 2021. (Year: 2021).
PubChem CID 3050135, National Center for Biotechnology Information. PubChem Compound Summary for CID 3050135, Pyrimidine, 2, 4-diamino-5-(4-pyridylmethyl)-, https://pubchem.ncbi.nlm.nih.gov/compound/Pyrimidine_-2_4-pyridylmethyl. Accessed May 18, 2021, create date Aug. 9, 2005. (Year: 2005).

* cited by examiner

P2X3 ANDOR P2X2/3 RECEPTOR ANTAGONIST, PHARMACEUTICAL COMPOSITION COMPRISING SAME, AND USE THEREOF

CROSS-REFERENCE TO RELATED APPLICATIONS

This application is a divisional application of U.S. application Ser. No. 16/760,911, which has a 371(c) Date of May 1, 2020, which is a U.S. Nat'l Phase of Int'l Appl. No. PCT/CN2018/112829, filed Oct. 31, 2018, which further claims priority to Int'l Appl. No. PCT/CN2017/108884, filed Nov. 1, 2017, each of which are incorporated by reference in their entireties.

FIELD OF THE INVENTION

The present invention relates to a P2X3 and/or P2X2/3 receptor antagonist, a pharmaceutical composition comprising the same, and use thereof for the prophylaxis or treatment of a disease mediated by the P2X3 and/or P2X2/3 receptor antagonist.

BACKGROUND OF THE INVENTION

Purine compounds, acting via cell surface purinoceptors, have been implicated as having a variety of physiological and pathological roles. ATP, and to a lesser extent, adenosine, can stimulate sensory nerve endings resulting in intense pain and a pronounced increase in sensory nerve discharge. ATP receptors have been classified into two major families, the P2Y- and P2X-purinoreceptors, on the basis of the molecular structure, transduction mechanisms, and pharmacological characterization. The P2Y-purinoceptors are G-protein coupled receptors, while the P2X-purinoceptors are a family of ATP-gated cation channels. Purinoceptors, in particular, P2X receptors, can form homomultimers or heteromultimers. To date, cDNAs for multiple P2X receptor subtypes (including six homologous receptors: P2X1, P2X2, P2X3, P2X4, P2X5 and P2X7; and three heterologous receptors: P2X2/3, P2X4/6 and P2X1/5) have been cloned. The structure and chromosomal mapping of mouse genomic P2X3 receptor subunits have also been reported.

Studies have shown that P2X3 and/or P2X2/3 receptor antagonists can be used to treat diseases such as pain, etc. The present invention provides compounds as P2X receptor modulators, particularly P2X3 and/or P2X2/3 receptor antagonists.

SUMMARY OF THE INVENTION

The present invention provides a compound for use as a P2X receptor modulator (particularly P2X3 and/or P2X2/3 receptor antagonist), it effectively antagonize the P2X receptor (particularly P2X3 and/or P2X2/3 receptor), and has better physicochemical properties (e.g., solubility, physical and/or chemical stability), improved pharmacokinetic properties (e.g., improved bioavailability, proper half-life and duration of action), improved safety (low toxicity and/or less side effects, wide therapeutic window), and the like.

An aspect of the present invention provides a compound or a pharmaceutically acceptable salt, ester, stereoisomer, polymorph, solvate, N-oxide, isotopically labeled compound, metabolite or prodrug thereof, wherein the compound has the structure of Formula (I):

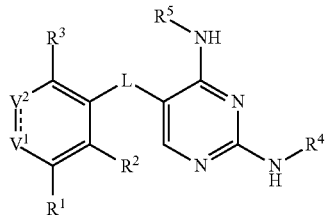

Formula (I)

L is selected from the group consisting of C(=O), CRR', NR, O, S, S=O and S(=O)$_2$;

$V^1$ is selected from the group consisting of N,

N—O and NR;

$V^2$ is selected from the group consisting of $CR^6$ and C(=O);

= represents either a single bond or a double bond, provided that when = is a single bond, $V^1$ is NR and $V^2$ is C(=O);

R and R' are each independently selected from the group consisting of H, halogen, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl, and at most 2 ring members in the cyclic hydrocarbyl and heterocyclyl are C(=O);

$R^1$, $R^2$, $R^3$ and $R^6$ are each independently selected from the group consisting of H, halogen, —CN, —NH$_2$, —OH, —SH, —Se—R, —Si(R)$_3$, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl, $C_{6-12}$ aralkyl, $C_{1-6}$ haloalkyl, —C(=O)R$^a$, —OC(=O)R$^a$, —C(=O)OR$^a$, —OR$^a$, —SR$^a$, —S(=O)R$^a$, —S(=O)$_2$R$^a$, —S(=O)$_2$NR$^a$R$^b$, —S(=O)(=NR)R$^a$, —NR$^a$R$^b$, —C(=O)NR$^a$R$^b$, —C(=S)NR$^a$R$^b$, —C(=NR)NR$^a$R$^b$, —NR$^a$—C(=O)R$^b$, —NR$^a$—C(=O)OR$^b$, —NR$^a$—S(=O)$_2$—R$^b$, —NR$^a$—C(=O)—NR$^a$R$^b$, —C$_{1-6}$ alkylene-NR$^a$R$^b$, —C$_{1-6}$ alkylene-OR$^a$, —C$_{1-6}$ alkylene-C(=O)R, —C$_{1-6}$ alkenylene-OR$^a$, —O—C$_{1-6}$ alkylene-NR$^a$R$^b$ and —P(=O)R$^a$R$^b$;

$R^4$ and $R^5$ are each independently selected from the group consisting of H, —C(=O)OR$^a$, —NR$^a$R$^b$, —NR$^a$—C(=O)R$^b$, —NR$^a$—C(=)OR, —C$_{1-6}$ alkylene-NR$^a$R$^b$, —C$_{1-6}$ alkylene-OR$^a$, —C$_{1-6}$ alkylene-O—C$_{1-6}$ alkylene-OR$^a$, C$_{1-6}$ alkyl, C$_{1-6}$ haloalkyl, C$_{2-6}$ alkenyl, C$_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl;

alternatively, $R^1$ and $R^4$ together form —NH—($C_{1-6}$ alkylene)-L-($C_{1-6}$ alkylene)-, preferably —NHCH$_2$CH$_2$—O—CH$_2$CH$_2$—;

the above alkyl, alkylene, alkenyl, alkynyl, cyclic hydrocarbyl, heterocyclyl, aryl, heteroaryl and aralkyl, at each occurrence, are each optionally substituted with one or more substituents independently selected from the group consisting of halogen, hydroxyl, oxo, amino, cyano, nitro, —Si(R)$_3$, $C_{1-6}$ alkyl, saturated or partially unsaturated $C_{3-6}$ cyclic hydrocarbyl, saturated or partially unsaturated 3- to 10-membered heterocyclyl, $C_{6-10}$ aryl, 5- to 14-membered heteroaryl, $C_{6-12}$ aralkyl, —C(=O)R$^a$, —OC(=O)R$^a$, —C(=O)OR$^a$, —OR$^a$, —SR$^a$, —S(=O)R$^a$, —S(=O)$_2$R$^a$, —S(=O)$_2$NR$^a$R$^b$, —NR$^a$R$^b$, —C(=O)NR$^a$R$^b$, —NR$^a$—C(=O)R$^b$, —NR$^a$—C(=O)OR$^b$, —NR$^a$—S(=O)$_2$—R$^b$, —NR$^a$—C(=O)—NR$^a$R$^b$, —C$_{1-6}$ alkylene-NR$^a$R$^b$, —C$_{1-6}$ alkylene-OR$^a$, —C$_{1-6}$ alkenylene-OR$^a$ and —O—C$_{1-6}$ alkylene-NR$^a$R$^b$, the alkyl, cyclic hydrocarbyl, heterocyclyl, aryl, heteroaryl and aralkyl are further optionally substituted with one or more substituents independently selected from the group consisting of halogen, hydroxyl, oxo, amino, cyano, nitro, —NR$^a$R$^b$, C$_{1-6}$ alkyl, —O—C$_{1-6}$ alkyl, saturated or partially unsaturated C$_{3-6}$ cyclic hydrocarbyl, saturated or partially unsaturated 3- to 10-membered heterocyclyl, C$_{6-10}$ aryl, 5- to 14-membered heteroaryl and C$_{6-12}$ aralkyl; and R$^a$ and R$^b$, at each occurrence, are each independently selected from the group consisting of H, —OH, C$_{1-6}$ alkyl, C$_{2-6}$ alkenyl, C$_{2-6}$ alkynyl, saturated or partially unsaturated C$_{3-10}$ cyclic hydrocarbyl, saturated or partially unsaturated 3- to 10-membered heterocyclyl, C$_{6-10}$ aryl, 5- to 14-membered heteroaryl and C$_{6-12}$ aralkyl; alternatively, R$^a$ and R$^b$ together with the atom to which they are attached form a 3- to 12-membered heterocycle or heteroaromatic ring, the above groups are further optionally substituted with one or more substituents independently selected from the group consisting of halogen, hydroxyl, oxo, amino, cyano, nitro, C$_{1-6}$ alkyl, —O—C$_{1-6}$ alkyl, saturated or partially unsaturated C$_{3-6}$ cyclic hydrocarbyl, saturated or partially unsaturated 3- to 10-membered heterocyclyl, C$_{6-10}$ aryl, 5- to 14-membered heteroaryl and C$_{6-12}$ aralkyl.

Another aspect of the present invention provides a pharmaceutical composition comprising a prophylactically or therapeutically effective amount of the compound of the present invention or a pharmaceutically acceptable salt, ester, stereoisomer, polymorph, solvate, N-oxide, isotopically labeled compound, metabolite or prodrug thereof, and one or more pharmaceutically acceptable carriers, and the pharmaceutical composition is preferably in the form of a solid, semi-solid, liquid, or gas preparation.

Another aspect of the present invention provides use of the compound of the present invention or a pharmaceutically acceptable salt, ester, stereoisomer, polymorph, solvate, N-oxide, isotopically labeled compound, metabolite or prodrug thereof or the pharmaceutical composition of the present invention in the manufacture of a medicament for the treatment of a disease mediated by the P2X3 and/or P2X2/3 receptor antagonist.

Another aspect of the present invention provides the compound of the present invention or a pharmaceutically acceptable salt, ester, stereoisomer, polymorph, solvate, N-oxide, isotopically labeled compound, metabolite or prodrug thereof or the pharmaceutical composition of the present invention for use in the treatment of a disease mediated by the P2X3 and/or P2X2/3 receptor antagonist.

Another aspect of the present invention provides a method for the prophylaxis or the treatment of a disease mediated by the P2X3 and/or P2X2/3 receptor antagonist, wherein the method comprises administering to a subject in need thereof an effective amount of the compound of the present invention or a pharmaceutically acceptable salt, ester, stereoisomer, polymorph, solvate, N-oxide, isotopically labeled compound, metabolite or prodrug thereof or the pharmaceutical composition of the present invention.

DETAILED DESCRIPTION OF THE INVENTION

Definition

Unless otherwise defined in the context, all technical and scientific terms used herein are intended to have the same meaning as commonly understood by a person skilled in the art. References to techniques employed herein are intended to refer to the techniques as commonly understood in the art, including variations on those techniques or substitutions of equivalent techniques which would be apparent to a person skilled in the art. While it is believed that the following terms will be readily understood by a person skilled in the art, the following definitions are nevertheless put forth to better illustrate the present invention.

The terms "contain", "include", "comprise", "have", or "relate to", as well as other variations used herein are inclusive or open-ended, and do not exclude additional, unrecited elements or method steps.

As used herein, the term "alkylene" refers to a saturated divalent hydrocarbyl, preferably refers to a saturated divalent hydrocarbyl having 1, 2, 3, 4, 5 or 6 carbon atoms, e.g., methylene, ethylene, propylene or butylene.

As used herein, the term "alkyl" is defined as a linear or branched saturated aliphatic hydrocarbon. In some embodiments, alkyl has 1-12, e.g., 1-6, carbon atoms. For example, as used herein, the term "C$_{1-6}$ alkyl" refers to a linear or branched group having 1-6 carbon atoms (such as methyl, ethyl, n-propyl, isopropyl, n-butyl, isobutyl, sec-butyl, tert-butyl, n-pentyl, isopentyl, neopentyl, or n-hexyl), which is optionally substituted with one or more (e.g., 1 to 3) suitable substituents such as halogen (in which case the group may be referred to as "haloalkyl") (e.g., CH$_2$F, CHF$_2$, CF$_3$, CCl$_3$, C$_2$F$_5$, C$_2$Cl$_5$, CH$_2$CF$_3$, CH$_2$Cl or —CH$_2$CH$_2$CF$_3$ etc.). The term "C$_{1-4}$ alkyl" refers to a linear or branched aliphatic hydrocarbon chain having 1-4 carbon atoms (i.e., methyl, ethyl, n-propyl, isopropyl, n-butyl, isobutyl, sec-butyl or tert-butyl).

As used herein, the term "alkenyl" refers to a linear or branched monovalent hydrocarbyl having a double bond and 2-6 carbon atoms ("C$_{2-6}$ alkenyl"). The alkenyl is e.g., vinyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl and 4-methyl-3-pentenyl. When the compound of the present invention contains an alkenylene group, the compound may exist as the pure E (entgegen) form, the pure Z (zusammen) form, or any mixture thereof.

As used herein, the term "alkynyl" refers to a monovalent hydrocarbyl containing one or more triple bond, and preferably having 2, 3, 4, 5 or 6 carbon atoms, e.g., ethynyl or propynyl.

As used herein, the term "cycloalkyl" refers to a saturated monocyclic or polycyclic (e.g., bicyclic) hydrocarbon ring (e.g., monocyclic, such as cyclopropyl, cyclobutyl, cyclopentyl, cyclohexyl, cycloheptyl, cyclooctyl, or cyclononyl, or bicyclic, including spiro, fused or bridged cyclic system (such as bicyclo[1.1.1]pentyl, bicyclo[2.2.1]heptyl, bicyclo[3.2.1]octyl or bicyclo[5.2.0]nonyl, or decahydronaphthalene etc.)), which is optionally substituted with one or more (e.g., 1 to 3) suitable substituents. The cycloalkyl has 3 to 15 carbon atoms. For example, the term "C$_{3-6}$ cycloalkyl" refers to a saturated monocyclic or polycyclic (e.g., bicyclic) hydrocarbon ring having 3 to 6 ring forming carbon atoms (e.g., cyclopropyl, cyclobutyl, cyclopentyl, or cyclohexyl), which is optionally substituted with one or more (e.g., 1 to 3) suitable substituents, e.g., methyl substituted cyclopropyl.

As used herein, the terms "cyclic hydrocarbylene", "cyclic hydrocarbyl" and "hydrocarbon ring" refer to a saturated (i.e., "cycloalkylene" and "cycloalkyl") or unsaturated (i.e., having one or more double and/or triple bonds in the ring) monocyclic or polycyclic hydrocarbon ring having e.g., 3-10 (suitably having 3-8, and more suitably having 3-6) ring carbon atoms, including but not limited to cyclopropyl(ene) (ring), cyclobutyl(ene) (ring), cyclopentyl(ene) (ring), cyclohexyl(ene) (ring), cycloheptyl(ene) (ring), cyclooctyl(ene) (ring), cyclononyl(ene) (ring), cyclohexenyl (ene) (ring), and the like.

As used herein, the terms "heterocyclyl", "heterocyclylene" and "heterocycle" refer to a saturated (i.e., heterocycloalkyl) or partially unsaturated (i.e., having one or more double and/or triple bonds in the ring) cyclic group having e.g. 3-10 (suitably having 3-8, and more suitably having 3-6) ring atoms, wherein at least one ring atom is a heteroatom selected from the group consisting of N, O and S, and the remaining ring atoms are C. For example, "3- to 10-membered heterocyclyl(ene)" of "3- to 10-membered heterocycle" refers to saturated or partially unsaturated heterocyclyl(ene) or heterocycle having 2-9 (e.g., 2, 3, 4, 5, 6, 7, 8 or 9) ring carbon atoms and one or more (e.g., 1, 2, 3, or 4) heteroatoms independently selected from the group consisting of N, O and S. Examples of heterocyclylene, heterocyclyl and heterocycle include, but are not limited to oxiranyl (ene), aziridinyl(ene), azetidinyl(ene), oxetanyl(ene), tetrahydrofuranyl(ene), dioxolinyl(ene), pyrrolidinyl(ene), pyrrolidonyl(ene), imidazolidinyl(ene), pyrazolidinyl(ene), pyrrolinyl(ene), tetrahydropyranyl(ene), piperidinyl(ene), morpholinyl(ene), dithianyl(ene), thiomorpholinyl(ene), piperazinyl(ene) or trithianyl(ene). Said group also encompasses a bicyclic system, including a spiro, fused, or bridged system (e.g., 8-azaspiro[4.5]decane, 3,9-diazaspiro[5.5]undecane, 2-azabicyclo[2.2.2]octane, etc.). Heterocyclylene, heterocyclyl and heterocycle may optionally be substituted with one or more (e.g. 1, 2, 3 or 4) suitable substituents.

As used herein, the terms "aryl(ene)" and "aromatic ring" refer to an all-carbon monocyclic or fused-ring polycyclic aromatic group having a conjugated π electron system. For example, as used herein, the terms "$C_{6-10}$ aryl(ene)" and "$C_{6-10}$ aromatic ring" refer to an aromatic group containing 6 to 10 carbon atoms, such as phenyl(ene) (benzene ring) or naphthyl(ene) (naphthalene ring). Aryl(ene) or aromatic ring is optionally substituted with one or more (such as 1 to 3) suitable substituents (e.g., halogen, —OH, —CN, —NO$_2$, and $C_{1-6}$ alkyl, etc.).

As used herein, the terms "heteroaryl(ene)" and "heteroaromatic ring" refer to a monocyclic, bicyclic or tricyclic aromatic ring system having 5, 6, 8, 9, 10, 11, 12, 13 or 14 ring atoms, particularly 1 or 2 or 3 or 4 or 5 or 6 or 9 or 10 carbon atoms, and containing at least one heteroatom (such as O, N, or S), which can be same to different. Moreover, in each case, it can be benzo-fused. In particular, "heteroaryl (ene)" or "heteroaromatic ring" is selected from the group consisting of thienyl(ene), furyl(ene), pyrrolyl(ene), oxazolyl(ene), thiazolyl(ene), imidazolyl(ene), pyrazolyl(ene), isoxazolyl(ene), isothiazolyl(ene), oxadiazolyl(ene), triazolyl(ene), thiadiazolyl(ene) etc., and benzo derivatives thereof; or pyridinyl(ene), pyridazinyl(ene), pyrimidinyl (ene), pyrazinyl(ene), triazinyl(ene), etc., and benzo derivatives thereof.

As used herein, the term "aralkyl" preferably means aryl or heteroaryl substituted alkyl, wherein aryl, heteroaryl and alkyl are as defined herein. Normally, the aryl group may have 6-14 carbon atoms, the heteroaryl group may have 5-14 ring atoms, and the alkyl group may have 1-6 carbon atoms. Exemplary aralkyl group includes, but is not limited to, benzyl, phenylethyl, phenylpropyl, phenylbutyl.

As used herein, the term "halo" or "halogen" are defined to include F, Cl, Br, or I.

As used herein, the term "nitrogen containing heterocycle" refers to a saturated or unsaturated monocyclic or bicyclic group having 2, 3, 4, 5, 6, 7, 8, 9, 10, 11, 12 or 13 carbon atoms and at least one nitrogen atom in the ring, which may further optionally comprise one or more (e.g., one, two, three or four) ring members selected from the group consisting of N, O, C=O, S, S=O and S(=O)$_2$. The nitrogen containing heterocycle is attached to the rest of the molecule through the nitrogen atom and any other ring atom in said nitrogen containing heterocycle. The nitrogen containing heterocycle is optionally benzo-fused, and is preferably attached to the rest of the molecule through the nitrogen atom in said nitrogen containing heterocycle and any carbon atom in the fused benzene ring.

The term "substituted" means that one or more (e.g., one, two, three, or four) hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

If a substituent is described as being "optionally substituted", the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more from a list of substituents, one or more of the hydrogens on the nitrogen (to the extent there are any) may each be replaced with an independently selected optional substituent.

If substituents are described as being "independently selected" from a group, each substituent is selected independent of the other(s). Each substituent therefore may be identical to or different from the other substituent(s).

As used herein, the term "one or more" means one or more than one (e.g., 2, 3, 4, 5 or 10) as reasonable.

As used herein, unless specified, the point of attachment of a substituent can be from any suitable position of the substituent.

When a bond to a substituent is shown to cross a bond connecting two atoms in a ring, then such substituent may be bonded to any of the ring-forming atoms in that ring that are substitutable.

The present invention also includes all pharmaceutically acceptable isotopically labeled compounds, which are identical to those of the present invention except that one or more atoms are replaced by an atom having the same atomic number, but an atomic mass or mass number different from the atomic mass or mass number which predominates in nature. Examples of isotopes suitable for inclusion in the compound of the present invention include, but are not limited to, isotopes of hydrogen, such as $^2$H, $^3$H; carbon, such as $^{11}$C, $^{13}$C, and $^{14}$C; chlorine, such as $^{36}$Cl; fluorine, such as $^{18}$F; iodine, such as $^{123}$I and $^{125}$I; nitrogen, such as $^{13}$N and $^{15}$N; oxygen, such as $^{15}$O, $^{17}$O, and $^{18}$O; phosphorus, such as $^{32}$P; and sulfur, such as $^{31}$S. Certain isotopically labeled compounds of the present invention, for example those incorporating a radioactive isotope, are useful in drug and/or substrate tissue distribution studies (e.g., assays). The radioactive isotopes tritium, i.e., $^3$H, and carbon-14, i.e., $^{14}$C, are particularly useful for this purpose in view of their ease of incorporation and ready means of detection. Substitution with positron-emitting isotopes, such as $^{11}$C, $^{18}$F, $^{15}$O and $^{13}$N, can be useful in positron emission tomography (PET) studies for examining substrate receptor occupancy. Isotopically labeled compounds of the present invention can generally be prepared by processes analogous to those described in the accompanying Schemes and/or in the Examples and Preparations, by using an appropriate isotopically labeled reagent in place of the non-labeled reagent previously employed. Pharmaceutically acceptable solvates in accordance with the invention include those wherein the solvent of crystallization may be isotopically substituted, e.g., D$_2$O, acetone-d$_6$, or DMSO-d$_6$.

The term "stereoisomer" refers to isomers with at least one asymmetric center. A compound having one or more (e.g., one, two, three or four) asymmetric centers can give rise to a racemic mixture, single enantiomer, diastereomer mixture and individual diastereomer. Certain individual molecules may exist as geometric isomers (cis/trans). Similarly, the compound of the present invention may exist as a mixture of two or more structurally different forms in rapid equilibrium (generally referred to as tautomer). Typical examples of a tautomer include a keto-enol tautomer, phenol-keto tautomer, nitroso-oxime tautomer, imine-enamine tautomer and the like. It is to be understood that all such isomers and mixtures thereof in any proportion (such as 60%, 65%, 70%, 75%, 80%, 85%, 90%, 95%, 96%, 97%, 98%, and 99%) are encompassed within the scope of the present invention.

The chemical bonds of the compound of the present invention may be depicted herein using a solid line ( — ), a solid wedge ( ◢ ), or a dotted wedge ( ┈┈ ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that the stereoisomer shown is present. When present in racemic compounds, solid and dotted wedges are used to define relative stereochemistry, rather than absolute stereochemistry. Unless stated otherwise, it is intended that the compound of the present invention can exist as stereoisomers, which include cis and trans isomers, optical isomers such as R and S enantiomers, diastereomers, geometric isomers, rotational isomers, conformational isomers, atropisomers, and mixtures thereof. The compound of the present invention may exhibit more than one type of isomerism, and consist of mixtures thereof (such as racemates and diastereomeric pairs).

The present invention includes all possible crystalline forms or polymorphs of the compound of the present invention, either as a single polymorph, or as a mixture of more than one polymorphs, in any ratio.

It also should be understood that, certain compounds of the present invention can be used for the treatment in a free from, or where appropriate, in a form of a pharmaceutically acceptable derivative. In the present invention, the pharmaceutically acceptable derivative includes, but is not limited to a pharmaceutically acceptable salt, ester, solvate, N-oxide, metabolite or prodrug, which can directly or indirectly provide the compound of the present invention or a metabolite or residue thereof after being administered to a patient in need thereof. Therefore, "the compound of the present invention" mentioned herein also means to encompass various derivative forms of the compound as mentioned above.

A pharmaceutically acceptable salt of the compound of the present invention includes an acid addition salt and a base addition salt thereof.

A suitable acid addition salt is formed from an acid which forms a pharmaceutically acceptable salt. Specific examples include acetate, adipate, aspartate, benzoate, besylate, bicarbonate/carbonate, bisulfate/sulfate, borate, camphorsulfonate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

A suitable base addition salt is formed from a base which forms a pharmaceutically acceptable salt. Specific examples include aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, 2002). The method for preparing a pharmaceutically acceptable salt of the compound of the present invention is known to a person skilled in the art.

As used herein, the term "ester" refers to those derived from the compounds of the various formulae in the present application, which include physiologically-hydrolyzable esters (which may be hydrolyzed under physiological conditions to release the compounds of the present invention in the form of free acids or alcohols). The compound of the present invention itself may be an ester as well.

The compound of the present invention can exist as a solvate (preferably a hydrate), wherein the compound of the present invention contains a polar solvent, in particular water, methanol or ethanol for example, as a structural element of the crystal lattice of the compound. The amount of the polar solvent, in particular water, may exist in a stoichiometric or non-stoichiometric ratio.

As can be appreciated by a person skilled in the art, not all nitrogen containing heterocycles can form N-oxides since the nitrogen requires an available lone-pair electron for oxidation to the oxide; a person skilled in the art will recognize those nitrogen containing heterocycles which can form N-oxides. A person skilled in the art will also recognize that tertiary amines can form N-oxides. Synthetic methods for the preparation of N-oxides of heterocycles and tertiary amines are well known to a person skilled in the art, and they include the oxidation of heterocycles and tertiary amines with peroxy acids such as peracetic acid and m-chloroperbenzoic acid (MCPBA), hydrogen peroxide, alkyl hydroperoxides such as tert-butyl hydroperoxide, sodium perborate, and dioxiranes such as dimethyldioxirane. These methods for the preparation of N-oxides have been extensively described and reviewed in literatures, see e.g., T. L. Gilchrist, *Comprehensive Organic Synthesis*, vol. 7, pp 748-750; A. R. Katritzky and A. J. Boulton, Eds., Academic Press; and G. W. H. Cheeseman and E. S. G. Werstiuk, Advances in Heterocyclic Chemistry, vol. 22, pp 390-392, A. R. Katritzky and A. J. Boulton, Eds., Academic Press.

The metabolite of the compound of the present invention, namely a substance formed in vivo upon administration of the compound of the present invention, is also included within the scope of the present invention. Such a product may result e.g., from the oxidation, reduction, hydrolysis, amidation, de-amidation, esterification, enzymolysis, and the like, of the administered compound. Accordingly, the present invention encompasses the metabolite of the compound of the present invention, including a compound produced by a method comprising contacting the compound of the present invention with a mammal for a period of time sufficient to result in a metabolic product thereof.

Also within the scope of the present invention is a prodrug of the compound of the invention, which is certain derivative of the compound of the invention that may have little or no pharmacological activity itself, but can, when administered into or onto the body, be converted into the compound of the invention having the desired activity, for example, by hydrolytic cleavage. In general, such prodrug will be a functional derivative of the compound which is readily converted in vivo into the compound with desired therapeutic activity. Further information on the use of the prodrug may be found in "Pro-drugs as Novel Delivery Systems", Vol. 14, ACS Symposium Series (T. Higuchi and V. Stella). The prodrug in accordance with the invention can, for example, be produced by replacing appropriate functionalities present in the compound of the present invention with certain moieties known to those skilled in the art as "pro-moieties" as described, for example, in "Design of Prodrugs" by H. Bundgaard (Elsevier, 1985).

The present invention further encompasses the compound of the present invention having a protecting group. During any of the processes for preparation of the compound of the present invention, it may be necessary and/or desirable to protect sensitive or reactive groups on any of the molecules concerned, thereby resulting in the chemically protected form of the compound of the present invention. This may be achieved by means of conventional protecting groups, e.g., those described in T. W. Greene & P. G. M. Wuts, Protective Groups in Organic Synthesis, John Wiley & Sons, 1991, which is incorporated herein by reference. The protecting groups may be removed at a convenient subsequent stage using methods known from the art.

The term "about" refers to a range within +10%, preferably within +5%, and more preferably within +2% of the specified value.

SPECIFIC EMBODIMENTS

Compound

In some embodiments, the present invention provides a compound or a pharmaceutically acceptable salt, ester, stereoisomer, polymorph, solvate, N-oxide, isotopically labeled compound, metabolite or prodrug thereof, wherein the compound has the structure of Formula (I):

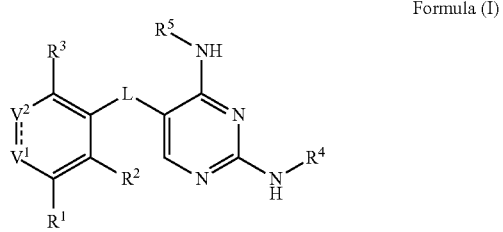

Formula (I)

wherein:

L is selected from the group consisting of C(=O), CRR', NR, O, S, S=O and S(=O)$_2$;

$V^1$ is selected from the group consisting of N,

and NR;

$V^2$ is selected from the group consisting of $CR^6$ and C(=O);

= represents either a single bond or a double bond, provided that when = is a single bond, $V^1$ is NR and $V^2$ is C(=O);

R and R' are each independently selected from the group consisting of H, halogen, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl, and at most 2 ring members in the cyclic hydrocarbyl and heterocyclyl are C(=O);

$R^1$, $R^2$, $R^3$ and $R^6$ are each independently selected from the group consisting of H, halogen, —CN, —NH$_2$, —OH, —SH, —Se—R, —Si(R)$_3$, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl, $C_{6-12}$ aralkyl, $C_{1-6}$ haloalkyl, —C(=O)R$^a$, —OC(=O)R$^a$, —C(=O)OR$^a$, —OR$^a$, —SR$^a$, —S(=O)R$^a$, —S(=O)$_2$R$^a$, —S(=O)$_2$NR$^a$R$^b$, —S(=O)(=NR)R$^a$, —NR$^a$R$^b$, —C(=O)NR$^a$R$^b$, —C(=S)NR$^a$R$^b$, —C(=NR)NR$^a$R$^b$, —NR$^a$—C(=O)R$^b$, —NR$^a$—C(=O)OR$^b$, —NR$^a$—S(=O)$_2$—R$^b$, —NR$^a$—C(=O)—NR$^a$R$^b$, —C$_{1-6}$ alkylene-NR$^a$R$^b$, —C$_{1-6}$ alkylene-OR$^a$, —C$_{1-6}$ alkylene-C(=O)R, —C$_{1-6}$ alkenylene-OR$^a$, —O—C$_{1-6}$ alkylene-NR$^a$R$^b$ and —P(=O)R$^a$R$^b$;

$R^4$ and $R^5$ are each independently selected from the group consisting of H, —C(=O)OR$^a$, —NR$^a$R$^b$, —NR$^a$—C(=O)R$^b$, —NR$^a$—C(=O)OR$^b$, —C$_{1-6}$ alkylene-NR$^a$R$^b$, —C$_{1-6}$ alkylene-OR$^a$, —C$_{1-6}$ alkylene-O—C$_{1-6}$ alkylene-OR$^a$, $C_{1-6}$ alkyl, $C_{1-6}$ haloalkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl;

alternatively, $R^1$ and $R^4$ together form —NH—(C$_{1-6}$ alkylene)-L-(C$_{1-6}$ alkylene)-, preferably —NHCH$_2$CH$_2$—O—CH$_2$CH$_2$—;

the above alkyl, alkylene, alkenyl, alkynyl, cyclic hydrocarbyl, heterocyclyl, aryl, heteroaryl and aralkyl, at each occurrence, are each optionally substituted with one or more substituents independently selected from the group consisting of halogen, hydroxyl, oxo, amino, cyano, nitro, —Si(R)$_3$, $C_{1-6}$ alkyl, saturated or partially unsaturated $C_{3-6}$ cyclic hydrocarbyl, saturated or partially unsaturated 3- to 10-membered heterocyclyl, $C_{6-10}$ aryl, 5- to 14-membered heteroaryl, $C_{6-12}$ aralkyl, —C(=O)R$^a$, —OC(=O)R$^a$, —C(=O)OR$^a$, —OR$^a$, —SR$^a$, —S(=O)R$^a$, —S(=O)$_2$R$^a$, —S(=O)$_2$NR$^a$R$^b$, —NR$^a$R$^b$, —C(=O)NR$^a$R$^b$, —NR$^a$—C(=O)R$^b$, —NR$^a$—C(=O)OR$^b$, —NR$^a$—S(=O)$_2$—R$^b$, —NR$^a$—C(=O)—NR$^a$R$^b$, —C$_{1-6}$ alkylene-NR$^a$R$^b$, —C$_{1-6}$ alkylene-OR$^a$, —C$_{1-6}$ alkenylene-OR$^a$ and —O—C$_{1-6}$ alkylene-NR$^a$R$^b$, the alkyl, cyclic hydrocarbyl, heterocyclyl, aryl, heteroaryl and aralkyl are further optionally substituted with one or more substituents independently selected from the group consisting of halogen, hydroxyl, oxo, amino, cyano, nitro, —NR$^a$R$^b$, $C_{1-6}$ alkyl, —O—C$_{1-6}$ alkyl, saturated or partially unsaturated $C_{3-6}$ cyclic hydrocarbyl, saturated or partially unsaturated 3- to 10-membered heterocyclyl, $C_{6-10}$ aryl, 5- to 14-membered heteroaryl and $C_{6-12}$ aralkyl; and $R^a$ and $R^b$, at each occurrence, are each independently selected from the group consisting of H, —OH, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl; alternatively, $R^a$ and $R^b$ together with the atom to which they are attached form a 3- to 12-membered heterocycle or heteroaromatic ring, the above groups are further optionally substituted with one or more substituents independently selected from the group consisting of halogen, hydroxyl, oxo, amino, cyano, nitro, $C_{1-6}$ alkyl, —O—$C_{1-6}$ alkyl, saturated or partially unsaturated $C_{3-6}$ cyclic hydrocarbyl, saturated or partially unsaturated 3- to 10-membered heterocyclyl, $C_{6-10}$ aryl, 5- to 14-membered heteroaryl and $C_{6-12}$ aralkyl.

In preferred embodiments, L is selected from the group consisting of $CH_2$, O, S and NH.

In preferred embodiments, $V^1$ is selected from the group consisting of N,

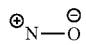

and $NCH_3$.

In preferred embodiments, $V^2$ is selected from the group consisting of CH, C—$NHCH_3$, C—$OCH_3$, C—F and C(=O).

In preferred embodiments, the present invention provides the compound or a pharmaceutically acceptable salt, ester, stereoisomer, polymorph, solvate, N-oxide, isotopically labeled compound, metabolite or prodrug thereof, wherein $R^a$ and $R^b$, at each occurrence, are each independently selected from the group consisting of H, —OH, methyl, ethyl, n-propyl, isopropyl, cyclopropyl, phenyl, benzyl, methoxy and ethoxy; alternatively, $R^a$ and $R^b$ together with the atom to which they are attached form a 5- to 8-membered heterocycle or heteroaromatic ring.

In preferred embodiments, the present invention provides the compound or a pharmaceutically acceptable salt, ester, stereoisomer, polymorph, solvate, N-oxide, isotopically labeled compound, metabolite or prodrug thereof, wherein $R^1$, $R^2$, $R^3$ and $R^6$ are each independently selected from the group consisting of H, F, Cl, Br, I, —CN, —$NH_2$, —OH, —SH, —Se—$CH_3$, —Si$(CH_3)_3$, —$CH_2NH_2$, —$CH_2NHCH_3$, —$CH_2N(CH_3)_2$, methyl, ethyl, n-propyl, isopropyl, n-butyl, isobutyl, tert-butyl, cyclopropyl, cyclobutyl, cyclopentyl, cyclohexyl, vinyl, propenyl, allyl, ethynyl, propynyl, trifluoromethyl, acetyl, —C(=O)OH, —C(=O)$NH_2$, —C(=S)$NH_2$, —C(=NH)$NH_2$, —$NHCH_3$, —$NHCH_2CH_3$, —$NHCH_2CF_3$, —N$(CH_3)_2$, —N$(CH_3)(C_2H_5)$, —N$(C_2H_5)_2$, —$NHCH_2CH_2OH$, —NH—C(=O)$CH_3$, —NH—C(=O)CH=$CH_2$, methoxy, ethoxy, propoxy, phenyl, —NH—C(=O)—$NH_2$, —NH—C(=O)$OCH_3$, —$SCH_3$, —$SCH_2CH_3$, —SC$(CH_3)_3$, —SBn, —S(=O)$CH_3$, —S(=O)Bn, —S(=O)$_2CH_3$, —S(=O)$_2$Bn, —S(=O)$_2NH_2$, —S(=O)$_2NHCH_3$, —S(=O)$_2$N$(CH_3)_2$, —S(=O)(=NH)$CH_3$, —P(=O)$(CH_3)_2$, —P(=O)$(C_2H_5)_2$,

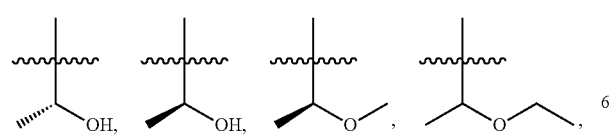

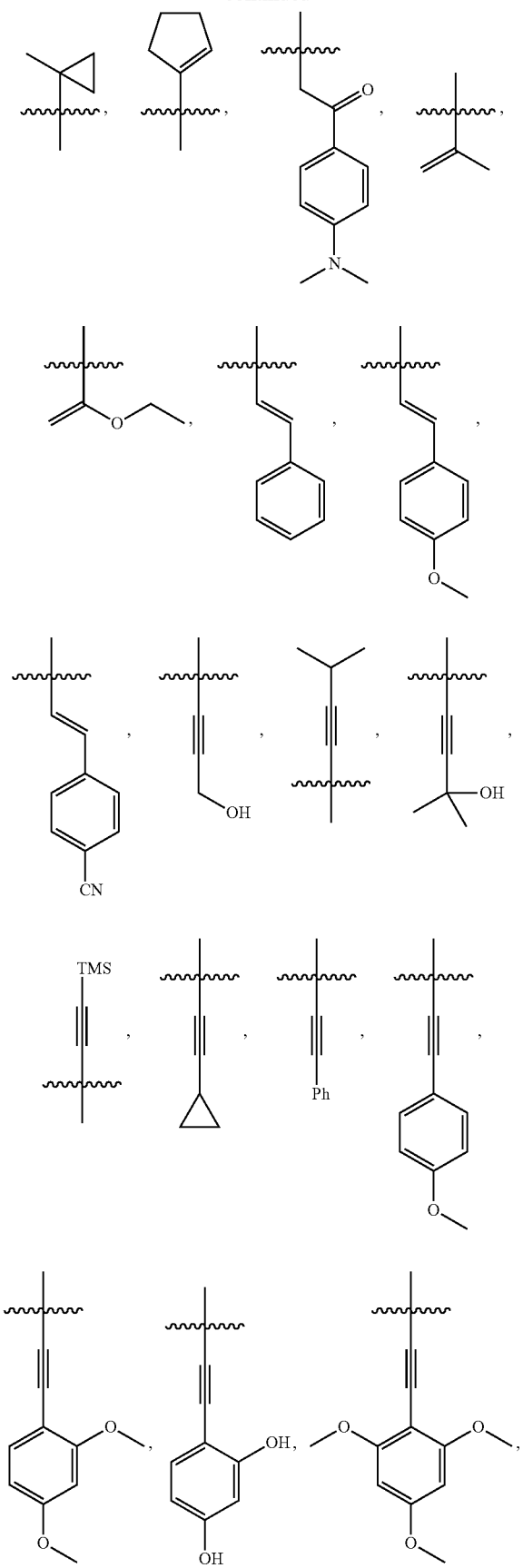

13
-continued

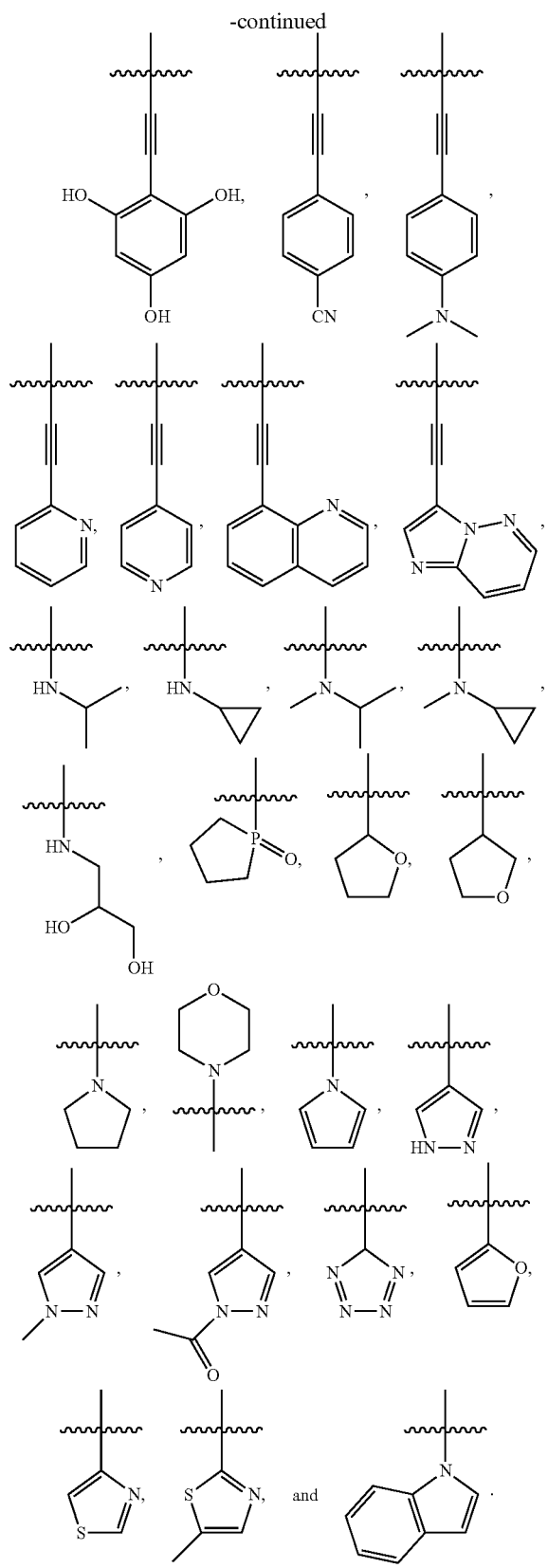

In preferred embodiments, the present invention provides the compound or a pharmaceutically acceptable salt, ester, stereoisomer, polymorph, solvate, N-oxide, isotopically labeled compound, metabolite or prodrug thereof, wherein $R^4$ and $R^5$ are each independently selected from the group consisting of H, —C(=O)OC(CH$_3$)$_3$, —NH$_2$, —NHCH$_3$, —NHPh, —NHC(=O)CH$_3$, —NHBoc, methyl, ethyl, —CH$_2$CF$_3$, n-propyl, isopropyl, n-butyl, isobutyl, tert-butyl, cyclopropyl, cyclobutyl, cyclopentyl, cyclohexyl, phenyl, benzyl,

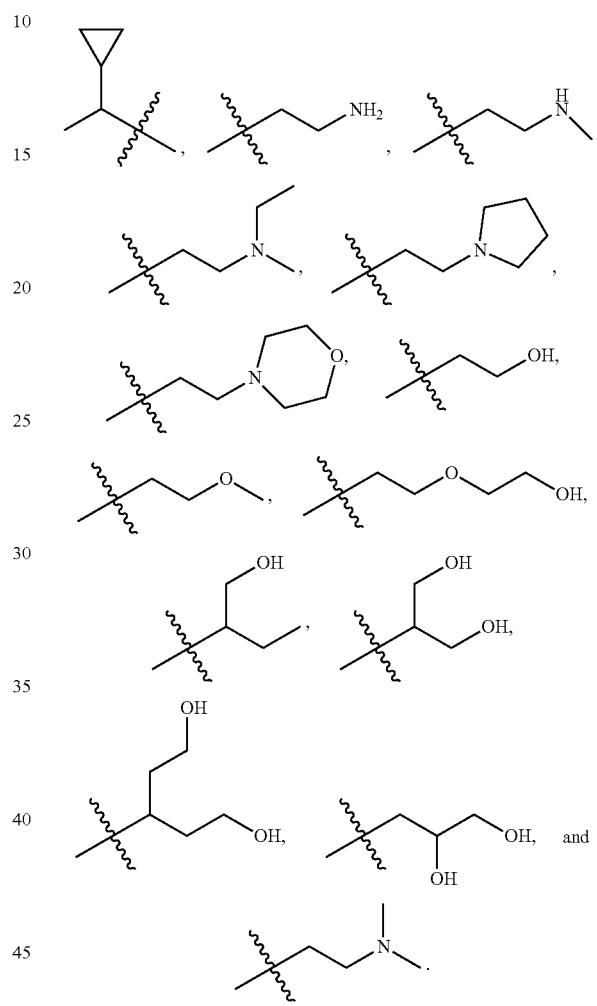

In preferred embodiments, the present invention provides the compound or a pharmaceutically acceptable salt, ester, stereoisomer, polymorph, solvate, N-oxide, isotopically labeled compound, metabolite or prodrug thereof, wherein the compound has the structure of any of the following formulae:

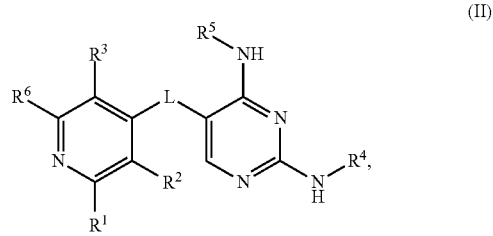

(II)

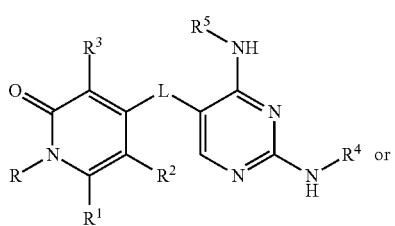
(III)
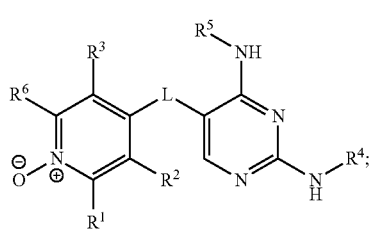
(IV)
preferably has the structure of any of the following formulae:
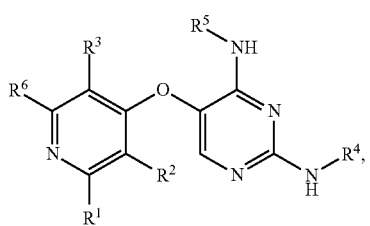
(II')
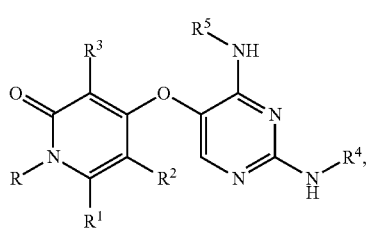
(III')
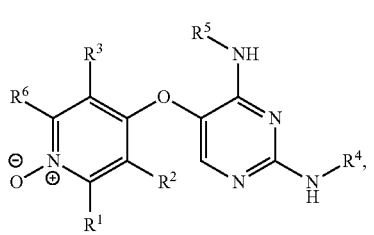
(IV')
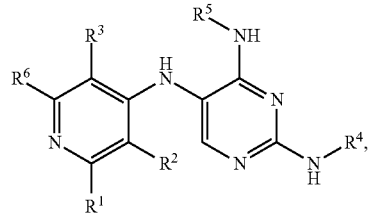
(II")
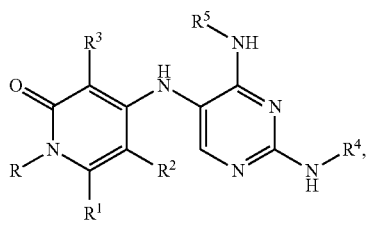
(III")
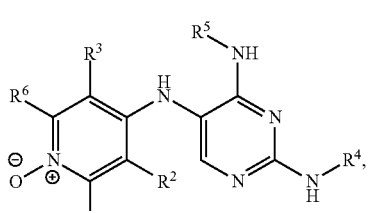
(IV")
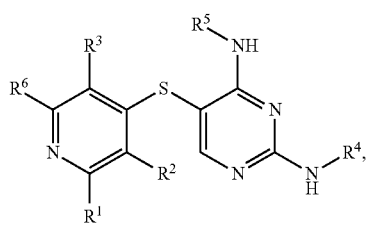
(II''')
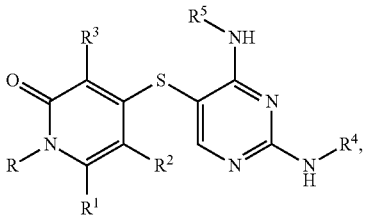
(III''')
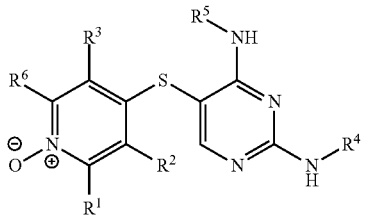
(IV''')
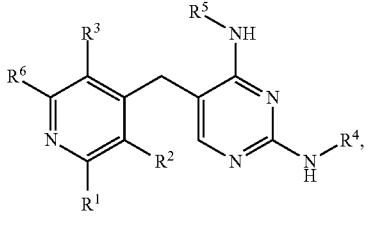
(II'''')
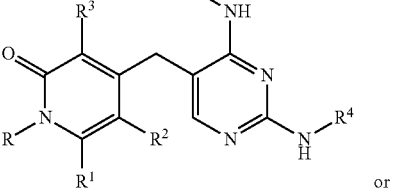
(III'''')
or

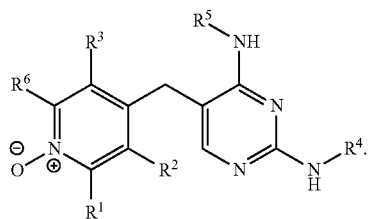
(IV'''')

The compound obtained by any combination of the various embodiments is encompassed by the invention.

In preferred embodiments, the present invention provides the compound or a pharmaceutically acceptable salt, ester, stereoisomer, polymorph, solvate, N-oxide, isotopically labeled compound, metabolite or prodrug thereof, wherein the compound has the following structure:

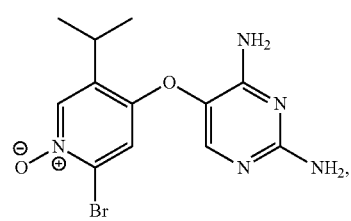
1

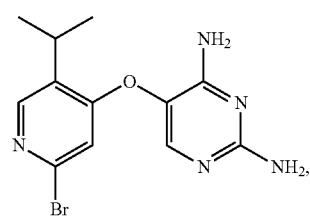
2

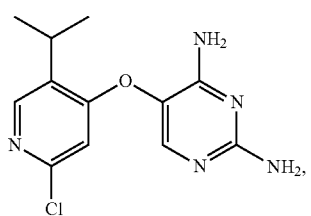
3

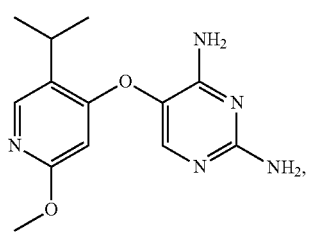
4

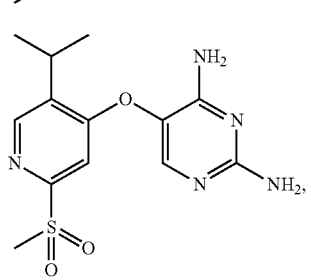
5

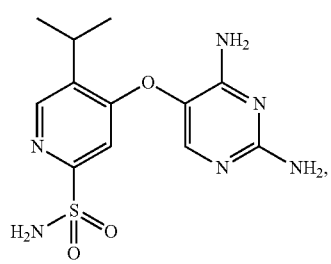
6

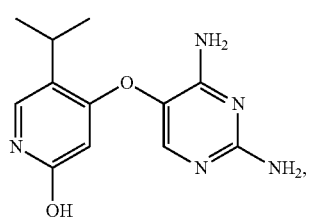
7

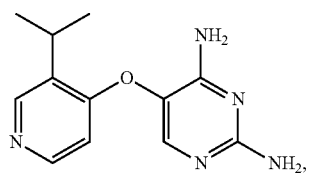
8

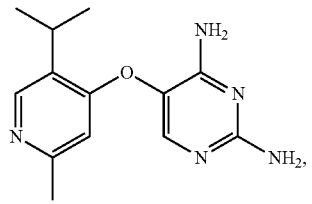
9

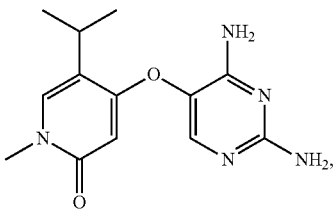
11

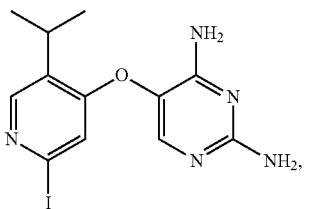
12

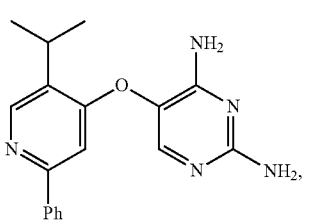
13

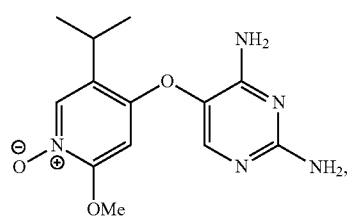
14
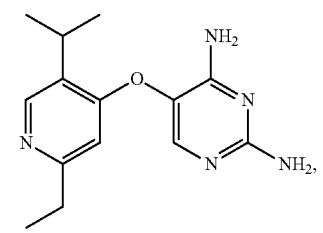
15
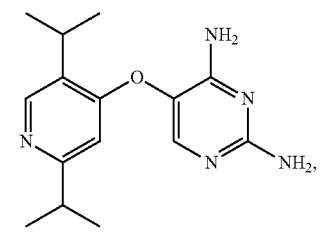
16
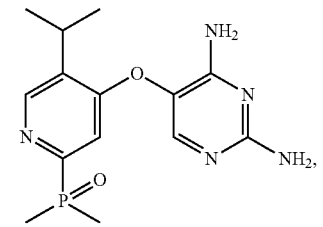
17
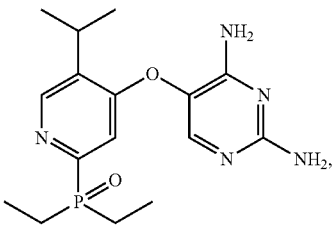
18
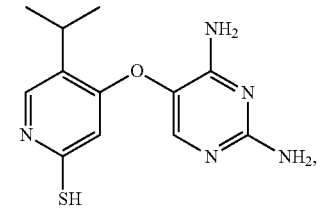
19
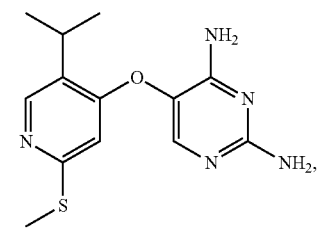
20
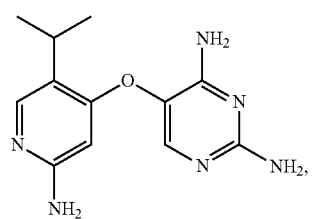
21
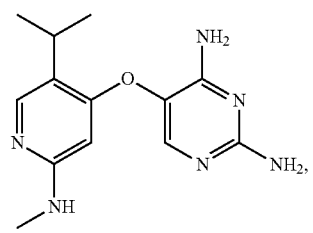
22
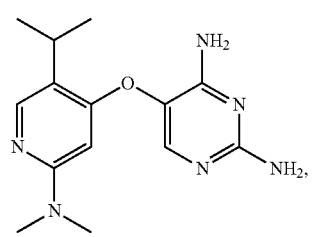
23
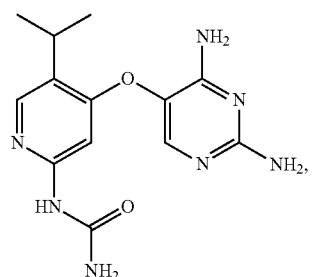
24
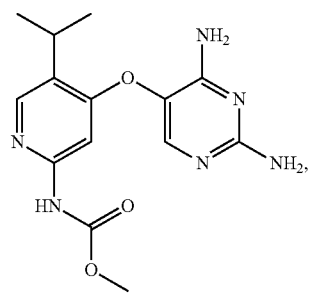
25
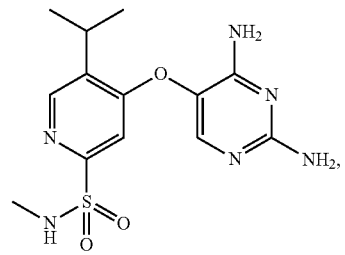
26

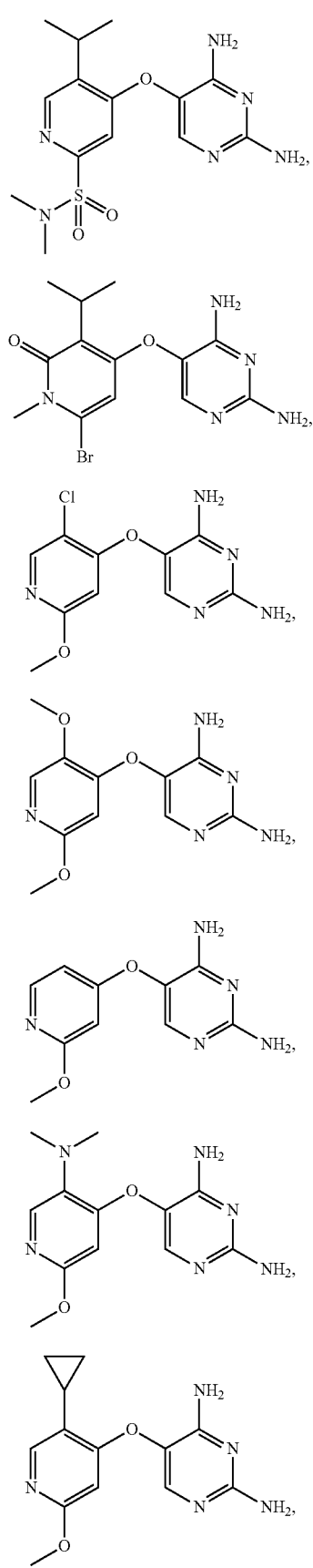
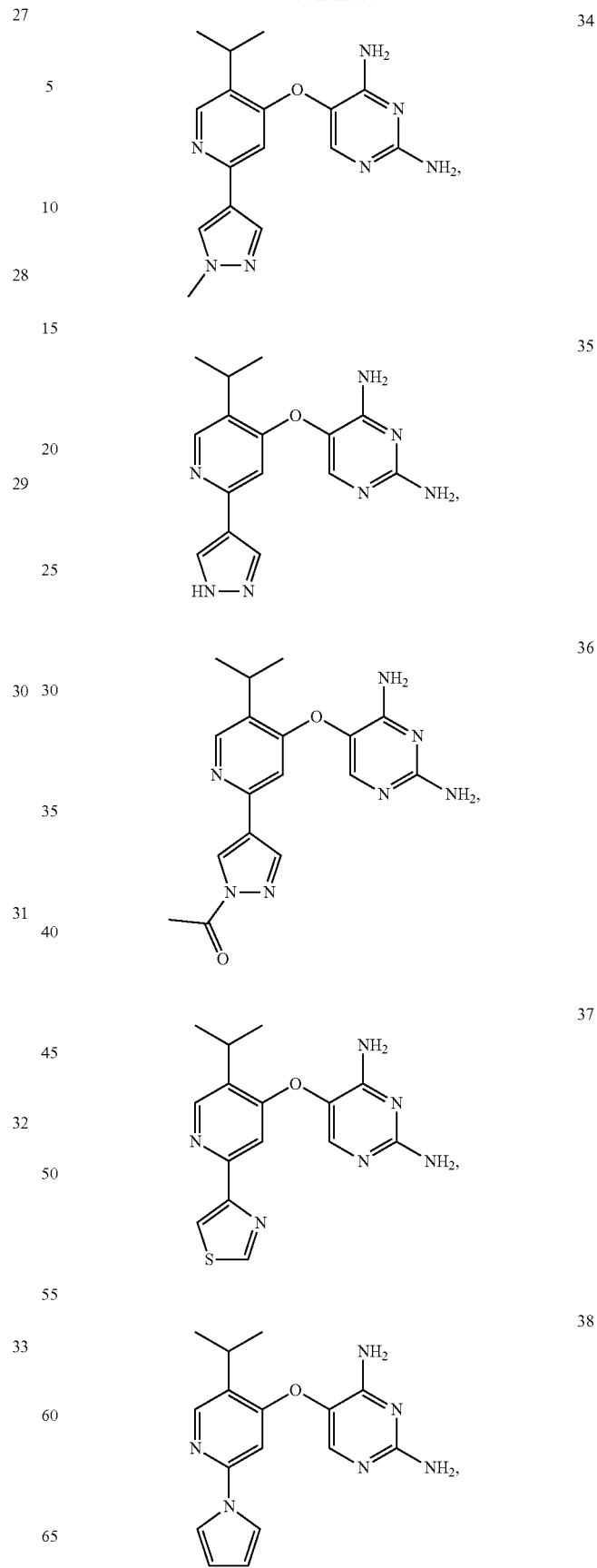

-continued
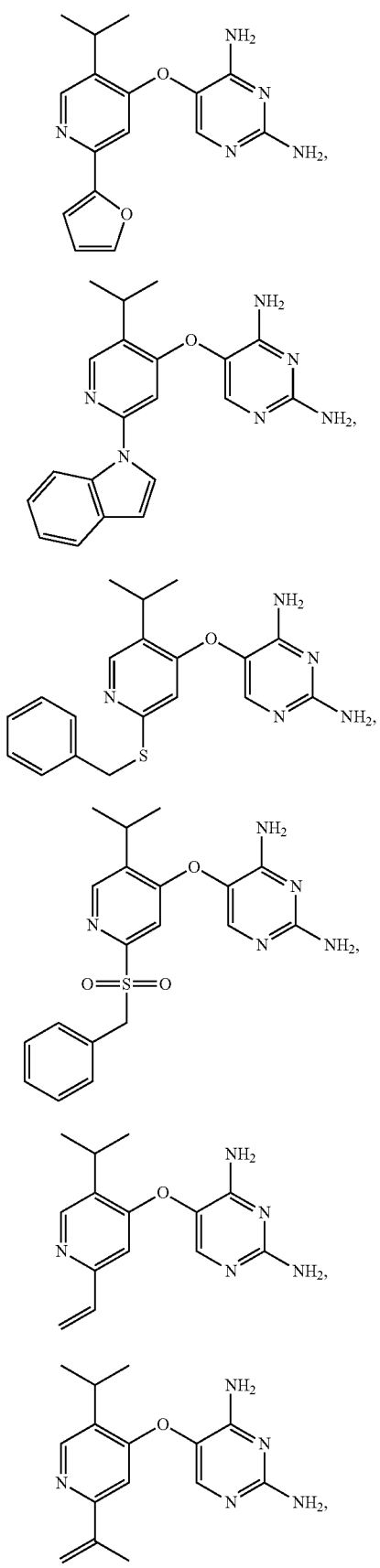
39
40
41
42
43
44
-continued
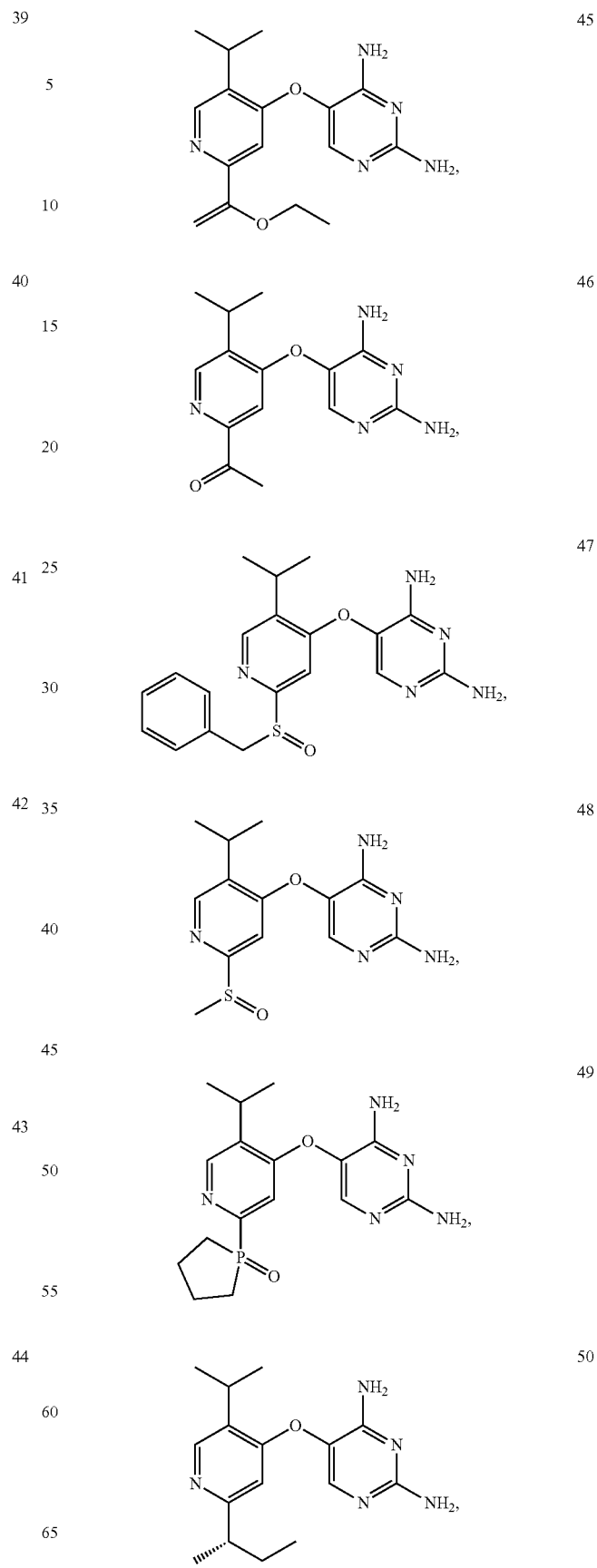
45
46
47
48
49
50

51 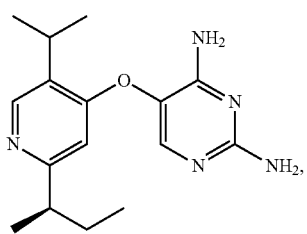
52 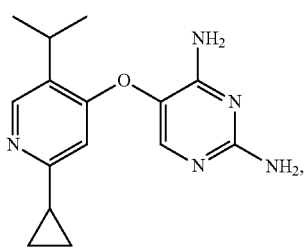
53 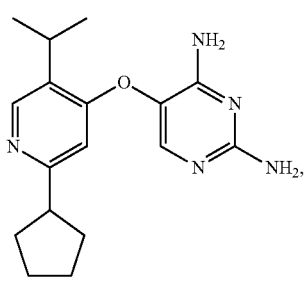
54 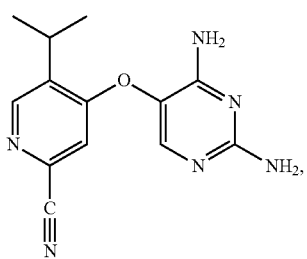
55 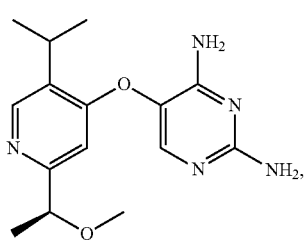
56 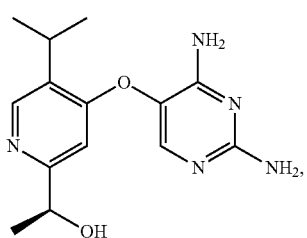
57 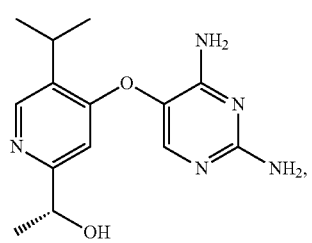
58 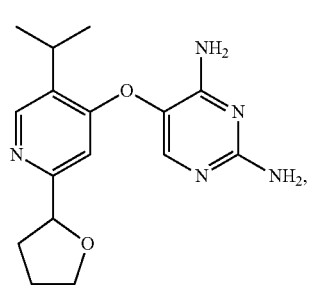
59 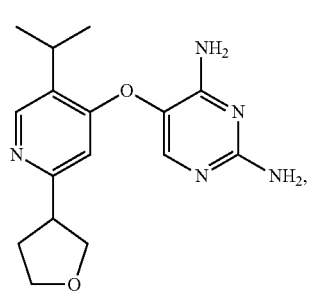
60 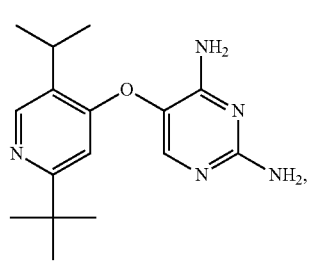
61 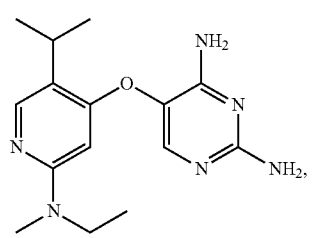
62 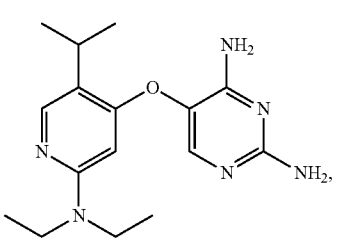

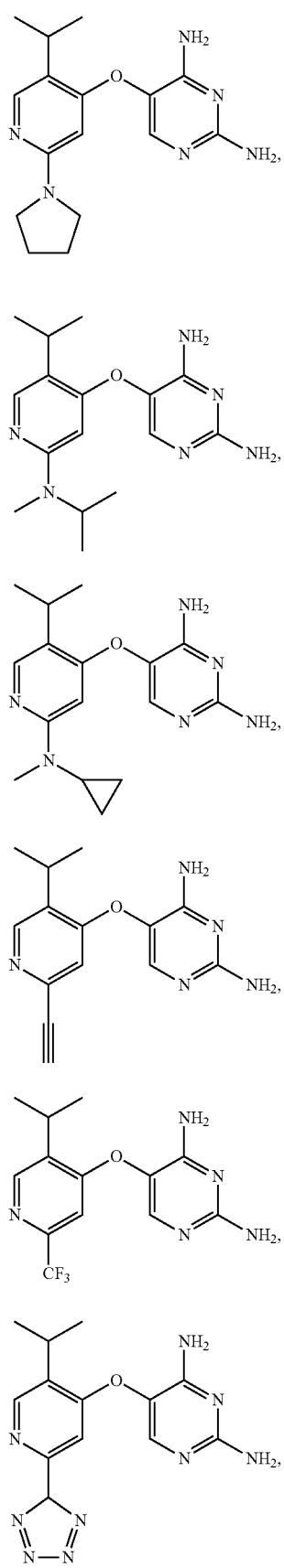
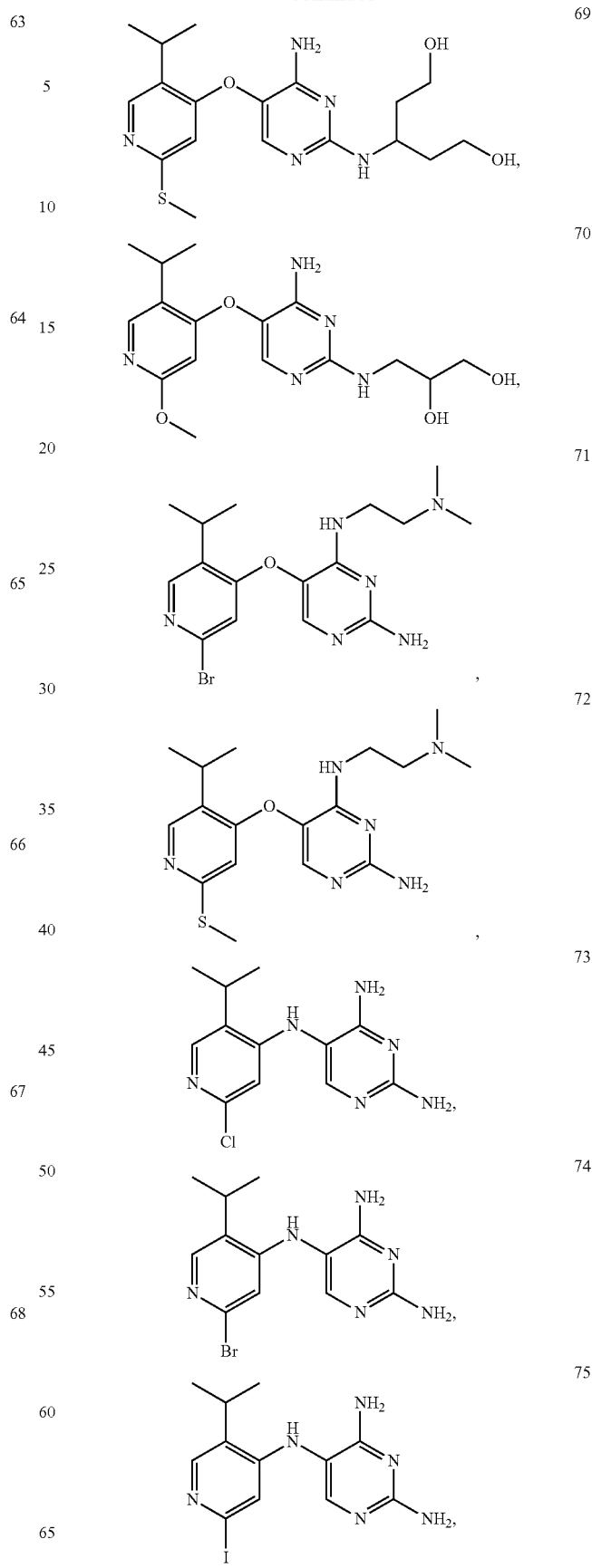

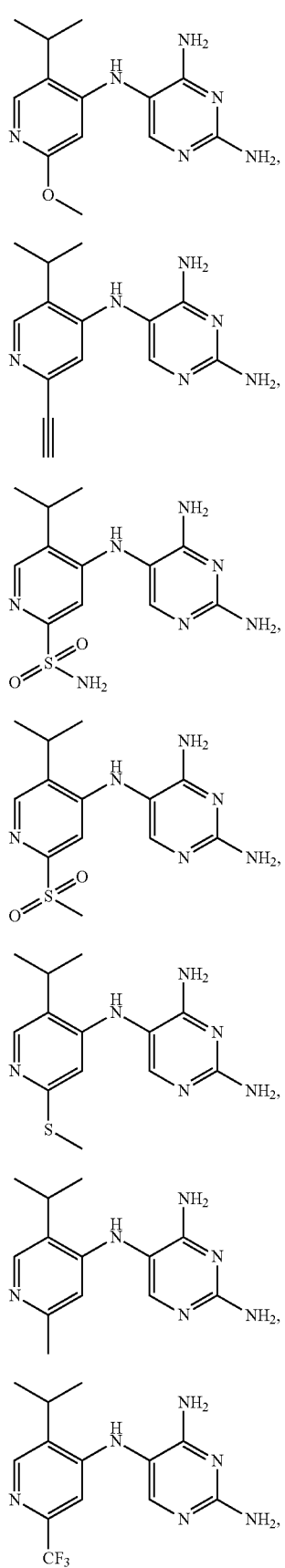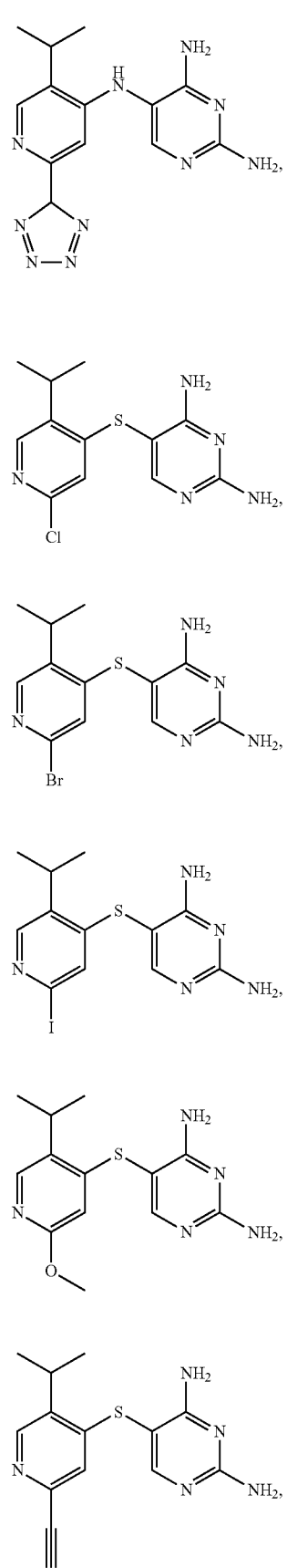

-continued
89
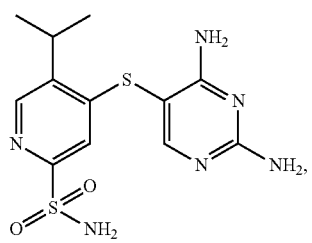
90
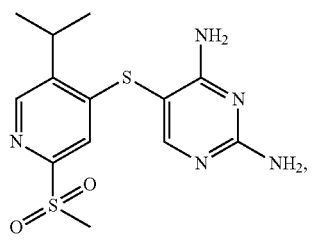
91
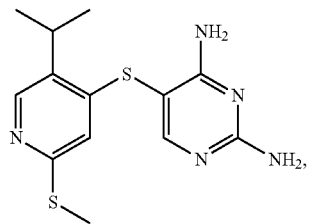
92
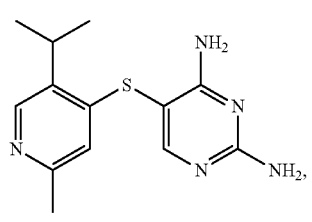
93
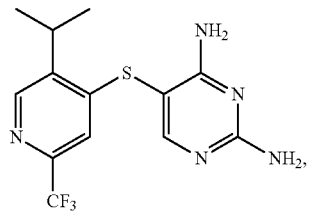
94
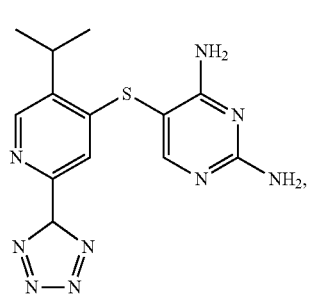
-continued
95
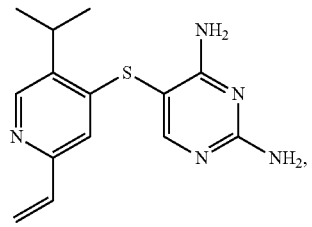
96
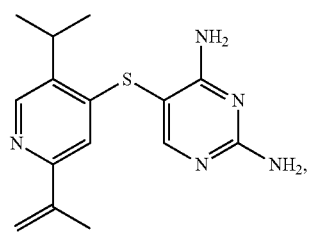
97
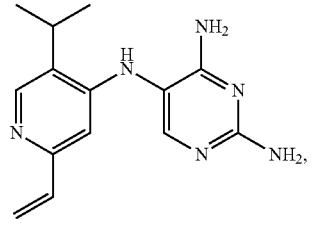
98
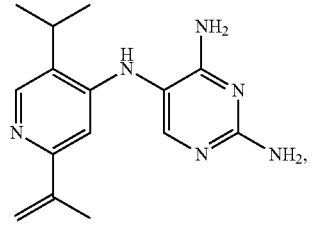
99
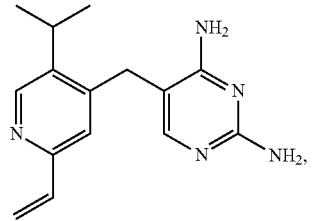
100
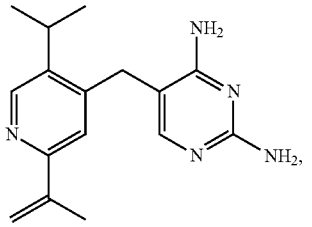
101
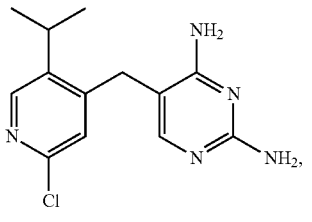

102 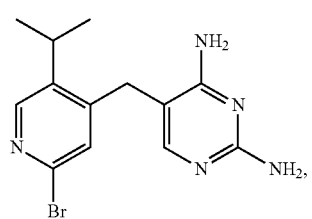
103 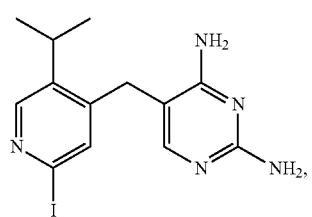
104 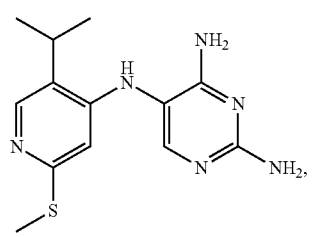
105 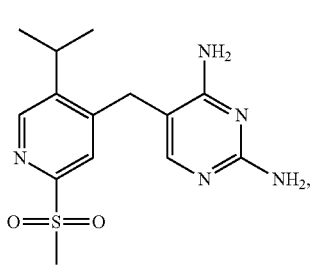
106 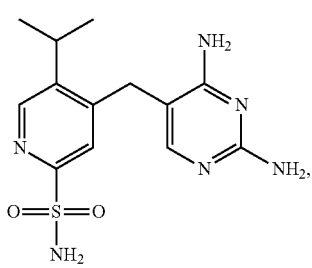
107 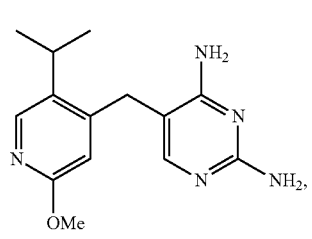
108 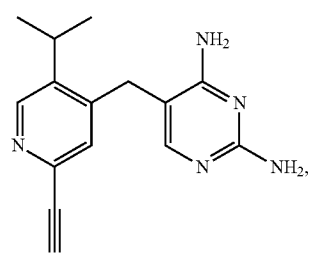
109 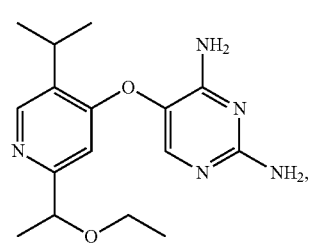
110 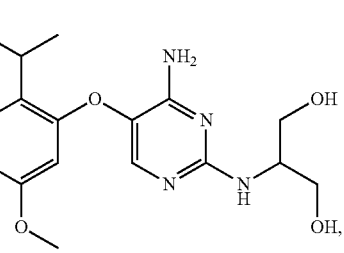
111 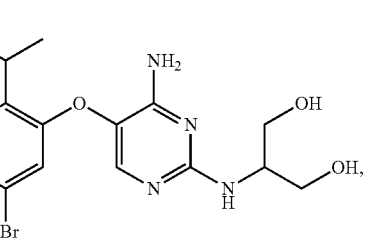
112 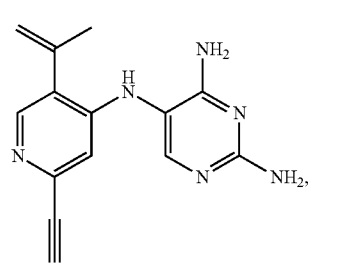
113 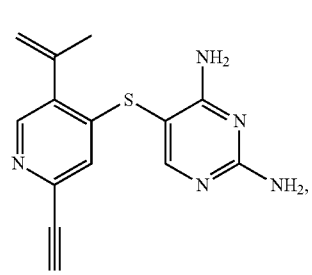

114
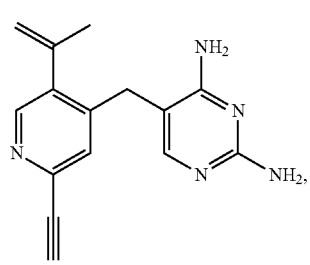
115
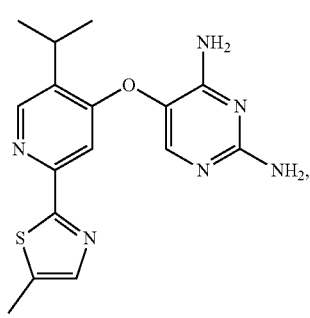
116
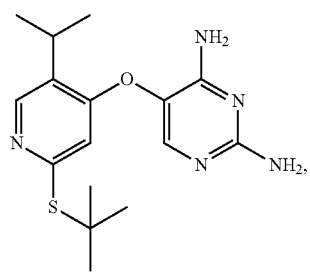
117
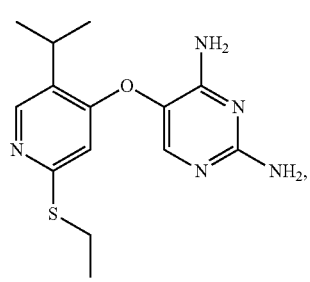
118
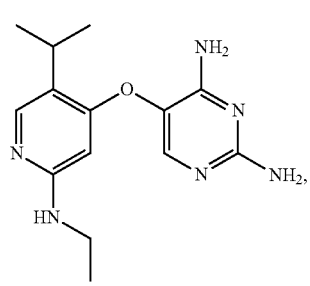
119
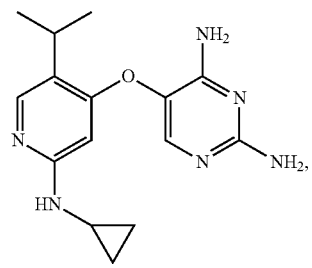
120
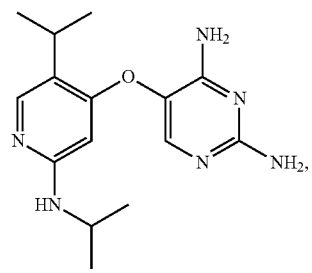
121
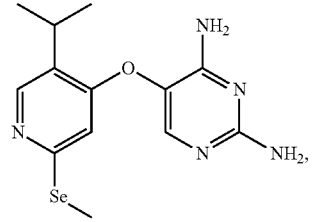
122
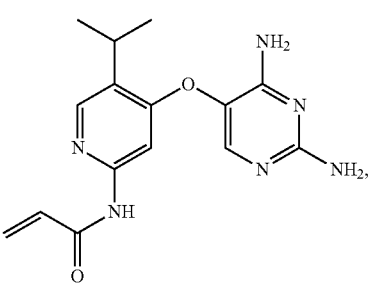
123
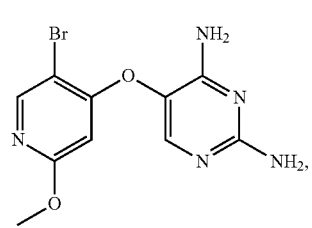
124

125 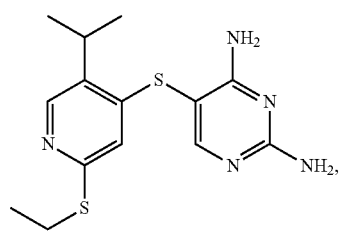
126 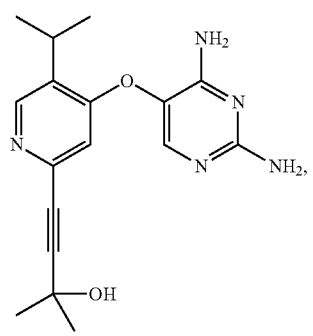
127 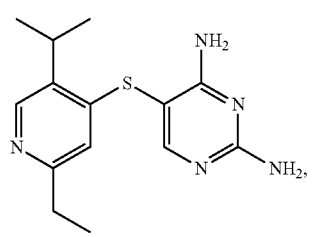
128 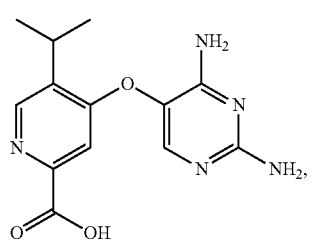
129 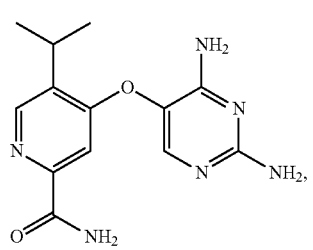
130 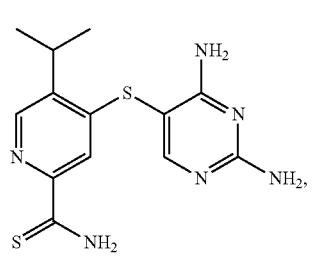
131 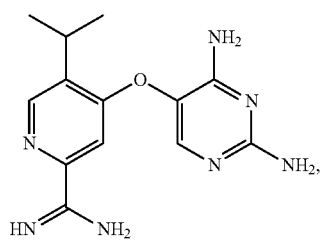
132 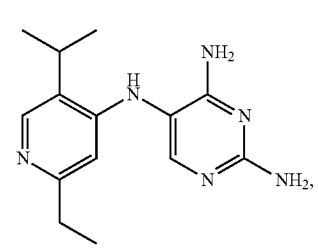
133 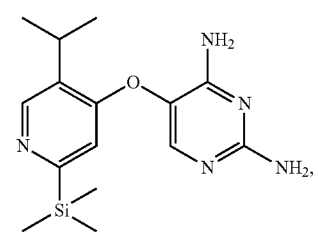
134 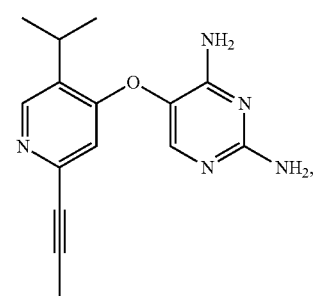
135 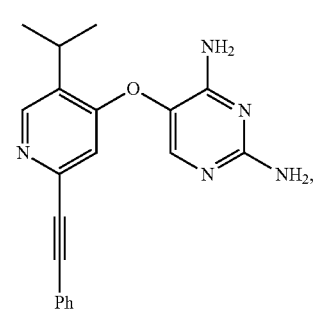

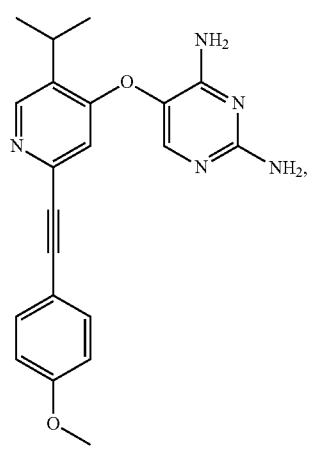
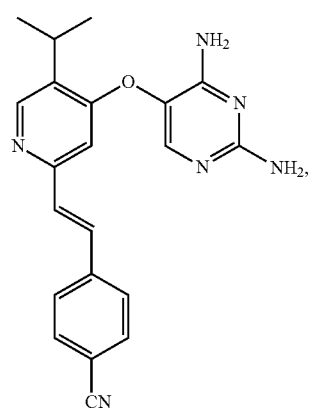
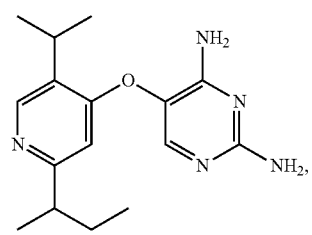
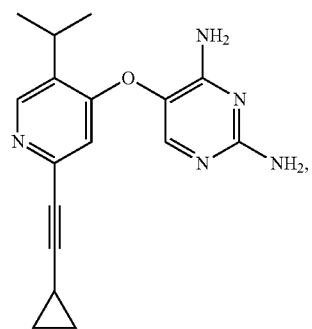
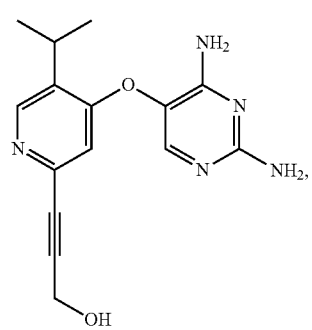

144
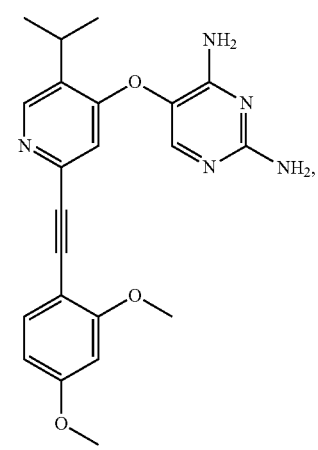
145
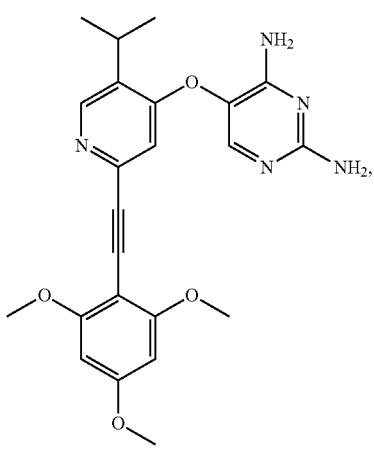
146
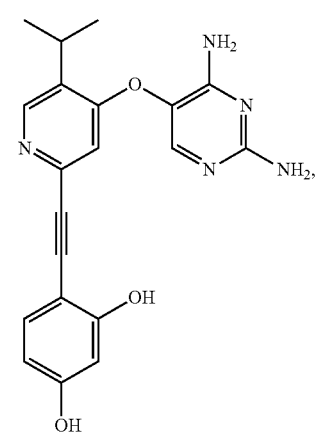
147
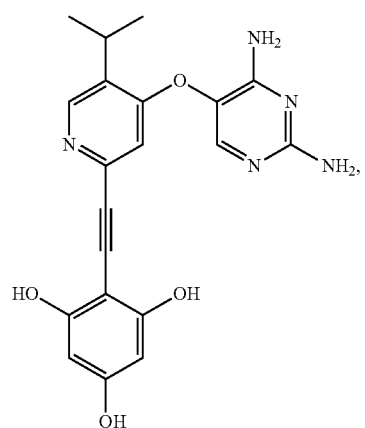
148
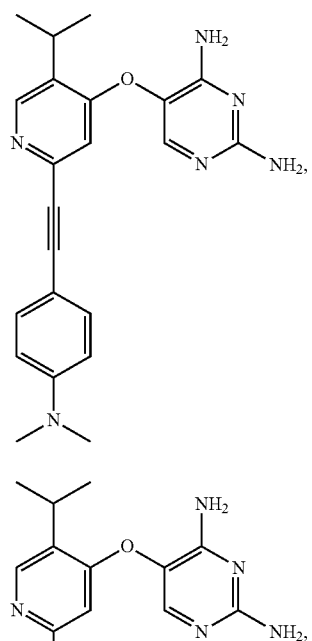
149
150
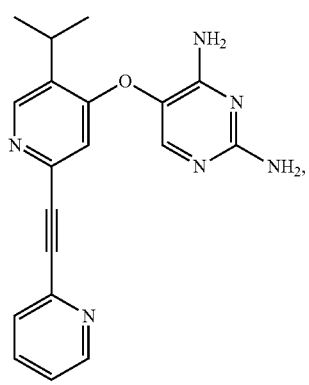

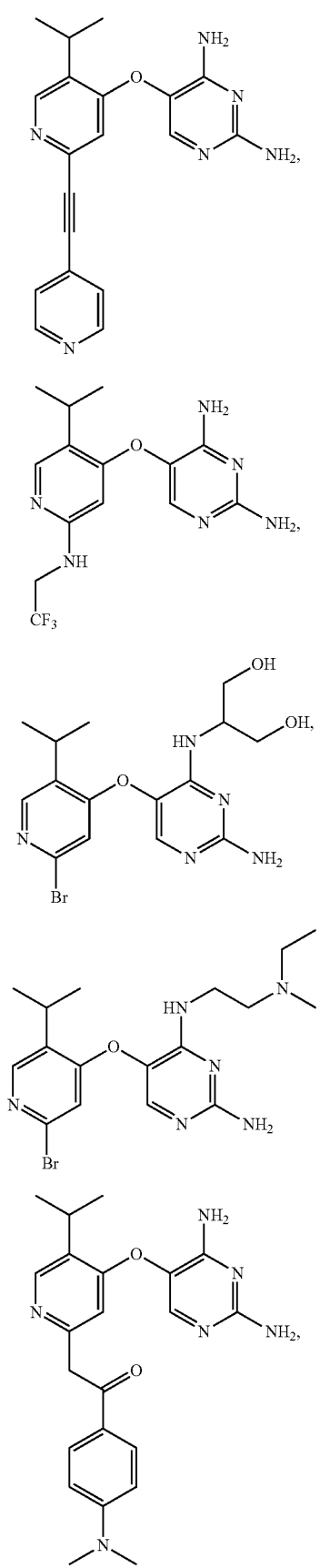
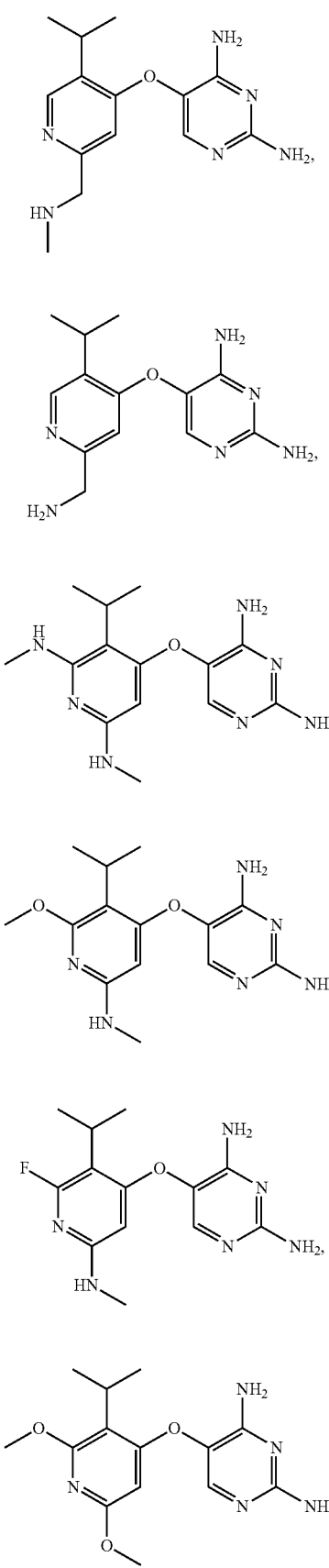

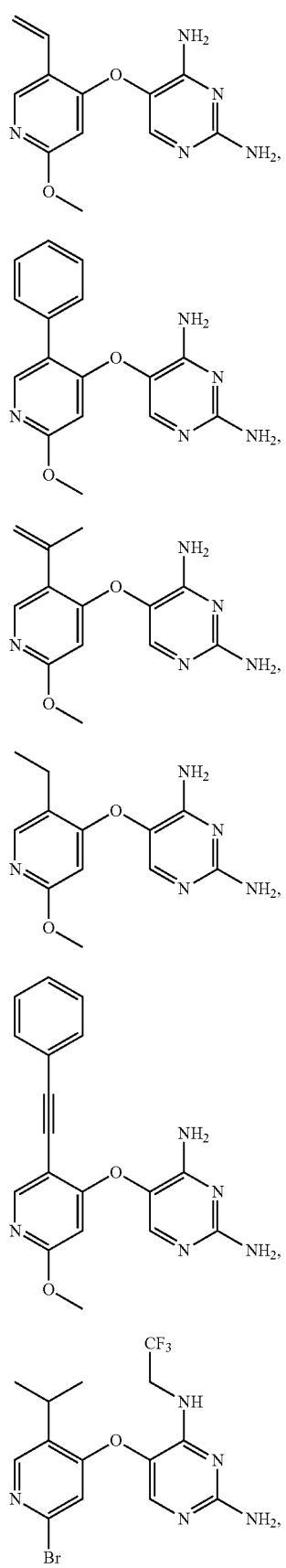
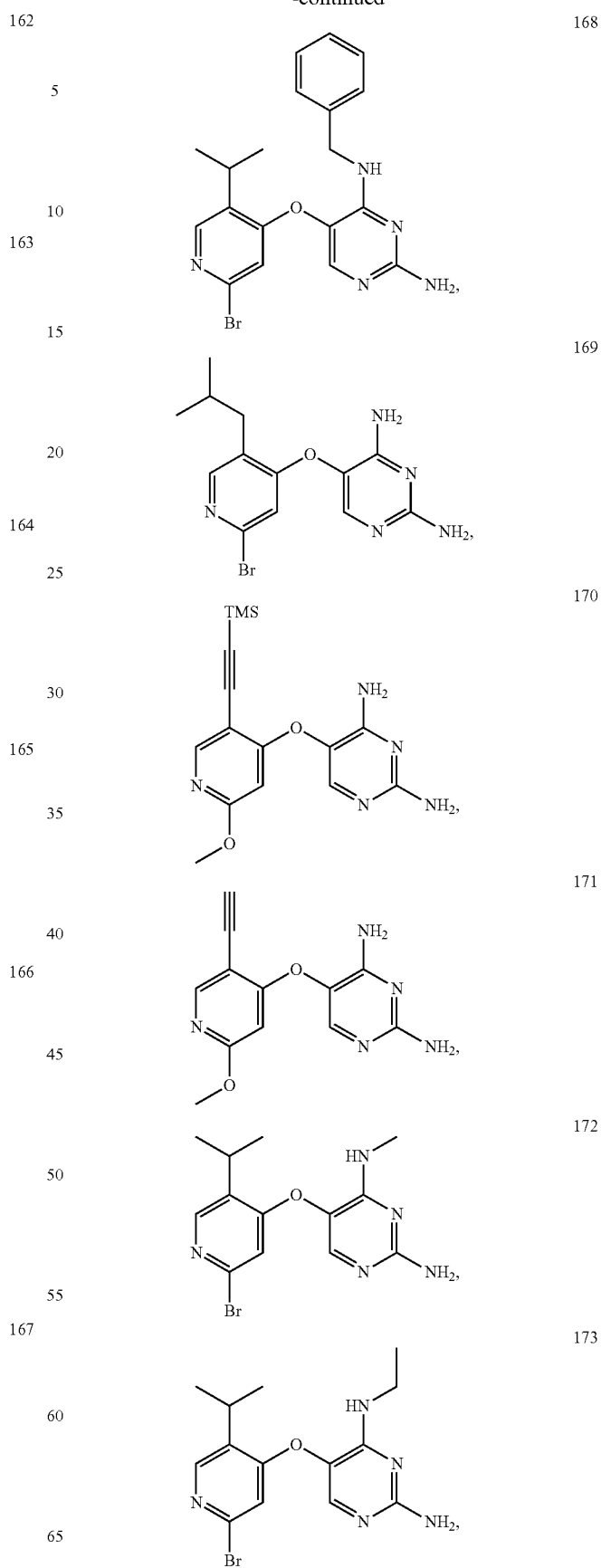

174 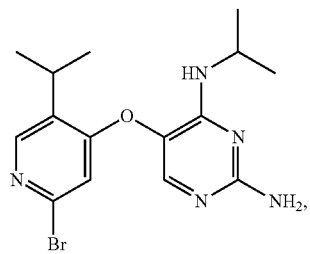
175 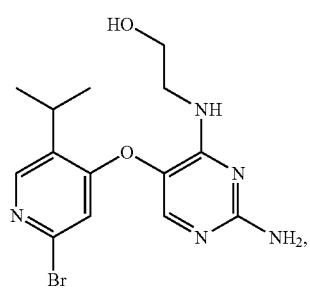
176 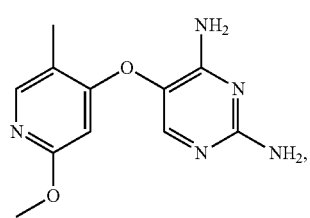
177 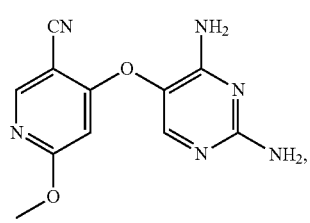
178 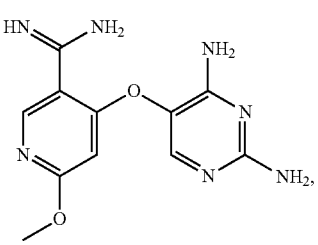
179 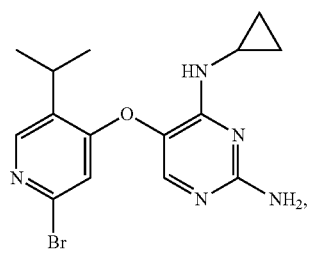
180 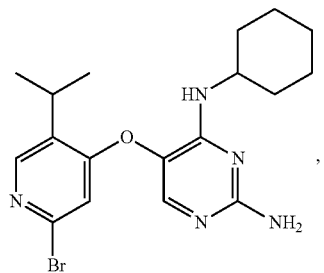
181 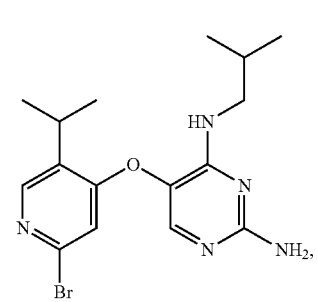
182 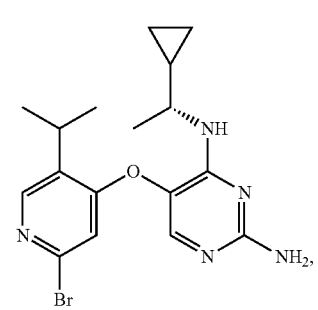
183 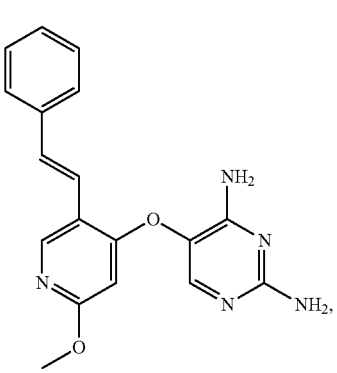
184 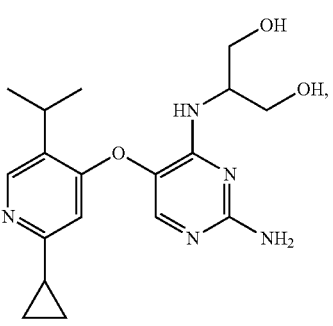

185 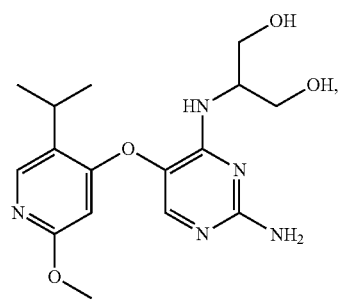
186 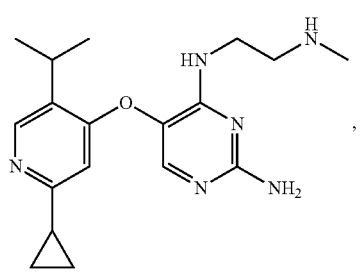
187 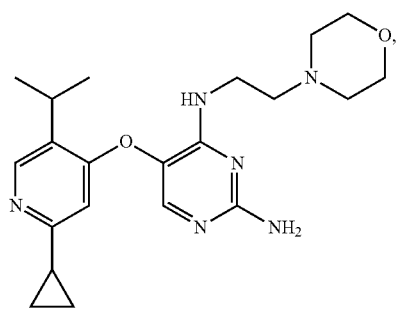
188 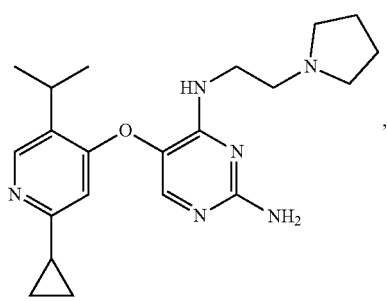
189 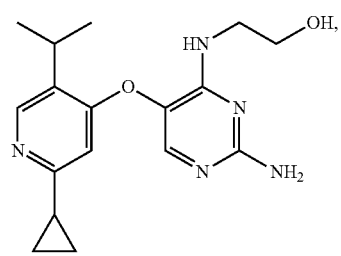
190 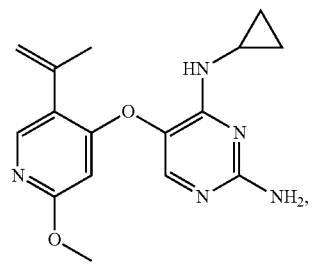
191 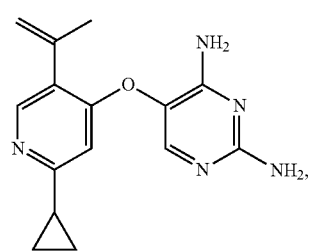
192 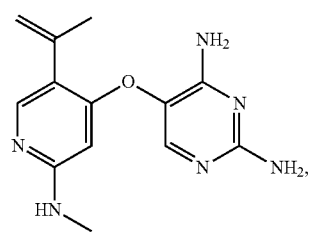
193 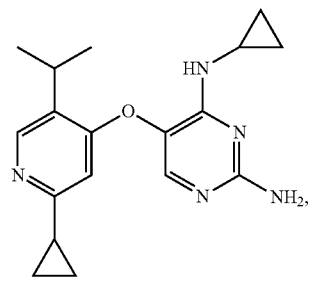
194 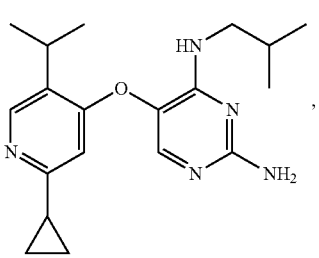

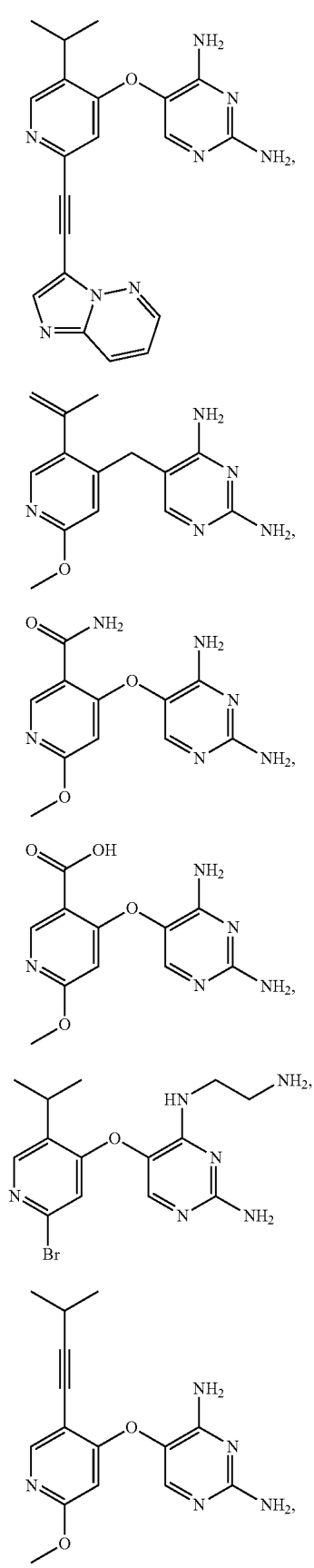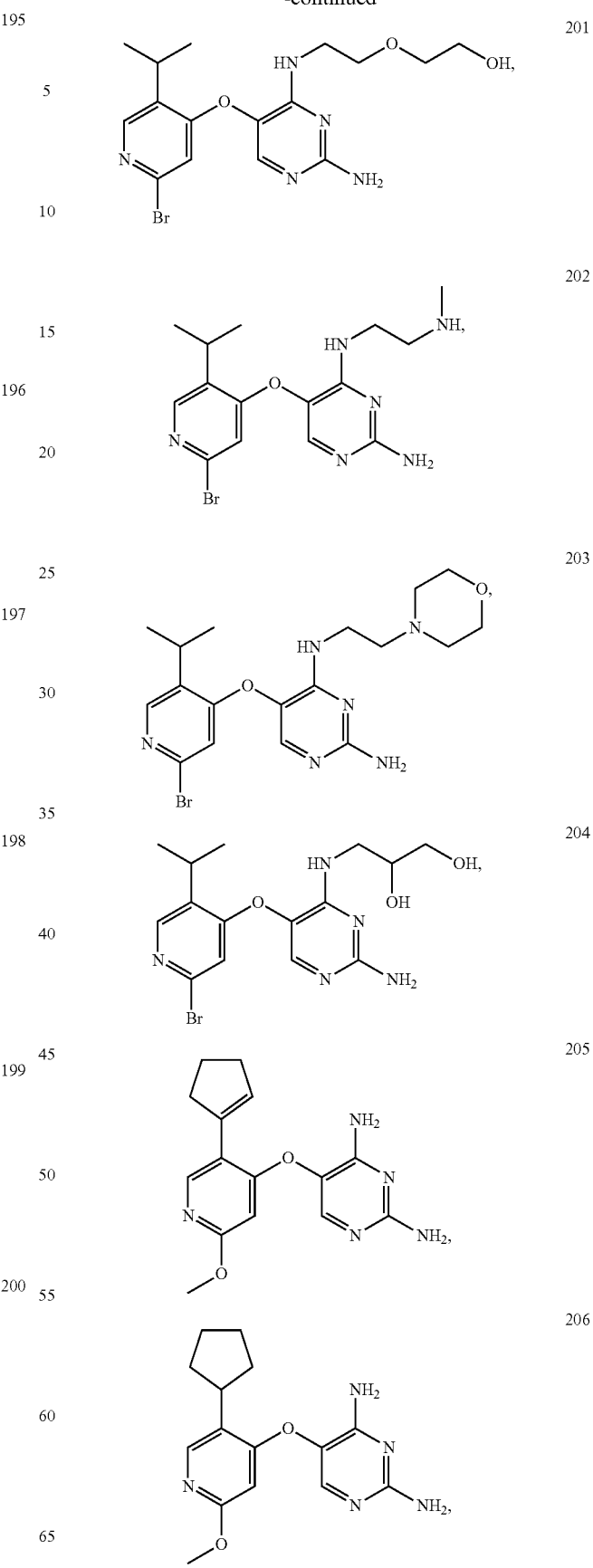

207 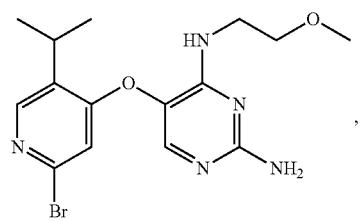
208 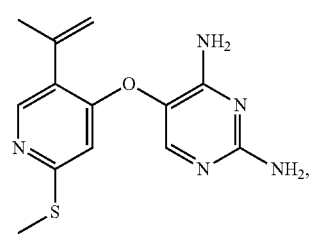
209 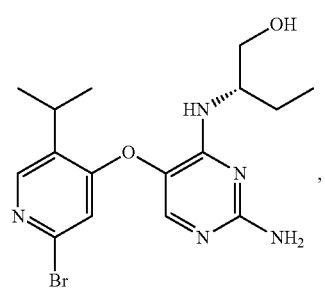
210 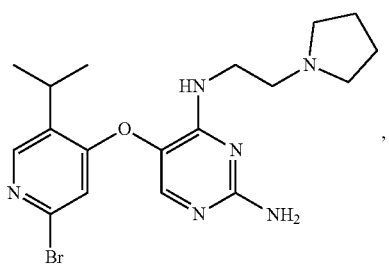
211 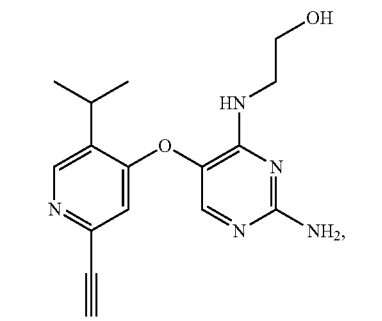
212 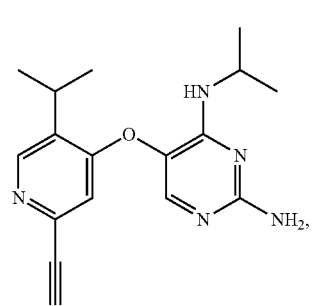
213 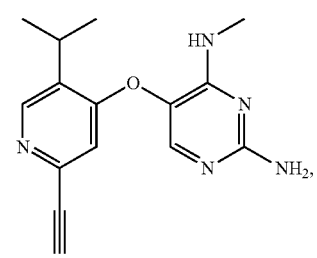
214 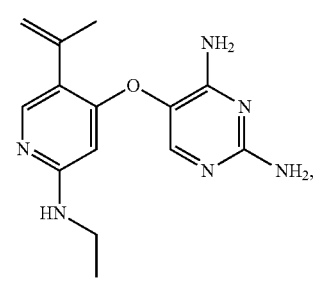
215 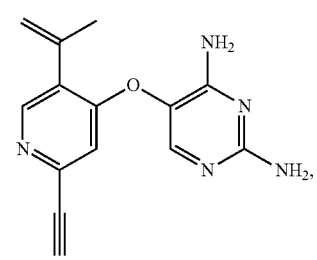
216 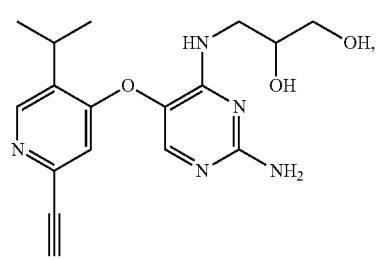
217 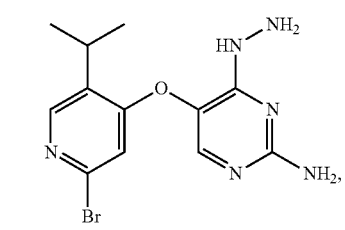
218 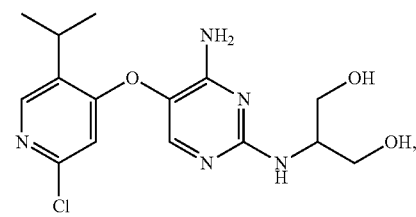

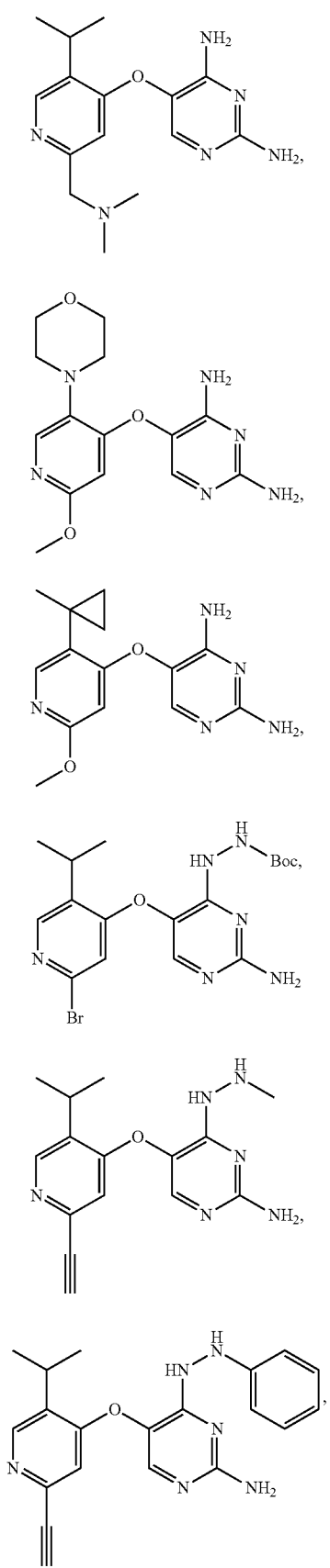
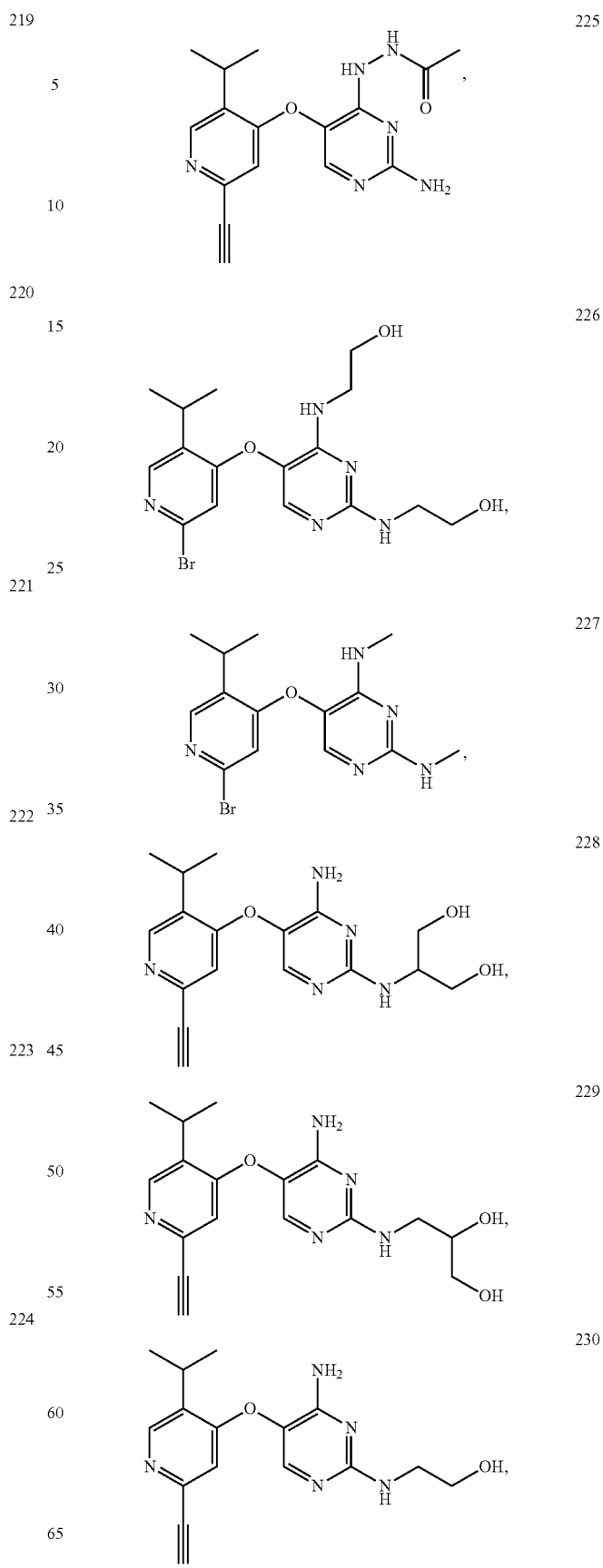

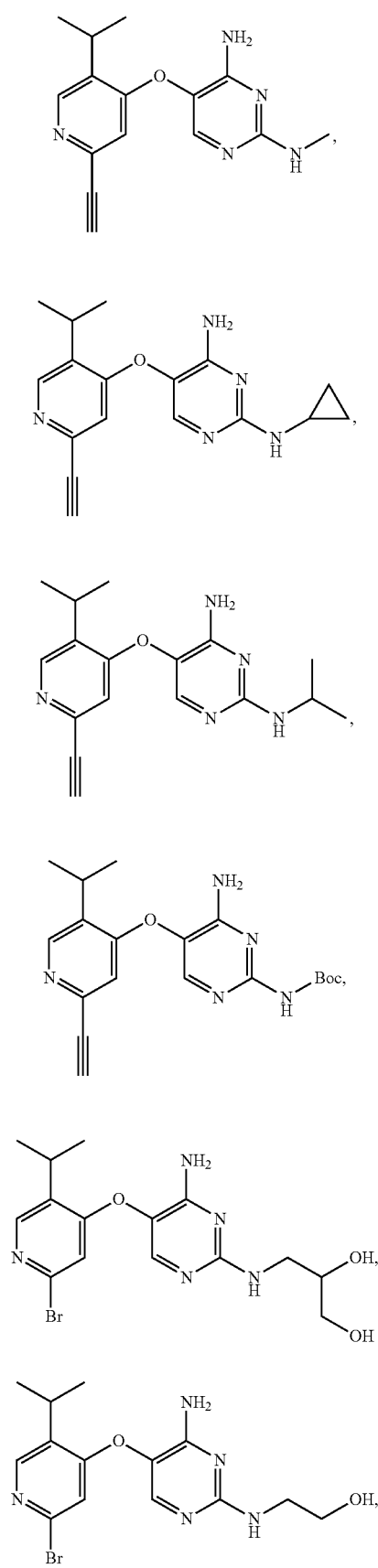
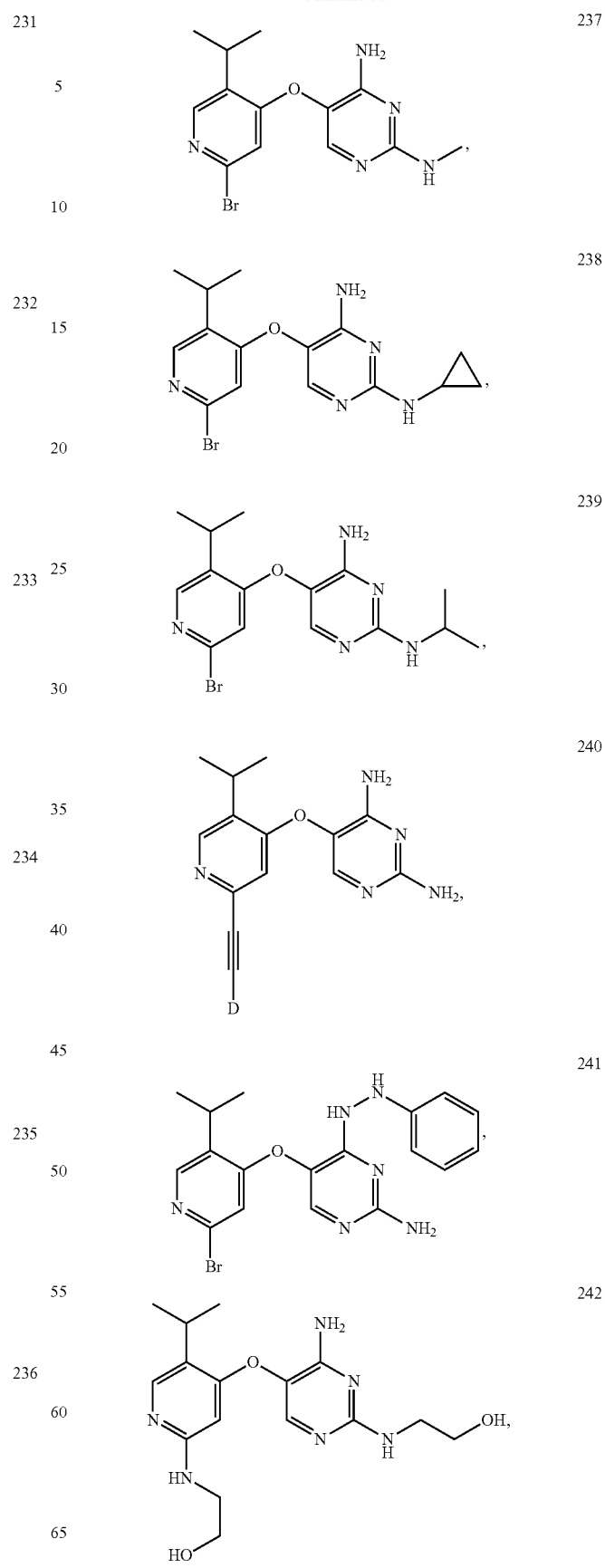

243 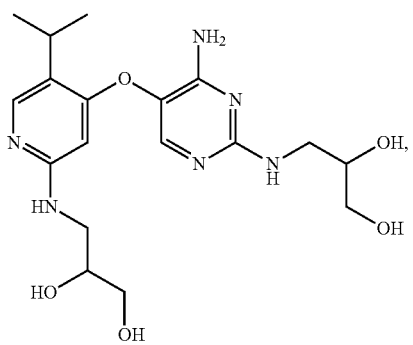

244 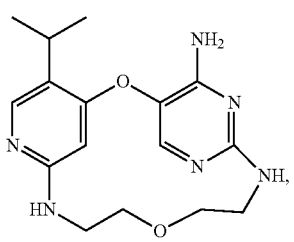

245 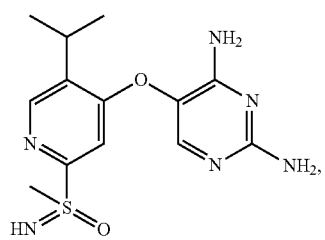

246 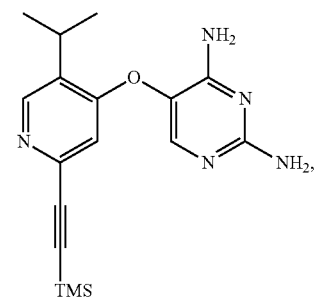

247 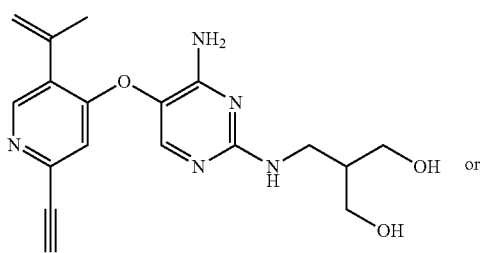 or

248 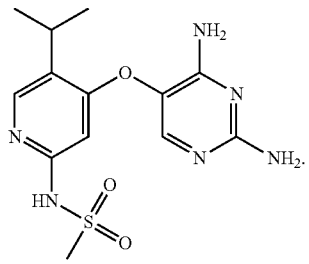

Pharmaceutical Composition and Therapeutic Method

In some embodiments, the present invention provides a pharmaceutical composition comprising a prophylactically or therapeutically effective amount of the compound of the present invention or a pharmaceutically acceptable salt, ester, stereoisomer, polymorph, solvate, N-oxide, isotopically labeled compound, metabolite or prodrug thereof and one or more pharmaceutically acceptable carriers, and the pharmaceutical composition is preferably in the form of a solid, semi-solid, liquid, or gas preparation. In some embodiments, the pharmaceutical composition can further comprise one or more additional therapeutic agents.

In some embodiments, the present invention provides use of the compound of the present invention or a pharmaceutically acceptable salt, ester, stereoisomer, polymorph, solvate, N-oxide, isotopically labeled compound, metabolite or prodrug thereof or the pharmaceutical composition of the present invention in the manufacture of a medicament for the treatment of a disease mediated by the P2X3 and/or P2X2/3 receptor antagonist.

In some embodiments, the present invention provides the compound of the present invention or a pharmaceutically acceptable salt, ester, stereoisomer, polymorph, solvate, N-oxide, isotopically labeled compound, metabolite or prodrug thereof or the pharmaceutical composition of the present invention for use in the treatment of a disease mediated by the P2X3 and/or P2X2/3 receptor antagonist.

In some embodiments, the present invention provides a method for the prophylaxis or the treatment of a disease mediated by the P2X3 and/or P2X2/3 receptor antagonist, wherein the method comprises administering to a subject in need thereof an effective amount of the compound of the present invention or a pharmaceutically acceptable salt, ester, stereoisomer, polymorph, solvate, N-oxide, isotopically labeled compound, metabolite or prodrug thereof or the pharmaceutical composition of the present invention.

In some embodiments, the disease mediated by the P2X3 and/or P2X2/3 receptor antagonist is selected from the group consisting of a urinary tract disease selected from reduced bladder capacity, frequent micturition, urge incontinence, stress incontinence, bladder hyperreactivity, benign prostatic hypertrophy, prostatitis, detrusor hyperreflexia, nocturia, urinary urgency, pelvic hypersensitivity, urethritis, pelvic pain syndrome, prostatodynia, cystitis, and idiopathic bladder hypersensitivity; pain disease selected from inflammatory pain, surgical pain, visceral pain, dental pain, premenstrual pain, central pain, pain due to burns, migraine and cluster headaches, nerve injury, neuritis, neuralgia, poisoning, ischemic injury, interstitial cystitis, cancer pain, viral, parasitic or bacterial infection, post-traumatic injury and pain associated with irritable bowel syndrome; cardiovascular system disease, preferably hypertension; respiratory disease selected from chronic obstructive pulmonary disease, asthma and bronchospasm; gastrointestinal disease selected from irritable bowel syndrome (preferably diarrhea-dominant irritable bowel syndrome), inflammatory bowel disease, biliary colic, renal colic, and pain associated with gastrointestinal distension.

The term "pharmaceutically acceptable carrier" in the present invention refers to a diluent, auxiliary material, excipient, or vehicle with which a therapeutic is administered, and it is, within the scope of sound medical judgment, suitable for contact with the tissues of human beings and animals without excessive toxicity, irritation, allergic response, or other problem or complication, commensurate with a reasonable benefit/risk ratio.

The pharmaceutically acceptable carrier which can be employed in the pharmaceutical composition of the present invention includes, but is not limited to sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Physiological salines as well as aqueous dextrose and glycerol solutions can also be employed as liquid carriers, particularly for injectable solutions. Suitable pharmaceutical excipients include starch, glucose, lactose, sucrose, gelatin, maltose, chalk, silica gel, sodium stearate, glycerol monostearate, talc, sodium chloride, dried skim milk, glycerol, propylene glycol, water, ethanol and the like. The pharmaceutical composition, if desired, can also contain minor amounts of wetting or emulsifying agents, or pH buffering agents. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in e.g. Remington's Pharmaceutical Sciences (1990).

The pharmaceutical composition of the present invention can act systemically and/or topically. To this end, it can be administered through a suitable route, such as through injection, (intravenous, intraarterial, subcutaneous, intraperitoneal, intramuscular injection, including dripping), or transdermal administration, or administered via oral, buccal, nasal, transmucosal, topical, as an ophthalmic formulation, or via inhalation.

For these routes of administration, the pharmaceutical composition of the present invention can be administered in a suitable dosage form.

Such dosage forms include, but are not limited to tablets, capsules, lozenges, hard candies, powders, sprays, creams, salves, suppositories, gels, pastes, lotions, ointments, aqueous suspensions, injectable solutions, elixirs, and syrups.

As used herein, the term "effective amount" refers to the amount of a compound being administered which will relieve to some extent one or more of the symptoms of the disorder being treated.

Dosage regimens may be adjusted to provide the optimum desired response. For example, a single bolus may be administered, several divided doses may be administered over time, or the dose may be proportionally reduced or increased as indicated by the exigencies of the therapeutic situation. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the composition.

The amount of the compound of the present invention administered will be dependent on the subject being treated, the severity of the disorder or condition, the rate of administration, the disposition of the compound and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases, still larger doses may be employed without causing any harmful side effect, provided that such larger doses are first divided into several small doses for administration throughout the day.

The content or dosage of the compound of the present invention in the pharmaceutical composition is about 0.01 mg to about 1000 mg, suitably 0.1-500 mg, preferably 0.5-300 mg, more preferably 1-150 mg, particularly preferably 1-50 mg, e.g., 1.5 mg, 2 mg, 4 mg, 10 mg, 25 mg, etc.

Unless otherwise indicated, the term "treating" or "treatment", as used herein, means reversing, alleviating, inhibiting the progress of, or preventing the disorder or condition to which such term applies, or one or more symptoms of such disorder or condition.

As used herein, the term "subject" includes a human or non-human animal. An exemplary human subject includes a human subject having a disease (such as one described herein) (referred to as a patient), or a normal subject. The term "non-human animal" as used herein includes all vertebrates, such as non-mammals (e.g. birds, amphibians, reptiles) and mammals, such as non-human primates, livestock and/or domesticated animals (such as sheep, dog, cat, cow, pig and the like).

In some embodiments, the pharmaceutical composition of the present invention can further comprise one or more additional therapeutic agents or prophylactic agents.

EXAMPLES

The present invention is further described with reference to the following examples, which are not provided to limit the scope of the present invention.

The structure of the compound was confirmed by nuclear magnetic resonance spectrum ($^1$H NMR) or mass spectrum (MS).

Chemical shifts (S) are expressed in parts per million (ppm). $^1$H NMR was recorded on a Bruker 400 or Varian 300 spectrometer, the test solvent was deuterated methanol ($CD_3OD$), deuterated chloroform ($CDCl_3$) or hexadeuterated dimethyl sulfoxide ($DMSO-d_6$), and the internal standard was tetramethylsilane (TMS).

The LC-MS assay was conducted on Agilent LC-MS-1110 liquid chromatography-mass spectrometer, Agilent LC-MS-6110 liquid chromatography-mass spectrometer, Agilent LC-MS-6120 liquid chromatography-mass spectrometer (Manufacturer: Agilent) or Shimadzu LC-MS-2020.

Preparative high-performance liquid chromatography was conducted on MS induced AutoPurification system (Waters), Gilson GX-281 (Gilson), or semi-preparative liquid chromatograph (Tong Heng Innovation Technology Co., Ltd., LC3000 (Ddlsogel, C18, 30 mm×250 mm 10 μm).

Thin layer chromatography (TLC) was performed with Huanghai HSGF 254 (5×20 cm) silica gel plates, and preparative thin layer chromatography was performed with GF 254 (0.4~0.5 nm) silica gel plates produced in Yantai.

The reaction was monitored by thin layer chromatography (TLC) or LC-MS, the developing solvent system included dichloromethane and methanol system, n-hexane and ethyl acetate system, as well as petroleum ether and ethyl acetate system, and was adjusted (by adjusting the volume ratio of the solvents, or by adding triethylamine, etc.) according to the polarity of the compound to be separated.

The microwave reaction was conducted by CEM Discovery Sp (400 W, RT~300° C.) microwave reactor.

Silica gel (200~300 mesh) produced by Yucheng Chemical Co., Ltd was normally employed as a stationary phase in column chromatography. The eluent system included dichloromethane and methanol system, as well as n-hexane and ethyl acetate system, and was adjusted (by adjusting the volume ratio of the solvents, or by adding triethylamine, etc.) according to the polarity of the compound to be separated.

In the following examples, unless otherwise specified, the reaction temperature was room temperature (20° C.~30° C.).

The reagents employed in the Examples were purchased from companies such as Aldrich Chemical Company, Shanghai Bide Pharmatech Co. Ltd., Beijing Greenchem Co. Ltd., Shanghai Shaoyuan Co. Ltd. or Ables Technology Co. Ltd. etc.

The abbreviations as used in the present invention have the following meanings:

| Abbreviation | Meaning |
|---|---|
| ACN | acetonitrile |
| $BBr_3$ | boron tribromide |
| BnBr | benzyl bromide |
| $Br_2$ | bromine |
| $CBr_4$ | carbon tetrabromide |
| DCM | dichloromethane |
| DIEA/DIPEA | N,N-diisopropylethylamine |
| DMA-DMF | N,N-dimethylformamide dimethyl acetal |
| DMAP | 4-dimethylaminopyridine |
| DMF | N,N-dimethylformamide |
| EA | ethyl acetate |
| $H_2$ | hydrogen |
| HBr | hydrobromic acid |
| HCl | hydrochloric acid |
| $H_2O$ | water |
| $K_2CO_3$ | potassium carbonate |
| LDA | lithium diisopropylamide |
| m-CPBA | meta-chloroperbenzoic acid |
| MeCN | acetonitrile |
| MeOH | methanol |
| MeONa | sodium methoxide |
| $Na_2CO_3$ | sodium carbonate |
| NaH | sodium hydride |
| NaOH | sodium hydroxide |
| NaSMe | sodium thiomethoxide |
| n-BuLi | n-butyl lithium |
| NCS | N-chlorosuccinimide |
| NMP | N-methylpyrrolidone |
| Oxone | potassium peroxymonosulfate |
| Pd/C | palladium/carbon |
| $Pd_2(dba)_3$ | tris(dibenzylideneacetone)dipalladium |
| $Pd(dppf)Cl_2$ | [1,1'-bis(diphenylphosphino)ferrocene]dichloropalladium |
| $Pd(PPh_3)_4$ | tetrakis(triphenylphosphine)palladium |
| $Pd(PPh_3)_2Cl_2$ | bis(triphenylphosphine)dichloropalladium |
| PE | petroleum ether |
| PMBCl | p-methoxybenzyl chloride |
| TBAF | tetrabutylammonium fluoride |
| TEA | triethylamine |
| TFA | trifluoroacetic acid |
| TFAA | trifluoroacetic anhydride |
| THF | tetrahydrofuran |
| Xantphos | 4,5-bis(diphenylphosphino)-9,9-dimethylxanthene |
| x-phos | 2-dicyclohexyl phosphino-2',4',6'-triisopropylbiphenyl |

Example 1: preparation of 5-((2-bromo-5-isopropylpyridin-4-yl)oxy)pyrimidine-2,4-diamine (C2, compound 2)

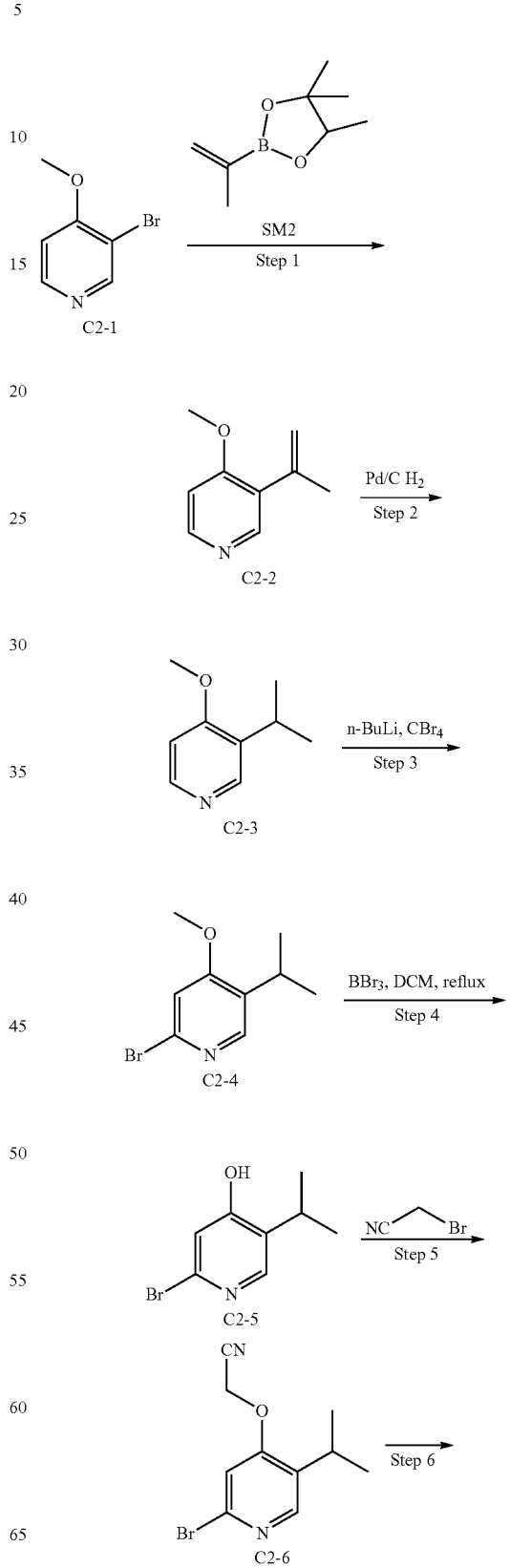

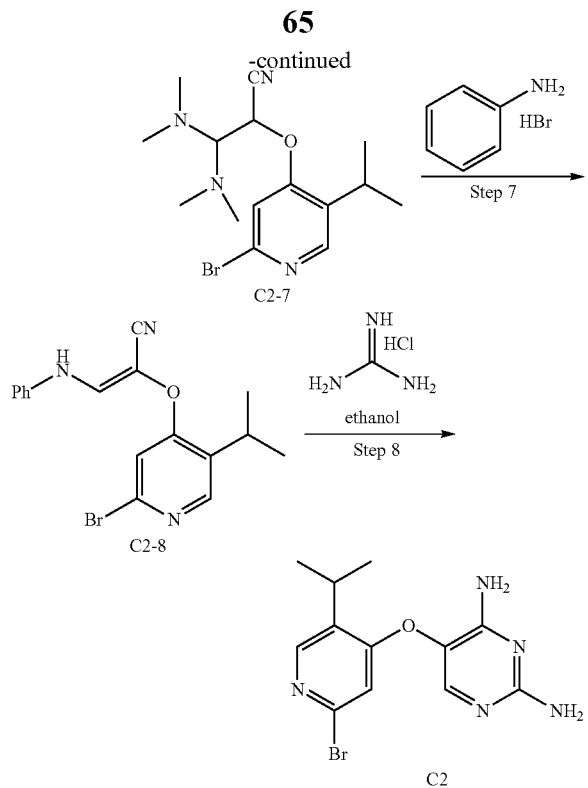

Step 1:

Compound C2-1 (100 g, 0.54 mol) was dissolved in 1,4-dioxane (700 mL), the starting material SM2 (136 g, 0.81 mol), K$_2$CO$_3$ (149 g, 1.08 mol) and Pd(PPh$_3$)$_4$ (6.2 g, 5.4 mmol) were sequentially added, followed by addition of purified water (35 mL), and purge with nitrogen was performed for 3 times. Under the protection of nitrogen, the reaction was performed at 100° C. for 18 hours. LC-MS indicated the reaction of the starting materials was substantially complete. The reaction solution was cooled to room temperature, filtered, and the filter cake was washed with 1,4-dioxane (200 mL). The filtrate was concentrated under reduced pressure to remove 1,4-dioxane, followed by addition of purified water (200 mL), and extraction with ethyl acetate (400 mL×3). The organic phases were combined, dried over anhydrous sodium sulfate (100 g) for 30 min, filtered, and concentrated under reduced pressure to afford a crude product. The crude product was purified by column chromatography on silica gel (petroleum ether:ethyl acetate=20:1~10:1), to afford compound C2-2 (79 g, yellow oil, yield: 99.75%).

$^1$H NMR (400 MHz, DMSO-d$_6$) δ 8.37 (d, J=5.6 Hz, 1H), 8.22 (s, 1H), 7.04 (d, J=5.6 Hz, 1H), 5.18 (s, 1H), 5.09 (s, 1H), 3.85 (s, 3H), 2.05 (s, 3H); MS m/z (ESI): 150.0 [M+H]$^+$.

Step 2:

Compound C2-2 (79 g, 0.53 mol) was dissolved in anhydrous methanol (700 mL), 10% palladium/carbon (16 g) was added, and the reaction was performed under hydrogen (0.4 MPa) at room temperature for 18 hours. LC-MS indicated a small amount of the starting material remained. palladium/carbon (4 g) was supplemented, and the reaction was continued under hydrogen (0.4 MPa) at room temperature for 18 hours. LC-MS indicated the reaction of the starting materials was complete. The reaction solution was filtered, the filter cake was washed with methanol (100 mL), and the filtrate was concentrated under reduced pressure to give a crude product, compound C2-3 (80 g, orange oily liquid, yield: 99.96%).

$^1$H NMR (400 MHz, DMSO-d$_6$) δ 8.31 (d, J=5.6 Hz, 1H), 8.28 (s, 1H), 6.98 (d, J=5.6 Hz, 1H), 3.86 (s, 3H), 3.21-3.09 (m, 1H), 1.21 (d, J=7.2 Hz, 6H); MS m/z (ESI): 152.1 [M+H]$^+$.

Step 3:

Compound N,N-dimethylethanolamine (46.3 g, 0.52 mol) was dissolved in n-hexane (400 mL). Under the protection of nitrogen, the reaction was cooled to −15° C.~−20° C., 2.4 M/L n-butyl lithium (434 mL, 1.04 mol) was slowly dropwise added. After the dropwise addition was complete, the reaction was kept at the temperature for 30 minutes, and then a solution of compound C2-3 (40 g, 0.26 mol) in toluene (200 mL) was slowly dropwise added at −15° C.~−20° C. After the dropwise addition was complete, the reaction was kept at the temperature for 30 minutes. The reaction solution was cooled to −70° C., a solution of carbon tetrabromide (172.4 g, 0.52 mol) in toluene (500 mL) was slowly dropwise added, and the temperature was controlled at −70° C.~−75° C. After the dropwise addition was complete, the reaction was kept at the temperature for 1 hour. LC-MS indicated the reaction of the starting materials was complete. The reaction was quenched by adding water (500 mL), and extracted with ethyl acetate (500 mL×3). The organic phases were combined, washed once with saturated brine (500 mL), dried over anhydrous sodium sulfate (400 g) for half an hour, filtered and concentrated. The crude product was isolated by column chromatography on silica gel (petroleum ether:ethyl acetate=200:1~50:1) to afford compound C2-4 (25 g, light yellow oily liquid, yield: 41.81%).

$^1$H NMR (400 MHz, DMSO-d$_6$) δ 8.06 (s, 1H), 7.20 (s, 1H), 3.89 (s, 3H), 3.13-3.05 (m, 1H), 1.18 (d, J=6.8 Hz, 6H); MS m/z (ESI): 229.9 [M+H]$^+$.

Step 4:

Compound C2-4 (25 g, 0.11 mol) was dissolved in dichloromethane (300 mL). Under the protection of nitrogen, the reaction was cooled to 0° C.~5° C., and a solution of boron tribromide (140.3 g, 0.55 mol) was slowly added. After completion of the addition, the reaction solution was warmed to reflux, and the reaction was performed for 18 hours. LC-MS indicated the reaction of the starting materials was complete.

The reaction solution was cooled to room temperature, and slowly dropwise added to 500 g ice. After the dropwise addition was complete, a saturated solution of sodium bicarbonate was dropwise added to adjust pH to 7~8. The reaction was filtered, the filter cake was washed thrice with ethyl acetate (400 mL), the filtrate was separated, and the aqueous phase was extracted with ethyl acetate (400 mL×3) again. All the organic phases were combined, dried over anhydrous sodium sulfate (500 g) for half an hour, filtered, and the filtrate was concentrated under reduced pressure to afford compound C2-5 (20 g, light yellow solid, yield: 84.17%).

$^1$H NMR (400 MHz, DMSO-d$_6$) δ 11.11 (s, 1H), 7.99 (s, 1H), 6.90 (s, 1H), 3.10-3.02 (m, 1H), 1.18 (d, J=6.8 Hz, 6H); MS m/z (ESI): 215.9 [M+H]$^+$.

Step 5:

Compound C2-5 (10 g, 0.047 mol) was dissolved in DMF (50 mL). Under the protection of nitrogen, potassium carbonate (12.8 g, 0.093 mol) and bromoacetonitrile (8.4 g, 0.07 mol) were sequentially added, and the reaction was stirred at room temperature for 2 hours. LC-MS indicated the reaction of the starting materials was complete. The reaction was quenched by adding water (50 mL), and extracted with ethyl acetate (50 mL×4). The combined organic phases were washed with saturated brine (50 mL×3), added with anhydrous sodium sulfate, dried for half an hour, and filtered. The filtrate was concentrated under reduced pressure, and the crude product was isolated by column chromatography on silica gel (petroleum ether:ethyl acetate=20:1~5:1) to afford compound C2-6 (4 g, light yellow solid, yield: 33.38%).

$^1$H NMR (400 MHz, DMSO-d$_6$) δ 8.18 (s, 1H), 7.40 (s, 1H), 5.37 (s, 2H), 3.14-3.06 (m, 1H), 1.21 (d, J=6.8 Hz, 6H); MS m/z (ESI): 254.8 [M+H]$^+$.

Step 6:

Compound C2-6 (4 g, 0.016 mol) was dissolved in DMF (50 mL). Under the protection of nitrogen, tert-butoxy bis(dimethylamino)methane (8.2 g, 0.048 mol) was added, the reaction was heated to 100° C., and stirred for 2 hours. LC-MS indicated the reaction of the starting materials was complete. The reaction solution was cooled to room temperature, quenched by adding water (50 mL), and then extracted with ethyl acetate (50 mL×3). The organic phase was then washed with saturated brine (50 mL×3), added with anhydrous sodium sulfate, dried for half an hour, and filtered. The filtrate was concentrated under reduced pressure, and the crude product was isolated by column chromatography on silica gel (petroleum ether:ethyl acetate=10:1~5:1) to afford compound C2-7 (3.8 g, light yellow solid, yield: 66.90%). MS m/z (ESI): 309.7 [M−45+H]*.

Step 7:

Compound C2-7 (3.54 g, 0.01 mol) was dissolved in DMF (25 mL). Under the protection of nitrogen, aniline hydrobromide (2.08 g, 0.012 mol) was added, the reaction was heated to 100° C., and stirred for 2 hours. LC-MS indicated the reaction of the starting materials was complete. The reaction solution was cooled to room temperature, quenched by adding water (25 mL), and extracted with ethyl acetate (20 mL×3). The organic phase was then washed with saturated brine (20 mL×3), added with anhydrous sodium sulfate, dried for half an hour, and filtered. The filtrate was concentrated under reduced pressure, and the crude product was isolated by column chromatography on silica gel (petroleum ether:ethyl acetate=20:1~5:1) to afford compound C2-8 (3.1 g, light yellow solid, yield: 86.59%).

$^1$H NMR (400 MHz, DMSO-d$_6$) δ 9.36 (d, J=12.8 Hz, 1H), 8.28 (s, 1H), 7.95 (d, J=12.8 Hz, 1H), 7.32-7.24 (m, 4H), 7.20 (s, 1H), 6.99 (t, J=7.2 Hz, 1H), 3.31-3.26 (m, 1H), 1.28 (d, J=6.8 Hz, 6H); MS m/z (ESI): 357.7 [M+H]$^+$.

Step 8:

Guanidine hydrochloride (2.4 g, 25.2 mmol) was added to anhydrous ethanol (50 mL). Under the protection of nitrogen, sodium methoxide (2.4 g, 25.2 mmol) was added, the reaction was stirred at room temperature for half an hour, followed by addition of compound C2-8 (3 g, 8.4 mmol). After completion of the addition, the reaction solution was heated to reflux, and the reaction was performed for 18 hours. LC-MS indicated the reaction of the starting materials was complete. The reaction solution was cooled to room temperature, filtered, the filtrate was concentrated under reduced pressure, and the crude product was isolated by column chromatography on silica gel (DCM:MeOH=50:1~20:1) to afford compound C2 (900 mg, light yellow solid, yield: 33.17%, compound 2).

$^1$H NMR (400 MHz, DMSO-d$_6$) δ 8.19 (s, 1H), 7.62 (s, 1H), 6.56 (s, 1H), 6.47 (s, 2H), 6.06 (s, 2H), 3.32-3.27 (m, 1H), 1.28 (d, J=6.8 Hz, 6H); MS m/z (ESI): 323.7 [M+H]$^+$.

The compounds in the following table were prepared according to methods similar to that described in Example 1.

| No. | Compound Structure | Compound Name | Starting material or regent different from that in Example 1 | Characterization Data |
|---|---|---|---|---|
| C3 (compound 3) | 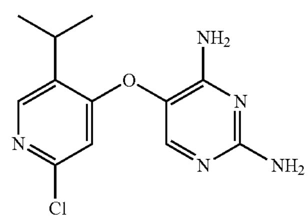 [SMILES: CC(C)c1cnc(Cl)cc1Oc1cnc(N)nc1N] | 5-((2-chloro-5-isopropylpyridin-4-yl)oxy)pyrimidine-2,4-diamine | Carbon tetrabromide in step 3 was replaced with hexachloroethane, and aniline hydrobromide in Step 7 was replaced with aniline hydrochloride. | $^1$H NMR (400 MHz, DMSO-d$_6$) δ 8.21 (s, 1H), 7.64 (s, 1H), 6.53 (s, 2H), 6.48 (s, 1H), 6.11 (s, 2H), 3.32-3.29 (m, 1H), 1.29 (d, J = 6.8 Hz, 6H); MS m/z (ESI): 279.8 [M + H]$^+$. |
| C12 (compound 12) | 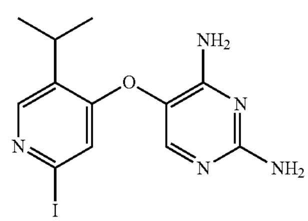 | 5-((2-iodo-5-isopropylpyridin-4-yl)oxy)pyrimidine-2,4-diamine | Carbon tetrabromide in Step 3 was replaced with iodine, and aniline hydrobromide in Step 7 was replaced with aniline hydroiodide. | $^1$H NMR (400 MHz, DMSO-d$_6$) δ 8.15 (s, 1H), 7.62 (s, 1H), 6.77 (s, 2H), 6.54 (s, 1H), 6.13 (s, 2H), 3.32-3.29 (m, 1H), 1.27 (d, J = 6.8 Hz, 6H); MS m/z (ESI): 371.7 [M + H]$^+$. |
| C67 (compound 67) | 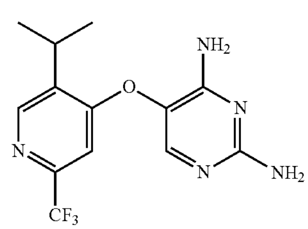 [SMILES: CC(C)c1cnc(C(F)(F)F)cc1Oc1cnc(N)nc1N] | 5-((5-isopropyl-2-(trifluoromethyl)pyridin-4-yl)oxy)pyrimidine-2,4-diamine | C2-5 in Step 5 was replaced with C67-4*. | $^1$H NMR (400 MHz, CD$_3$OD) δ 8.63 (s, 1H), 7.82 (s, 1H), 7.30 (s, 1H), 3.53-3.49 (m, 1H), 1.43-1.41 (d, J = 7.2 Hz, 6H). MS m/z (ESI): 313.9 [M + H]$^+$. |

-continued

| No. | Compound Structure | Compound Name | Starting material or regent different from that in Example 1 | Characterization Data |
|---|---|---|---|---|
| C215-1 | 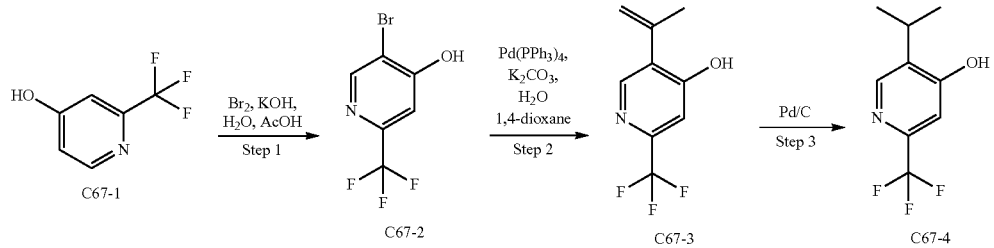 | 5-((2-bromo-5-(prop-1-en-2-yl)pyridin-4-yl)oxy)pyrimidine-2,4-diamine | Step 2 in Example 1 was omitted. | MS m/z (ESI): 321.7 [M + H]+. |

*preparation of intermediate C67-4:

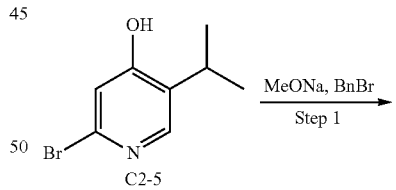

Step 1:

Compound C67-1 (10 g, 0.061 mol) was dissolved in acetic acid (100 mL), bromine (11.7 g, 0.073 mol) was dissolved in an aqueous solution of potassium hydroxide (10.3 g, 0.183 mol, 20 mL), which was then slowly added dropwise to the reaction solution under ice bath cooling. The reaction solution was stirred overnight at room temperature. LC-MS indicated the reaction of the starting materials was substantially complete. The reaction was rotary evaporated to remove acetic acid, then adjusted to pH 7 with sodium bicarbonate, and extracted with ethyl acetate (200 mL×3). The organic phases were combined, washed once with saturated brine (100 mL), then dried over anhydrous sodium sulfate (50 g) for half an hour, filtered, and concentrated under reduced pressure to afford a crude product. The crude product was isolated by column chromatography on silica gel (petroleum ether:ethyl acetate=5:1) to afford compound C67-2 (6 g, white solid, yield 40.5%).

$^1$H NMR (400 MHz, CD$_3$OD) δ 8.24 (s, 1H), 6.84 (s, 1H). MS m/z (ESI): 241.7 [M+H]+.

Step 2:

Compound C67-2 (6 g, 0.025 mol) was dissolved in 1,4-dioxane (100 mL), and isopropenyl pinacol borate (6.27 g, 0.037 mol), potassium carbonate (6.87 g, 0.050 mol), Pd(PPh$_3$)$_4$ (0.6 g) and water (10 mL) were added. Purge with nitrogen was performed for 3 times, and the reaction solution was stirred at 100° C. for 16 hours. LC-MS indicated the reaction of the starting materials was complete. The reaction solution was cooled to room temperature, quenched by adding water (100 mL), and extracted with ethyl acetate (100 mL×3). The organic phases were combined, then washed with saturated brine (100 mL), added with anhydrous sodium sulfate (50 g), dried for half an hour, and filtered. The filtrate was concentrated under reduced pressure to afford a crude product, which was isolated by column chromatography on silica gel (petroleum ether:ethyl acetate=10:1~5:1) to afford compound C67-3 (1 g, yellow oily liquid, yield 20%). MS m/z (ESI): 203.9 [M+H]+.

Step 3:

Compound C67-3 (1 g, 0.0049 mol) was dissolved in methanol (10 mL), wet palladium/carbon (0.3 g) was added, and the reaction solution was stirred at room temperature for 16 hours. LC-MS indicated the reaction of the starting materials was substantially complete. The reaction was filtered, concentrated under reduced pressure to afford a crude product, C67-4, which was directly used in the next step (1 g, light yellow oily liquid, yield 100%). MS m/z (ESI): 205.9 [M+H]+.

Example 2: preparation of 5-((5-isopropyl-2-methoxypyridin-4-yl)oxy)pyrimidine-2,4-diamine (Compound C4, Compound 4)

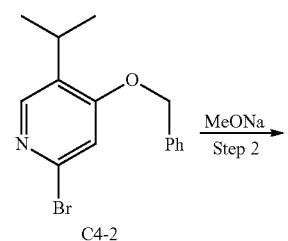

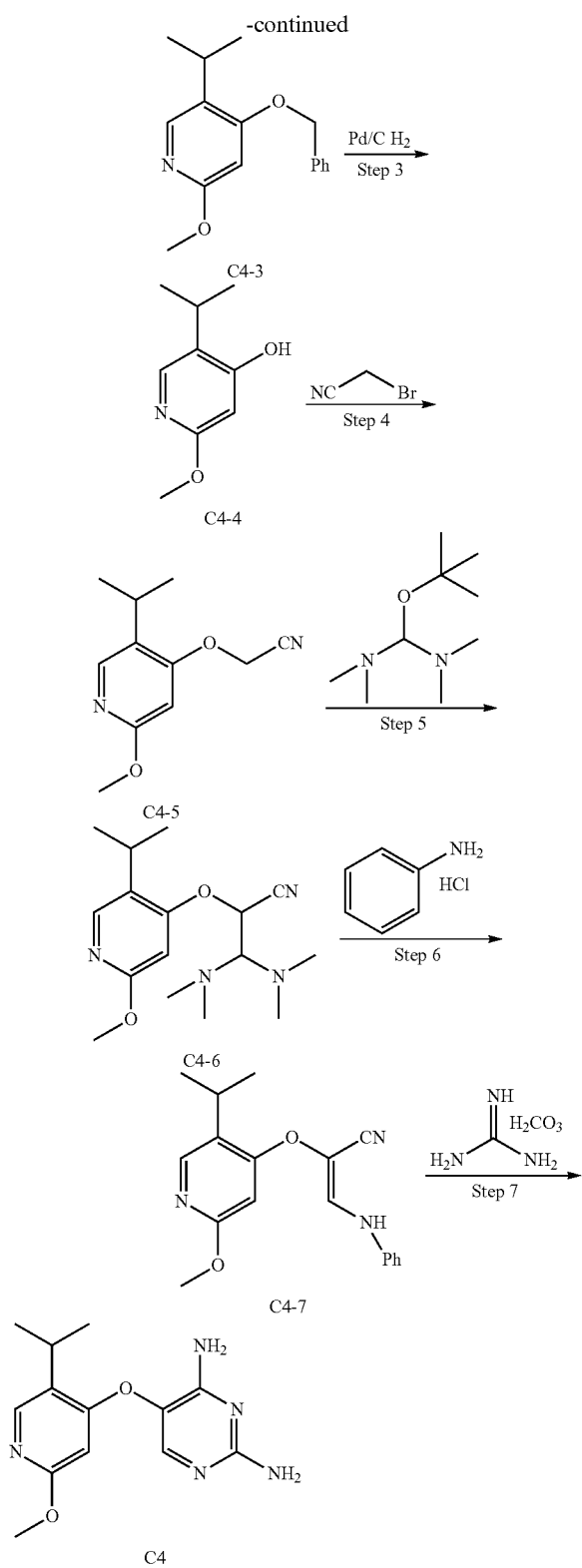

Step 1:

Compound C2-5 (440 mg, 2.03 mmol) and methanol (6 mL) was added to a 50 mL flask, sodium methoxide (220 mg, 4.06 mmol) was added, followed by slow dropwise addition of benzyl bromide (694 mg, 4.06 mmol), and the reaction was performed at room temperature overnight. Thin layer chromatography (ethyl acetate) and LC-MS analysis indicated the reaction was complete. The reaction solution was directly used in the next step. MS m/z (ESI): 305.8/307.8 [M+H]$^+$.

Step 2:

Sodium methoxide (220 mg, 4.06 mmol) was added to the reaction solution obtained in the previous step, and the reaction was performed under microwave radiation at 100° C. for 1 hour. Thin layer chromatography (ethyl acetate) and LC-MS analysis indicated the reaction was complete. The reaction solution was cooled to room temperature, concentrated under reduced pressure to give a crude product, which was isolated by preparative chromatography (ethyl acetate-~dichloromethane:methanol=10:1) to afford compound C4-3 (470 mg, colorless oil, yield: 75.66%).

$^1$H NMR (400 MHz, DMSO-d$_6$) δ 7.46 (s, 1H), 7.38-7.28 (m, 3H), 7.18-7.16 (m, 2H), 5.63 (s, 1H), 5.06 (s, 2H), 3.76 (s, 3H), 2.98-2.87 (m, 1H), 1.07 (d, J=6.8 Hz, 6H); MS m/z (ESI): 257.9 [M+H]$^+$.

Step 3:

In a 50 mL flask, compound C4-3 (470 mg, 1.83 mmol) was dissolved in methanol (15 mL), 10% Pd/C (200 mg) was added, purge with hydrogen was performed 3 times, and the reaction was performed under hydrogen overnight. LC-MS analysis indicated the reaction was complete. The reaction solution was filtered, the filter cake was rinsed with methanol (15 mL), and the filtrate was concentrated under reduced pressure to afford compound C4-4 (270 mg, white solid, yield: 88.35%).

$^1$H NMR (400 MHz, DMSO-d$_6$) δ 10.50 (bs, 1H), 7.76 (s, 1H), 6.11 (s, 1H), 3.74 (s, 3H), 3.04-2.97 (m, 1H), 1.17 (d, J=6.4 Hz, 6H); MS m/z (ESI): 168.0 [M+H]$^+$.

Step 4:

In a 50 mL flask, compound C4-4 (260 mg, 1.56 mmol) was dissolved in N,N-dimethylformamide (5 mL), potassium carbonate (430 mg, 3.11 mmol) was added, followed by slow dropwise addition of bromoacetonitrile (374 mg, 3.11 mmol), and the reaction was performed at room temperature for 1 hour. LC-MS analysis indicated the reaction was complete. The reaction was quenched by water (10 mL), and then extracted with ethyl acetate (20 mL) for 4 times. The organic phases were combined, washed with saturated brine (10 mL) 1 times, then dried over sodium sulfate, filtered, and concentrated to give a crude product, which was purified by preparative chromatography (petroleum ether:ethyl acetate=3:1~1:1) to afford compound C4-5 (220 mg, colorless oil, yield: 68.45%). MS m/z (ESI): 207.0 [M+H]$^+$.

Step 5:

In a 50 mL flask, compound C4-5 (170 mg, 0.83 mmol) was dissolved in N,N-dimethylformamide (5 mL), tert-butoxy bis(dimethylamino)methane (435 mg, 2.5 mmol) was added, the reaction solution was heated to 100° C., and the reaction was performed for 18 hours. LC-MS analysis indicated the reaction was complete. The reaction was quenched by water (10 mL), and then extracted with ethyl acetate (20 mL) for 4 times. The organic phases were combined, washed with saturated brine (10 mL×2), then dried over sodium sulfate, filtered, and concentrated under reduced pressure. The crude product was purified by preparative chromatography (petroleum ether:ethyl acetate=3:1~1:1) to afford compound C4-6 (100 mg, colorless oil, yield: 39.37%). MS m/z (ESI): 307.0 [M+H]$^+$.

Step 6:

In a 50 mL flask, compound C4-6 (80 mg, 0.26 mmol) was dissolved in N,N-dimethylformamide (2 mL), aniline hydrochloride (40 mg, 0.29 mmol) was added, and the reaction was heated to 100° C., and stirred for 2 hours. LC-MS indicated the reaction of the starting materials was complete. The reaction was added with 25 mL water, and extracted with ethyl acetate 20 mL×3. Then, the organic phase was washed with saturated brine (20 mL×3), added with anhydrous sodium sulfate, dried for half an hour, and filtered. The filtrate was concentrated under reduced pressure, and the crude product was purified by preparative chromatography (petroleum ether:ethyl acetate=2:1) to afford compound C4-7 (40 mg, colorless oil, yield: 49.79%). MS m/z (ESI): 310.0 [M+H]$^+$.

Step 7:

In a 50 mL flask, compound C4-7 (40 mg, 0.13 mmol) was dissolved in anhydrous ethanol (2 mL), guanidine carbonate (29 mg, 0.29 mmol) was added, and the reaction was performed under microwave radiation at 100° C. for 2 hours. LC-MS indicated the reaction of the starting materials was complete. The reaction was cooled to room temperature, and concentrated under reduced pressure. The crude product was purified by preparative chromatography (dichloromethane:methanol=10:1) to afford compound C4 (20 mg, white solid, yield: 55.94%, compound 4).

$^1$H NMR (400 MHz, DMSO-d$_6$) δ 7.95 (s, 1H), 7.60 (s, 1H), 6.65 (s, 2H), 6.26 (s, 2H), 5.85 (s, 1H), 3.76 (s, 3H), 3.28-3.22 (m, 1H), 1.26 (d, J=6.8 Hz, 6H); MS m/z (ESI): 275.9 [M+H]$^+$.

Example 3: preparation of 4-((2,4-diaminopyrimidin-5-yl)oxy)-5-isopropylpyridin-2-ol (Compound C7, Compound 7)

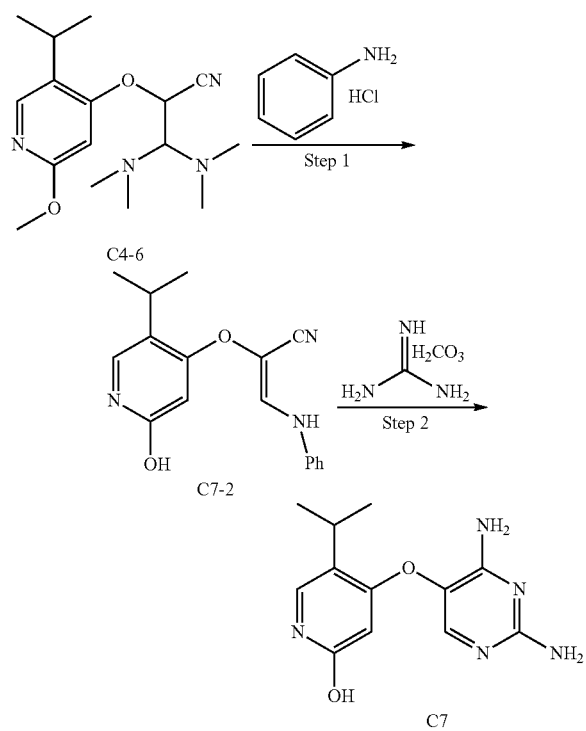

Step 1:

In a 50 mL flask, compound C4-6 (25 mg, 0.08 mmol) was dissolved in N,N-dimethylformamide (2 mL), aniline hydrochloride (12 mg, 0.09 mmol) was added, the reaction was heated to 100° C., and stirred for 2 hours. LC-MS indicated the reaction of the starting materials was complete. The reaction was added with water (25 mL), and extracted with ethyl acetate (20 mL×3). The organic phase was then washed with saturated brine (20 mL×3), added with anhydrous sodium sulfate, dried for half an hour, and filtered. The filtrate was concentrated under reduced pressure, and the crude product was purified by preparative thin layer chromatography (petroleum ether:ethyl acetate=2:1) to afford compound C7-2 (15 mg, colorless oil, yield: 63.56%). MS m/z (ESI): 295.9 [M+H]$^+$.

Step 2:

In a 50 mL flask, compound C7-2 (40 mg, 0.13 mmol) was dissolved in anhydrous ethanol (2 mL), guanidine carbonate (29 mg, 0.29 mmol) was added, and the reaction was performed under microwave radiation at 100° C. for 2 hours. LC-MS indicated the reaction of the starting materials was complete. The reaction was cooled to room temperature, and concentrated under reduced pressure. The crude product was purified by preparative chromatography (dichloromethane:methanol=10:1) to afford compound C7 (2 mg, white solid, yield: 55.89%, compound 7).

$^1$H NMR (400 MHz, CD$_3$OD) δ 7.64 (s, 1H), 7.25 (s, 1H), 5.67 (s, 1H), 3.23-3.18 (m, 1H), 1.30 (d, J=6.8 Hz, 6H); MS m/z (ESI): 261.9 [M+H]$^+$.

Example 4: preparation of 5-((3-isopropylpyridin-4-yl)oxy)pyrimidine-2,4-diamine (C8, compound 8)

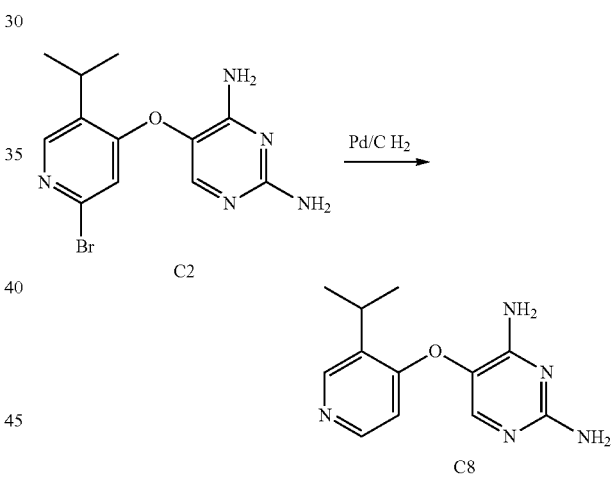

Step 1:

Compound C2 (20 mg, 0.06 mmol) was dissolved in anhydrous methanol (5 mL), followed by addition of 10% palladium/carbon (5 mg), purge with hydrogen was performed for 3 times, and the reaction was performed under hydrogen (0.4 Mpa) at room temperature for 18 hours. LC-MS indicated the reaction of the starting materials was complete. The reaction solution was filtered, the filtrate was concentrated under reduced pressure, and the crude product was isolated by column chromatography on silica gel (dichloromethane:methanol=10:1) to afford compound C8 (2 mg, white solid, yield: 13.61%, compound 8).

$^1$H NMR (400 MHz, CD$_3$OD) δ 8.39 (s, 1H), 8.25 (s, 1H), 7.60 (s, 1H), 6.7 (s, 1H), 3.48-3.46 (m, 1H), 1.38 (d, J=6.4 Hz, 6H); MS m/z (ESI): 246.0 [M+H]$^+$.

Example 5: preparation of 5-((5-isopropyl-2-methylpyridin-4-yl)oxy)pyrimidine-2,4-diamine (C9, compound 9)

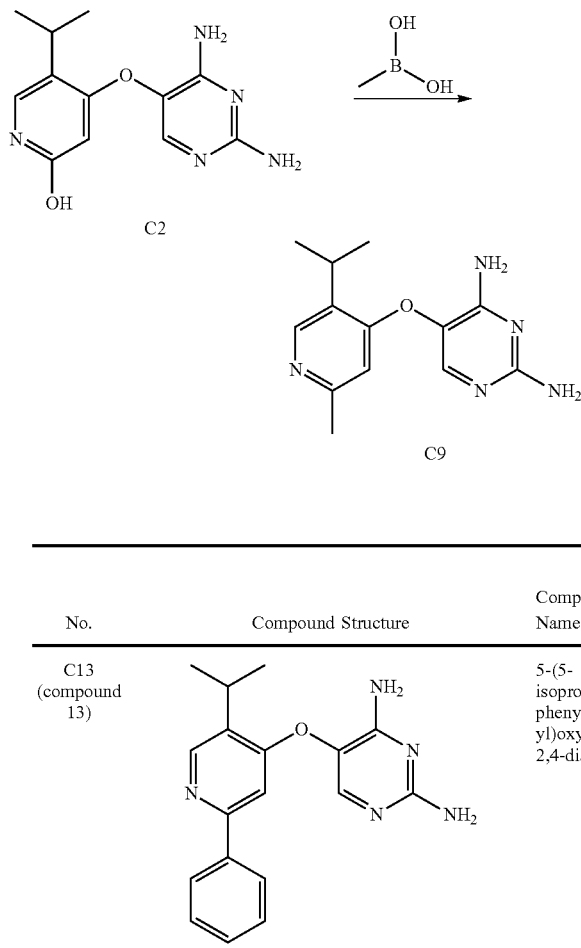

Compound C2 (30 mg, 0.1 mmol) was dissolved in 1,4-dioxane (1 mL), methylboronic acid (12 mg, 0.2 mmol), $K_2CO_3$ (136 mg, 0.3 mmol) and Pd(dppf)Cl$_2$ (7.5 mg, 0.01 mmol) were sequentially added, followed by addition of purified water (0.1 mL), and purge with nitrogen was performed for 3 times. Under the protection of nitrogen, the reaction solution was heated to 110° C., and the reaction was performed under microwave radiation for 1 hour. LC-MS indicated the reaction of the starting materials was complete. The reaction solution was cooled to room temperature, filtered, the filtrate was concentrated under reduced pressure to dryness, and the crude product was isolated by column chromatography on silica gel (dichloromethane:methanol=10:1) to afford compound C9 (3 mg, white solid, yield: 11.58%, compound 9).

$^1$H NMR (400 MHz, DMSO-d$_6$) δ 8.25 (s, 1H), 7.62 (s, 1H), 6.84 (s, 2H), 6.50 (s, 1H), 6.41 (s, 2H), 3.30-3.28 (m, 1H), 2.34 (s, 3H), 1.27 (d, J=6.8 Hz, 6H); MS m/z (ESI): 259.9 [M+H]$^+$.

The following compounds were prepared according to methods similar to that described in Example 5.

| No. | Compound Structure | Compound Name | Starting material or regent different from that in Example 5 | Characterization Data |
|---|---|---|---|---|
| C13 (compound 13) | 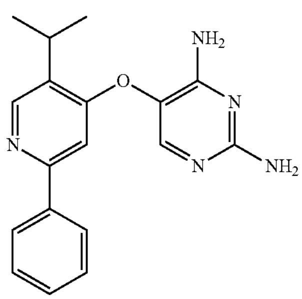 [SMILES: CC(C)c1cnc(-c2ccccc2)cc1Oc1cnc(N)nc1N] | 5-(5-isopropyl-2-phenylpyridin-4-yl)oxy)pyrimidine-2,4-diamine | Methylboronic acid was replaced with phenylboronic acid. | $^1$H NMR (400 MHz, DMSO-d$_6$) δ 8.50 (s, 1H), 7.84 (d, J = 7.6 Hz, 2H), 7.65 (s, 1H), 7.47-7.39 (m 3H), 6.95 (s, 1H), 6.63 (s, 2H), 6.18 (s, 2H), 3.43-3.37 (m, 1H), 1.34 (d, J = 7.2 Hz, 6H); MS m/z (ESI): 321.9 [M + H]$^+$. |
| C43 (compound 43) | 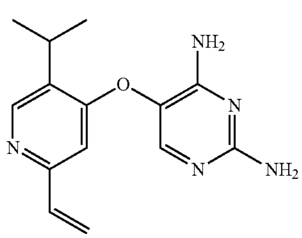 [SMILES: C=Cc1cc(Oc2cnc(N)nc2N)c(C(C)C)cn1] | 5-(5-isopropyl-2-vinylpyridin-4-yl)oxy)pyrimidine-2,4-diamine | Methylboronic acid was replaced with vinylboronic acid. | $^1$H NMR (400 MHz, CD$_3$OD) δ 8.31 (s, 1H), 7.59 (s, 1H), 6.76 (s, 1H), 6.71-6.67 (m, 1H), 6.00 (d, J = 17.6 Hz, 1H), 5.43 (d, J = 10.8 Hz, 1H), 3.45-3.41 (m, 1H), 1.38 (d, J = 6.8 Hz, 6H); MS m/z (ESI): 271.9 [M + H]$^+$. |
| C44 (compound 44) | 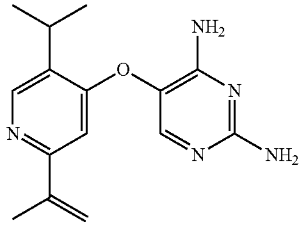 [SMILES: C=C(C)c1cc(Oc2cnc(N)nc2N)c(C(C)C)cn1] | 5-(5-isopropyl-2-(prop-1-en-2-yl)pyridin-4-yl)oxy)pyrimidine-2,4-diamine | Methylboronic acid was replaced with prop-1-en-2-ylboronic acid. | $^1$H NMR (400 MHz, DMSO-d$_6$) δ 8.38 (s, 1H), 7.60 (s, 1H), 6.68 (s, 1H), 6.62 (s, 2H), 6.18 (s, 2H), 5.61 (s, 1H), 5.20 (s, 1H), 3.30-3.28 (m, 1H), 2.03 (s, 3H), 1.30 (d, J = 7.2 Hz, 6H); MS m/z (ESI): 285.9 [M + H]$^+$. |

-continued

| No. | Compound Name | Starting material or regent different from that in Example 5 | Characterization Data |
|---|---|---|---|
| C35 (compound 35) | 5-((5-isopropyl-2-(1H-pyrazol-4-yl)pyridin-4-yl)oxy) pyrimidine-2,4-diamine | Methylboronic acid was replaced with 1H-pyrazol-4-boronic acid. | $^1$H NMR (400 MHz, CD$_3$OD) δ 8.30 (s, 1H), 8.01 (s, 2H), 7.61 (s, 1H), 6.86 (s, 1H), 3.45-3.43 (m, 1H), 1.39 (d, J = 6.8 Hz, 6H); MS m/z (ESI): 311.9 [M + H]$^+$. |
| C19 (compound 19) | 4-((2,4-diaminopyrimidin-5-yl)oxy)-5-isopropylpyridine-2-thiol | Methylboronic acid was replaced with triisopropylsilan ethiol; Pd(dppf)Cl$_2$ was replaced with Pd$_2$(dba)$_3$ and Xantphos; potassium carbonate was replaced with DIPEA. | $^1$H NMR (400 MHz, CD$_3$OD) δ 7.70 (s, 1H), 7.55 (s, 1H), 6.71 (s, 1H), 3.30-3.23 (m, 1H), 1.40 (d, J = 6.8 Hz, 6H). MS m/z (ESI): 277.9 [M + H]$^+$. |
| C34 (compound 34) | 5-((5-isopropyl-2-(1-methyl-1H-pyrazol-4-yl)pyridin-4-yl)oxy) pyrimidine-2,4-diamine | Methylboronic acid was replaced with (1-methyl-1H-pyrazol-4-yl)boronic acid; Pd(dppf)Cl$_2$ was replaced with Pd(PPh$_3$)$_4$. | $^1$H NMR (400 MHz, CD$_3$OD) δ 8.29 (s, 1H), 8.05 (s, 1H), 7.86 (s, 1H), 7.60 (s, 1H), 6.81 (s, 1H), 3.89 (s, 3H), 3.45-3.41 (m, 1H). MS m/z (ESI): 325.9 [M + H]$^+$. |
| C38 (compound 38) | 5-((5-isopropyl-2-(1H-pyrrol-1-yl)pyridin-4-yl)oxy) pyrimidine-2,4-diamine | Methylboronic acid was replaced with 1H-pyrrole; potassium carbonate was replaced with potassium tert-butoxide; Pd(dppf)Cl$_2$ was replaced with x-phos and Pd$_2$(dba)$_3$; no water was added. | $^1$H NMR (400 MHz, DMSO-d$_6$) δ 12.24 (s, 1H), 8.48 (s, 1H), 8.29 (s, 1H), 8.09 (s, 1H), 7.95 (s, 1H), 7.69-7.68 (m, 4H), 7.17 (s, 1H), 6.25 (s, 2H), 3.32-3.27 (m, 1H), 1.31-1.29 (d, J = 7.2 Hz, 6H). MS m/z (ESI): 310.9 [M + H]$^+$. |
| C39 (compound 39) | 5-((2-(furan-2-yl)-5-isopropylpyridin-4-yl)oxy) pyrimidine-2,4-diamine | Methylboronic acid was replaced with furan-2-ylboronic acid; Pd(dppf)Cl$_2$ was replaced with Pd(PPh$_3$)$_4$. | $^1$H NMR (400 MHz, CD$_3$OD) δ 8.43 (s, 1H), 7.92 (s, 1H), 7.83 (s, 1H), 7.50 (s, 1H), 7.45 (s, 1H), 6.71 (s, 1H), 3.47-3.44 (m, 1H), 1.41 (d, J = 6.8 Hz, 6H). MS m/z (ESI): 311.9 [M + H]$^+$. |

| No. | Compound Structure | Compound Name | Starting material or regent different from that in Example 5 | Characterization Data |
|---|---|---|---|---|
| C40 (compound 40) | 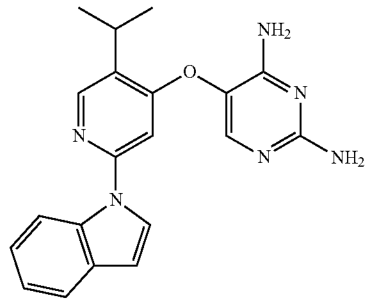 [SMILES: CC(C)c1cnc(-n2ccc3ccccc32)cc1Oc1cnc(N)nc1N] | 5-((2-(1H-indol-1-yl)-5-isopropylpyridin-4-yl)oxy)pyrimidine-2,4-diamine | Methylboronic acid was replaced with 1H-indole; potassium carbonate was replaced with potassium phosphate; Pd(dppf)Cl₂ was replaced with cyclohexane-1,2-diamine and cuprous iodide; no water was added. | 1H NMR (400 MHz, DMSO-d₆) δ 8.39 (s, 1H), 8.04 (d, J = 7.6 Hz, 1H), 7.77 (d, J = 3.6 Hz, 1H), 7.70 (s, 1H), 7.63 (d, J = 7.6 Hz, 1H), 7.22-7.12 (m, 2H), 6.72 (s, 1H), 6.68 (d, J = 3.6 Hz, 1H), 6.58 (s, 2H), 6.10 (s, 2H), 3.42-3.33 (m, 1H), 1.36 (d, J = 7.2 Hz, 6H). MS m/z (ESI): 360.9 [M + H]⁺. |
| C45 (compound 45) | 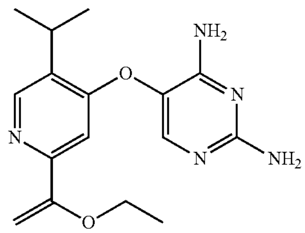 [SMILES: C=C(OCC)c1cc(Oc2cnc(N)nc2N)c(C(C)C)cn1] | 5-((2-(1-ethoxyvinyl)-5-isopropylpyridin-4-yl)oxy)pyrimidine-2,4-diamine | Methylboronic acid was replaced with tributyl(1-ethoxyvinyl)stannane; Pd(dppf)Cl₂ was replaced with Pd(PPh₃)₄; no water was added. | ¹H NMR (400 MHz, CD₃OD) δ 8.32 (s, 1H), 7.57 (s, 1H), 6.97 (s, 1H), 5.15 (s, 1H), 4.37 (s, 1H), 3.92-3.89 (m, 2H), 3.46-3.46 (m, 1H), 1.39 (d, J = 8.0 Hz, 6H), 1.33 (d, J = 6.4 Hz, 3H). MS m/z (ESI): 315.9 [M + H]⁺. |
| C52 (compound 52) | 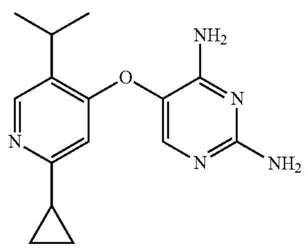 [SMILES: CC(C)c1cnc(C2CC2)cc1Oc1cnc(N)nc1N] | 5-((2-cyclopropyl-5-isopropylpyridin-4-yl)oxy)pyrimidine-2,4-diamine | Methylboronic acid was replaced with cyclopropylboronic acid; potassium carbonate was replaced with potassium phosphate; Pd(dppf)Cl₂ was replaced with palladium acetate and tricyclohexylphosphine; the solvent, 1,4-dioxane, was replaced with toluene; no water was added. | ¹H NMR (400 MHz, DMSO-d₆) δ 12.31 (s, 1H), 8.52 (s, 1H), 8.34 (s, 1H), 8.11 (s, 1H), 7.96 (s, 1H), 7.74 (s, 2H), 7.00 (s, 1H), 2.34 (s, 1H), 1.27 (d, J = 6.8, 6H), 1.04-0.98 (m, 4H). MS m/z (ESI): 286.0 [M + H]⁺. |
| C115 (compound 115) | 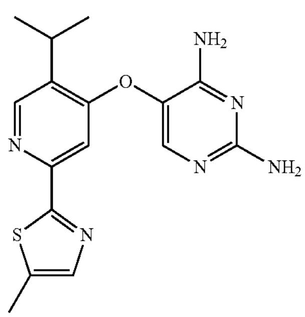 [SMILES: Cc1cnc(-c2cc(Oc3cnc(N)nc3N)c(C(C)C)cn2)s1] | 5-((5-isopropyl-2-(5-methylthiazol-2-yl)pyridin-4-yl)oxy)pyrimidine-2,4-diamine | Methylboronic acid was replaced with 5-methyl-2-(tributylstannyl)thiazole; Pd(dppf)Cl₂ was replaced with Pd(PPh₃)₄. | ¹H NMR (400 MHz, CD₃OD) δ 8.37 (s, 1H), 7.62 (s, 1H), 6.49 (s, 1H), 7.39 (s, 1H), 3.49-3.46 (m, 1H), 2.50 (s, 3H), 1.40 (d, J = 6.8 Hz, 6H). MS m/z (ESI): 342.8 [M + H]⁺. |
| C116 (compound 116) | 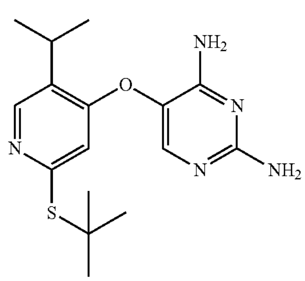 [SMILES: CC(C)c1cnc(SC(C)(C)C)cc1Oc1cnc(N)nc1N] | 5-((2-(tert-butylthio)-5-isopropylpyridin-4-yl)oxy)pyrimidine-2,4-diamine | Methylboronic acid was replaced with potassium tert-butanethiol; potassium carbonate was replaced with DIPEA; Pd(dppf)Cl₂ was replaced with Xantphos and Pd₂(dba)₃. | ¹H NMR (400 MHz, CD₃OD) δ 8.35 (s, 1H), 7.63 (s, 1H), 6.74 (s, 1H), 3.46-3.43 (m, 1H), 1.40-1.37 (m, 15H). MS m/z (ESI): 333.9 [M + H]⁺. |

| No. | Compound Structure | Compound Name | Starting material or regent different from that in Example 5 | Characterization Data |
| --- | --- | --- | --- | --- |
| C117 (compound 117) | 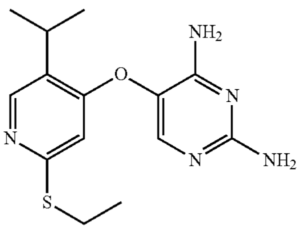 [SMILES: CCSc1cc(Oc2cnc(N)nc2N)c(C(C)C)cn1] | 5-((2-(ethylthio)-5-isopropylpyridin-4-yl)oxy)pyrimidine-2,4-diamine | Methylboronic acid was replaced with sodium ethanethiolate; potassium carbonate was replaced with DIPEA; Pd(dppf)Cl$_2$ was replaced with Xantphos and Pd$_2$(dba)$_3$. | $^1$H NMR (400 MHz, CD$_3$OD) δ 8.23 (s, 1H), 7.60 (s, 1H), 6.48 (s, 1H), 3.40-3.36 (m, 1H), 3.06-3.04 (m, 2H) 1.38-1.29 (m, 9H). MS m/z (ESI): 305.8 [M + H]$^+$. |
| C208 (compound 208) | 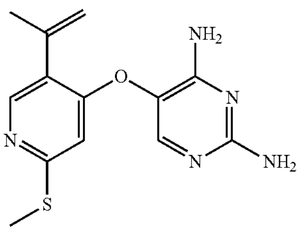 [SMILES: C=C(C)c1cnc(SC)cc1Oc1cnc(N)nc1N] | 5-((2-(methylthio)-5-(prop-1-en-2-yl)pyridin-4-yl)oxy)pyrimidine-2,4-diamine | C2 was replaced with C215-1; methylboronic acid was replaced with sodium thiomethoxide; potassium carbonate was replaced with DIPEA; Pd(dppf)Cl$_2$ was replaced with X-phos and Pd$_2$(dba)$_3$; no water was added. | $^1$H NMR (400 MHz, CD$_3$OD) δ 8.29 (s, 1H), 7.62 (s, 1H), 6.78 (s, 1H), 5.29 (s, 1H), 5.27 (s, 1H), 2.53 (s, 3H), 2.18 (s, 3H). MS m/z (ESI): 290.0 [M + H]$^+$. |

Example 6: preparation of 4-((2,4-diaminopyrimidin-5-yl)oxy)-5-isopropyl-1-methylpyridin-2(1H)-one (C11, compound 11)

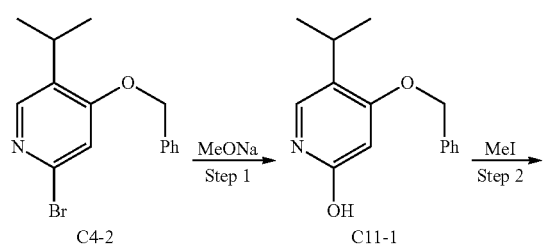

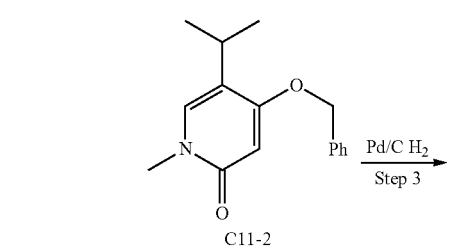

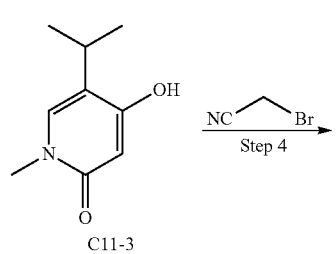

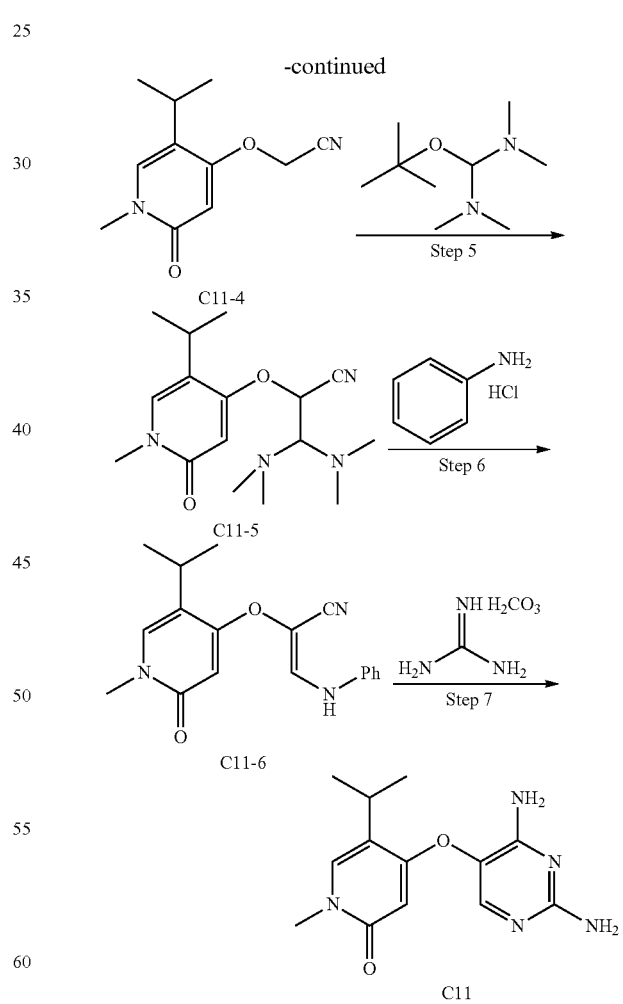

Step 1:

Compound C4-2 (2.2 g, 7 mmol) was dissolved in methanol (10 mL), sodium methoxide (610 mg, 7.7 mmol) was added, and the reaction was performed under reflux for 16 hours. LC-MS indicated the reaction of the starting materials was substantially complete. The reaction solution was concentrated under reduced pressure to afford a crude product, C11-1 (1.9 g), which was directly used in the next step. MS m/z (ESI): 243.9 [M+H]$^+$.

Step 2:

In a 50 mL flask, compound C11-1 (crude product, 1.2 g, 5 mmol) was dissolved in N,N-dimethylformamide (10 mL), potassium carbonate (1.38 g, 10 mmol) was added, followed by slow dropwise addition of iodomethane (840 mg, 6 mmol), and the reaction was performed at room temperature for 4 hours. LC-MS analysis indicated the reaction was complete. The reaction was quenched by water (10 mL), then extracted with ethyl acetate (20 mL×4). The organic phases were combined, washed with saturated brine (10 mL×2), then dried over sodium sulfate, filtered, and concentrated to give a crude product, which was purified by column chromatography on silica gel (petroleum ether:ethyl acetate=10:1~1:1), to afford compound C11-2 (240 mg, colorless oil, yield: 18.62%).

$^1$H NMR (400 MHz, DMSO-d$_6$) δ 7.45 (s, 1H), 7.34-7.22 (m, 5H), 5.82 (s, 1H), 5.03 (s, 2H), 3.76 (s, 3H), 2.89-2.82 (m, 1H), 1.10 (d, J=6.8 Hz, 6H); MS m/z (ESI): 257.9 [M+H]$^+$.

Step 3:

In a 50 mL flask, compound C11-2 (240 mg, 0.93 mmol) was dissolved in methanol (5 mL), 10% Pd/C (20 mg) was added, purge with hydrogen was performed 3 times, and the reaction was performed under hydrogen at room temperature for 72 hours. LC-MS analysis indicated the reaction was complete. The reaction solution was filtered, the filter cake was rinsed with methanol (5 mL), and the filtrate was concentrated under reduced pressure to afford compound C11-3 (150 mg, white solid, yield: 95.58%).

$^1$H NMR (400 MHz, DMSO-d$_6$) δ 6.93 (s, 1H), 5.68 (s, 1H), 3.74 (s, 3H), 2.87-2.77 (m, 1H), 1.08 (d, J=6.8 Hz, 6H); MS m/z (ESI): 168.0 [M+H]$^+$.

Step 4:

In a 50 mL flask, compound C11-3 (150 mg, 0.93 mmol) was dissolved in N,N-dimethylformamide (5 mL), potassium carbonate (380 mg, 1.86 mmol) was added, followed by slow dropwise addition of bromoacetonitrile (162 mg, 1.41 mmol), and the reaction was performed at room temperature for 18 hours. LC-MS analysis indicated the reaction was complete. The reaction was quenched by water (10 mL), then extracted with ethyl acetate (20 mL) for 4 times. The organic phases were combined, washed once with saturated brine (10 mL), then dried over sodium sulfate, filtered, and concentrated to give a crude product. The crude product was purified by preparative chromatography (petroleum ether:ethyl acetate=3:1~1:1) to afford compound C11-4 (110 mg, colorless oil, yield: 57.42%).

$^1$H NMR (400 MHz, DMSO-d$_6$) δ 7.48 (s, 1H), 5.88 (s, 1H), 4.91 (s, 2H), 3.79 (s, 3H), 2.89-2.83 (m, 1H), 1.11 (d, J=6.8 Hz, 6H); MS m/z (ESI): 207.0 [M+H]$^+$.

Step 5:

In a 50 mL flask, compound C11-4 (86 mg, 0.42 mmol) was dissolved in N,N-dimethylformamide (5 mL), tert-butoxy bis(dimethylamino)methane (208 mg, 1.26 mmol) was added, and the reaction solution was heated to 100° C. and allowed to proceed for 2 hours. LC-MS analysis indicated the reaction was complete. The reaction was quenched by water (10 mL), then extracted with ethyl acetate (20 mL) for 4 times. The organic phases were combined, washed twice with saturated brine (10 mL), then dried over sodium sulfate, filtered, and concentrated under reduced pressure. The crude product was purified by preparative chromatography (petroleum ether:ethyl acetate=3:1~1:1) to afford compound C11-5 (60 mg, colorless oil, yield: 46.69%). MS m/z (ESI): 307.0 [M+H]$^+$.

Step 6:

In a 50 mL flask, compound C11-5 (60 mg, 0.2 mmol) was dissolved in N,N-dimethylformamide (2 mL), aniline hydrochloride (32 mg, 0.24 mmol) was added, the reaction was heated to 100° C., and stirred for 2 hours. LC-MS indicated the reaction of the starting materials was complete. The reaction was added with 25 mL water, and extracted with ethyl acetate (20 mL×3). The organic phase was washed twice with saturated brine (20 mL), dried over anhydrous sodium sulfate for half an hour, and filtered. The filtrate was concentrated under reduced pressure, and the crude product was purified by preparative chromatography (petroleum ether:ethyl acetate=2:1) to afford compound C11-6 (30 mg, colorless oil, yield: 48.54%).

$^1$H NMR (400 MHz, DMSO-d$_6$) δ 9.23 (d, J=13.2 Hz, 1H), 8.00 (d, J=13.2 Hz, 1H), 7.37-7.21 (m, 4H), 7.09 (s, 1H), 6.99 (d, J=6.8 Hz, 1H), 5.91 (s, 1H), 3.82 (s, 3H), 2.89-2.82 (m, 1H), 1.13 (d, J=6.8 Hz, 6H); MS m/z (ESI): 309.9 [M+H]$^+$.

Step 7:

In a 50 mL flask, compound C11-6 (20 mg, 0.07 mmol) was dissolved in anhydrous ethanol (2 mL), guanidine carbonate (38 mg, 0.21 mmol) was added, the reaction was heated to 100° C. under microwave radiation, and stirred for 2 hours. LC-MS indicated the reaction of the starting materials was complete. The reaction was cooled to room temperature, and concentrated under reduced pressure. The crude product was purified by preparative chromatography (dichloromethane:methanol=10:1) to afford compound C11 (5 mg, white solid, yield: 25.97%, compound 11).

$^1$H NMR (400 MHz, DMSO-d$_6$) δ 7.52 (s, 1H), 6.98 (s, 1H), 6.12 (s, 4H), 5.85 (s, 1H), 3.80 (s, 3H), 2.83-2.91 (m, 1H), 1.12 (d, J=6.8 Hz, 6H); MS m/z (ESI): 275.9 [M+H]$^+$.

Example 7: preparation of 4-((2,4-diaminopyrimidin-5-yl)oxy)-5-isopropyl-2-methoxypyridine 1-oxide (C14, compound 14)

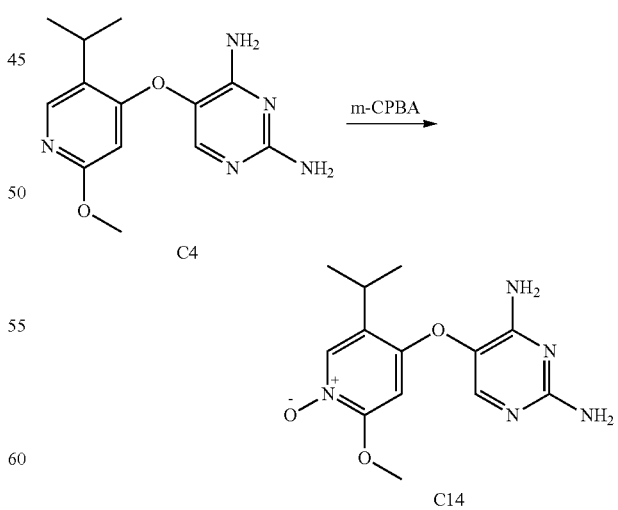

Compound C4 (10 mg, 0.036 mmol) was dissolved in anhydrous dichloromethane (5 mL), followed by addition of meta-chloroperbenzoic acid (13 mg, 0.072 mmol), and the reaction was performed at room temperature for 18 hours.

LC-MS indicated the reaction of the starting materials was complete. The reaction solution was filtered, the filtrate was concentrated under reduced pressure, and the crude product was separated by thin layer chromatography (dichloromethane:methanol=10:1) to afford compound C14 (2 mg, white solid, yield: 19.16%, compound 14).

$^1$H NMR (400 MHz, CD$_3$OD) δ 7.95 (s, 1H), 7.59 (s, 1H), 6.02 (s, 1H), 3.82 (s, 3H), 3.31-3.28 (m, 1H), 1.35 (d, J=6.8 Hz, 6H); MS m/z (ESI): 291.9 [M+H]$^+$.

The following compound was prepared according to a method similar to that described in Example 7.

LC-MS indicated the reaction was complete. The reaction solution was filtered, the filtrate was concentrated under reduced pressure, and the crude product was isolated by thin layer chromatography (dichloromethane:methanol=10:1) to afford compound C15 (2 mg, white solid, yield: 52.33%, compound 15).

$^1$H NMR (400 MHz, CD$_3$OD) δ 8.25 (s, 1H), 7.58 (s, 1H), 6.56 (s, 1H), 3.44-3.37 (m, 1H), 2.68 (q, J=7.6 Hz, 2H), 1.36 (d, J=7.2 Hz, 6H), 1.19 (t, J=7.6 Hz, 3H); MS m/z (ESI): 274.0 [M+H]$^+$.

| No | Compound Structure | Compound Name | Starting material or regent different from that in Example 7 | Characterization Data |
| --- | --- | --- | --- | --- |
| C1 (compound 1) | 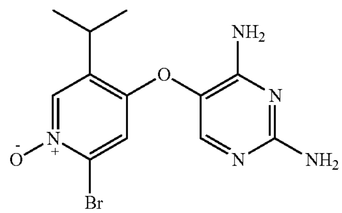 | 2-bromo-4-((2,4-diaminopyrimidin-5-yl)oxy)-5-isopropylpyridine 1-oxide | C4 was replaced with C2. | $^1$H NMR (400 MHz, CD$_3$OD) δ 8.19 (s, 1H), 7.65 (s, 1H), 6.88 (s, 1H), 3.45-3.38 (m, 1H), 1.37 (d, J = 6.8 Hz, 6H). MS m/z (ESI): 339.8 [M + H]$^+$. |

Example 8: preparation of 5-((2-ethyl-5-isopropylpyridin-4-yl)oxy)pyrimidine-2,4-diamine (C15, compound 15)

Example 9: preparation of 5-((2,5-diisopropylpyridin-4-yl)oxy)pyrimidine-2,4-diamine (C16, compound 16)

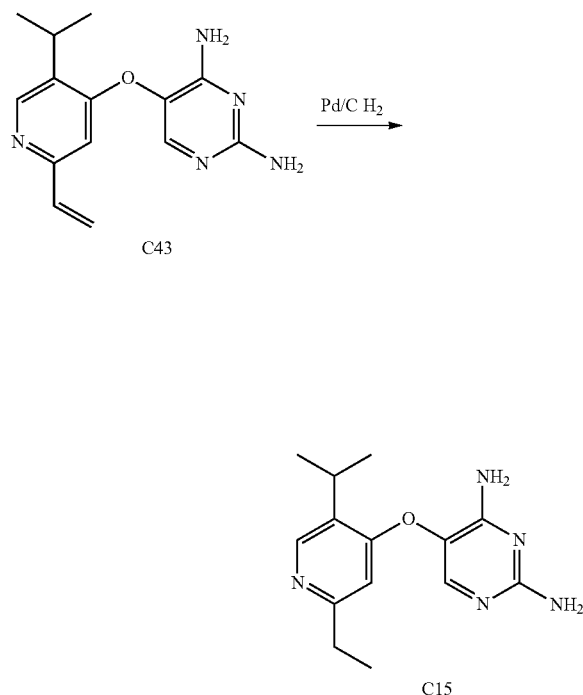

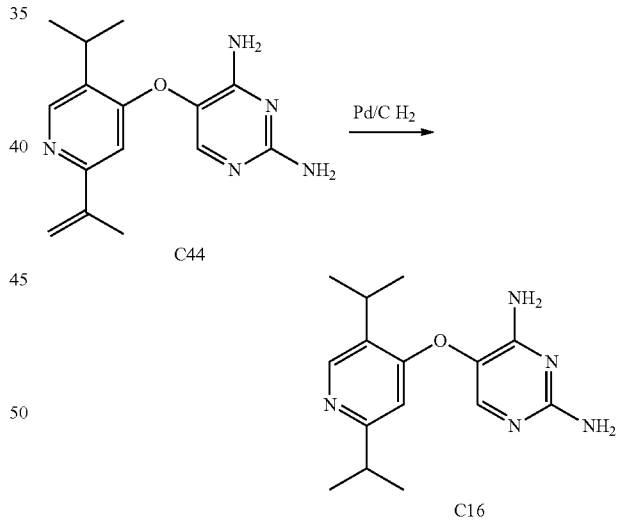

Compound C43 (4 mg, 0.014 mmol) was dissolved in anhydrous methanol (5 mL), followed by addition of 10% palladium/carbon (4 mg), purge with hydrogen was performed for 3 times, and the reaction was performed under hydrogen (0.4 Mpa) at room temperature for 18 hours.

Compound C44 (4 mg, 0.014 mmol) was dissolved in anhydrous methanol (5 mL), followed by addition of 10% palladium/carbon (4 mg), purge with hydrogen was performed for 3 times, and the reaction was performed under hydrogen (0.4 Mpa) at room temperature for 18 hours. LC-MS indicated the reaction of the starting materials was complete. The reaction solution was filtered, the filtrate was concentrated under reduced pressure, and the crude product was separated by thin layer chromatography (dichloromethane:methanol=10:1) to afford compound C16 (2 mg, white solid, yield: 49.78%).

$^1$H NMR (400 MHz, CD$_3$OD) δ 8.26 (s, 1H), 7.58 (s, 1H), 6.57 (s, 1H), 3.46-3.39 (m, 1H), 3.31-3.29 (m, 1H), 1.36 (d, J=7.2 Hz, 6H), 1.20 (d, J=6.8 Hz, 6H); MS m/z (ESI): 288.0 [M+H]$^+$.

Example 10: preparation of (4-((2,4-diaminopyrimidin-5-yl)oxy)-5-isopropylpyridin-2-yl)diethylphosphine oxide (C18, compound 18)

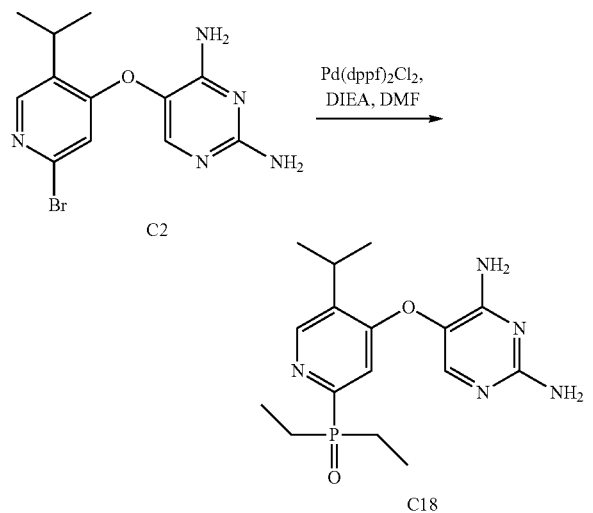

At 25° C. and under the protection of nitrogen, Pd(dppf)$_2$Cl$_2$ (10 mg) was added to a mixed solution of C2 (20 mg, 0.062 mmol), diethylphosphine oxide (65.72 mg, 0.62 mmol), DIEA (80 mg, 0.62 mmol) and DMF (5 mL). the reaction was stirred at 100° C. overnight. The reaction solution was concentrated to give a black oil, which was purified by preparative high-performance liquid chromatography to afford C18 (2.19 mg, white solid, yield: 10.12%, compound 18).

$^1$H NMR (400 MHz, CD$_3$OD) δ 8.71 (s, 1H), 7.84 (s, 1), 7.46 (d, J=6 Hz, 1H), 3.55-3.52 (m, 1H), 2.13-2.04 (m, 4H), 1.43 (d, J=6.8 Hz, 6H), 1.08-1.02 (m, 6H); MS m/z (ESI): 349.9 [M+H]$^+$.

Example 11: preparation of 5-((5-isopropyl-2-(methylthio)pyridin-4-yl)oxy)pyrimidine-2,4-diamine (C20, compound 20), 5-((5-isopropyl-2-(methylsulfonyl)pyridin-4-yl)oxy)pyrimidine-2,4-diamine (C5, compound 5) and 5-((5-isopropyl-2-(methylsulfinyl)pyridin-4-yl)oxy)pyrimidine-2,4-diamine (C48, compound 48)

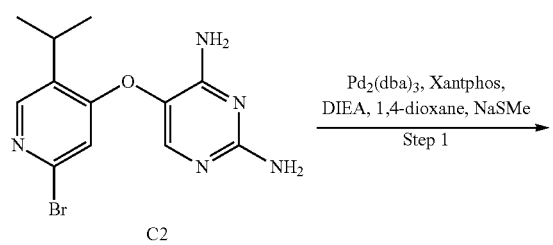

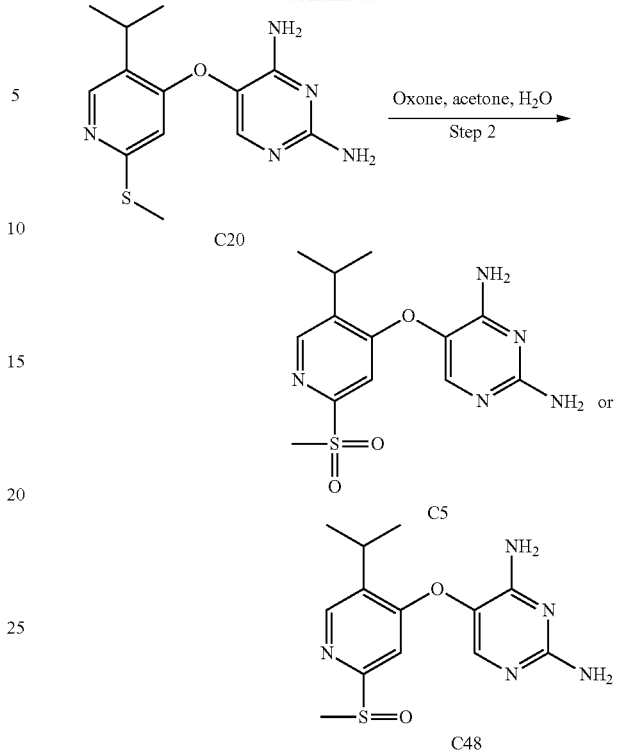

Step 1:

At 25° C. and under the protection of nitrogen, Pd$_2$(dba)$_3$ (5 mg) was added to a mixed solution of C2 (15 mg, 0.046 mmol), sodium thiomethoxide (20 mg, 0.285 mmol), DIEA (20 mg, 0.188 mmol) and Xantphos (15 mg, 0.026 mmol) (dissolved in 1,4-dioxane (10 mL)). The reaction was stirred at 100° C. overnight. The reaction was concentrated to dryness to give a black oil, and the residue was purified by preparative thin layer chromatography (DCM:MeOH=20:1) to afford compound C20 (13 mg, white solid, yield: 97.12%, compound 20).

$^1$H NMR (400 MHz, CD$_3$OD) δ 8.22 (s, 1H), 7.60 (s, 1H), 6.47 (s, 1H), 3.40-3.33 (m, 1H), 2.46 (s, 3H), 1.38-1.36 (d, J=7.2 Hz, 1H); MS m/z (ESI): 291.8 [M+H]$^+$.

Step 2:

At 0° C., Oxone (42.4 mg, 0.069 mmol) was added to a mixed solution of C20 (10 mg, 0.034 mmol) in acetone (4 mL) and water (1 mL). The reaction was stirred at 0° C. for 1 h. The reaction was quenched by water, and then extracted with ethyl acetate. The organic phase was washed with saturated brine, dried over anhydrous sodium sulfate, filtered, and concentrated under reduced pressure to dryness to give a yellow residue. The residue was purified by preparative thin layer chromatography (DCM:MeOH=20:1) to afford compound C5 (4 mg, white solid, yield: 36.42%, compound 5).

$^1$H NMR (400 MHz, DMSO-d$_6$) δ 8.62 (s, 1H), 7.69 (s, 1H), 7.05 (s, 1H), 6.66 (s, 2H), 6.20 (s, 2H), 3.48-3.44 (m, 1H), 3.24 (s, 3H), 1.35-1.34 (d, J=6.8 Hz, 6H); MS m/z (ESI): 323.8 [M+H]$^+$.

Compound C20 (20 mg, 68.6 mmol) was dissolved in acetone (5 mL), an aqueous solution (1 mL) of oxone (30 mg, 84.4 mmol) was added at 0° C., and the reaction solution was stirred at 0° C. for 0.5 hour. The reaction was added with water (5 mL), extracted with dichloromethane (5 mL×3). The organic phase was dried over sodium sulfate, concentrated under reduced pressure to afford a crude product. The crude product was purified by preparative thin layer chromatography on silica gel (dichloromethane:methanol=20:1) to afford compound C48 (10 mg, white solid, yield 47.5%).

$^1$H NMR (400 MHz, CD$_3$OD) δ 8.53 (s, 1H), 7.67 (s, 1H), 7.25 (s, 1H), 3.56-3.52 (m, 1H), 1.43 (d, J=6.8 Hz, 6H). MS m/z (ESI): 307.9 [M+H]$^+$.

Example 12: preparation of 5-((5-isopropyl-2-(pyrrolidin-1-yl)pyridin-4-yl)oxy)pyrimidine-2,4-diamine (C63, compound 63)

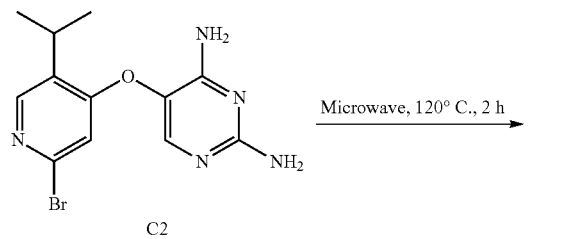

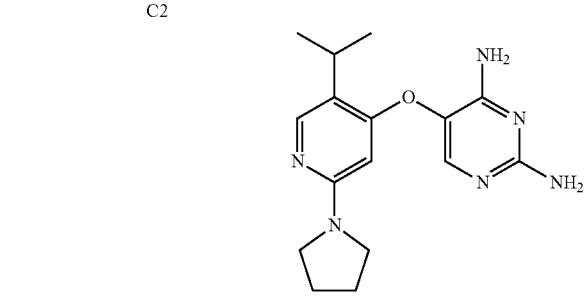

At 25° C., a solution of C2 (10 mg, 0.031 mmol) in pyrrolidine (1 mL) was stirred at 120° C. (microwave) for 2 hours. The reaction was concentrated to dryness to give a yellow oil, which was purified by preparative thin layer chromatography (DCM:MeOH=20:1) to afford C63 (1.62 mg, light yellow solid, yield: 16.64%, compound 63).

$^1$H NMR (400 MHz, CD$_3$OD) δ 7.72 (s, 1H), 7.65 (s, 1H), 5.85 (s, 1H), 3.42-3.38 (m, 4H), 3.33-3.27 (m, 1H), 2.07-2.04 (m, 4H), 1.35-1.33 (d, J=7.2 Hz, 6H); MS m/z (ESI): 314.9 [M+H]$^+$.

Example 13: preparation of 5-((2-(dimethylamino)-5-isopropylpyridin-4-yl)oxy)pyrimidine-2,4-diamine (C23, compound 23)

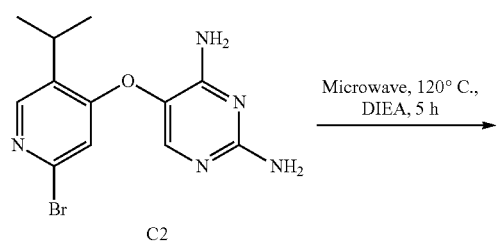

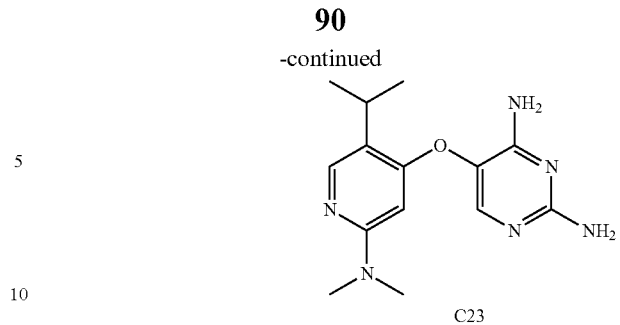

At 25° C., dimethylamine hydrochloride (20 mg) was added to a solution of C2 (10 mg, 0.031 mmol) in DIEA (1 mL). The reaction was stirred at 120° C. (microwave) for 5 hours. The reaction solution was concentrated to dryness to give a yellow oil, which was purified by preparative thin layer chromatography to afford compound C23 (2 mg, light yellow solid, yield: 22.40%, compound 23).

$^1$H NMR (400 MHz, CD$_3$OD) δ 7.947 (s, 1H), 7.686 (s, 1H), 6.390 (s, 1H), 3.330-3.233 (m, 1H), 3.218 (s, 6H), 1.340 (d, J=6.8 Hz, 6H); MS m/z: 288.9 [M+H]$^+$.

Example 14: preparation of 5-((2-(benzylsulfonyl)-5-isopropylpyridin-4-yl)oxy)pyrimidine-2,4-diamine (C42, compound 42) and 5-((2-(benzylthio)-5-isopropylpyridin-4-yl)oxy)pyrimidine-2,4-diamine (C41, compound 41)

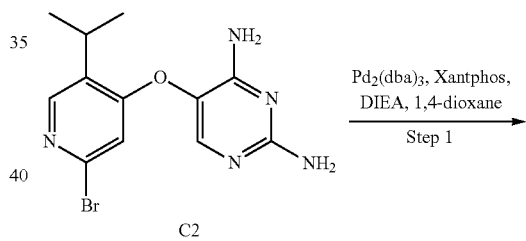

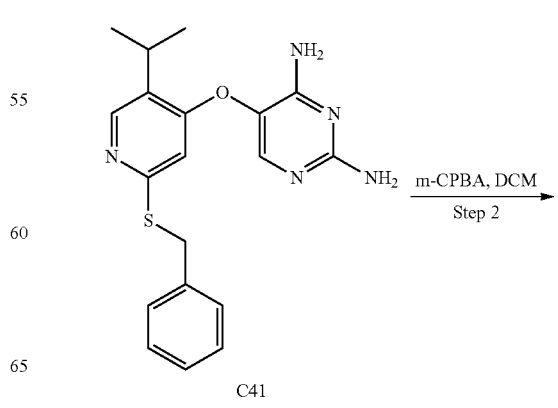

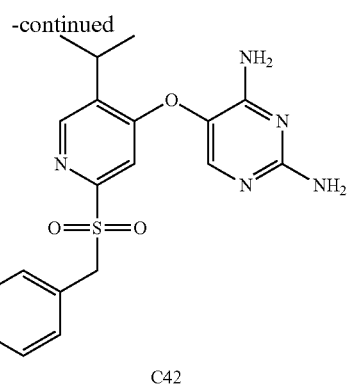

C42

Example 15: preparation of 4-((2,4-diaminopyrimidin-5-yl)oxy)-5-isopropylpyridine-2-sulfonamide (C6, compound 6)

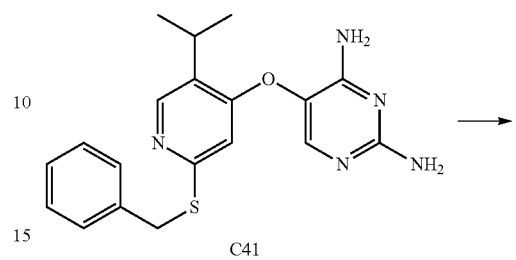

C41

Step 1:

At 25° C. and under the protection of nitrogen, Pd$_2$(dba)$_3$ (10 mg) was added to a mixed system of C2 (25 mg, 0.077 mmol), benzyl mercaptan (19 mg, 015 mmol), DIEA (24.6 mg, 0.23 mmol), Xantphos (19 mg, 0.033 mmol) and dioxane (10 mL). The reaction solution was stirred at 100° C. overnight. The reaction solution was concentrated to dryness to give a yellow oil, which was purified by preparative thin layer chromatography on silica gel (DCM: MeOH=15:1) to afford compound C41 (12 mg, white solid, yield: 42.27%, compound 41).

$^1$H NMR (400 MHz, CD$_3$OD) δ 8.20 (s, 1H), 7.49 (s, 1H), 7.28-7.21 (m, 5H), 6.44 (s, 1H), 4.24 (s, 2H), 2.98-2.94 (q, J=6.8 Hz, 1H), 1.36 (d, J=6.8 Hz, 6H); MS m/z (ESI): 367.8 [M+H]$^+$.

Step 2:

At 25° C., m-CPBA (8.3 mg) was added to a solution of C41 (8 mg, 0.0217 mmol) in dichloromethane (10 mL). The reaction was stirred at 25° C. for 1 h. The reaction was concentrated to dryness to give a yellow oil, which was purified by preparative thin layer chromatography (DCM: MeOH=10:1) to afford C42 (1 mg, white solid, yield: 11.55%, compound 42).

$^1$H NMR (400 MHz, CD$_3$OD) δ 8.64 (s, 1H), 7.40 (s, 1H), 7.33-7.24 (m, 3H), 7.14-7.13 (m, 2H), 6.88 (s, 1H), 4.62 (s, 2H), 3.54-3.51 (q, J=6.8 Hz, 1H), 1.43 (d, J=6.8 Hz, 6H); MS m/z (ESI): 399.8 [M+H]$^+$.

C6

C41 (0.1 g, 0.27 mmol) was dissolved in dichloromethane (5 mL) and acetic acid (5 mL), and NCS (3.0 g, 0.027 mol) was added. The reaction was stirred at room temperature for 1 hour. The reaction solution was poured into aqueous ammonia (10 mL), stirred for half an hour, and then extracted with ethyl acetate. The organic phase was concentrated to dryness to give a crude product, which was purified by Prep-HPLC to afford C6 (10 mg, white solid, yield 11.3%).

$^1$H NMR (400 MHz, CD$_3$OD) δ 8.60 (s, 1H), 7.85 (s, 1H), 7.37 (s, 1H), 3.53-3.50 (m, 1H), 1.42 (d, J=7.2 Hz, 6H). MS m/z (ESI): 324.7 [M+H]$^+$.

The compounds in the following table were prepared according to methods similar to that described in Example 15.

| No. | Compound Structure | Compound Name | Starting material or regent different from that in Example 15 | Characterization Data |
| --- | --- | --- | --- | --- |
| C26 (compound 26) | 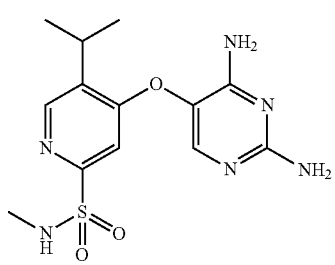 [SMILES: CNS(=O)(=O)c1cc(Oc2cnc(N)nc2N)c(C(C)C)cn1] | 4-((2,4-diaminopyrimidin-5-yl)oxy)-5-isopropyl-N-methylpyridine-2-sulfonamide | The aqueous ammonia was replaced with a solution of methylamine in tetrahydrofuran. | $^1$H NMR (400 MHz, CD$_3$OD) δ 8.62 (s, 1H), 7.86 (s, 1H), 7.33 (s, 1H), 3.52-3.48 (m, 1H), 2.65 (s, 3H), 1.42 (d, J = 7.2 Hz, 6H). MS m/z (ESI): 338.9 [M + H]$^+$. |

| No. | Compound Structure | Compound Name | Starting material or regent different from that in Example 15 | Characterization Data |
|---|---|---|---|---|
| C27 (compound 27) | 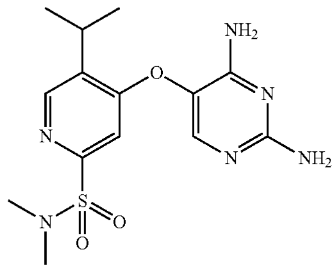 [SMILES: CC(C)c1cnc(S(=O)(=O)N(C)C)cc1Oc1cnc(N)nc1N] | 4-((2,4-diaminopyrimidin-5-yl)oxy)-5-isopropyl-N,N-dimethylpyridine-2-sulfonamide | The aqueous ammonia was replaced with a solution of dimethylamine in tetrahydrofuran. | $^1$H NMR (400 MHz, CD$_3$OD) δ 8.64 (s, 1H), 7.88 (s, 1H), 7.30 (s, 1H), 3.54-3.51 (m, 1H), 2.89 (s, 6H), 1.43 (d, J = 6.8 Hz, 6H). MS m/z (ESI): 352.9 [M + H]$^+$. |
| C47 (compound 47) | 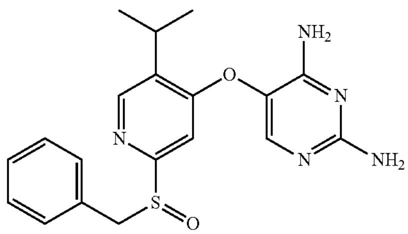 [SMILES: CC(C)c1cnc(S(=O)Cc2ccccc2)cc1Oc1cnc(N)nc1N] | 5-((2-(benzylsulfinyl)-5-isopropylpyridin-4-yl)oxy)pyrimidine-2,4-diamine | It is a by-product isolated during the synthesis of Example 15. | $^1$H NMR (400 MHz, DMSO-d$_6$) δ 7.36-7.23 (m, 6H), 7.00 (s, 1H), 6.66 (s, 1H), 6.41 (s, 2H), 6.05 (s, 2H), 5.33 (s, 2H), 3.42-3.38 (m, 1H), 1.33 (m, 6H). MS m/z (ESI): 383.8 [M + H]$^+$. |

Example 16: preparation of (4-((2,4-diaminopyrimidin-5-yl)oxy)-5-isopropylpyridin-2-yl)dimethylphosphine oxide (C17, compound 17)

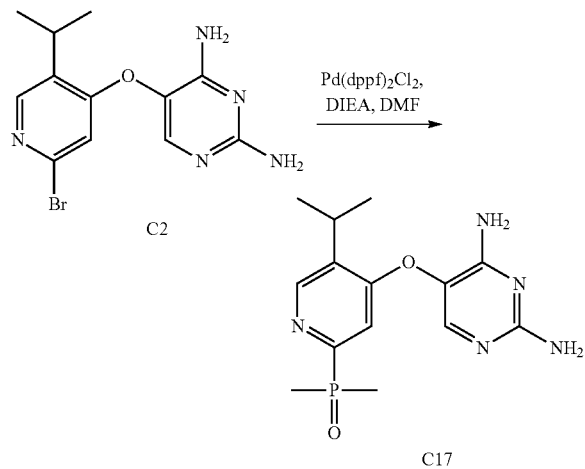

At 25° C. and under the protection of nitrogen, Pd(dppf)$_2$Cl$_2$ (10 mg) was added to a mixed solution of C2 (20 mg, 0.062 mmol), dimethylphosphine oxide (15 mg, 0.186 mmol), DIEA (24 mg, 0.186 mmol) and DMF (5 mL). The reaction was stirred at 100° C. overnight. The reaction solution was concentrated to give a black oil, and the residue was purified by preparative high-performance liquid chromatography to afford compound C17 (3 mg, white solid, 15.1%).

$^1$H NMR (400 MHz, DMSO-d$_6$) δ 8.67 (s, 1H), 8.60 (s, 1H), 8.23 (s, 1H), 8.03 (s, 1H), 7.81 (s, 2H), 7.25 (d, J=6 Hz, 1H), 3.45-3.38 (m, 1H), 1.65 (s, 3H), 1.61 (s, 3H), 1.33 (d, J=6.8 Hz, 6H). MS m/z (ESI): 321.8 [M+H]$^+$.

The compound in the following table was prepared according to methods similar to that described in Example 16.

| No. | Compound Structure | Compound Name | Starting material or regent different from that in Example 16 | Characterization Data |
|---|---|---|---|---|
| C49 (compound 49) | 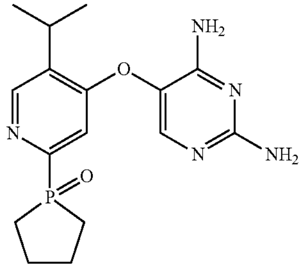 [SMILES: CC(C)c1cnc(P2(=O)CCCC2)cc1Oc1cnc(N)nc1N] | 1-(4-((2,4-diaminopyrimidin-5-yl)oxy)-5-isopropylpyridin-2-yl)phospholane 1-oxide | The dimethylphosphine oxide was replaced with phospholane 1-oxide. | $^1$H NMR (400 MHz, DMSO-d$_6$) δ 8.61 (s, 1H), 7.63 (s, 1H), 7.11 (d, J = 6.4 Hz, 1H), 6.55 (s, 2H), 6.12 (s, 2H), 3.44-3.40 (m, 1H), 2.00-1.48 (m, 8H), 1.32 (d, J = 7.2 Hz, 6H). MS m/z (ESI): 347.8 [M + H]$^+$. |

Example 17: preparation of 5-((2-amino-5-isopropylpyridin-4-yl)oxy)pyrimidine-2,4-diamine (C21, compound 21)

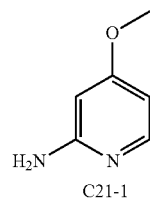
C21-1

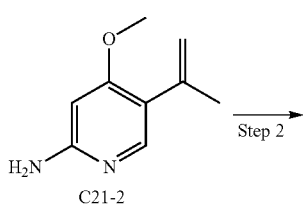
C21-2

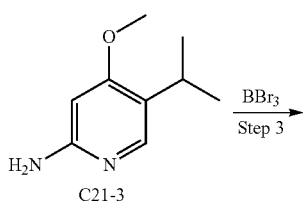
C21-3

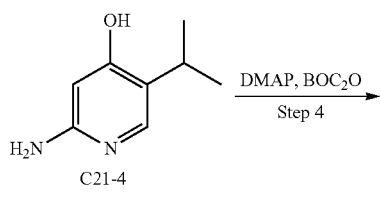
C21-4

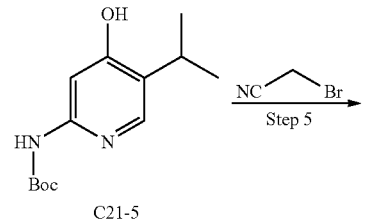
C21-5

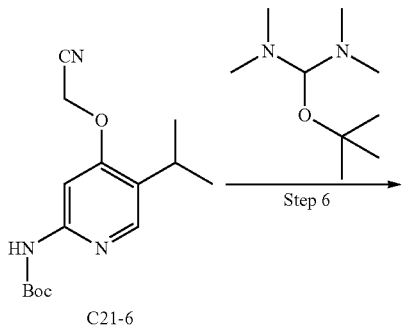
C21-6

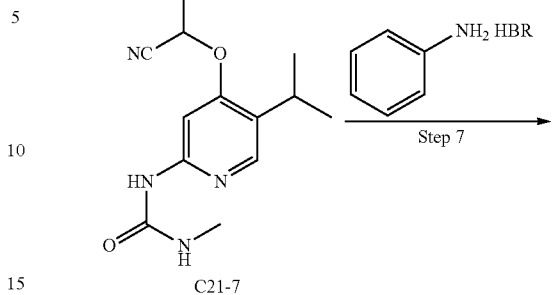
C21-7

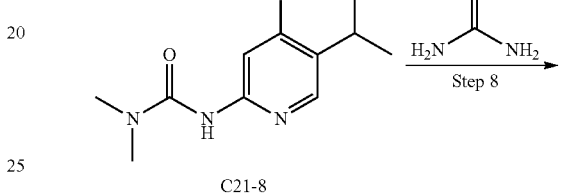
C21-8

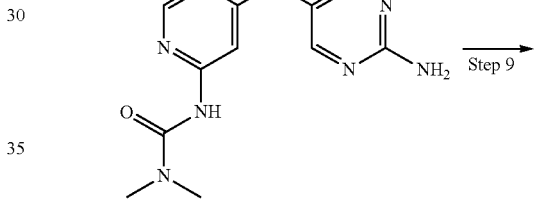
C21-9

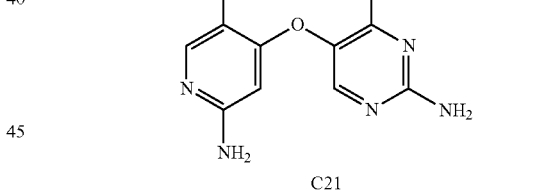
C21

Step 1:

Compound C21-1 (28 g, 0.138 mol) was dissolved in 1,4-dioxane (300 mL), isopropenylpinacol borate (46.3 g, 0.275 mol), potassium carbonate (38.6 g, 0.276 mol), Pd(PPh$_3$)$_4$ (3.5 g) and water (30 mL) were added. Purge with nitrogen was performed for 3 times, and the reaction solution was stirred at 100° C. for 16 hours. LC-MS indicated the reaction of the starting materials was complete. The reaction solution was cooled to room temperature, quenched by adding water (300 mL), and extracted with ethyl acetate (300 mL×3). The organic phases were combined, washed with saturated brine (100 mL), added with anhydrous sodium sulfate (50 g), dried for half an hour, and filtered. The filtrate was concentrated under reduced pressure to afford a crude product, which was purified by column chromatography on silica gel (petroleum ether:ethyl acetate=20:1~5:1) to afford compound C21-2 (14 g, yellow solid, yield 61.9%).

¹H NMR (400 MHz, DMSO-d₆) δ 7.63 (s, 1H), 6.01 (s, 1H), 5.88 (s, 2H), 5.01-4.95 (m, 2H), 3.74-3.70 (m, 3H), 1.99 (s, 3H). MS m/z (ESI): 165.0 [M+H]⁺.

Step 2:

Compound C21-2 (14 g, 0.085 mol) was dissolved in ethanol (200 mL), 10% wet palladium/carbon (10 g) was added, and the reaction solution was stirred under hydrogen at room temperature overnight. LC-MS indicated the reaction of the starting materials was substantially complete. The reaction was filtered, concentrated under reduced pressure to afford a crude product, which was purified by column chromatography on silica gel (dichloromethane:methanol=20:1) to afford compound C21-3 (12 g, white solid, yield 84.5%).

¹H NMR (400 MHz, DMSO-d₆) δ 7.58 (s, 1H), 5.99 (s, 1H), 5.61 (s, 2H), 3.73 (s, 3H), 2.94-2.93 (m, 1H), 1.16-1.08 (m, 6H). MS m/z (ESI): 167.0 [M+H]⁺.

Step 3:

Compound C21-3 (5 g, 0.030 mol) was dissolved in dichloromethane (20 mL), boron tribromide (10 mL) was added, the reaction solution was stirred at 40° C. for 16 hours. LC-MS indicated the reaction of the starting materials was complete. The reaction solution was slowly dropwise added to ice water, adjusted to pH 8 with sodium carbonate, and extracted with ethyl acetate (100 mL×3). The organic phases were combined, washed once with saturated brine (100 mL), then dried over anhydrous sodium sulfate (10 g) for half an hour, filtered, and concentrated to give a crude product, C21-4, and the crude product was directly used in the next step (4 g, crude product, yellow oily liquid, yield 89%).

¹H NMR (400 MHz, DMSO-d₆) δ 10.23 (s, 1H), 7.13 (s, 1H), 6.55 (s, 1H), 5.77-5.43 (m, 2H), 2.85 (m, 1H), 1.13-1.05 (m, 6H). MS m/z (ESI): 153.0 [M+H]⁺.

Step 4:

Compound C21-4 (3 g, 0.020 mol) was dissolved in acetonitrile (30 mL), di-tert-butyl dicarbonate (8.6 g, 0.039 mol), triethylamine (3.9 g, 0.039 mol) and DMAP (2.4 g, 0.019 mol) were sequentially added, and the reaction solution was stirred at 30° C. for 3 hours. LC-MS indicated the reaction of the starting materials was substantially complete. The reaction was quenched by adding water (100 mL), and extracted with ethyl acetate (100 mL×3). The organic phases were combined, washed once with saturated brine (100 mL), then dried over anhydrous sodium sulfate (10 g) for half an hour, filtered, and concentrated under reduced pressure to afford a crude product, which was purified by column chromatography on silica gel (petroleum ether:ethyl acetate=10:1) to afford compound C21-5 (1.4 g, white solid, yield 29%).

¹H NMR (400 MHz, DMSO-d₆) δ 10.48 (s, 1H), 9.39 (s, 1H), 7.84 (s, 1H), 7.35 (s, 1H), 3.02 (s, 1H), 1.47 (s, 9H), 1.17 (s, 6H). MS m/z (ESI): 253.1 [M+H]⁺.

Step 5:

Compound C21-5 (1.4 g, 5.56 mmol) was dissolved in DMF (15 mL), bromoacetonitrile (1 g, 8.30 mmol) and potassium carbonate (1.5 g, 11.10 mmol) were sequentially added, and the reaction solution was stirred at room temperature for 16 hours. LC-MS indicated the reaction of the starting materials was complete. The reaction was quenched by adding water (100 mL), and extracted with ethyl acetate (100 mL×3). The organic phases were combined, washed once with saturated brine (100 mL), then dried over anhydrous sodium sulfate (10 g) for half an hour, filtered, and concentrated under reduced pressure to afford a crude product, which was purified by column chromatography on silica gel (petroleum ether:ethyl acetate=5:1~1:1) to afford compound C21-6 (790 mg, yellow solid, yield 38%).

¹H NMR (400 MHz, DMSO-d₆) δ 9.77 (s, 1H), 8.02 (s, 1H), 7.53 (s, 1H), 5.27 (s, 2H), 3.06-3.02 (m, 1H), 1.48 (s, 9H), 1.20-1.19 (m, 6H). MS m/z (ESI): 291.9 [M+H]⁺.

Step 6:

Compound C21-6 (300 mg, 1.03 mmol) was dissolved in DMF (5 mL), tert-butoxy bis(dimethylamino)methane (718 mg, 4.12 mmol) was added, and the reaction solution was stirred at 100° C. for 1 hour. LC-MS indicated the reaction of the starting materials was complete. The reaction solution was concentrated under reduced pressure, to afford a crude product, C21-7, and the crude product was directly used in the next step (0.4 g, yellow oily liquid, yield 99%). MS m/z (ESI): 318.0 [M+H]⁺.

Step 7:

Compound C21-7 (400 mg, 1.03 mmol) was dissolved in DMF (5 mL), aniline hydrobromide (285 mg, 3.07 mmol) was added, and the reaction solution was stirred at 100° C. for 16 hours. LC-MS indicated the reaction of the starting materials was complete. The reaction solution was cooled to room temperature, quenched by adding water (30 mL), and extracted with ethyl acetate (50 mL×3). The organic phases were combined, washed with saturated brine (50 mL), added with anhydrous sodium sulfate (10 g), dried for half an hour, and filtered. The filtrate was concentrated under reduced pressure to afford a crude product, which was purified by column chromatography on silica gel (petroleum ether:ethyl acetate=5:1~1:1) to afford compound C21-8, (230 mg, yellow oily liquid, yield 61%). MS m/z (ESI): 365.9 [M+H]⁺.

Step 8:

Compound C21-8 (120 mg, 0.33 mmol) was dissolved in ethanol (5 mL), guanidine hydrochloride (150 mg, 0.99 mmol) and sodium methoxide (53 mg, 0.99 mmol) were sequentially added, and the reaction solution was stirred at 90° C. for 16 hours. LC-MS indicated the reaction of the starting materials was complete. The reaction solution was cooled to room temperature, concentrated under reduced pressure to afford a crude product, C21-9, and the crude product was directly used in the next step (180 mg, brown oily liquid, yield 100%). MS m/z (ESI): 331.8 [M+H]⁺.

Step 9:

Compound C21-9 (90 mg, 0.27 mmol) was dissolved in ethanol (5 mL), an aqueous solution of sodium hydroxide (109 mg, 2.7 mmol, 1 mL H₂O) was added, and the reaction was stirred at 90° C. for 6 hours. LC-MS indicated the reaction of the starting materials was complete. The reaction solution was cooled to room temperature, concentrated under reduced pressure, and the crude product was isolated by preparative liquid chromatography to afford compound C21 (15 mg, white solid, yield 21%).

¹H NMR (400 MHz, CD₃OD) δ 7.96 (s, 1H), 7.70 (s, 1H), 6.33 (s, 1H), 3.30-3.28 (m, 1H), 1.34-1.30 (d, J=7.2 Hz, 6H). MS m/z (ESI): 260.9 [M+H]⁺.

99

Example 18: preparation of 5-((5-isopropyl-2-(methylamino)pyridin-4-yl)oxy)pyrimidine-2,4-diamine (C22, compound 22)

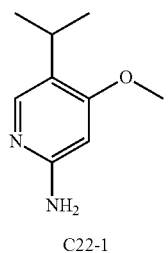

C22-1

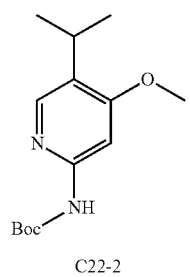

C22-2

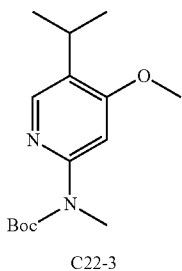

C22-3

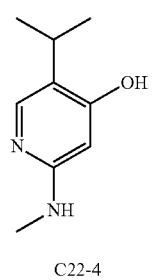

C22-4

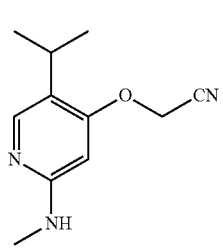 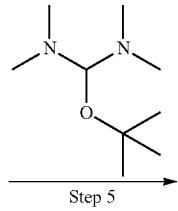

C22-5

100

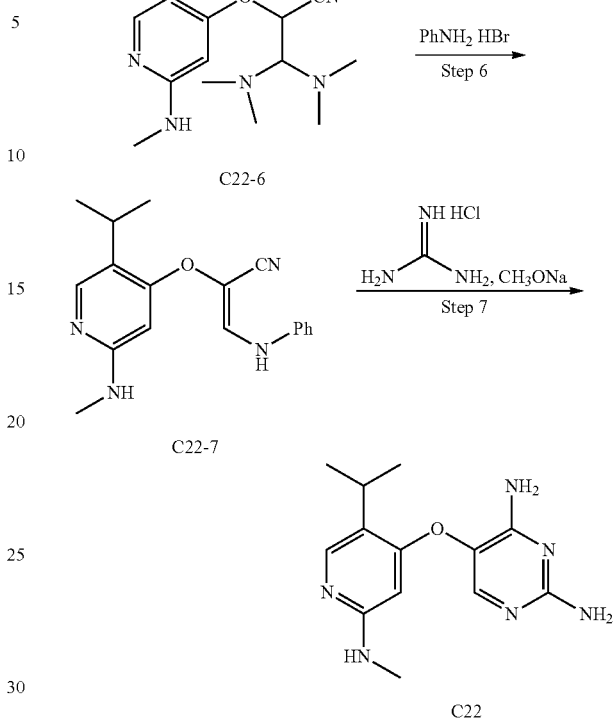

Step 1:

Compound C22-1 (3 g, 0.018 mol) was dissolved in tert-butanol (200 mL), di-tert-butyl dicarbonate (4.73 g, 0.021 mol) was added, and the reaction solution was stirred at 20° C. for 16 hours. LC-MS indicated the reaction of the starting materials was substantially complete. The reaction solution was concentrated under reduced pressure to afford a crude product, which was purified by column chromatography on silica gel (petroleum ether:ethyl acetate=100:1~50:1) to afford compound C22-2 (2.5 g, white solid, yield 52%).

$^1$H NMR (400 MHz, DMSO-$d_6$) δ 9.72 (s, 1H), 7.92 (s, 1H), 7.45 (s, 1H), 3.84 (s, 3H), 3.07-3.05 (m, 1H), 1.48 (s, 9H), 1.18 (d, J=7.2 Hz, 6H). MS m/z (ESI): 267.0 [M+H]$^+$.

Step 2:

Compound C22-2 (2.5 g, 0.094 mol) was dissolved in DMF (25 mL), sodium hydride (451 mg, 18.8 mmol) was added, and the reaction solution was stirred at 0° C. for 15 minutes. Iodomethane (2.0 g, 14.1 mmol) was then added, and the reaction solution was stirred at 0° C. for 1 hour. LC-MS indicated the reaction of the starting materials was substantially complete. Then, the reaction was added with purified water (150 mL), and extracted with ethyl acetate (200 mL×3). The organic phases were combined, washed with an aqueous solution of NaCl (100 mL), added with anhydrous sodium sulfate (20 g), dried for 30 min, filtered, and concentrated under reduced pressure to afford a crude product, which was purified by column chromatography on silica gel (petroleum ether:ethyl acetate=30:1~20:1) to afford compound C22-3 (2.2 g, brown oily liquid, yield 84%). MS m/z (ESI): 280.9 [M+H]$^+$.

Step 3:

Compound C22-3 (1.2 g, 0.043 mol) was dissolved in dichloromethane (10 mL), boron tribromide (10 mL) was added, and the reaction solution was stirred at 40° C. for 16 hours. LC-MS indicated the reaction of the starting materials was complete. The reaction solution was slowly dropwise added to ice water, adjusted to pH 8 with sodium carbonate, and extracted with ethyl acetate (100 mL×3). The organic phases were combined, washed once with saturated brine (100 mL), then dried over anhydrous sodium sulfate (10 g) for half an hour, filtered, and concentrated to give a crude product, C22-4, and the crude product was directly used in the next step (1 g crude product, yellow oily liquid, yield 80%). MS m/z (ESI): 167.0 [M+H]$^+$.

Step 4:

Compound C22-4 (1 g, 6.02 mmol) was dissolved in DMF (10 mL), bromoacetonitrile (723 mg, 6.02 mmol) and sodium carbonate (1.92 g, 18.06 mmol) were sequentially added, and the reaction solution was stirred at room temperature for 16 hours. LC-MS indicated the reaction of the starting materials was complete. The reaction was quenched by adding water (100 mL), and extracted with ethyl acetate (100 mL×3). The organic phases were combined, washed once with saturated brine (100 mL), then dried over anhydrous sodium sulfate (10 g) for half an hour, filtered, and concentrated under reduced pressure to afford a crude product, which was purified by column chromatography on silica gel (petroleum ether:ethyl acetate=5:1~1:1) to afford compound C22-5 (0.17 g, yellow solid, yield 15%).

$^1$H NMR (400 MHz, DMSO-d$_6$) δ 7.73 (s, 1H), 6.11 (s, 1H), 5.22 (s, 2H), 2.93-2.95 (m, 1H), 2.77 (s, 3H), 1.16 (d, J=6.8 Hz, 6H). MS m/z (ESI): 206.0 [M+H]$^+$.

Step 5:

Compound C22-5 (170 mg, 0.83 mmol) was dissolved in DMF (2 mL), tert-butoxy bis(dimethylamino)methane (577 mg, 3.32 mmol) was added, and the reaction solution was stirred at 100° C. for 1 hour. LC-MS indicated the reaction of the starting materials was complete. The reaction solution was concentrated under reduced pressure to afford a crude product, C22-6, and the crude product was directly used in the next step (0.2 g, yellow oily liquid, yield 79%). MS m/z (ESI): 260.9 [M−45+H]*.

Step 6:

Compound C22-6 (100 mg, 0.33 mmol) was dissolved in DMF (2 mL), aniline hydrobromide (54 mg, 0.39 mmol) was added, and the reaction solution was stirred at 100° C. for 16 hours. LC-MS indicated the reaction of the starting materials was complete. The reaction solution was cooled to room temperature, quenched by adding water (30 mL), and extracted with ethyl acetate (50 mL×3). The organic phases were combined, washed with saturated brine (50 mL), added with anhydrous sodium sulfate (10 g), dried for half an hour, and filtered. The filtrate was concentrated under reduced pressure to afford a crude product, C22-7, and the crude product was directly used in the next step (70 mg, brown oily liquid, yield 70%). MS m/z (ESI): 308.9 [M+H]$^+$.

Step 7:

Compound C22-7 (70 mg, 0.23 mmol) was dissolved in ethanol (15 mL), guanidine hydrochloride (65 mg, 0.68 mmol) and sodium methoxide (37 mg, 0.68 mmol) were sequentially added, and the reaction was stirred at 90° C. for 16 hours. LC-MS indicated the reaction of the starting materials was complete. The reaction solution was cooled to room temperature, concentrated under reduced pressure, and the crude product was isolated by preparative liquid chromatography to afford compound C22 (12 mg, light yellow solid, yield 19%).

$^1$H NMR (400 MHz, CD$_3$OD) δ 7.97 (s, 1H), 7.64 (s, 1H), 6.32 (s, 1H), 3.30-3.28 (m, 1H), 2.99 (s, 3H), 1.34 (d, J=6.8 Hz, 6H). MS m/z (ESI): 274.9 [M+H]$^+$.

The compounds in the following table were prepared according to methods similar to that described in Example 18.

| No. | Compound Structure | Compound Name | Starting material or regent different from that in Example 18 | Characterization Data |
|---|---|---|---|---|
| C120 (compound 120) | 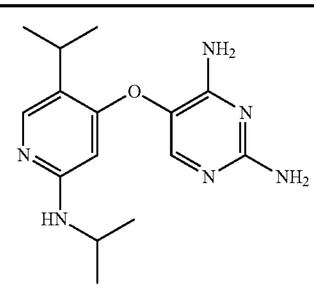 | 5-((5-isopropyl-2-(isopropylamino)pyridin-4-yl)oxy)pyrimidine-2,4-diamine | Iodomethane in Step 2 was replaced with isopropyl iodine. | $^1$H NMR (400 MHz, CD$_3$OD) δ 7.98 (s, 1H), 7.61 (s, 1H), 6.27 (s, 1H), 3.88-3.84 (m, 1H), 3.33-3.32 (m, 1H), 1.34 (d, J = 6.8 Hz, 6H), 1.29 (d, J = 6.4 Hz, 6H). MS m/z (ESI): 302.9 [M + H]$^+$. |
| C118 (compound 118) | 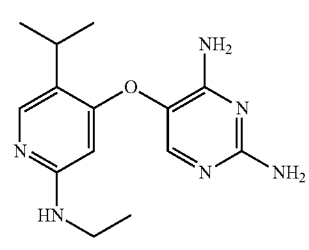 [SMILES: CCNc1cc(Oc2cnc(N)nc2N)c(C(C)C)cn1] | 5-((2-(ethylamino)-5-isopropylpyridin-4-yl)oxy)pyrimidine-2,4-diamine | C118-1 was prepared from C22-1$^i$, and the preparation started from Step 3 of Example 18. | $^1$H NMR (400 MHz, CD$_3$OD) δ 7.74 (s, 1H), 7.56 (s, 1H), 5.77 (s, 1H), 3.26-3.17 (m, 3H), 1.33 (d, J = 6.8 Hz, 6H), 1.17-1.14 (m, 3H). MS m/z (ESI): 288.8 [M + H]$^+$. |

-continued

| No. | Compound Structure | Compound Name | Starting material or regent different from that in Example 18 | Characterization Data |
|---|---|---|---|---|
| C119 (compound 119) | | 5-((2-(cyclopropylamino)-5-isopropylpyridin-4-yl)oxy)pyrimidine-2,4-diamine | Step 2 of Example 18 was replaced with the preparation of C119-1[iii]. | $^1$H NMR (400 MHz, CD₃OD) δ 7.79 (s, 1H), 7.58 (s, 1H), 5.99 (s, 1H), 3.37 (s, 1H), 2.23-2.19 (m, 1H), 1.34-1.31 (m, 6H), 1.02-0.94 (m, 2H), 0.64-0.62 (m, 1H), 0.38-0.37 (m, 1H). MS m/z (ESI): 301.0 [M + H]⁺. |
| C61 (compound 61) | | 5-((2-(ethyl(methyl)amino)-5-isopropylpyridin-4-yl)oxy)pyrimidine-2,4-diamine | The preparation started from Step 3 of Example 18, and C22-3 in Step 3 was replaced with C61-1[ii]. | $^1$H NMR (400 MHz, DMSO-d₆) δ 7.88 (s, 1H), 7.52 (s, 1H), 6.32 (s, 2H), 5.98 (s, 2H), 5.62 (s, 1H), 3.42-3.40 (m, 2H), 3.17-3.16 (m, 1H), 2.80 (s, 3H), 1.23 (d, J = 6.8 Hz, 6H), 0.98-0.95 (m, 3H). MS m/z (ESI): 303.0 [M + H]⁺. |
| C65 (compound 65) | | 5-((2-(cyclopropyl(methyl)amino)-5-isopropylpyridin-4-yl)oxy)pyrimidine-2,4-diamine | The preparation started from Step 3 of Example 18, and C22-3 in Step 3 was replaced with C65-5[ii]. | $^1$H NMR (400 MHz, CD₃OD) δ 7.99 (s, 1H), 7.76 (s, 1H), 6.53 (s, 1H), 3.21 (s, 3H), 2.91-2.81 (m, 1H), 2.25-2.18 (m, 1H), 1.35 (d, J = 7.0 Hz, 6H), 1.09-1.04 (m, 2H), 0.84-0.80 (m, 2H). MS m/z (ESI): 315.1 [M + H]⁺. |
| C152 (compound 152) | | 5-((5-isopropyl-2-(2,2,2-trifluoroethyl)amino)pyridin-4-yl)oxy)pyrimidine-2,4-diamine | The preparation started from Step 3 of Example 18, and C22-3 in Step 3 was replaced with C152-3[iv]. | $^1$H NMR (400 MHz, DMSO-d₆) δ 7.81 (s, 1H), 7.54 (s, 1H), 6.91 (t, J = 6.4 Hz, 1H), 6.31 (s, 2H), 5.99 (s, 2H), 5.84 (s, 1H), 4.09-4.02 (m, 2H), 3.20-3.16 (m, 1H), 1.24 (d, J = 6.8 Hz, 6H). MS m/z (ESI): 343.0 [M + H]⁺. | i Preparation of Intermediate Example C118-1

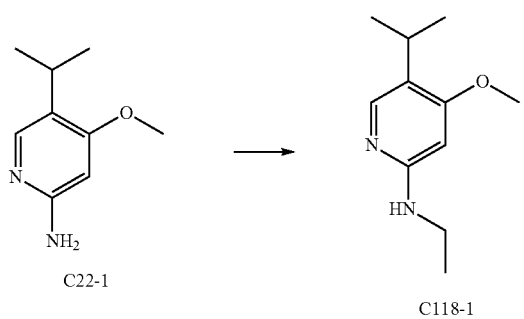

Compound C22-1 (10 g, 0.060 mol) was dissolved in ethanol (30 mL), acetaldehyde (2.7 g, 0.06 mol) was added, then sodium borohydride (6.9 g, 0.18 mol) was slowly added, and the reaction solution was stirred at 25° C. for 4 hours. LC-MS indicated the reaction of the starting materials was substantially complete. The reaction solution was quenched by adding water (100 mL), and extracted with ethyl acetate (120 mL×3). The organic phases were combined, washed with saturated brine (100 mL), added with anhydrous sodium sulfate (10 g), dried for half an hour, and filtered. The reaction solution was concentrated under reduced pressure to afford a crude product, which was purified by column chromatography on silica gel (petroleum ether:ethyl acetate=10:1~5:1) to afford compound C118-1 (8.5 g, yellow solid, yield 52%). MS m/z (ESI): 195.0 [M+H]⁺.

ii Preparation of Intermediate Example C65-5 and C61-1

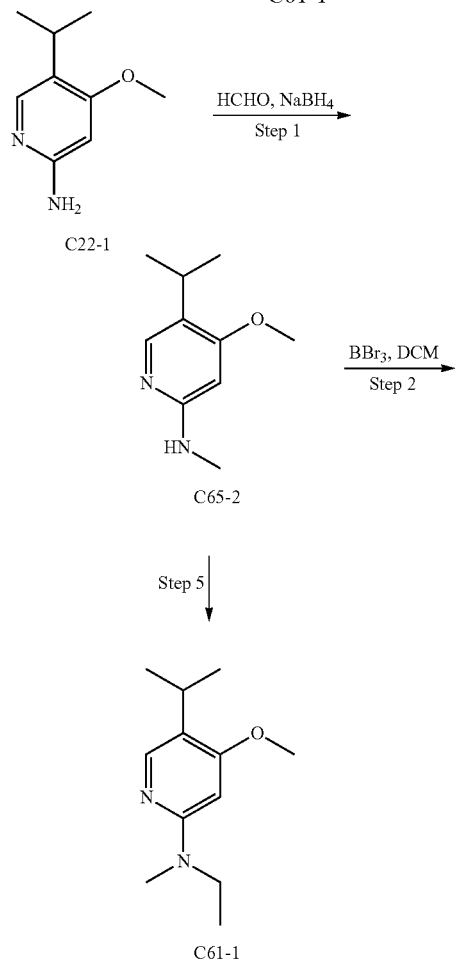

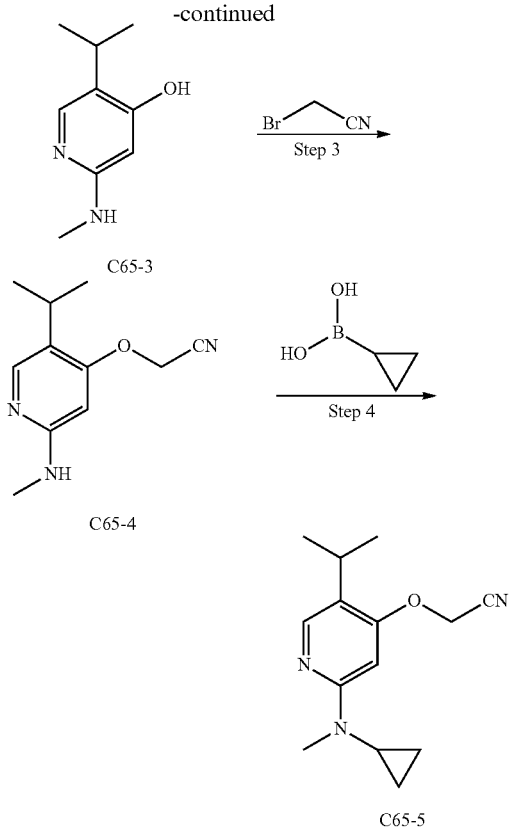

Step 1:

To a solution of C22-1 (10 g, 0.06 mol) in dichloromethane (200 mL), an aqueous solution of formaldehyde (10 mL, 0.12 mol) and anhydrous magnesium sulfate (30 g) as well as several drops of acetic acid were added, and the reaction was stirred at room temperature for 1 h. The reaction solution was added with sodium borohydride (12 g, 0.31 mol), and then stirred at room temperature for 18 h. The reaction was complete. The reaction was filtered, the filter cake was washed with dichloromethane (100 mL), and the filtrate was sequentially washed with water (200 mL) and saturated brine (200 mL×2). The organic phase was dried over anhydrous sodium sulfate, filtered, and concentrated under reduced pressure. The residue was purified by column chromatography on silica gel (petroleum ether:ethyl acetate=1:3) to afford C65-2 (2.1 g, light yellow oil, yield 19.4%).

¹H NMR (300 MHz, CDCl₃) δ 7.79 (s, 1H), 5.83 (s, 1H), 3.83 (s, 3H), 3.11-3.02 (m, 1H), 2.92 (d, J=5.0 Hz, 3H), 1.21 (d, J=6.9 Hz, 6H). MS m/z (ESI): 181.2 [M+H]⁺.

Step 2:

C65-2 (1.9 g, 11 mmol) was dissolved in dichloromethane (40 mL), boron tribromide (10 g, 40 mmol) was dropwise added at room temperature, after the dropwise addition, the reaction was placed in an oil bath at 50° C., and allowed to proceed for 18 h. After the reaction was complete, the reaction system was quenched by adding methanol (50 mL) under ice bath cooling, and concentrated under reduced pressure. The residue was adjusted to pH 6~7 with a saturated aqueous solution of sodium bicarbonate, extracted with tetrahydrofuran (50 mL×8), the combined organic phase was dried over anhydrous sodium sulfate, filtered, and then the filtrate was concentrated under reduced pressure, to afford C65-3 (1.2 g, light yellow solid, yield 68.5%).

$^1$H NMR (400 MHz, DMSO-d$_6$) δ 10.90 (s, 1H), 7.35 (s, 1H), 6.52 (s, 1H), 5.72 (s, 1H), 2.96-2.89 (m, 1H), 2.70 (d, J=4.7 Hz, 3H), 1.11 (d, J=6.9 Hz, 6H). MS m/z (ESI): 167.1 [M+H]$^+$.

Step 3:

C65-3 (1.14 g, 6.86 mmol) was dissolved in anhydrous DMF (10 mL), silver oxide (3.2 g, 13.7 mmol) and 2-bromoacetonitrile (905 mg, 7.55 mmol) were sequentially added to the solution, and the reaction was performed at room temperature for 4 h. The reaction solution was filtered, the filtrate was diluted with ethyl acetate (30 mL), then washed with a saturated aqueous solution of sodium chloride (20 mL×3), dried over anhydrous sodium sulfate, and filtered. The filtrate was concentrated under reduced pressure, and the residue was purified by column chromatography on silica gel (petroleum ether:ethyl acetate=1:4), to afford C65-4 (837 mg, yellow solid, yield 59.4%).

$^1$H NMR (400 MHz, CDCl$_3$) δ 7.87 (s, 1H), 5.84 (s, 1H), 4.81 (s, 2H), 4.75 (m, 1H), 3.08-3.02 (m, 1H), 2.92 (d, J=4.9 Hz, 3H), 1.20 (d, J=6.9 Hz, 6H). MS m/z (ESI): 206.2 [M+H]$^+$.

Step 4:

C65-4 (720 mg, 3.5 mmol), cyclopropylboronic acid (903 mg, 10.5 mmol), anhydrous cupric acetate (636 mg, 3.5 mmol) and DMAP (640 mg, 5.25 mmol) were added to acetonitrile (35 mL), and the reaction was placed in an oil bath at 50° C., and allowed to proceed for 18 h. The reaction solution was filtered, the filtrate was concentrated, and then the residue was purified by column chromatography on silica gel (petroleum ether:ethyl acetate=4:1), to afford C65-5 (410 mg, colorless oil, yield 47.6%).

$^1$H NMR (400 MHz, CDCl$_3$) δ 7.98 (s, 1H), 6.51 (s, 1H), 4.84 (s, 2H), 3.15 (s, 3H), 3.10-3.02 (m, 1H), 2.54-2.49 (m, 1H), 1.21 (d, J=7.0 Hz, 6H), 0.94-0.89 (m, 2H), 0.73-0.69 (m, 2H). MS m/z (ESI): 246.2 [M+H]$^+$.

Step 5:

Compound C65-2 (800 mg, 4.4 mmol) was dissolved in DMF (5 mL), NaH (320 mg, 13.2 mmol) was added at 0° C., and the reaction solution was stirred at 0° C. for 30 min. Then, iodoethane (687 mg, 4.4 mmol) was added, and the reaction was stirred at room temperature for 18 hours. LC-MS indicated the reaction of the starting materials was complete. The reaction was quenched by adding water (10 mL), and extracted with ethyl acetate (20 mL×3). The organic phases were combined, washed with saturated brine (40 mL), added with anhydrous sodium sulfate (10 g), dried for half an hour, and filtered. The filtrate was concentrated under reduced pressure to afford a crude product, which was purified by column chromatography on silica gel (petroleum ether:ethyl acetate=20:1~5:1) to afford compound C61-1 (360 mg, oil, yield 39.0%). MS m/z (ESI): 208.7 [M+H]$^+$.

iii Preparation of Intermediate Example C119-1

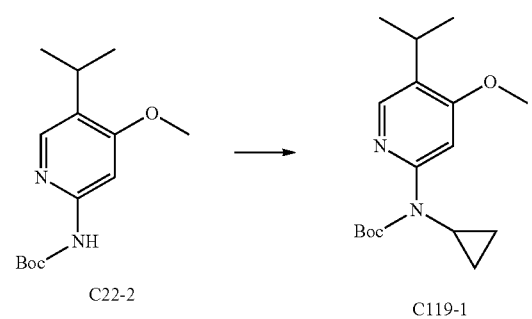 [SMILES: COc1cc(NC(=O)OC(C)(C)C)ncc1C(C)C ; COc1cc(N(C(=O)OC(C)(C)C)C2CC2)ncc1C(C)C ; "C22-2" ; "C119-1"]

Compound C22-2 (2.2 g, 0.010 mol) was dissolved in acetonitrile (30 mL), cyclopropylboronic acid (1.72 g, 0.020 mol), DMAP (1.8 g, 0.015 mol), molecular sieves (2.7 g) and cupric acetate (1.8 g, 0.010 mol) were sequentially added, and the reaction solution was stirred at 50° C. for 48 hours. LC-MS indicated the reaction of the starting materials was substantially complete. The reaction solution was cooled to room temperature, filtered, and the filtrate was concentrated under reduced pressure to afford a crude product, which was purified by column chromatography on silica gel (petroleum ether:ethyl acetate=10:1~5:1) to afford compound C119-1 (1.2 g, yellow solid, yield 48%). MS m/z (ESI): 306.8 [M+H]$^+$.

iv Preparation of Intermediate Example C152-3

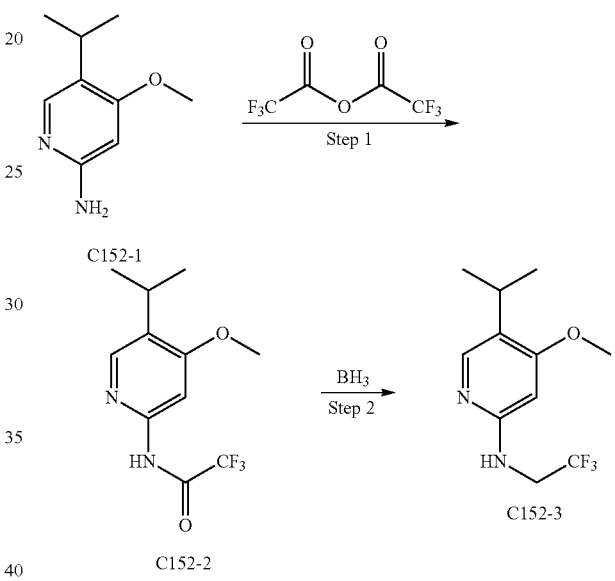

Step 1:

Compound C152-1 (5 g, 0.030 mol) was dissolved in dichloromethane (30 mL), triethylamine (4.0 g, 0.040 mol) and trifluoroacetic anhydride (7.6 g, 0.036 mol) were added, and the reaction solution was stirred at room temperature for 16 hours. The reaction solution was quenched by water (20 mL), and then extracted with dichloromethane (50 mL). The organic phase was washed with saturated brine (20 mL), dried, concentrated, and the crude product was purified by column chromatography on silica gel (petroleum ether:ethyl acetate=10:1), to afford compound C152-2 (2.4 g, white solid, yield 30.5%).

$^1$H NMR (400 MHz, CDCl$_3$) δ 7.94 (s, 1H), 7.61 (s, 1H), 7.26 (s, 1H), 3.95 (s, 3H), 3.24-3.13 (m, 1H), 1.24 (d, J=6.8 Hz, 6H). MS m/z (ESI): 262.9 [M+H]$^+$.

Step 2:

Compound C152-2 (2.4 g, 9.16 mmol) was dissolved in THF (30 mL), a solution of borane (27 mL, 27 mmol) was added, and the reaction solution was stirred at 50° C. overnight. The reaction was quenched by adding water (5 mL), then extracted with ethyl acetate (20 mL×3). The organic phase was washed with water (15 mL), dried over sodium sulfate, and then concentrated to give a crude product, C152-3 (1.3 g, brown solid, yield 57.2%). MS m/z (ESI): 248.9 [M+H]$^+$.

Example 19: preparation of 5-((5-bromo-2-methoxypyridin-4-yl)oxy)pyrimidine-2,4-diamine (C124, compound 124)

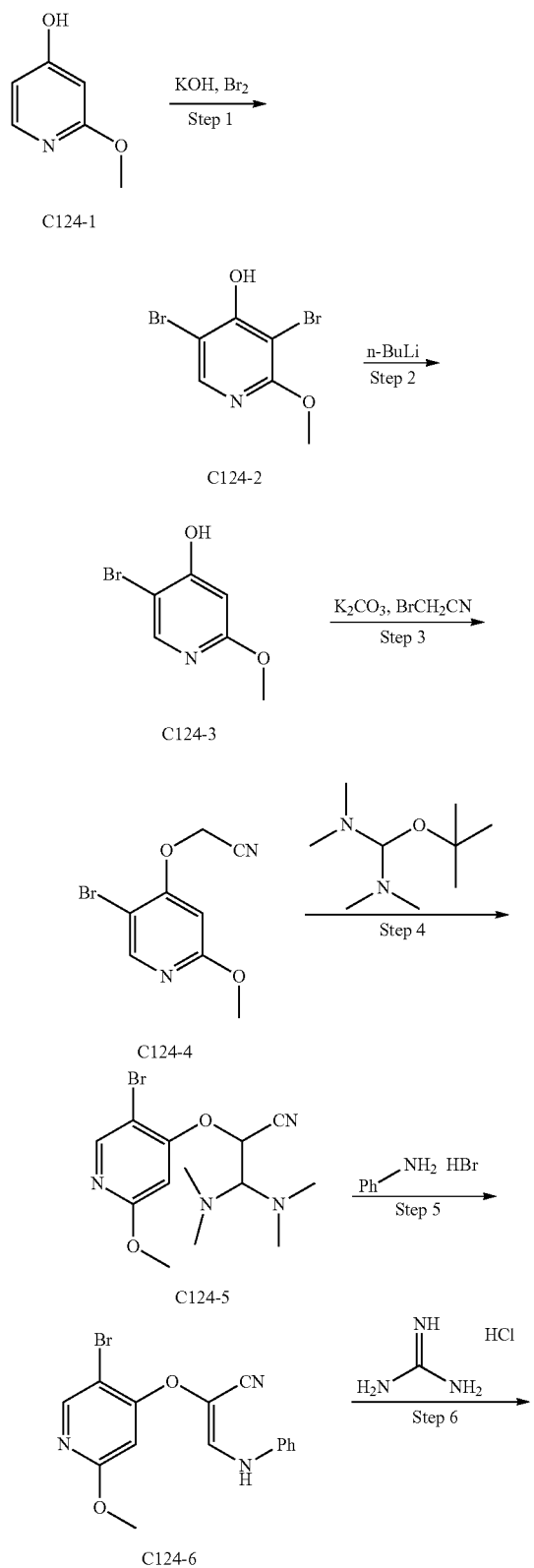

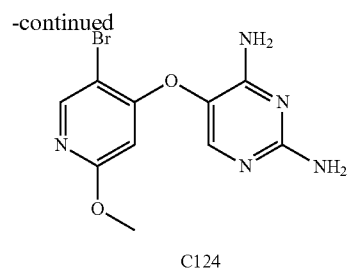

Step 1:

C124-1 (1.2 g, 9.6 mmol) was dissolved in acetic acid (50 mL), and then an aqueous solution (10 mL) of KOH (2.15 g, 38.4 mmol) and bromine (3.07 g, 19.2 mmol) were dropwise added. The reaction was performed at 0° C. for 0.5 hour, and was then stirred at room temperature for 16 hours. A large amount of white solid precipitated, the reaction was filtered, and the filter cake was rinsed with petroleum ether (10 mL). The filter cake was collected and dried to afford compound C124-2 (2.34 g, white solid, yield 86%).

$^1$H NMR (400 MHz, DMSO-$d_6$) δ 8.14 (s, 1H), 3.88 (s, 3H). MS m/z (ESI): 283.7 [M+H]$^+$.

Step 2:

C124-2 (2.34 g, 8.26 mmol) was dissolved in tetrahydrofuran (50 mL), and then a solution of n-butyl lithium (7.5 mL, 18.2 mmol) was dropwise added under the protection of nitrogen at −78° C., and the reaction was performed at −78° C. for 1 hour. The reaction was quenched by adding water (10 mL), adjusted to pH 7 with a 1N solution of hydrochloric acid, and then extracted with ethyl acetate (40 mL×2). The organic phases were combined, washed once with saturated brine (20 mL), then dried over anhydrous sodium sulfate (5 g) for half an hour, filtered, and concentrated. The crude product was isolated by column chromatography on silica gel (petroleum ether:ethyl acetate=3:1) to afford compound C124-3 (1.2 g, white solid, yield 71.2%).

$^1$H NMR (400 MHz, DMSO-$d_6$) δ 11.53 (s, 1H), 8.09 (s, 1H), 3.78 (s, 3H). MS m/z (ESI): 203.8 [M+H]$^+$.

Step 3:

C124-3 (204 mg, 1 mmol) was dissolved in DMF (2 mL), followed by addition of potassium carbonate (276 mg, 2 mmol) and bromoacetonitrile (240 mg, 2 mmol), and the reaction was stirred at room temperature for 1 h. The reaction was quenched by adding water (5 mL), and then extracted with ethyl acetate (20 mL×2). The organic phase was dried over anhydrous sodium sulfate, concentrated, and the crude product was isolated by column chromatography on silica gel (petroleum ether:ethyl acetate=4:1) to afford compound C124-4 (100 mg, white solid, yield 43.3%).

$^1$H NMR (400 MHz, DMSO-$d_6$) δ 8.19 (s, 1H), 6.32 (s, 1H), 4.85 (s, 3H), 3.93 (s, 3H). MS m/z (ESI): 242.7 [M+H]$^+$.

Step 4:

C124-4 (100 mg, 0.433 mmol) was dissolved in DMF (2 mL), and tert-butoxy bis(dimethylamino)methane (226 mg, 1.3 mmol) was added to the reaction solution. The reaction was stirred at 100° C. for 2 hours. After LC-MS indicated the reaction was complete, the reaction was quenched by adding water, and extracted with ethyl acetate (15 mL×2). The organic phase was dried over anhydrous sodium sulfate and concentrated to afford a crude product, compound C124-5 (110 mg, crude). MS m/z (ESI): 297.8 [M−45+H]$^+$.

Step 5:

C124-5 (242 mg, 0.705 mmol) was dissolved in DMF (2 mL), and aniline hydrobromide (24 mg, 0.14 mmol) was added to the reaction solution. The reaction was stirred at 100° C. for 3 hours. The reaction was quenched by adding water, and extracted with ethyl acetate (25 mL×3). The organic phase was dried and concentrated to afford compound C124-6 (110 mg, brown solid, yield 42.5%). MS m/z (ESI): 345.8 [M+H]$^+$.

Step 6:

C124-6 (110 mg, 0.3 mmol) was dissolved in ethanol (5 mL), and guanidine hydrochloride (56 mg, 0.6 mmol) and sodium methoxide (32 mg, 0.6 mmol) were added to the reaction solution. The reaction was stirred at 90° C. overnight. After LC-MS indicated the reaction was complete, the reaction was concentrated to dryness, and the residue was purified by the Prep-HPLC method to afford C124 (10 mg, yellow solid, yield 10%).

$^1$H NMR (400 MHz, CD$_3$OD) δ 8.23 (s, 1H), 7.23 (s, 1H), 6.37 (s, 1H), 3.88 (s, 3H). MS m/z (ESI): 311.8 [M+H]$^+$.

The compounds in the following table were prepared according to methods similar to that described in Example 19.

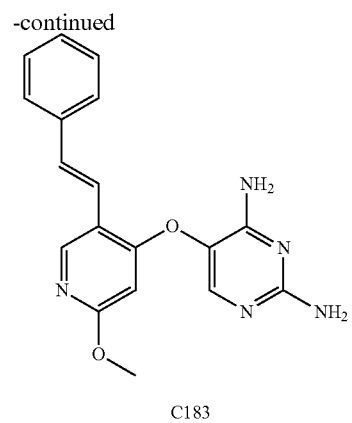

C183

C124 (32 mg, 0.1 mmol), (E)-styrylboronic acid (SM3, 29.6 mg, 0.2 mmol), potassium carbonate (41.4 mg, 0.3 mmol) and Pd(PPh$_3$)$_4$ (20 mg) were added to a 50 mL single-neck flask, followed by addition of the solvent, 1,4-dioxane (5 mL) and water (1 mL). Under the protection of

| No. | Compound Structure | Compound Name | Starting material or regent different from that in Example 19 | Characterization Data |
|---|---|---|---|---|
| C30 (compound 30) | 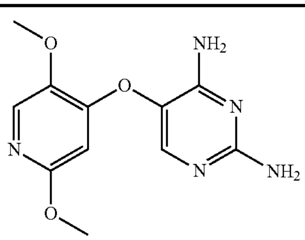 | 5-(2,5-dimethoxypyridin-4-yl)oxy)pyrimidine-2,4-diamine | The preparation started from Step 3 of Example 19, and C124-3 in Step 3 was replaced with 2,5-dimethoxypyridin-4-ol. | $^1$H NMR (400 MHz, CD$_3$OD) δ 7.77 (s, 1H), 7.60 (s, 1H), 6.08 (s, 1H), 3.93 (s, 3H), 3.82 (s, 3H). MS m/z (ESI): 264.0 [M + H]$^+$. |
| C31 (compound 31) | 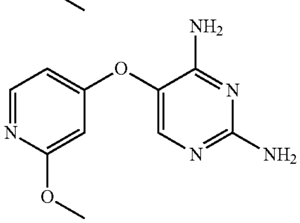 | 5-((2-methoxy-4-yl)oxy)pyrimidine-2,4-diamine | The preparation started from Step 3 of Example 19, and C124-3 in Step 3 was replaced with 2-methoxypyridin-4-ol. | $^1$H NMR (400 MHz, DMSO-d$_6$) δ 8.47 (s, 1H), 8.08 (s, 2H), 7.97 (s, 1H), 7.69 (s, 2H), 6.78 (s, 1H), 6.47 (s, 1H), 3.84 (s, 3H). MS m/z (ESI): 234.1 [M + H]$^+$. |

Example 20: preparation of (E)-(5-((2-methoxy-5-styrylpyridin-4-yl)oxy)pyrimidine-2,4-diamine (C183, compound 183)

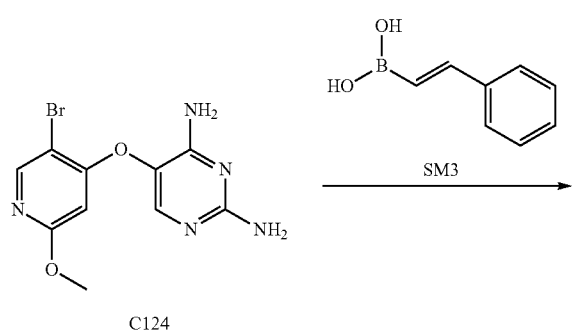

nitrogen, the reaction solution was heated to 100° C., and the reaction was performed for 18 h. LC-MS analysis confirmed that the target product was obtained. The reaction solution was cooled to room temperature, filtered, and the filtrate was concentrated under reduced pressure to give an oily crude product, which was purified by preparative thin layer chromatography on silica gel (dichloromethane:methanol=10:1) to afford compound C183 (6 mg, white solid, yield 17.9%).

$^1$H NMR (400 MHz, CD$_3$OD) δ 8.37 (s, 1H), 7.67 (s, 1H), 7.58 (d, J=8.0 Hz, 2H), 7.35-7.38 (m, 3H), 7.25 (d, J=8.0 Hz, 2H), 6.05 (s, 1H), 3.90 (s, 3H). MS m/z (ESI): 335.8 [M+H]$^+$.

The compounds in the following table were prepared according to methods similar to that described in Example 20.

| No. | Compound Structure | Compound Name | Starting material or regent different from that in Example 20 | Characterization Data |
|---|---|---|---|---|
| C177 (compound 177) | 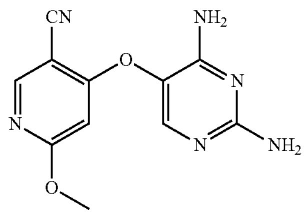 [SMILES: COc1cc(Oc2cnc(N)nc2N)c(C#N)cn1] | 4-((2,4-diamino-pyrimidin-5-yl)oxy)-6-methoxy-nicotinonitrile | Potassium carbonate and SM3 were replaced with zinc powder and zinc cyanide; 1,4-dioxane was replaced with DMF. | $^1$H NMR (400 MHz, CD$_3$OD) δ 8.47 (s, 1H), 7.72 (s, 1H), 6.13 (s, 1H), 3.96 (s, 3H). MS m/z (ESI): 259.0 [M + H]$^+$. |
| C176 (compound 176) | 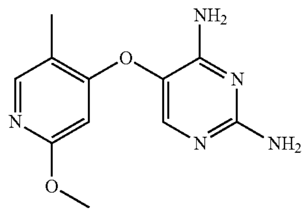 [SMILES: COc1cc(Oc2cnc(N)nc2N)c(C)cn1] | 5-((2-methoxy-5-methylpyridin-4-yl)oxy)pyrimidine-2,4-diamine | SM3 was replaced with methylboronic acid. | $^1$H NMR (400 MHz, CD$_3$OD) δ 7.87 (s, 1H), 7.60 (s, 1H), 5.96 (s, 1H), 3.83 (s, 3H), 2.27 (s, 3H). MS m/z (ESI): 247.9 [M + H]$^+$. |
| C164 (compound 164) | 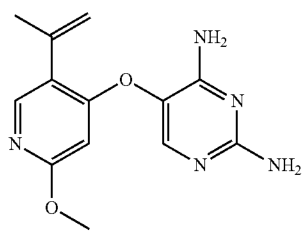 [SMILES: C=C(C)c1cnc(OC)cc1Oc1cnc(N)nc1N] | 5-((2-methoxy-5-(prop-1-en-2-yl)pyridin-4-yl)oxy)pyrimidine-2,4-diamine | SM3 was replaced with isopropenyl-boronic acid. | $^1$H NMR (400 MHz, CD$_3$OD) δ 7.96 (s, 1H), 7.58 (s, 1H), 6.02 (s, 1H), 5.22 (d, J = 8.0 Hz, 2H), 3.87 (s, 3H), 2.20 (s, 3H). MS m/z (ESI): 273.9 [M + H]$^+$. |
| C162 (compound 162) | 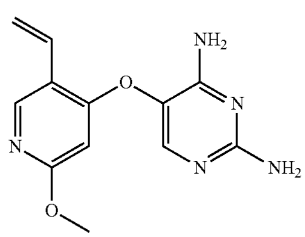 [SMILES: C=Cc1cnc(OC)cc1Oc1cnc(N)nc1N] | 5-((2-methoxy-5-vinylpyridin-4-yl)oxy)pyrimidine-2,4-diamine | SM3 was replaced with 4,4,5,5-tetramethyl-2-vinyl-1,3,2-dioxaborolane. | $^1$H NMR (400 MHz, CD$_3$OD) δ 8.21 (s, 1H), 7.61 (s, 1H), 7.01-6.92 (m, 1H), 6.01 (s, 1H), 5.85 (d, J = 18.0 Hz, 1H), 5.33 (d, J = 11.6 Hz, 1H), 3.87 (s, 3H). MS m/z (ESI): 259.9 [M + H]$^+$. |
| C163 (compound 163) | 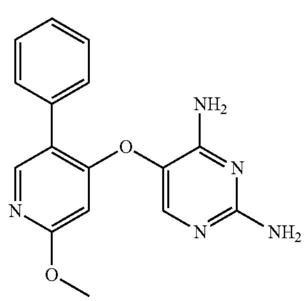 [SMILES: COc1cc(Oc2cnc(N)nc2N)c(-c2ccccc2)cn1] | 5-((2-methoxy-5-phenylpyridin-4-yl)oxy)pyrimidine-2,4-diamine | SM3 was replaced with phenylboronic acid. | $^1$H NMR (400 MHz, CD$_3$OD) δ 8.07 (s, 1H), 7.64-7.44 (m, 5H), 7.39-7.36 (m, 1H), 6.12 (s, 1H), 3.91 (s, 3H). MS m/z (ESI): 309.9 [M + H]$^+$. |

-continued

| No. | Compound Structure | Compound Name | Starting material or regent different from that in Example 20 | Characterization Data |
|---|---|---|---|---|
| C138 (compound 138) | 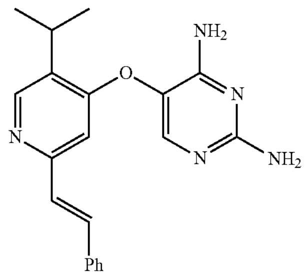 [SMILES: CC(C)c1cnc(/C=C/c2ccccc2)cc1Oc1cnc(N)nc1N] | (E)-5-((5-isopropyl-2-styrylpyridin-4-yl)oxy)pyrimidine-2,4-diamine | C124 was replaced with C2. | $^1$H NMR (400 MHz, DMSO) δ 8.40 (s, 1H), 7.65-7.55 (m, 4H), 7.36-7.28 (m, 4H), 6.67 (s, 1H), 6.51 (s, 2H), 6.12 (s, 2H), 3.34-3.36 (m, 1H), 1.32 (d, J = 6.8 Hz, 6H). MS m/z (ESI): 347.9 [M + H]$^+$. |
| C33 (compound 33) | 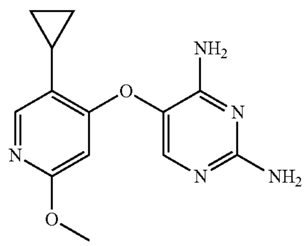 [SMILES: COc1cc(Oc2cnc(N)nc2N)c(C2CC2)cn1] | 5-((5-cyclopropyl-2-methoxypyridin-4-yl)oxy)pyrimidine-2,4-diamine | SM3 was replaced with cyclopropyl-boronic acid. | $^1$H NMR (400 MHz, CD$_3$OD) δ 7.73 (s, 1H), 7.60 (s, 1H), 5.98 (s, 1H), 3.83 (s, 3H), 2.11-2.08 (m, 1H), 0.95-0.74 ((m, 4H). MS m/z (ESI): 273.9 [M + H]$^+$. |
| C205 (compound 205) | 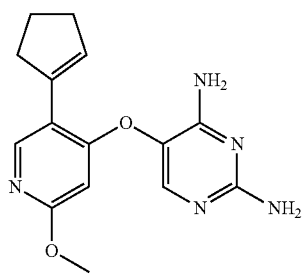 [SMILES: COc1cc(Oc2cnc(N)nc2N)c(C2=CCCC2)cn1] | 5-((5-(cyclopent-1-en-1-yl)-2-methoxypyridin-4-yl)oxy)pyrimidine-2,4-diamine | SM3 was replaced with cyclopentenyl-pinacol borate; the catalyst and ligand was replaced with tri-tert-butylphosphine and Pd$_2$(dba)$_3$; potassium carbonate was replaced with cesium carbonate; the solvent was dioxane only, no water was added. | $^1$H NMR (400 MHz, DMSO) δ 8.45 (s, 1H), 8.11 (s, 1H), 8.08 (s, 1H), 7.88 (s, 1H), 7.61 (s, 2H), 6.38-6.35 (m, 2H), 3.83 (s, 3H), 2.74-2.67 (m, 4H), 1.93-1.89 (m, 2H). MS m/z (ESI): 299.9 [M + H]$^+$. |
| C54 (compound 54) | 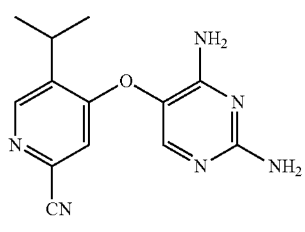 [SMILES: CC(C)c1cnc(C#N)cc1Oc1cnc(N)nc1N] | 4-((2,4-diamino-pyrimidin-5-yl)oxy)-5-isopropyl-2-cyanopyridine | Potassium carbonate and SM3 were replaced with zinc powder and zinc cyanide; 1,4-dioxane was replaced with DMF; C124 was replaced with C2. | $^1$H NMR (400 MHz, CD$_3$OD) δ 8.52 (s, 1H), 7.63 (s, 1H), 7.09 (s, 1H), 3.52-3.49 (m, 1H), 1.39 (d, J = 6.8 Hz, 6H). MS m/z (ESI): 270.9 [M + H]$^+$. |
| C129 (compound 129) | 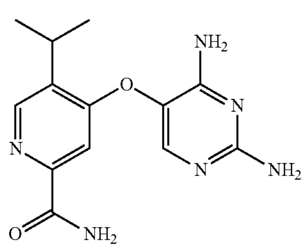 [SMILES: CC(C)c1cnc(C(N)=O)cc1Oc1cnc(N)nc1N] | 4-((2,4-diamino-pyrimidin-5-yl)oxy)-5-isopropyl-picolinamide | It is a by-product isolated during the synthesis of C54. | $^1$H NMR (400 MHz, DMSO-d) δ 8.43 (s, 1H), 8.03 (s, 1H), 7.62 (s, 2H), 7.14 (s, 1H), 6.55 (s, 2H), 6.15 (s, 2H), 3.43-3.41 (m, 1H), 1.32 (d, J = 6.8 Hz, 6H). MS m/z (ESI): 288.9 [M + H]$^+$. |

Example 21: preparation of 1-(4-((2,4-diaminopyrimidin-5-yl)oxy)-5-isopropylpyridin-2-yl)ethanone (C46, compound 46)

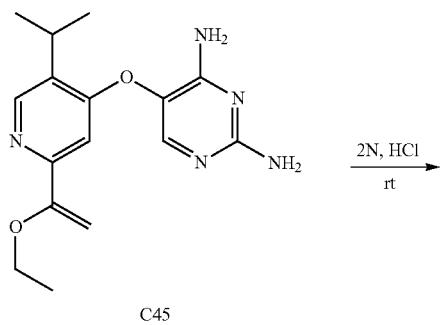

C45 (20 mg, 0.06 mmol) was dissolved in 2M HCl (10 mL), and the reaction was performed at room temperature for 18 h. After the reaction was complete, the reaction solution was concentrated under reduced pressure to afford a crude product, which was purified by prep-HPLC to afford compound C46 (5 mg, yield 27.47%).

1H NMR (400 MHz, CD$_3$OD) δ 8.60 (s, 1H), 7.75 (s, 1H), 7.38 (s, 1H), 3.48-3.45 (m, 1H), 2.64 (s, 3H), 1.41 (d, J=6.0 Hz, 6H). MS m/z (ESI): 287.9 [M+H]$^+$.

Example 22: preparation of 5-((5-isopropyl-2-((trimethylsilyl)ethynyl)pyridin-4-yl)oxy)pyrimidine-2,4-diamine (C246, compound 246) and 5-((2-ethynyl-5-isopropylpyridin-4-yl)oxy)pyrimidine-2,4-diamine (C66, compound 66)

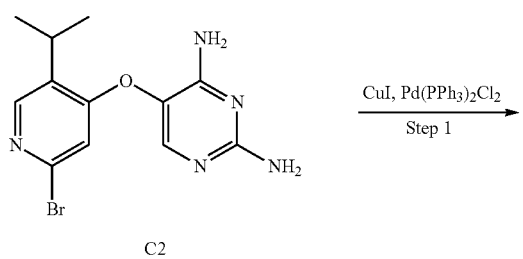

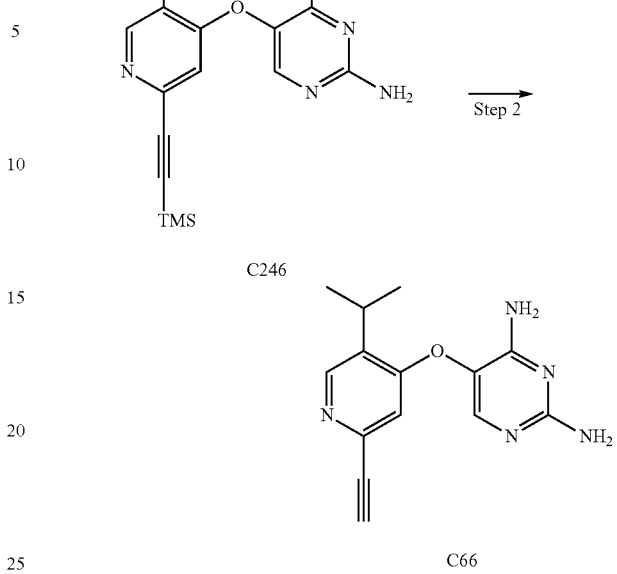

Step 1:

Compound C2 (3 g, 9.29 mmol) was dissolved in 1,4-dioxane (40 mL), trimethylsilylacetylene (9 g, 92.9 mmol), DIEA (12 g, 92.9 mmol), CuI (0.6 g) and Pd(PPh$_3$)$_2$Cl$_2$ (0.6 g) were sequentially added, and purge with nitrogen was performed for 3 times. Under the protection of nitrogen, the reaction was performed at 50° C. for 2 hours. LC-MS indicated the reaction of the starting materials was substantially complete. The reaction solution was cooled to room temperature, filtered, the filter cake was washed with 1,4-dioxane (10 mL), the filtrate was concentrated under reduced pressure to remove dioxane, followed by addition of purified water (100 mL), and extraction with ethyl acetate (100 mL×3). The organic phases were combined, added with anhydrous sodium sulfate (20 g), dried for 30 min, filtered, and concentrated under reduced pressure to afford a crude product, which was purified by column chromatography on silica gel (petroleum ether:ethyl acetate=20:1~5:1) to afford compound C246 (2 g, yield 63.1%). MS m/z (ESI): 341.9 [M+H]$^+$.

Step 2:

Compound C246 (2 g, 5.87 mmol) was dissolved in THF (20 mL), and TBAF (1.53 g, 5.87 mmol) was added. The reaction was performed at room temperature for 10 minutes. LC-MS indicated the reaction of the starting materials was complete. The reaction solution was rotary evaporated to dryness to give an oily residue. The residue was purified by column chromatography on silica gel (petroleum ether:ethyl acetate=1:3) to afford compound C66 (0.7 g, yellow solid, yield 44.6%).

$^1$H NMR (300 MHz, DMSO-d$_6$) δ 8.33 (s, 1H), 7.56 (s, 1H), 6.50 (s, 1H), 6.41 (s, 2H), 6.01 (s, 2H), 4.20 (s, 1H), 3.37-3.31 (m, 1H), 1.28 (d, J=6.8 Hz, 6H). MS m/z (ESI): 269.8 [M+H]$^+$.

The compounds in the following table were prepared according to methods similar to that described in Example 22.

| No. | Compound Structure | Compound Name | Starting material or regent different from that in Example 22 | Characterization Data |
| --- | --- | --- | --- | --- |
| C88 (compound 88) | 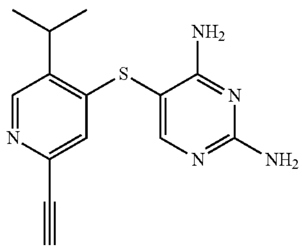 | 5-((2-ethynyl-5-isopropyl-pyrdin-4-yl)thio)pyrimidine-2,4-diamine | C2 in Step 1 was replaced with C85. | $^1$H NMR (400 MHz, CD$_3$OD) δ 8.28 (s, 1H), 7.96 (s, 1H), 6.80 (s, 1H), 3.66 (s, 1H), 3.37-3.30 (m, 1H), 1.39 (d, J = 6.8 Hz, 6H). MS m/z (ESI): 285.8 [M + H]$^+$. |
| C136 (compound 136) | 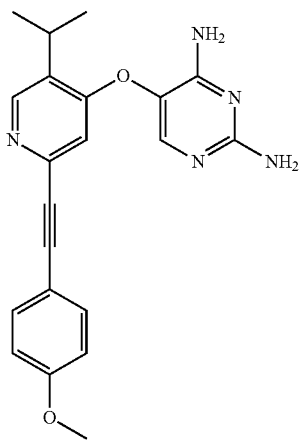 [SMILES: COc1ccc(C#Cc2cc(Oc3cnc(N)nc3N)c(C(C)C)cn2)cc1] | 5-((5-isopropyl-2-((4-methoxyphenyl)ethynyl)pyridin-4-yl)oxy)pyrimidine-2,4-diamine | Trimethylsilylacetylene in Step 1 was replaced with 4-methoxyphenylacetylene. | $^1$H NMR (400 MHz, DMSO-d$_6$) δ 8.50-8.46 (m, 2H), 8.24 (s, 1H), 8.10 (s, 1H), 7.95 (s, 2H), 7.52 (d, J = 8.8 Hz, 2H), 7.19 (s, 1H), 7.01 (d, J = 8.8 Hz, 2H), 3.81 (s, 3H), 3.35 (m, 1H), 1.30 (d, J = 6.8 Hz, 6H). MS m/z (ESI): 375.9 [M + H]$^+$. |
| C137 (compound 137) | 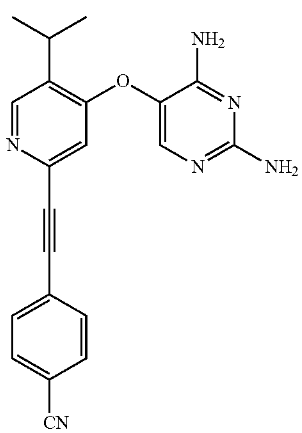 [SMILES: CC(C)c1cnc(C#Cc2ccc(C#N)cc2)cc1Oc1cnc(N)nc1N] | 4-((4-(2,4-diaminopyrimidin-5-yl)oxy)-5-isopropylpyridin-2-yl)ethynyl)benzonitrile | Trimethylsilylacetylene in Step 1 was replaced with 4-ethynylbenzonitrile. | $^1$H NMR (400 MHz, DMSO-d$_6$) δ 8.51 (s, 2H), 8.11 (s, 1H), 7.98 (s, 1H), 7.92 (d, J = 8.4 Hz, 2H), 7.78 (d, J = 8.8 Hz, 2H), 7.68 (s, 2H), 7.31 (s, 1H), 3.38 (m, 1H), 1.32 (d, J = 6.8 Hz, 6H). MS m/z (ESI): 370.9 [M + H]$^+$. |
| C148 (compound 148) | 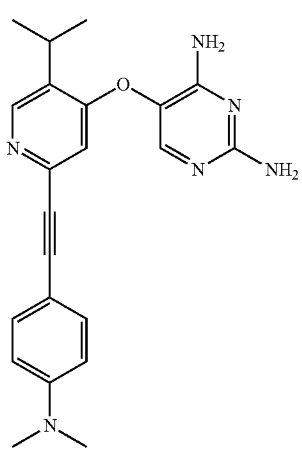 [SMILES: CC(C)c1cnc(C#Cc2ccc(N(C)C)cc2)cc1Oc1cnc(N)nc1N] | 5-((2-((4-(dimethylamino)phenyl)ethynyl)-5-isopropylpyridin-4-yl)oxy)pyrimidine-2,4-diamine | Trimethylsilylacetylene in Step 1 was replaced with 4-dimethylaminophenylacetylene. | $^1$H NMR (400 MHz, CDCl$_3$) δ 8.42 (s, 1H), 7.76 (s, 1H), 7.47 (d, J = 8.4 Hz, 2H), 6.80 (s, 1H), 6.65 (d, J = 8.8 Hz, 2H), 5.09 (s, 2H), 4.92 (s, 2H), 3.38 (m, 1H), 3.02 (s, 6H), 1.39 (d, J = 6.8 Hz, 6H). MS m/z (ESI): 388.9 [M + H]$^+$. |

| No. | Compound Structure | Compound Name | Starting material or regent different from that in Example 22 | Characterization Data |
| --- | --- | --- | --- | --- |
| C155 (compound 155) | 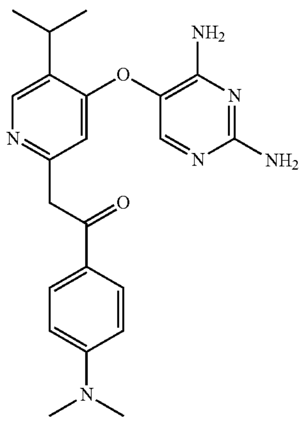 [SMILES: CC(C)c1cnc(CC(=O)c2ccc(N(C)C)cc2)cc1Oc1cnc(N)nc1N] | 2-(4-(2,4-diamino-pyrimidin-5-yl)oxy)-5-isopropylpyridin-2-yl)-1-(4-(dimethylamino)phenyl)ethanone | It is a by-product resulted from the work-up of C148. | $^1$H NMR (400 MHz, DMSO-d$_6$) δ 8.26 (s, 1H), 7.83 (m, 2H), 7.52 (s, 1H), 6.70 (m, 2H), 6.54 (s, 1H), 6.36 (s, 2H), 5.96 (s, 2H), 4.22 (s, 2H), 3.32 (m, 1H), 2.95 (s, 6H), 1.27 (d, J = 6.8 Hz, 6H). MS m/z (ESI): 406.7 [M + H]$^+$. |
| C170 (compound 170) | 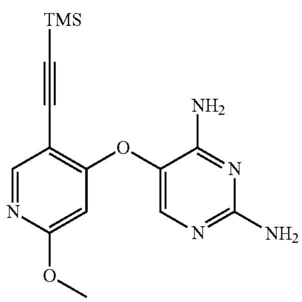 [SMILES: COc1cc(Oc2cnc(N)nc2N)c(C#C[Si](C)(C)C)cn1] | 5-((2-methoxy-5-((trimethylsilyl)ethynyl)pyridin-4-yl)oxy)pyrimidine-2,4-diamine | C2 in Step 1 was replaced with C124. | $^1$H NMR (400 MHz, CDCl$_3$) δ 8.24 (s, 1H), 7.65 (s, 1H), 6.15 (s, 1H), 5.73 (s, 2H), 5.28 (s, 2H), 3.92 (s, 3H), 0.25 (s, 9H). MS m/z (ESI): 330.0 [M + H]$^+$. |
| C126 (compound 126) | 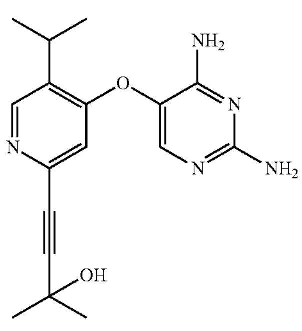 [SMILES: CC(C)c1cnc(C#CC(C)(C)O)cc1Oc1cnc(N)nc1N] | 4-(4-(2,4-diamino-pyrimidin-5-yl)oxy)-5-isopropyl-pyridin-2-yl)-2-methylbut-3-yn-2-ol | Trimethylsilylacetylene in Step 1 was replaced with 2-methylbut-3-yn-2-ol; 1,4-dioxane was replaced with acetonitrile; DIEA was replaced with triethylamine. | $^1$H NMR (400 MHz, DMSO-d$_6$) δ 8.37 (s, 1H), 6.54-6.48 (m, 3H), 6.09 (s, 2H), 5.54 (s, 1H), 3.39-3.33 (m, 1H), 1.42 (s, 6H), 1.30 (d, J = 7.2 Hz, 6H). MS m/z (ESI): 327.9 [M + H]$^+$. |
| C171 (compound 171) | 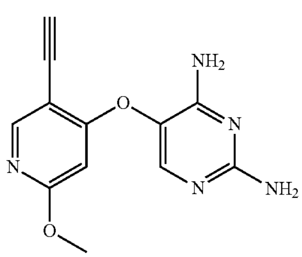 [SMILES: C#Cc1cnc(OC)cc1Oc1cnc(N)nc1N] | 5-((5-ethynyl-2-methoxy-pyridin-4-yl)oxy)pyrimidine-2,4-diamine | The preparation started from Step 2, C246 in Step 2 was replaced with C170. | $^1$H NMR (400 MHz, CD$_3$OD) δ 8.47 (s, 1H), 7.64 (s, 1H), 6.06 (s, 1H), 3.89 (s, 3H), 3.68 (s, 1H). MS m/z (ESI): 257.9 [M + H]$^+$. |

-continued

| No. | Compound Structure | Compound Name | Starting material or regent different from that in Example 22 | Characterization Data |
|---|---|---|---|---|
| C143 (compound 143) | 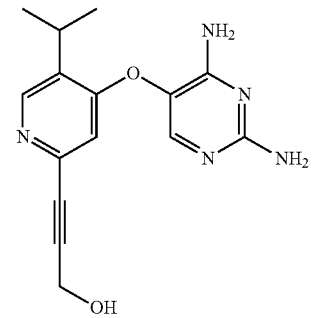 [SMILES: CC(C)c1cnc(C#CCO)cc1Oc1cnc(N)nc1N] | 3-(4-((2,4-diaminopyrimidin-5-yl)oxy)-5-isopropylpyridin-2-yl)prop-2-yn-1-ol | Trimethylsilylacetylene in Step 1 was replaced with prop-2-yn-1-ol. | $^1$H NMR (400 MHz, DMSO-d$_6$) δ 8.36 (s, 1H), 7.59 (s, 1H), 6.48 (s, 1H), 6.45 (s, 2H), 6.05 (s, 2H), 5.35-5.32 (m, 1H), 4.26-4.25 (m, 2H), 3.38-3.33 (m, 1H), 1.30 (d, J = 6.8 Hz, 6H). MS m/z (ESI): 299.9 [M + H]$^+$. |
| C142 (compound 142) | 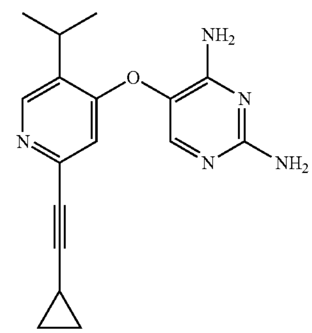 [SMILES: CC(C)c1cnc(C#CC2CC2)cc1Oc1cnc(N)nc1N] | 5-((2-(cyclopropylethynyl)-5-isopropylpyrdin-4-yl)oxy)pyrimidine-2,4-diamine | Trimethylsilylacetylene in Step 1 was replaced with cyclopropylacetylene. | $^1$H NMR (400 MHz, DMSO-d$_6$) δ 8.46-8.37 (m, 2H), 8.04 (s, 1H), 7.90 (s, 1H), 7.63 (s, 2H), 7.00 (s, 1H), 3.33-3.29 (m, 1H), 1.55-1.52 (m, 1H), 1.27 (d, J = 6.8 Hz, 6H), 0.91-0.89 (m, 2H), 0.76-0.74 (m, 2H). MS m/z (ESI): 310.1 [M + H]$^+$. |
| C215 (compound 215) | 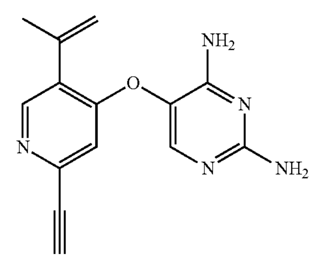 [SMILES: C#Cc1cc(Oc2cnc(N)nc2N)c(C(=C)C)cn1] | 5-((2-ethynyl-5-(prop-1-en-2-yl)pyridin-4-yl)oxy)pyrimidine-2,4-diamine | C2 in Step 1 was replaced with C215-1. | $^1$H NMR (400 MHz, DMSO-d$_6$) δ 8.48 (bs, 1H), 8.42 (s, 1H), 8.02 (s, 1H), 7.92 (s, 1H), 7.69 (bs, 2H), 7.67 (s, 1H), 5.35 (d, J = 7.2 Hz, 2H), 4.38 (s, 1H), 2.15 (s, 3H). MS m/z (ESI): 267.8 [M + H]$^+$. |
| C134 (compound 134) | 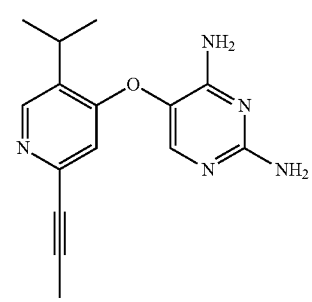 [SMILES: CC#Cc1cc(Oc2cnc(N)nc2N)c(C(C)C)cn1] | 5-((5-isopropyl-2-(prop-1-yn-1-yl)pyridin-4-yl)oxy)pyrimidine-2,4-diamine | Trimethylsilylacetylene in Step 1 was replaced with propyne. | $^1$H NMR (400 MHz, DMSO-d$_6$) δ 8.31 (s, 1H), 7.60 (s, 1H), 6.58 (s, 2H), 6.48 (s, 1H), 6.17 (s, 2H), 3.36-3.31 (m, 1H), 2.00 (s, 3H), 1.28 (d, J = 6.8 Hz, 6H). MS m/z (ESI): 283.8 [M + H]$^+$. |

-continued

| No. | Compound Structure | Compound Name | Starting material or regent different from that in Example 22 | Characterization Data |
|---|---|---|---|---|
| C135 (compound 135) | 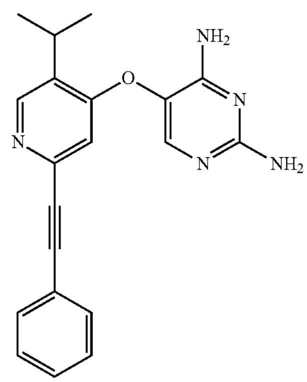 [SMILES: CC(C)c1cnc(C#Cc2ccccc2)cc1Oc1cnc(N)nc1N] | 5-((5-isopropyl-2-(phenyl-ethynyl)pyridin-4-yl)oxy) pyrimidine-2,4-diamine | Trimethylsilylacetylene in Step 1 was replaced with phenylacetylene. | $^1$H NMR (400 MHz, DMSO-d$_6$) δ 8.46 (s, 2H), 8.08 (s, 1H), 7.95 (s, 1H), 6.65-7.55 (m, 4H), 7.73-7.42 (m, 3H) 7.25 (s, 1H), 3.42-3.26 (m, 1H), 1.31 (d, J = 8.8 Hz, 6H). MS m/z (ESI): 346.2 [M + H]$^+$. |
| C228 (compound 228) | 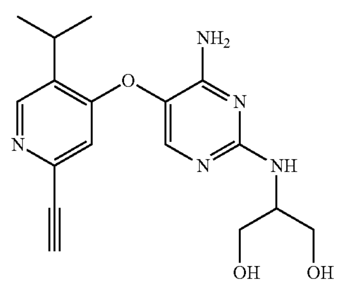 [SMILES: C#Cc1cc(Oc2cnc(NC(CO)CO)nc2N)c(C(C)C)cn1] | 2-((4-amino-5-((2-ethynyl-5-isopropyl-pyrdin-4-yl)oxy) pyrimidin-2-yl)amino) propane-1,3-diol | C2 in Step 1 was replaced with C111. | $^1$H NMR (400 MHz, CD$_3$OD) δ 8.34 (s, 1H), 7.65 (s, 1H), 6.77 (s, 1H), 3.74-3.73 (m, 1H), 3.70 (d, 4H), 3.50-3.49 (m, 1H), 3.47-3.46 (m, 1H), 1.40 (d, J = 6.8 Hz, 6H). MS m/z (ESI): 343.8 [M + H]$^+$. |
| C231 (compound 231) | 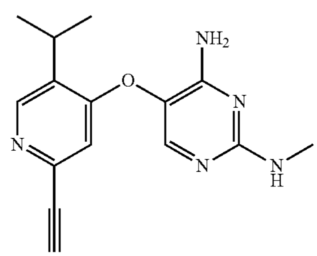 [SMILES: C#Cc1cc(Oc2cnc(NC)nc2N)c(C(C)C)cn1] | 5-((2-ethynyl-5-isopropyl-pyridin-4-yl)oxy)-N$^2$-methyl-pyrimidine-2,4-diamine | C2 in Step 1 was replaced with C237. | $^1$H NMR (400 MHz, CD$_3$OD) δ 8.33 (s, 1H), 7.63 (s, 1H), 6.76 (s, 1H), 3.69 (s, 1H), 3.45-3.40 (m, 1H), 2.91 (s, 3H), 1.40 (d, J = 5.2 Hz, 6H). MS m/z (ESI): 283.9 [M + H]$^+$. |
| C230 (compound 230) | 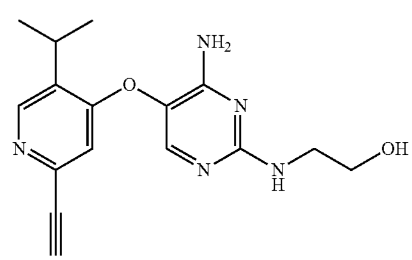 [SMILES: C#Cc1cc(Oc2cnc(NCCO)nc2N)c(C(C)C)cn1] | 2-((4-amino-5-((2-ethynyl-5-isopropyl-pyridin-4-yl)oxy) pyrimidin-2-yl)amino) ethanol | C2 in Step 1 was replaced with C236. | $^1$H NMR (400 MHz, CD$_3$OD) δ 8.33 (s, 1H), 7.64 (s, 1H), 6.76 (s, 1H), 3.74-3.72 (m, 3H), 3.49-3.47 (m, 3H), 1.39 (m, J = 6.8 Hz, 6H). MS m/z (ESI): 313.9 [M + H]$^+$. |
| C229 (compound 229) | 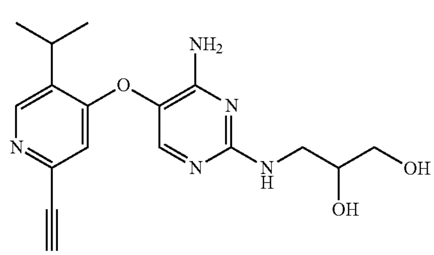 [SMILES: C#Cc1cc(Oc2cnc(NCC(O)CO)nc2N)c(C(C)C)cn1] | 3-((4-amino-5-((2-ethynyl-5-isopropyl-pyridin-4-yl)oxy) pyrimidin-2-yl)amino) propane-1,2-diol | C2 in Step 1 was replaced with C235. | $^1$H NMR (400 MHz, CD$_3$OD) δ 8.33 (s, 1H), 7.64 (s, 1H), 6.75 (s, 1H), 3.81-3.79 (m, 1H), 3.70 (s, 1H), 3.46-3.41 (m, 2H), 3.39-3.34 (m, 3H), 1.40 (d, J = 6.8 Hz, 6H). MS m/z (ESI): 343.8 [M + H]$^+$. |

| No. | Compound Structure | Compound Name | Starting material or regent different from that in Example 22 | Characterization Data |
|---|---|---|---|---|
| C233 (compound 233) | 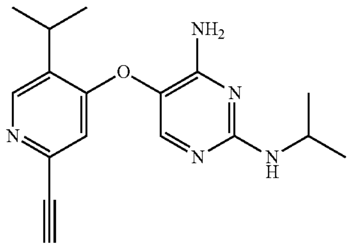 [SMILES: C#Cc1cc(Oc2cnc(NC(C)C)nc2N)c(C(C)C)cn1] | 5-((2-ethynyl-5-isopropyl-pyrdin-4-yl)oxy)-$N^2$-isopropyl-pyrmidine-2,4-diamine | C2 in Step 1 was replaced with C239. | $^1$H NMR (400 MHz, CD$_3$OD) δ 8.33 (s, 1H), 7.62 (s, 1H), 6.77 (s, 1H), 4.09-4.06 (m, 1H), 3.69 (s, 1H), 3.47 (m, 1H), 1.41-1.38 (m, 6H), 1.24-1.21 (m, 6H). MS m/z (ESI): 311.9 [M + H]$^+$. |

Example 23: preparation of 5-((2-bromo-5-isopropylpyridin-4-yl)oxy)-$N^4$-(2-(ethyl(methyl)amino)ethyl)pyrimidine-2,4-diamine (C154, compound 154)

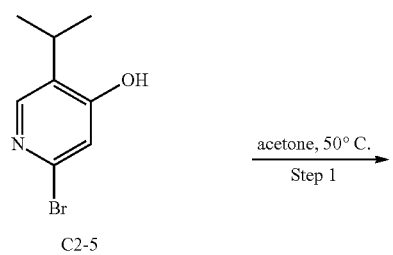
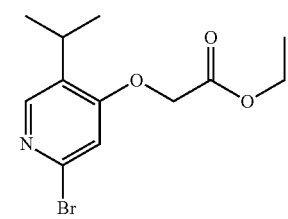
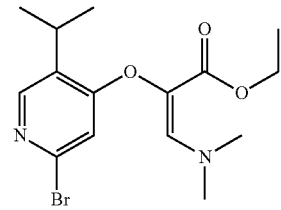
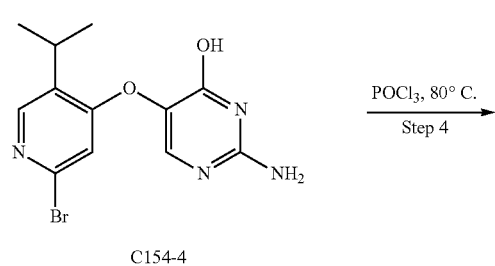
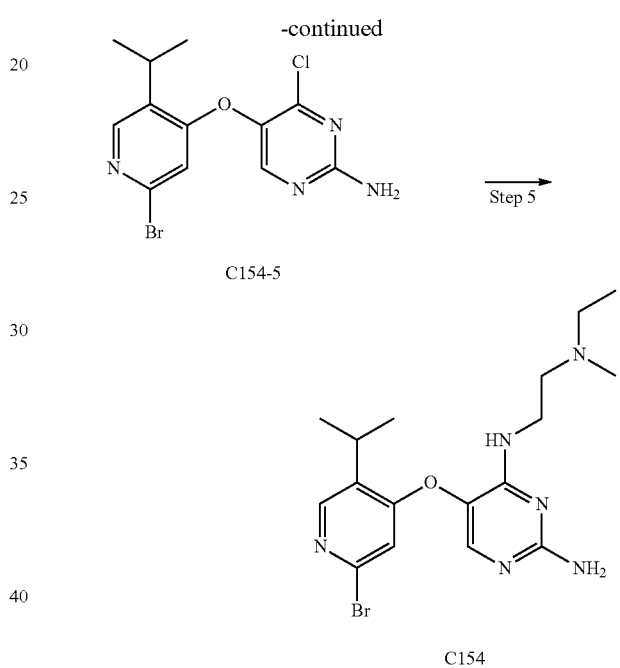

Step 1:

Compound C2-5 (5 g, 0.023 mol) was dissolved in acetone (200 mL), ethyl bromoacetate (5.8 g, 0.035 mol) and potassium carbonate (6.4 g, 0.046 mol) were sequentially added, and the reaction solution was stirred at 50° C. for 16 hours. LC-MS indicated the reaction of the starting materials was complete. The reaction was quenched by adding water (100 mL), and extracted with ethyl acetate (100 mL×3). The organic phases were combined, washed once with saturated brine (100 mL), then dried over anhydrous sodium sulfate (10 g) for half an hour, filtered, and concentrated, to afford a crude product, compound C154-2, which was directly used in the next step (5 g crude product, brown oily liquid, yield 74%). MS m/z (ESI): 288.0 [M+H]$^+$.

Step 2:

Compound C154-2 (4.5 g, 0.015 mol) was dissolved in DMF (30 mL), DMF-DMA (5.6 g, 0.047 mol) was added, and the reaction solution was stirred at 130° C. for 16 hours. LC-MS indicated the reaction of the starting materials was complete. The reaction was quenched by adding water (100 mL), and extracted with ethyl acetate (100 mL×3). The organic phases were combined, washed once with saturated brine (100 mL), then dried over anhydrous sodium sulfate (10 g) for half an hour, filtered, and concentrated under reduced pressure to afford a crude product, which was purified by column chromatography on silica gel (petroleum ether:ethyl acetate=10:1~5:1) to afford compound C154-3 (2 g, yellow oily liquid, yield 40%). MS m/z (ESI): 342.8 [M+H]$^+$.

Step 3:

Compound C154-3 (2 g, 0.0056 mol) was dissolved in ethanol (20 mL), guanidine hydrochloride (3.2 g, 0.034 mol) and sodium methoxide (1.82 g, 0.034 mol) were sequentially added, and the reaction solution was stirred at 90° C. for 16 hours. LC-MS indicated the reaction of the starting materials was complete. The reaction solution was filtered, the filtrate was concentrated under reduced pressure, added with purified water (50 mL), then adjusted to a pH value of 7 with 1 M HCl, and extracted with ethyl acetate (100 mL×3). The organic phases were combined, washed once with saturated brine (100 mL), then dried over anhydrous sodium sulfate (10 g) for half an hour, filtered, and concentrated to afford a crude product, which was isolated by column chromatography on silica gel (petroleum ether:ethyl acetate=20:1~5:1) to afford compound C154-4 (0.7 g, light yellow solid, yield 38%).

$^1$H NMR (400 MHz, DMSO-d$_6$) δ 8.19 (s, 1H), 7.88 (s, 1H), 7.67 (s, 2H), 7.16 (s, 1H), 3.25-3.18 (m, 1H), 1.27 (d, J=6.8 Hz, 6H). MS m/z (ESI): 324.8 [M+H]$^+$.

Step 4:

Compound C154-4 (200 mg, 0.617 mmol) was dissolved in phosphorus oxychloride (1 mL), heated to 80° C., and stirred for 16 hours. LC-MS indicated the reaction of the starting materials was complete. The reaction solution was cooled to room temperature, quenched by adding water (30 mL), then adjusted to a pH value of 7-8 with sodium bicarbonate, and extracted with dichloromethane (50 mL×3). The organic phases were combined, washed with saturated brine (50 mL), added with anhydrous sodium sulfate, dried for half an hour, and filtered. The filtrate was concentrated under reduced pressure, and the crude product was isolated by column chromatography on silica gel (petroleum ether:ethyl acetate=10:1~1:1) to afford compound C154-5 (90 mg, light yellow solid, yield 42%).

$^1$H NMR (400 MHz, CDCl$_3$) δ 8.24 (s, 1H), 8.16 (s, 1H), 6.58 (s, 1H), 5.35 (s, 2H), 3.38-3.35 (m, 1H), 1.38 (d, J=6.8 Hz, 6H). MS m/z (ESI): 342.7 [M+H]$^+$.

Step 5:

Compound C154-5 (10 mg, 0.029 mmol) was dissolved in acetonitrile (2 mL), N-methyl-N-ethylethylenediamine (12.4 mg, 0.18 mmol) was added, and the reaction solution was stirred at 90° C. for 16 hours. LC-MS indicated the reaction of the starting materials was substantially complete. The reaction solution was concentrated under reduced pressure to afford a crude product, which was purified by preparative thin layer chromatography on silica gel (dichloromethane:methanol=10:1) to afford compound C154 (3 mg, white solid, yield 31%).

$^1$H NMR (400 MHz, CD$_3$OD) δ 8.18 (s, 1H), 7.59 (s, 1H), 6.77 (s, 1H), 3.61 (m, 2H), 3.34-3.32 (m, 1H), 2.85-2.77 (m, 4H), 2.50 (s, 3H), 1.38 (d, J=6.8 Hz, 6H), 1.14 (s, 3H). MS m/z (ESI): 410.8 [M+H]$^+$.

The compounds in the following table were prepared according to methods similar to that described in Example 23.

| No. | Compound Structure | Compound Name | Starting material or regent different from that in Example 23 | Characterization Data |
|---|---|---|---|---|
| C71 (compound 71) | 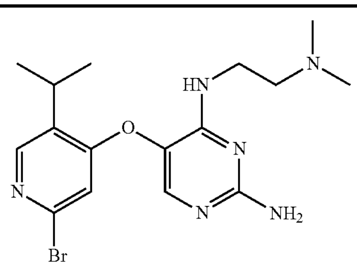 | 5-((2-bromo-5-isopropylpyridin-4-yl)oxy)-N$^4$-(2-(dimethylamino)ethyl)pyrimidine-2,4-diamine | N-methyl-N-ethylethylene diamine in Step 5 was replaced with N,N-dimethylethylenediamine. | $^1$H NMR (400 MHz, CD$_3$OD) δ 8.19 (s, 1H), 7.62 (s, 1H), 6.82 (s, 1H), 3.74-3.71 (m, 2H), 3.37-3.34 (m, 1H), 3.12 (s, 2H), 2.78 (s, 6H), 1.38 (d, J = 6.8 Hz, 6H). MS m/z (ESI): 394.9 [M + H]$^+$. |
| C153 (compound 153) | 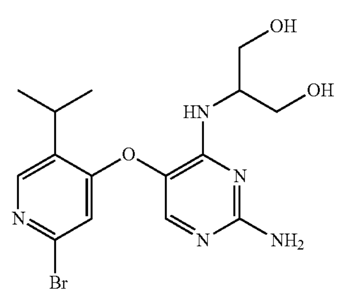 [SMILES: CC(C)c1cnc(Br)cc1Oc1cnc(N)nc1NC(CO)CO] | 2-((2-amino-5-((2-bromo-5-isopropylpyridin-4-yl)oxy)pyrimidin-4-yl)amino)propane-1,3-diol | N-methyl-N-ethylethylene diamine in Step 5 was replaced with serinol. | $^1$H NMR (400 MHz, CD$_3$OD) δ 8.18 (s, 1H), 7.61 (s, 1H), 6.89 (s, 1H), 4.30 (s, 1H), 3.68-3.60 (m, 4H), 3.31 (s, 1H), 1.36 (d, J = 6.8 Hz, 6H). MS m/z (ESI): 397.8 [M + H]$^+$. |
| C172 (compound 172) | 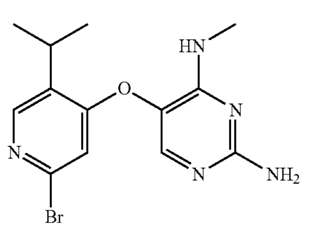 [SMILES: CNc1nc(N)ncc1Oc1cc(Br)ncc1C(C)C] | 5-((2-bromo-5-isopropylpyridin-4-yl)oxy)-N$^4$-methyl-pyrimidine-2,4-diamine | N-methyl-N-ethylethylene diamine in Step 5 was replaced with methylamine. | $^1$H NMR (400 MHz, CD$_3$OD) δ 8.17 (s, 1H), 7.52 (s, 1H), 6.73 (s, 1H), 3.41 (s, 1H), 2.92 (s, 3H), 1.37 (d, J = 6.8 Hz, 6H). MS m/z (ESI): 337.8 [M + H]$^+$. |

-continued

| No. | Compound Structure | Compound Name | Starting material or regent different from that in Example 23 | Characterization Data |
|---|---|---|---|---|
| C173 (compound 173) | 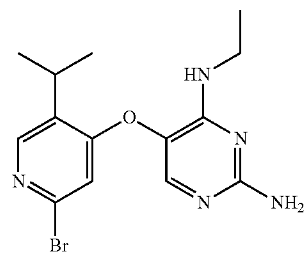 [SMILES: CCNc1nc(N)ncc1Oc1cc(Br)ncc1C(C)C] | 5-((2-bromo-5-isopropylpyridin-4-yl)oxy)-N⁴-ethylpyrimidine-2,4-diamine | N-methyl-N-ethylethylene diamine in Step 5 was replaced with ethylamine. | ¹H NMR (400 MHz, CD₃OD) δ 8.17 (s, 1H), 7.52 (s, 1H), 6.73 (s, 1H), 3.50-3.45 (m, 3H), 1.37 (m, J = 6.8 Hz, 6H), 1.19-1.12 (m, 3H). MS m/z (ESI): 351.8 [M + H]⁺. |
| C174 (compound 174) | 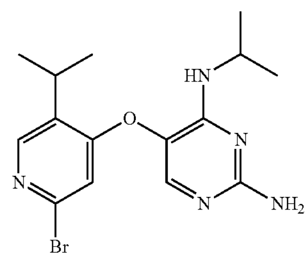 [SMILES: CC(C)Nc1nc(N)ncc1Oc1cc(Br)ncc1C(C)C] | 5-((2-bromo-5-isopropylpyridin-4-yl)oxy)-N⁴-isopropyl-pyrimidine-2,4-diamine | N-methyl-N-ethylethylene diamine in Step 5 was replaced with isopropylamine. | ¹H NMR (400 MHz, CDCl₃) δ 8.28 (s, 1H), 7.54 (s, 1H), 6.83 (s, 1H), 4.33-4.30 (m, 1H), 3.31-3.27 (m, 1H), 1.36 (d, J = 6.8 Hz, 6H), 1.26 (d, J = 6.4 Hz, 6H). MS m/z (ESI): 365.8 [M + H]⁺. |
| C175 (compound 175) | 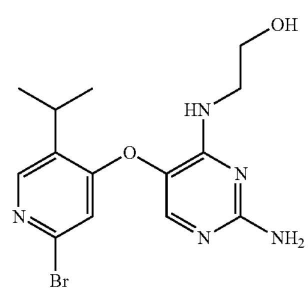 [SMILES: CC(C)c1cnc(Br)cc1Oc1cnc(N)nc1NCCO] | 2-((2-amino-5-((2-bromo-5-isopropylpyridin-4-yl)oxy) pyrimidin-4-yl)amino)ethanol. | N-methyl-N-ethylethylene diamine in Step 5 was replaced with ethanolamine. | ¹H NMR (400 MHz, CD₃OD) δ 8.17 (s, 1H), 7.56 (s, 1H), 6.79 (s, 1H), 3.67-3.69 (m, 2H), 3.57-3.54 (m, 2H), 3.44-3.37 (m, 1H), 1.38 (d, J = 6.8 Hz, 6H). MS m/z (ESI): 367.8 [M + H]⁺. |
| C179 (compound 179) | 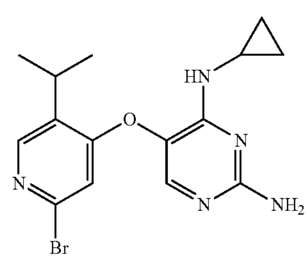 [SMILES: CC(C)c1cnc(Br)cc1Oc1cnc(N)nc1NC1CC1] | 5-((2-bromo-5-isopropylpyridin-4-yl)oxy)-N⁴-cyclopropyl-pyrimidine-2,4-diamine | N-methyl-N-ethylethylene diamine in Step 5 was replaced with cyclopropylamine. | ¹H NMR (400 MHz, CD₃OD) δ 8.16 (s, 1H), 7.53 (s, 1H), 6.71 (s, 1H), 3.42-3.39 (m, 1H), 2.82-2.80 (m, 1H), 1.37-1.31 (d, J = 7.2 Hz, 6H), 0.79-0.76 (m, 2H), 0.55 (s, 2H). MS m/z (ESI): 363.7 [M + H]⁺. |
| C180 (compound 180) | 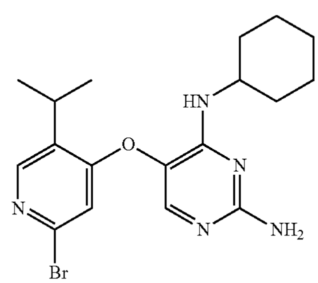 [SMILES: CC(C)c1cnc(Br)cc1Oc1cnc(N)nc1NC1CCCCC1] | 5-((2-bromo-5-isopropylpyridin-4-yl)oxy)-N⁴-cyclohexyl-pyrimidine-2,4-diamine | N-methyl-N-ethylethylene diamine in Step 5 was replaced with cyclohexylamine. | ¹H NMR (400 MHz, CD₃OD) δ 8.17 (s, 1H), 7.52 (s, 1H), 6.74 (s, 1H), 4.07-4.01 (m, 1H), 3.46-3.39 (m, 1H), 1.92 (d, J = 12.4 Hz, 2H), 1.78 (d, J = 13.2 Hz, 2H), 1.67 (d, J = 13.2 Hz, 2H), 1.38-1.36 (m, 10H). MS m/z (ESI): 407.8 [M + H]⁺. |

-continued

| No. | Compound Structure | Compound Name | Starting material or regent different from that in Example 23 | Characterization Data |
|---|---|---|---|---|
| C181 (compound 181) | 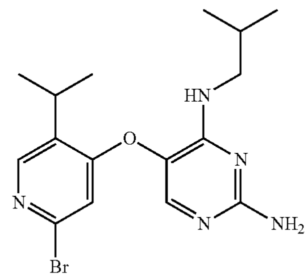 [SMILES: CC(C)CNc1nc(N)ncc1Oc1cc(Br)ncc1C(C)C] | 5-((2-bromo-5-isopropylpyridin-4-yl)oxy)-N⁴-isobutyl-pyrimidine-2,4-diamine | N-methyl-N-ethylethylene diamine in Step 5 was replaced with isobutylamine. | ¹H NMR (400 MHz, CD₃OD) δ 8.19 (s, 1H), 7.53 (s, 1H), 6.75 (s, 1H), 3.44-3.39 (m, 1H), 3.24 (d, J = 6.8 Hz, 2H), 1.96-1.93 (m, 1H), 1.38 (d, J = 7.2 Hz, 6H), 0.90 (d, J = 6.8 Hz, 6H). MS m/z (ESI): 381.8 [M + H]⁺. |
| C182 (compound 182) | 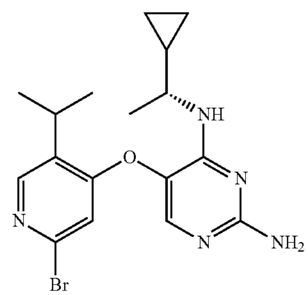 [SMILES: CC(C)c1cnc(Br)cc1Oc1cnc(N)nc1N[C@H](C)C1CC1] | (R)-5-((2-bromo-5-isopropyl pyridin-4-yl)oxy)-N⁴-(1-cyclopropylethyl) pyrimidine-2,4-diamine | N-methyl-N-ethylethylene diamine in Step 5 was replaced with (R)-1-cyclopropylethylamine. | ¹H NMR (300 MHz, CD₃OD) δ 8.13 (s, 1H), 7.48 (s, 1H), 6.70 (s, 1H), 3.65 (m, 1H), 3.42-3.40 (m, 1H), 1.36 (d, J = 4.5 Hz, 6H), 1.29 (s, 3H), 0.92-0.90 (m, 1H), 0.49-0.43 (m, 2H), 0.32-0.21 (m, 2H). MS m/z (ESI): 393.9 [M + H]⁺. |
| C201 (compound 201) | 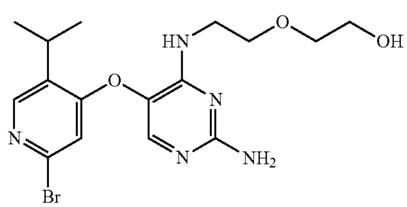 [SMILES: CC(C)c1cnc(Br)cc1Oc1cnc(N)nc1NCCOCCO] | 2-(2-((2-amino-5-((2-bromo-5-isopropylpyridin-4-yl)oxy) pyrimidin-4-yl)amino)ethoxy) ethanol | N-methyl-N-ethylethylene diamine in Step 5 was replaced with 2-(2-aminoethoxy) ethanol. | ¹H NMR (400 MHz, CD₃OD) δ 8.18 (s, 1H), 7.56 (s, 1H), 6.76 (s, 1H), 3.63-3.61 (m, 6H), 3.55-3.54 (m, 2H), 3.44-3.42 (m, 1H), 1.38 (d, J = 7.2 Hz, 6H). MS m/z (ESI): 411.7 [M + H]⁺. |
| C202 (compound 202) | 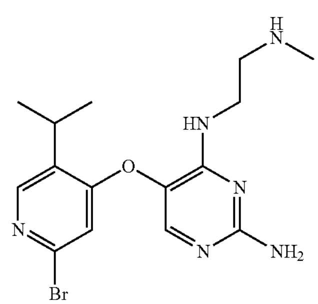 [SMILES: CNCCNc1nc(N)ncc1Oc1cc(Br)ncc1C(C)C] | 5-((2-bromo-5-isopropylpyridin-4-yl)oxy)-N⁴-(2-(methylamino) ethyl)pyrimidine-2,4-diamine | N-methyl-N-ethylethylene diamine in Step 5 was replaced with N-methyl-ethylenediamine. | ¹H NMR (400 MHz, CD₃OD) δ 8.28 (s, 1H), 7.83 (s, 1H), 7.23 (s, 1H), 3.89-3.86 (m, 2H), 3.37-3.35 (m, 1H), 3.35-3.33 (m, 2H), 2.81 (s, 3H), 1.37 (d, J = 7.2 Hz, 6H). MS m/z (ESI): 380.8 [M + H]⁺. |
| C203 (compound 203) | 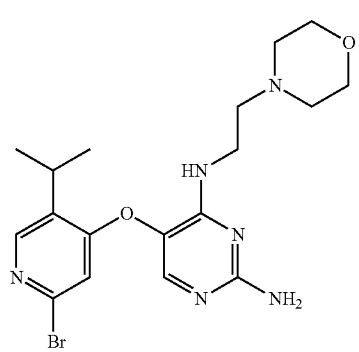 [SMILES: CC(C)c1cnc(Br)cc1Oc1cnc(N)nc1NCCN1CCOCC1] | 5-((2-bromo-5-isopropylpyridin-4-yl)oxy)-N⁴-(2-morpholinoethyl)pyrimidine-2,4-diamine | N-methyl-N-ethylethylene diamine in Step 5 was replaced with 2-morpholino-ethylamine. | ¹H NMR (400 MHz, CD₃OD) δ 8.20 (s, 1H), 7.58 (s, 1H), 6.77 (s, 1H), 3.60 (m, 6H), 3.44-3.41 (m, 1H), 2.57-2.49 (m, 6H), 1.40 (d, J = 6.8 Hz, 6H). MS m/z (ESI): 436.7 [M + H]⁺. |

-continued

| No. | Compound Structure | Compound Name | Starting material or regent different from that in Example 23 | Characterization Data |
|---|---|---|---|---|
| C204 (compound 204) | 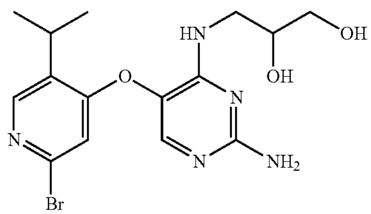 [SMILES: CC(C)c1cnc(Br)cc1Oc1cnc(N)nc1NCC(O)CO] | 3-((2-amino-5-((2-bromo-5-isopropylpyridin-4-yl)oxy)pyrimidin-4-yl)amino)propane-1,2-diol | N-methyl-N-ethylethylene diamine in Step 5 was replaced with 3-amino propane-1,2-diol. | $^1$H NMR (400 MHz, CD$_3$OD) δ 8.26 (s, 1H), 7.75 (s, 1H), 7.19 (s, 1H), 3.89 (m, 1H), 3.74-3.71 (m, 1H), 3.61-3.56 (m, 3H), 3.41-3.38 (m, 1H), 1.37 (d, J = 7.2 Hz, 6H). MS m/z (ESI): 399.7 [M + H]$^+$. |
| C207 (compound 207) | 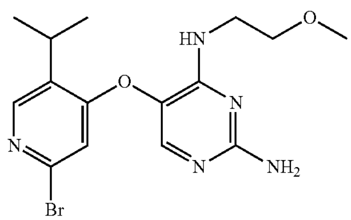 [SMILES: COCCNc1nc(N)ncc1Oc1cc(Br)ncc1C(C)C] | 5-((2-bromo-5-isopropylpyridin-4-yl)oxy)-N$^4$-(2-methoxyethyl)pyrimidine-2,4-diamine | N-methyl-N-ethylethylene diamine in Step 5 was replaced with 2-methoxyethyl amine. | $^1$H NMR (400 MHz, CD$_3$OD) δ 8.18 (s, 1H), 7.56 (s, 1H), 6.76 (s, 1H), 3.62-3.60 (m, 2H), 3.54-3.52 (m, 2H), 3.42 (m, 1H), 3.35-3.33 (m, 3H), 1.38 (d, J = 6.8 Hz, 6H). MS m/z (ESI): 383.7 [M + H]$^+$. |
| C209 (compound 209) | 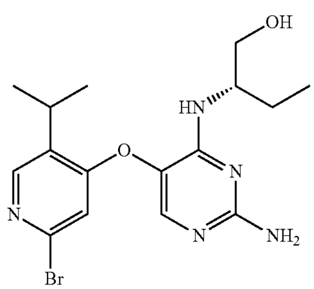 [SMILES: CC[C@@H](CO)Nc1nc(N)ncc1Oc1cc(Br)ncc1C(C)C] | (S)-2-((2-amino-5-((2-bromo-5-isopropylpyridin-4-yl)oxy)pyrimidin-4-yl)amino)but-1-ol | N-methyl-N-ethylethylene diamine in Step 5 was replaced with (S)-2-aminobut-1-ol. | $^1$H NMR (400 MHz, CD$_3$OD) δ 8.18 (s, 1H), 7.57 (s, 1H), 6.82 (s, 1H), 3.60-3.58 (m, 2H), 3.45-3.40 (m, 1H), 1.53-1.47 (m, 1H), 1.40-1.38 (m, 2H), 1.37-1.31 (m, 6H), 0.95-0.92 (m, 3H). MS m/z (ESI): 395.8 [M + H]$^+$. |
| C210 (compound 210) | 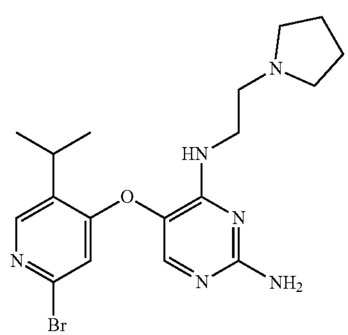 [SMILES: CC(C)c1cnc(Br)cc1Oc1cnc(N)nc1NCCN1CCCC1] | 5-((2-bromo-5-isopropylpyridin-4-yl)oxy)-N$^4$-(2-(pyrrolidin-1-yl)ethyl)pyrimidine-2,4-diamine | N-methyl-N-ethylethylene diamine in Step 5 was replaced with 1-(2-aminoethyl)pyrrolidine. | $^1$H NMR (400 MHz, CD$_3$OD) δ 8.19 (s, 1H), 7.59 (s, 1H), 6.77 (s, 1H), 3.64 (s, 2H), 3.50 (s, 1H), 2.92-2.78 (s, 6H), 1.89 (s, 4H), 1.38 (d, J = 6.4 Hz, 6H). MS m/z (ESI): 423.1 [M + H]$^+$. |
| C222 (compound 222) | 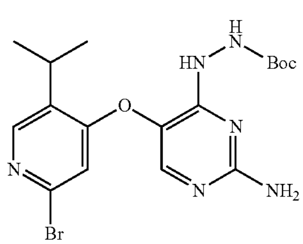 [SMILES: CC(C)c1cnc(Br)cc1Oc1cnc(N)nc1NNC(=O)OC(C)(C)C] | tert-butyl 2-(2-amino-5-((2-bromo-5-isopropylpyridin-4-yl)oxy)pyrimidin-4-yl)hydrazine-1-carboxylate | N-methyl-N-ethylethylene diamine in Step 5 was replaced with tert-butyl hydrazine-carboxylate. | $^1$H NMR (400 MHz, CD$_3$OD) δ 8.17 (s, 1H), 7.66 (s, 1H), 6.92 (s, 1H), 3.43-3.41 (s, 1H), 1.50 (s, 9H), 1.37 (d, J = 6.8 Hz, 6H). MS m/z (ESI): 438.9 [M + H]$^+$. |

| No. | Compound Structure | Compound Name | Starting material or regent different from that in Example 23 | Characterization Data |
|---|---|---|---|---|
| C241 (compound 241) | 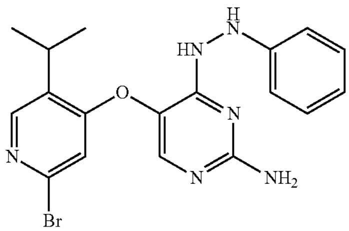 [SMILES: CC(C)c1cnc(Br)cc1Oc1cnc(N)nc1NNc1ccccc1] | 5-((2-bromo-5-isopropylpyridin-4-yl)oxy)-4-(2-phenylhydrazinyl)pyrimidin-2-amine | N-methyl-N-ethylethylene diamine in Step 5 was replaced with phenylhydrazine. | $^1$H NMR (400 MHz, CD$_3$OD) δ 7.99 (s, 1H), 7.46 (s, 5H), 7.35-7.32 (m, 1H), 7.14-7.12 (m, 1H), 3.10-3.05 (m, 1H), 1.35 (d, J = 6.8 Hz, 6H). MS m/z (ESI): 414.7 [M + H]$^+$. |

Example 24: preparation of 5-((2-bromo-5-isopropylpyridin-4-yl)thio)pyrimidine-2,4-diamine (C85, compound 85)

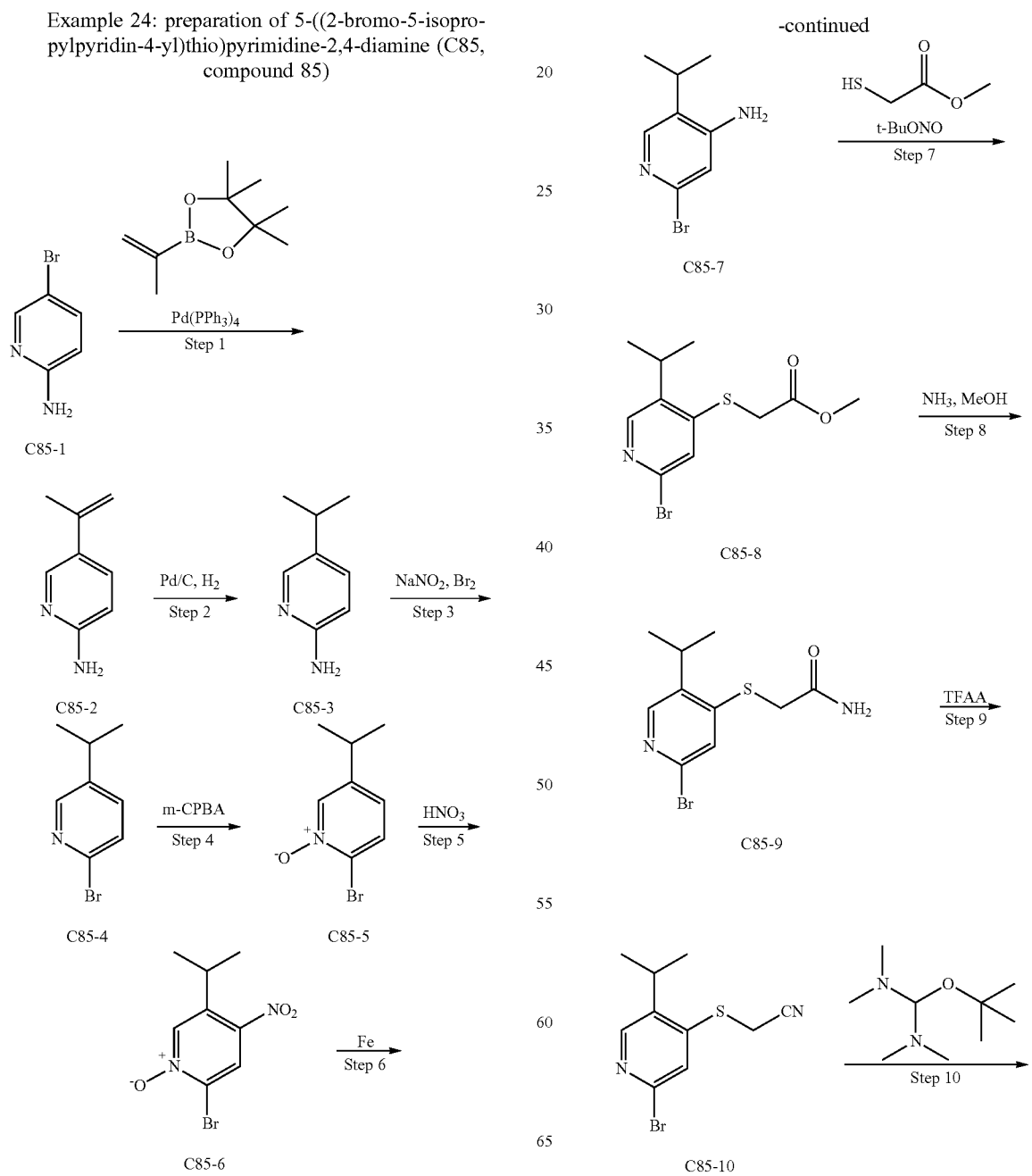

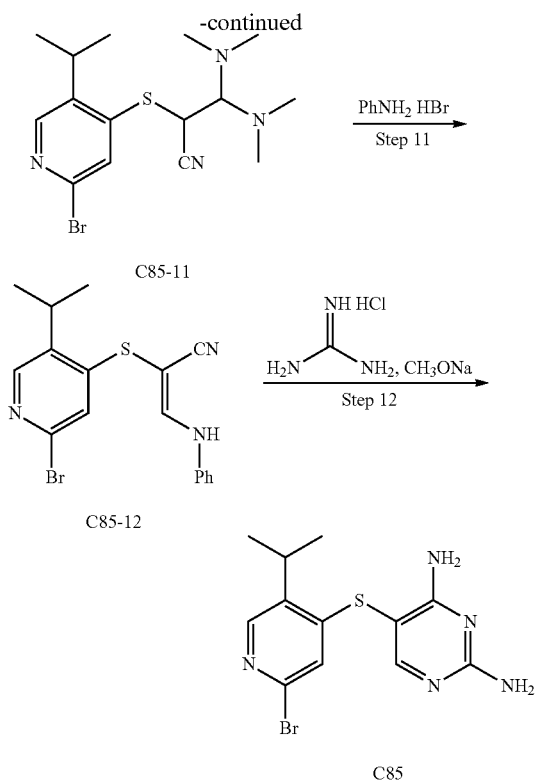

Step 1:

Compound C85-1 (100 g, 0.58 mol) was dissolved in 1,4-dioxane (700 mL), isopropenylpinacol borate (147 g, 0.87 mol), $K_2CO_3$ (160 g, 1.16 mol) and $Pd(PPh_3)_4$ (10 g, 5.4 mmol) were sequentially added, followed by addition of purified water (35 mL). Under the protection of nitrogen, the reaction was performed at 100° C. for 18 hours. LC-MS indicated the reaction of the starting materials was substantially complete, and the target product was obtained. The reaction solution was cooled to room temperature, filtered, the filter cake was washed with 1,4-dioxane (200 mL), concentrated under reduced pressure to remove the organic solvent, added with purified water (200 mL), and extracted with ethyl acetate (400 ml×3). The organic phases were combined, added with 100 g anhydrous sodium sulfate, dried for 30 min, and filtered. The filter cake was washed with 200 ml ethyl acetate, concentrated under reduced pressure to dryness, and the crude product was purified by column chromatography on silica gel (mobile phase: petroleum ether:ethyl acetate=20:1~2:1), to afford compound C85-2 (70 g, light yellow solid, yield 89.60%). MS m/z (ESI): 135.1 $[M+H]^+$.

Step 2:

Compound C2-2 (70 g, 0.52 mol) was dissolved in anhydrous methanol (700 mL), 10% palladium/carbon (14 g) was added, and the reaction was performed under hydrogen (0.4 MPa) at room temperature for 18 hours. LC-MS indicated a small amount of the starting material remained. Palladium/carbon 4 g was supplemented, and the reaction was continued under hydrogen (0.4 MPa) at room temperature for 18 hours. LC-MS indicated the reaction of the starting materials was complete. The reaction solution was filtered, the filter cake was washed with 100 ml methanol, and concentrated under reduced pressure to give a crude product, compound C85-3 (70 g, orange oily liquid, yield 98.1%). MS m/z (ESI): 137.1 $[M+H]^+$.

Step 3:

C85-3 (70 g, 0.52 mol) was dissolved in hydrobromic acid (40%) (400 mL). Under the protection of nitrogen, the reaction was cooled to −15° C.~−20° C., and liquid bromine (200 g, 1.25 mol) was slowly dropwise added. After the dropwise addition was complete, the reaction was kept at the temperature for 1 h, sodium nitrite (103.5 g, 1.5 mol) was dissolved in water (90 mL), and this solution was slowly dropwise added. After the dropwise addition was complete, the reaction was stirred at room temperature for 18 h. LC-MS indicated the reaction of the starting materials was complete. The reaction was adjusted to pH 8~10 with a saturated solution of sodium bicarbonate, and extracted with ethyl acetate (200 ml×3). The organic phases were combined, washed once with saturated brine (200 mL), then dried over anhydrous sodium sulfate (400 g) for half an hour, filtered, and concentrated. The crude product was purified by column chromatography on silica gel (petroleum ether:ethyl acetate=50:1~20:1), to afford compound C85-4 (30 g, light yellow oily liquid, yield 29.4%). MS m/z (ESI): 199.8 $[M+H]^+$.

Step 4:

Compound C85-4 (30 g, 0.15 mol) was dissolved in dichloromethane (300 mL). Under the protection of nitrogen, meta-chloroperbenzoic acid (52 g, 0.3 mol) was added at room temperature. After the addition, the reaction was performed for 18 hours. LC-MS indicated the reaction of the starting materials was complete (if there is remaining starting material, meta-chloroperbenzoic acid can supplemented appropriately). The reaction was filtered, the filter cake was washed twice with dichloromethane (100 mL), the filtrate was concentrated under reduced pressure to dryness to afford compound C85-5 (30 g, light-colored solid, yield 92.6%).

$^1H$ NMR (400 MHz, DMSO) δ 8.41 (s, 1H), 7.82 (d, J=6.8 Hz, 1H), 7.19 (d, J=8.4 Hz, 1H), 4.07-4.06 (m, 1H), 1.19 (d, J=6.8 Hz, 6H). MS m/z (ESI): 215.9 $[M+H]^+$.

Step 5:

Compound C85-5 (30 g, 0.14 mol) was slowly added to concentrated sulfuric acid (50 mL), the reaction was cooled to 0° C., fuming nitric acid (100 mL) was slowly dropwise added, and the reaction was heated to 100° C. and allowed to proceed for 18 h. LC-MS indicated the reaction of the starting materials was complete. The reaction solution was cooled to room temperature, slowly poured into ice water, adjusted to pH 9 with a solution of sodium hydroxide, then extracted with ethyl acetate (300 ml×3). The organic phases were combined, dried over sodium sulfate, and then filtered. The filtrate was concentrated under reduced pressure to afford a crude product, which was then purified by column chromatography on silica gel (petroleum ether:ethyl acetate=20:1~5:1) to afford the product C85-6 (25 g, oily liquid, yield 68.5%). MS m/z (ESI): 260.8 $[M+H]^+$.

Step 6:

Compound C85-6 (20 g, 0.08 mol) was dissolved in tetrahydrofuran (50 mL), methanol (50 mL) and water (50 mL), iron powder (22.4 g, 0.4 mol) and ammonium chloride (21.6 g, 0.4 mol) were added at room temperature, and the reaction solution was heated to reflux for 18 h. LC-MS indicated the reaction of the starting materials was complete. The reaction solution was cooled to room temperature, filtered, and the filtrate was concentrated under reduced pressure to dryness to afford compound C85-7 (12 g, oily liquid, yield 62.8%). MS m/z (ESI): 214.9 $[M+H]^+$.

Step 7:

Compound C85-7 (10 g, 0.047 mol) was dissolved in acetonitrile (100 mL), followed by addition of ethyl mercaptoacetate (9.9 g, 0.094 mol), the reaction was heated to 50° C., and stirred for 0.5 hour. Tert-butyl nitrite was slowly added, and after completion of the addition, the reaction was stirred at the former temperature for 18 h. LC-MS indicated the reaction of the starting materials was complete. The reaction was cooled to room temperature, added with 50 ml water, and extracted with ethyl acetate (100 ml×3). The organic phase was washed with saturated brine (20 mL×3), added with anhydrous sodium sulfate, dried for half an hour, and filtered. The filtrate was concentrated under reduced pressure, and the crude product was purified by column chromatography on silica gel (petroleum ether:ethyl acetate=20:1~5:1), to afford compound C85-8 (8 g, oily liquid, yield 56.8%). MS m/z (ESI): 303.8 $[M+H]^+$.

Step 8:

Compound C85-8 (8 g, 0.026 mol) was dissolved in anhydrous methanol (100 mL). Under the protection of nitrogen, a solution of ammonia in methanol (7 mol/L, 40 mL) was added, and the reaction was stirred at room temperature for 18 hours. LC-MS indicated the reaction of the starting materials was complete. The reaction was concentrated under reduced pressure to afford compound C85-9 (6.5 g, light yellow solid, yield 86.7%). MS m/z (ESI): 288.8 $[M+H]^+$.

Step 9:

Compound C85-9 (6.5 g, 0.023 mol) was dissolved in anhydrous dichloromethane (50 mL), triethylamine (9.3 g, 0.092 mol) was added, the reaction solution was cooled to 0° C., trifluoroacetic anhydride (9.7 g, 0.046 mol) was slowly dropwise added, and the reaction was stirred at room temperature for 1 hour. LC-MS indicated the reaction of the starting materials was complete. The reaction was added with water (50 mL), extracted with dichloromethane (50 mL×3), dried over sodium sulfate, and then filtered. The filtrate was concentrated under reduced pressure, and the crude product was purified by column chromatography on silica gel (petroleum ether:ethyl acetate=20:1~10:1) to afford compound C85-10 (3.5 g, light yellow solid, yield 56.4%). MS m/z (ESI): 270.8 $[M+H]^+$.

Step 10:

Compound C85-10 (3.5 g, 0.013 mol) was dissolved in anhydrous DMF (30 mL), tert-butoxy bis(dimethylamino) methane (6.8 g, 0.039 mol) was added, and the reaction solution was heated to 100° C., and stirred for 2 hours. LC-MS indicated the reaction of the starting materials was complete. The reaction was cooled to room temperature, added with water (100 mL), extracted with ethyl acetate (50 mL×3), dried over sodium sulfate, and then filtered. The filtrate was concentrated under reduced pressure, and the crude product was purified by column chromatography on silica gel (petroleum ether:ethyl acetate=20:1~5:1) to afford compound C85-11 (2.2 g, light yellow oily liquid, yield 45.7%). MS m/z (ESI): 325.8 $[M+H]^+$.

Step 11:

Compound C85-11 (2.2 g, 0.006 mol) was dissolved in anhydrous DMF (20 mL), aniline hydrobromide (1.6 g, 0.009 mol) was added, and the reaction solution was heated to 100° C., and stirred for 18 hours. LC-MS indicated the reaction of the starting materials was complete. The reaction was cooled to room temperature, added with water (20 mL), extracted with ethyl acetate (20 mL×3), washed twice with saturated brine, dried over sodium sulfate, and then filtered. The filtrate was concentrated under reduced pressure, and the crude product was purified by column chromatography on silica gel (petroleum ether:ethyl acetate=20:1~5:1) to afford compound C85-12 (1.2 g, light yellow solid, yield 53.6%). MS m/z (ESI): 373.8 $[M+H]^+$.

Step 12:

Guanidine hydrochloride (920 mg, 0.0096 mmol) was dissolved in anhydrous ethanol (20 mL). Under the protection of nitrogen, sodium methoxide (0.864 g, 0.016 mol) was added, the reaction was stirred at room temperature for half an hour, and then compound C85-12 (1.2 g, 0.0032 mol) was added. The reaction solution was heated to reflux, and stirred for 18 hours. LC-MS indicated the reaction of the starting materials was complete. The reaction solution was cooled to room temperature, filtered, the filtrate was concentrated under reduced pressure, and the crude product was purified by column chromatography on silica gel (DCM: MeOH=50:1~20:1) to afford compound C85 (500 mg, light yellow solid, yield 46.7%).

$^1$H NMR (400 MHz, DMSO) δ 8.19 (s, 1H), 7.91 (s, 1H), 6.71 (s, 2H), 6.58 (s, 1H), 6.54 (s, 2H), 3.15~3.19 (m, 1H), 1.31 (d, J=6.8 Hz, 6H). MS m/z (ESI): 339.7 $[M+H]^+$.

The compound in the following table was prepared according to a method similar to that described in Example 24.

| No. | Compound Structure | Compound Name | Starting material or regent different from that in Example 24 | Characterization Data |
|---|---|---|---|---|
| C84 (compound 84) | 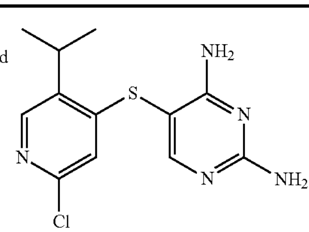 | 5-((2-chloro-5-isopropylpyridin-4-yl)thio)pyrimidine-2,4-diamine | Hydrobromic acid and liquid bromine in Step 3 was replaced with concentrated hydrochloric acid; aniline hydrobromide in Step 11 was replaced with aniline hydrochloride. | $^1$H NMR (400 MHz, CD$_3$OD) δ 8.12 (s, 1H), 7.94 (s, 1H), 6.12 (s, 1H), 3.35-3.33 (m, 1H), 1.37 (d, J = 6.8 Hz, 6H). MS m/z (ESI): 295.8 $[M + H]^+$. |

Example 25: preparation of 5-((5-isopropyl-2-vinylpyridine-4-yl)thio)pyrimidine-2,4-diamine (C95, compound 95) and 5-((2-ethyl-5-isopropylpyridin-4-yl)thio)pyrimidine-2,4-diamine (C127, compound 127)

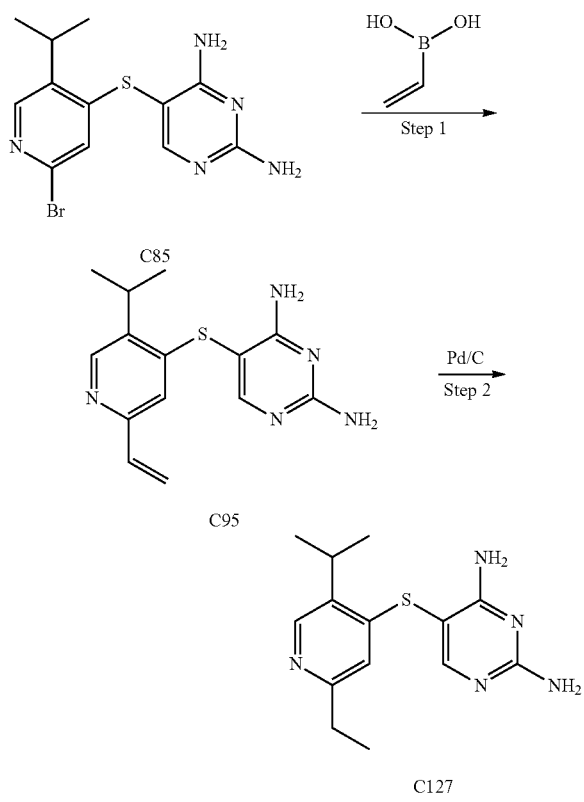

Step 1:

Compound C85 (50 mg, 0.15 mol) was dissolved in 1,4-dioxane (10 mL) and water (1 mL), vinylboronic acid (47 mg, 0.3 mmol), $K_2CO_3$ (42 mg, 0.3 mol) and $Pd(PPh_3)_4$ (12 mg) were sequentially added. Under the protection of nitrogen, the reaction was performed at 100° C. for 18 hours. LC-MS indicated the reaction of the starting materials was substantially complete, and the target product was obtained. The reaction solution was cooled to room temperature, and filtered. The filter cake was washed with 1,4-dioxane (10 mL), and concentrated under reduced pressure to dryness. The crude product was purified by column chromatography on silica gel (dichloromethane:methanol=50:1-10:1) to afford compound C95 (15 mg, white solid, yield 34.8%).

$^1$H NMR (400 MHz, CD$_3$OD) δ 8.27 (s, 1H), 7.97 (s, 1H), 6.79 (s, 1H), 6.67 (dd, J=17.6, 11.2 Hz, 1H), 5.93 (d, J=17.6 Hz, 1H), 5.42 (d, J=11.2 Hz, 1H), 3.42-3.3 (n, 1H), 1.38 (d, J=6.8 Hz, 6H). MS m/z (ESI): 287.9 [M+H]S.

Step 2:

Compound C95 (10 mg, 0.03 mol) was dissolved in anhydrous methanol (5 mL), 10% palladium/carbon (5 mg) was added, and the reaction was performed under hydrogen (0.4 MPa) at room temperature for 18 hours. LC-MS indicated the reaction of the starting materials was complete. The reaction solution was filtered, the filter cake was washed with 10 ml methanol, concentrated under reduced pressure, and purified by column chromatography on silica gel (dichloromethane:methanol=10:1) to afford compound C127 (3 mg, white solid, yield 29.8%).

$^1$H NMR (400 MHz, CD$_3$OD) δ 8.20 (s, 1H), 7.94 (s, 1H), 6.60 (s, 1H), 3.39-3.30 (m, 1H), 2.64 (d, J=7.6 Hz, 2H), 1.39 (d, J=6.8 Hz, 6H), 1.17 (t, J=7.6 Hz, 3H). MS m/z (ESI): 289.9 [M+H]7.

The compounds in the following table were prepared according to methods similar to that described in Example 25.

| No. | Compound Structure | Compound Name | Starting material or regent different from that in Example 25 | Characterization Data |
|---|---|---|---|---|
| C92 (compound 92) | 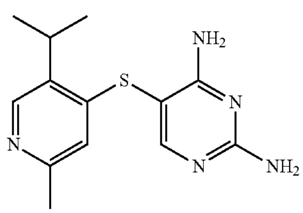 [SMILES: Cc1cc(Sc2cnc(N)nc2N)c(C(C)C)cn1] | 5-((5-isopropyl-2-methylpyridin-4-yl)thio)pyrimidine-2,4-diamine | Vinylboronic acid in Step 1 was replaced with methylboronic acid, and Step 2 was omitted. | $^1$H NMR (400 MHz, CD$_3$OD) δ 8.18 (s, 1H), 7.95 (s, 1H), 6.60 (s, 1H), 3.39-3.29 (m, 1H), 2.37 (s, 3H), 1.38 (d, J = 6.8 Hz, 6H). MS m/z (ESI): 275.8 [M + H]$^+$. |
| C109 (compound 109) | 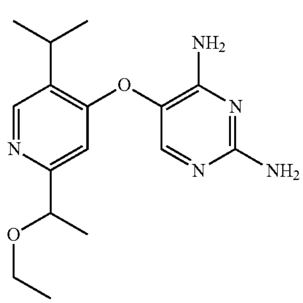 [SMILES: CCOC(C)c1cc(Oc2cnc(N)nc2N)c(C(C)C)cn1] | 5-((2-(1-ethoxyethyl)-5-isopropyl-pyridin-4-yl)oxy)pyrimidine-2,4-diamine | The preparation started from Step 2, and C95 in Step 2 was replaced with C45. | $^1$H NMR (400 MHz, CD$_3$OD) δ 8.51 (s, 1H), 8.02 (s, 1H), 7.51 (s, 1H), 4.81-4.76 (m, 1H), 3.62-3.52 (m, 3H), 1.48 (d, J = 5.2 Hz, 3H), 1.41 (d, J = 6.0 Hz, 6H), 1.23 (t, J = 6.8 Hz, 3H). MS m/z (ESI): 317.9 [M + H]$^+$. |

-continued

| No. | Compound Structure | Compound Name | Starting material or regent different from that in Example 25 | Characterization Data |
|---|---|---|---|---|
| C91 (compound 91) | 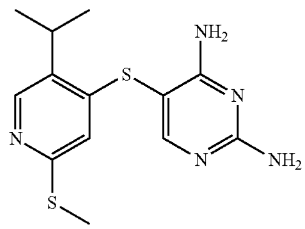 [SMILES: CSc1cc(Sc2cnc(N)nc2N)c(C(C)C)cn1] | 5-((5-isopropyl2-(methylthio)pyridin-4-yl)thio)pyrimidine-2,4-diamine | Vinylboronic acid in Step 1 was replaced with sodium thiomethoxide, Pd(PPh$_3$)$_4$ was replaced with Pd$_2$(dba)$_3$ and Xantphos, K$_2$CO$_3$ was replaced with DIEA, and Step 2 was omitted. | $^1$H NMR (400 MHz, CD$_3$OD) δ 8.25 (s, 1H), 8.15 (s, 1H), 6.67 (s, 1H), 3.36-3.27 (m, 1H), 2.50 (s, 3H), 1.38 (d, J = 6.8 Hz, 6H). MS m/z (ESI): 307.8 [M + H]$^+$. |
| C125 (compound 125) | 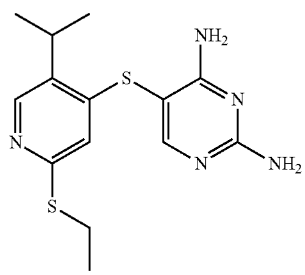 [SMILES: CCSc1cc(Sc2cnc(N)nc2N)c(C(C)C)cn1] | 5-((2-(ethylthio)-5-isopropyl-pyridin-4-yl)thio)pyrimidine-2,4-diamine | Vinylboronic acid in Step 1 was replaced with sodium ethanethiolate, Pd(PPh$_3$)$_4$ was replaced with Pd$_2$(dba)$_3$ and Xantphos, K$_2$CO$_3$ was replaced with DIEA. | $^1$H NMR (400 MHz, CD$_3$OD) δ 8.16 (s, 1H), 7.94 (s, 1H), 6.51 (s, 1H), 3.34-3.28 (m, 1H), 3.01-2.88 (m, 2H), 1.38-1.31 (m, 3H). 1.27 (d, J = 6.8 Hz, 6H). MS m/z (ESI): 321.9 [M + H]$^+$. |
| C165 (compound 165) | 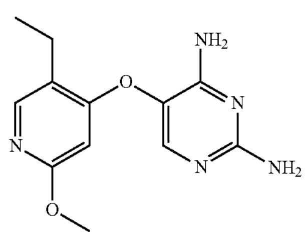 [SMILES: CCc1cnc(OC)cc1Oc1cnc(N)nc1N] | 5-((5-ethyl-2-methoxy-pyridin-4-yl)oxy)pyrimidine-2,4-diamine | The preparation started from Step 2, and C95 in Step 2 was replaced with C162. | $^1$H NMR (400 MHz, CD$_3$OD) δ 7.88 (s, 1H), 5.97 (s, 1H), 5.51 (s, 1H), 3.84 (s, 3 H). 2.75-2.73 (m, 2H), 1.32-1.22 (m, 3H). MS m/z (ESI): 261.9 [M + H]$^+$. |
| C194 (compound 194) | 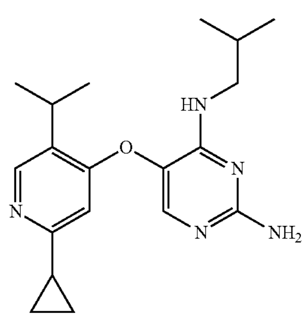 [SMILES: CC(C)CNc1nc(N)ncc1Oc1cc(C2CC2)ncc1C(C)C] | 5-((2-cyclopropyl-5-isopropyl-pyridin-4-yl)oxy)-N$^4$-isobutyl-pyrimidine-2,4-diamine | C85 in Step 1 was replaced with C181; vinylboronic acid was replaced with cyclopropyl-boronic acid, and Step 2 was omitted. | $^1$H NMR (400 MHz, CD$_3$OD) δ 8.39 (s, 1H), 7.86 (s, 1H), 7.09 (s, 1H), 3.50-3.46 (m, 1H), 3.37-3.33 (m, 2H), 2.27 (m, 1H), 2.03 (m, 1H), 1.41-1.33 (m, 8H), 1.14 (s, 2H), 0.94 (m, 6H). MS m/z (ESI): 341.9 [M + H]$^+$. |

Example 26: preparation of 5-((2-bromo-5-isopropylpyridin-4-yl)oxy)-N²-methylpyrimidine-2,4-diamine (C237, compound 237)

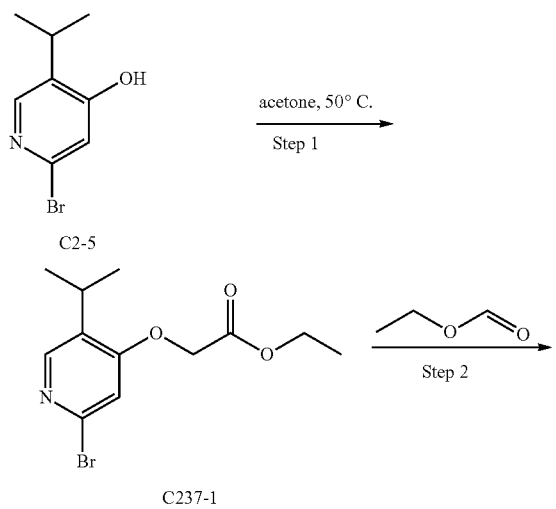

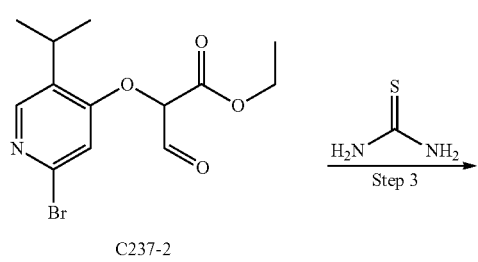

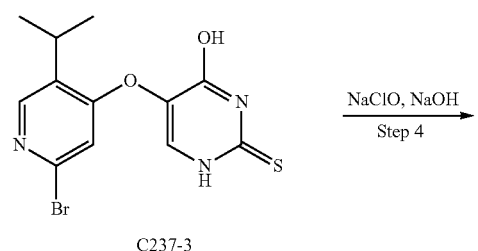

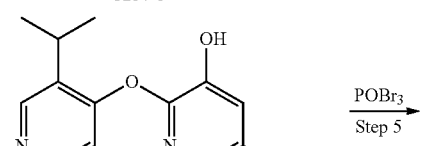

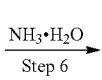

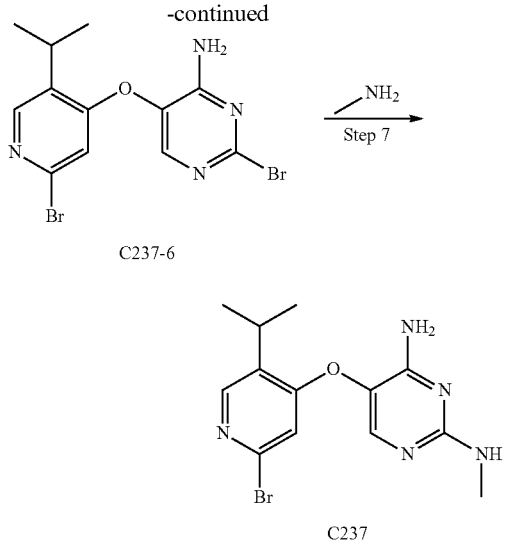

Step 1:
Compound C2-5 (5 g, 0.023 mol) was dissolved in acetone (200 mL), ethyl bromoacetate (5.8 g, 0.035 mol), and potassium carbonate (6.4 g, 0.046 mol) were sequentially added, and the reaction solution was stirred at 50° C. for 16 hours. LC-MS indicated the reaction of the starting materials was complete. The reaction was quenched by adding water (100 mL), and extracted with ethyl acetate (100 mL×3). The organic phases were combined, washed once with saturated brine (100 mL), then dried over anhydrous sodium sulfate (10 g) for half an hour, filtered, and concentrated to afford a crude product, compound C237-1 (5 g crude product, brown oily liquid, yield 74%), which was directly used in the next step. MS m/z (ESI): 288.0 [M+H]⁺.

Step 2:
C237-1 (30 g, 0.091 mol) was dissolved in 1,2-dimethoxyethane (100 mL), and ethyl formate (10 g, 0.14 mol) and potassium tert-butoxide (20 g, 0.18 mol) were added to the solution. The reaction was performed at 25° C. for 1 hour. LC-MS indicated the reaction was complete. The reaction solution was poured into petroleum ether (100 mL), a large amount of white solid precipitated, which was filtered and dried to afford C237-2 (35 g, white solid, yield 95.6%). MS m/z (ESI): 329.9 [M+H]⁺.

Step 3:
C237-2 (35 g, 0.11 mol) was dissolved in ethanol (100 mL), thiourea (24.3 g, 0.32 mol) and sodium methoxide (17.3 g, 0.32 mol) were added to the solution. The reaction was performed at 100° C. overnight. LC-MS indicated the reaction was complete. The reaction solution was rotary evaporated to dryness to afford a yellow residue, which was purified by column chromatography on silica gel (petroleum ether:ethyl acetate=1:1) to afford compound C237-3 (5 g, yellow solid, yield 13.8%). MS m/z (ESI): 341.7 [M+H]⁺.

Step 4:
C237-3 (5 g, 0.015 mol) was added to water (20 mL), sodium hypochlorite (10 mL) and sodium hydroxide (1.2 g) were added to the solution. The reaction was performed at 90° C. for 20 hours. LC-MS indicated the reaction was complete. The reaction was adjusted to pH 7 with 1M HCl, and extracted with ethyl acetate (100 mL×3). The organic phases were combined, washed once with saturated brine (100 mL), then dried over anhydrous sodium sulfate (10 g) for half an hour, filtered, and concentrated. The crude product was isolated by column chromatography on silica gel (petroleum ether:ethyl acetate=1:1) to afford compound C237-4 (3 g, light yellow solid, yield 63%). MS m/z (ESI): 325.7 [M+H]$^+$.

Step 5:

Phosphorus oxybromide (10 g) was added to C237-4 (3 g, 9.23 mmol), and the reaction was performed at 70° C. for 2 hours. LC-MS indicated the reaction was complete. The reaction solution was slowly added to ice water, adjusted to pH 7 with an aqueous solution of sodium bicarbonate, then extracted with ethyl acetate (50 mL×3). The organic phases were combined, washed once with saturated brine (50 mL), then dried over anhydrous sodium sulfate (10 g) for half an hour, filtered, and concentrated. The crude product was isolated by column chromatography on silica gel (petroleum ether:ethyl acetate=10:1) to afford compound C237-5 (2 g, light yellow solid, yield 48.3%). MS m/z (ESI): 449.4 [M+H]$^+$.

Step 6:

C237-5 (1.8 g, 0.004 mol) was added to DCM (10 mL), and aqueous ammonia (20 ml) was added to the solution. The reaction was performed at 40° C. for 4 hours. LC-MS indicated the reaction was complete. The reaction was extracted with ethyl acetate (50 mL×3), the organic phases were combined, washed once with saturated brine (40 mL), then dried over anhydrous sodium sulfate (10 g) for half an hour, filtered, and concentrated. The crude product was isolated by column chromatography on silica gel (petroleum ether:ethyl acetate=1:1) to afford compound C237-6 (1.2 g, white solid, yield 77.4%). MS m/z (ESI): 386.5 [M+H]$^+$.

Step 7:

Compound C237-6 (100 mg, 0.26 mmol) was dissolved in NMP (3 mL), methylamine hydrochloride (20 mg) was added to the solution, and the reaction was performed under microwave radiation at 150° C. for 1 hour. The reaction solution was directly purified by preparative liquid chromatography to afford C237 (30 mg, white solid, yield 34.4%).

$^1$H NMR (400 MHz, CD$_3$OD) δ 8.24 (s, 1H), 7.82 (s, 1H), 7.12 (s, 1H), 3.34-3.32 (m, 1H), 3.02 (s, 3H), 1.37 (d, J=7.2 Hz, 6H). MS m/z (ESI): 337.9 [M+H]$^+$.

The compounds in the following table were prepared according to methods similar to that described in Example 26.

| No. | Compound Structure | Compound Name | Starting material or regent different from that in Example 26 | Characterization Data |
|---|---|---|---|---|
| C111 (compound 111) | 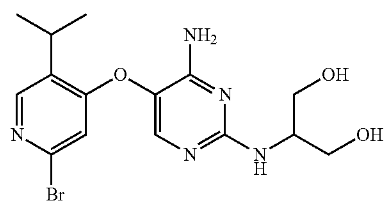 [SMILES: CC(C)c1cnc(Br)cc1Oc1cnc(NC(CO)CO)nc1N] | 2-((4-amino-5-((2-bromo-5-isopropyl-pyridin-4-yl)oxy)pyrimidin-2-yl)amino)propane-1,3-diol | Phosphorus oxybromide in Step 5 was replaced with phosphorus oxychloride; methylamine hydrochloride in Step 7 was replaced with serinol. | $^1$H NMR (400 MHz, CD$_3$OD) δ 8.16 (s, 1H), 7.65 (s, 1H), 6.76 (s, 1H), 4.05 (m, 1H), 3.74 (d, J = 5.6 Hz, 4H), 3.36-3.33 (m, 1H), 1.38 (d, J = 6.8 Hz, 6H). MS m/z (ESI): 397.8 [M + H]$^+$. |
| C218 (compound 218) | 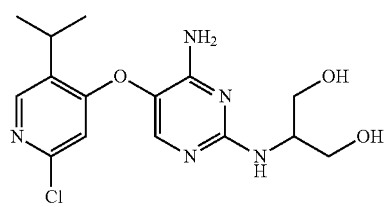 [SMILES: CC(C)c1cnc(Cl)cc1Oc1cnc(NC(CO)CO)nc1N] | 2-((4-amino-5-((2-chloro-5-isopropyl-pyridin-4-yl)oxy)pyrimidin-2-yl)amino)propane-1,3-diol | C2-5 in Step 1 was replaced with 2-chloro-5-isopropylpyridin-4-ol; phosphorus oxybromide in Step 5 was replaced with phosphorus oxychloride; methylamine hydrochloride in Step 7 was replaced with serinol. | $^1$H NMR (400 MHz, CD$_3$OD) δ 8.18 (s, 1H), 7.65 (s, 1H), 6.64 (s, 1H), 4.04 (m, 1H), 3.73 (d, J = 5.2 Hz, 4H), 3.43-3.39 (m, 1H), 1.38 (d, J = 6.8 Hz, 6H). MS m/z (ESI): 353.8 [M + H]$^+$. |
| C235 (compound 235) | 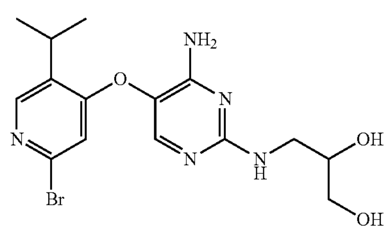 [SMILES: CC(C)c1cnc(Br)cc1Oc1cnc(NCC(O)CO)nc1N] | 3-((4-amino-5-((2-bromo-5-isopropyl-pyridin-4-yl)oxy)pyrimidin-2-yl)amino)propane-1,2-diol | Methylamine hydrochloride in Step 7 was replaced with 3-aminopropane-1,2-diol. | $^1$H NMR (400 MHz, DMSO-d$_6$) δ 8.65 (s, 1H), 8.24 (m, 2H), 8.03 (s, 1H), 7.72 (s, 1H), 7.25 (s, 1H), 3.67 (m, 1H), 3.45-3.22 (m, 7H), 1.27 (d, J = 6.8, 6H). MS m/z (ESI): 397.7 [M + H]$^+$. |

| No. | Compound Structure | Compound Name | Starting material or regent different from that in Example 26 | Characterization Data |
|---|---|---|---|---|
| C243 (compound 243) | 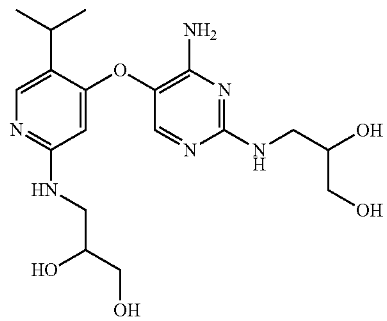 [SMILES: CC(C)c1cnc(NCC(O)CO)cc1Oc1cnc(NCC(O)CO)nc1N] | 3-((4-((4-amino-2-((2,3-dihydroxypropyl)amino)pyrimidin-5-yl)oxy)-5-isopropylpyridin-2-yl)amino)propane-1,2-diol | Methylamine hydrochloride in Step 7 was replaced with 3-aminopropane-1,2-diol. | $^1$H NMR (400 MHz, CD$_3$OD) δ 7.98 (s, 1H), 7.68 (s, 1H), 6.48 (s, 1H), 3.88-3.83 (m, 2H), 3.61-3.28 (m, 9H), 1.33 (d, J = 6.8 Hz, 6H). MS m/z (ESI): 408.6 [M + H]$^+$. |
| C236 (compound 236) | 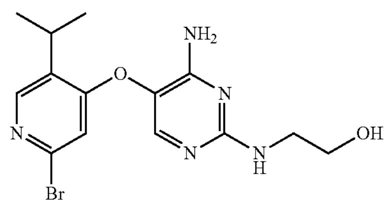 [SMILES: CC(C)c1cnc(Br)cc1Oc1cnc(NCCO)nc1N] | 2-((4-amino-5-((2-bromo-5-isopropyl-pyridin-4-yl)oxy)pyrimidin-2-yl)amino)ethanol | Methylamine hydrochloride in Step 7 was replaced with ethanolamine. | $^1$H NMR (400 MHz, DMSO-d$_6$) δ 8.63 (s, 1H), 8.24-8.18 (m, 2H), 8.03-7.94 (m, 2H), 7.25 (s, 1H), 3.60-3.57 (m, 2H), 3.55-3.34 (m, 2H), 3.32-3.26 (m, 1H), 1.27 (d, J = 7.2 Hz, 6H). MS m/z (ESI): 367.9 [M + H]$^+$. |
| C242 (compound 242) | 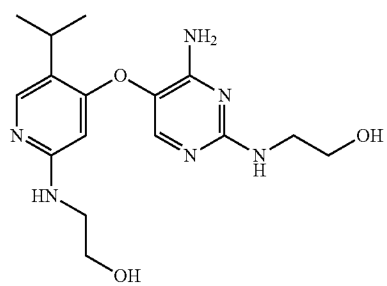 [SMILES: CC(C)c1cnc(NCCO)cc1Oc1cnc(NCCO)nc1N] | 2-((4-((4-amino-2-((2-hydroxyethyl)amino)pyrimidin-5-yl)oxy)-5-isopropyl-pyridin-2-yl)amino)ethanol | Methylamine hydrochloride in Step 7 was replaced with ethanolamine. | $^1$H NMR (400 MHz, CD$_3$OD) δ 7.98 (s, 1H), 7.67 (s, 1H), 6.43 (s, 1H), 3.79-3.75 (m, 4H), 3.47-3.45 (m, 2H), 3.34-3.33 (m, 2H), 3.31-3.28 (m, 1H), 1.33 (d, J= 7.2 Hz, 6H). MS m/z (ESI): 348.8 [M + H]$^+$. |
| C238 (compound 238) | 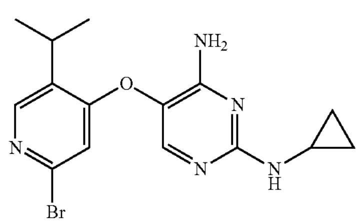 [SMILES: CC(C)c1cnc(Br)cc1Oc1cnc(NC2CC2)nc1N] | 5-((2-bromo-5-isopropylpyridin-4-yl)oxy)-N$^2$-cyclopropyl-pyrimidine-2,4-diamine | Methylamine hydrochloride in Step 7 was replaced with cyclopropylamine. | $^1$H NMR (400 MHz, CD$_3$OD) δ 8.25 (s, 1H), 7.81 (s, 1H), 7.16 (s, 1H), 3.42-3.38 (m, 1H), 2.74 (m, 1H), 1.38 (d, J = 6.8 Hz, 6H), 0.95 (m, 2H), 0.74 (m, 2H). MS m/z (ESI): 363.9 [M + H]$^+$. |
| C239 (compound 239) | 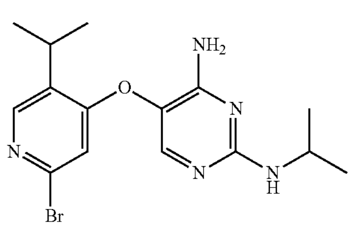 [SMILES: CC(C)Nc1ncc(Oc2cc(Br)ncc2C(C)C)c(N)n1] | 5-((2-bromo-5-isopropylpyridin-4-yl)oxy)-N$^2$-isopropyl-pyrimidine-2,4-diamine | Methylamine hydrochloride in Step 7 was replaced with isopropylamine. | $^1$H NMR (400 MHz, CD$_3$OD) δ 8.24 (s, 1H), 7.78 (s, 1H), 7.14 (s, 1H), 4.24-4.22 (m, 1H), 3.41-3.38 (m, 1H), 1.37 (d, J = 6.8 Hz, 6H), 1.31 (d, J = 6.4 Hz, 6H). MS m/z (ESI): 367.9 [M + H]$^+$. |

Example 27: preparation of 5-((5-isopropyl-2-(methylselanyl)pyridin-4-yl)oxy)pyrimidine-2,4-diamine (C121, compound 121)

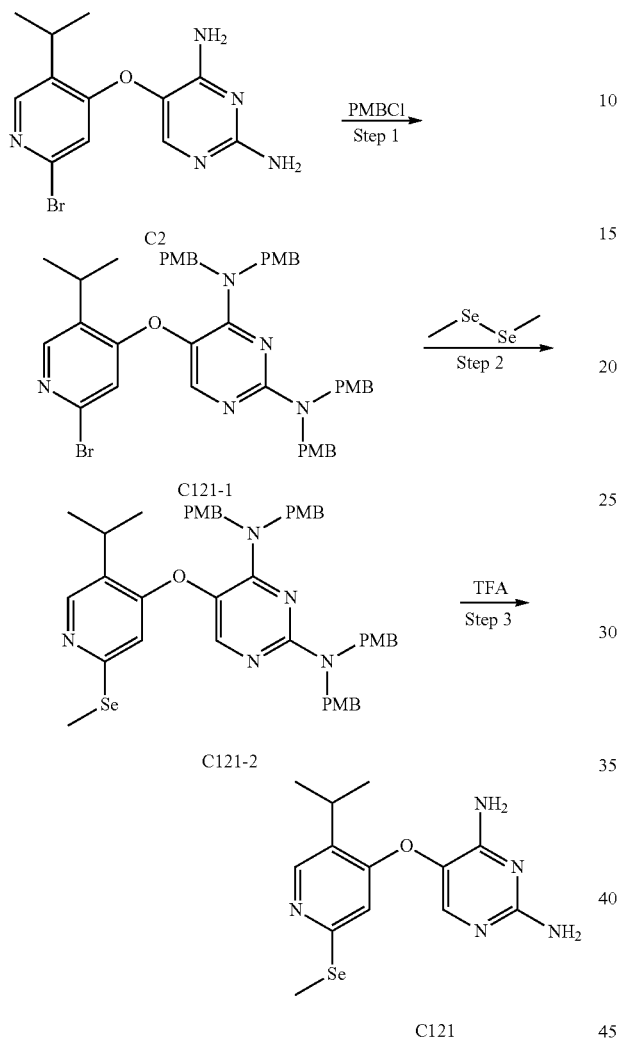

Step 1:

Compound C2 (50 mg, 0.15 mol) was dissolved in anhydrous DMF (5 mL), sodium hydride (18 mg, 0.75 mmol) was added under ice bath cooling, the reaction was stirred for 30 minutes, followed by addition of p-methoxybenzyl chloride (118 mg, 0.75 mmol). Under the protection of nitrogen, the reaction was performed at room temperature for 2 hours. LC-MS indicated the reaction of the starting materials was substantially complete, and the target product was obtained. The reaction solution was slowly dropwise added with water (5 mL), and extracted with ethyl acetate (10 mL×3). The organic phases were combined, added with 10 g anhydrous sodium sulfate, dried for 30 min, and filtered. The filter cake was washed with ethyl acetate (10 mL), and concentrated under reduced pressure to dryness. The crude product was purified by column chromatography on silica gel (mobile phase: petroleum ether:ethyl acetate=20:1~5:1), to afford compound C121-1 (20 mg, oil, yield 16.5%). MS m/z (ESI): 339.8 [M+H]$^+$.

Step 2:

Compound C121-1 (20 mg, 0.025 mmol) was dissolved in anhydrous tetrahydrofuran (5 mL), the reaction was cooled to −78° C., a solution of n-butyl lithium (2.4 mol/L, 0.04 ml) was slowly dropwise added under the protection of nitrogen, and the reaction was stirred at this temperature for 15 minutes. Dimethyldiselenide was added, the reaction was stirred at this temperature for 15 minutes, then allowed to slowly warm to room temperature, and the reaction was performed at room temperature for 2 hours. LC-MS indicated the reaction of the starting materials was substantially complete, and the target product was obtained. The reaction solution was slowly dropwise added with 5 ml water, and extracted with ethyl acetate (12 ml×3). The organic phases were combined, added with 10 g anhydrous sodium sulfate, dried for 30 min, and filtered. The filter cake was washed with ethyl acetate (10 mL), the filtrate was concentrated, and then purified by column chromatography on silica gel (mobile phase: petroleum ether:ethyl acetate=20:1~3:1), to afford compound C121-2 (5 mg, oil, yield 24.4%). MS m/z (ESI): 819.6 [M+H]$^+$.

Step 3:

Compound C121-2 (4 mg, 0.005 mmol) was dissolved in trifluoroacetic acid (1 mL), the reaction was stirred at room temperature for 1 hour, and then warmed to 45° C. and stirred for 2 hours. LC-MS indicated the reaction of the starting materials was substantially complete, and the target product was obtained. The solvent was concentrated under reduced pressure to dryness, and the crude product was purified by thin layer chromatography on silica gel (DCM:MeOH=10:1) to afford compound C121 (1.12 mg, white solid, yield 66.1%).

$^1$H NMR (400 MHz, CD$_3$OD) δ 8.61 (s, 1H), 8.21 (s, 1H), 7.42 (s, 1H), 3.08-3.12 (m, 1H), 2.48 (s, 3H), 1.38 (d, J=6.8 Hz, 6H). MS m/z (ESI): 339.8 [M+H]$^+$.

Example 28: preparation of N$^4$-(2-(dimethylamino)ethyl)-5-((5-isopropyl-2-(methylthio)pyridin-4-yl)oxy)pyrimidine-2,4-diamine (C72, compound 72)

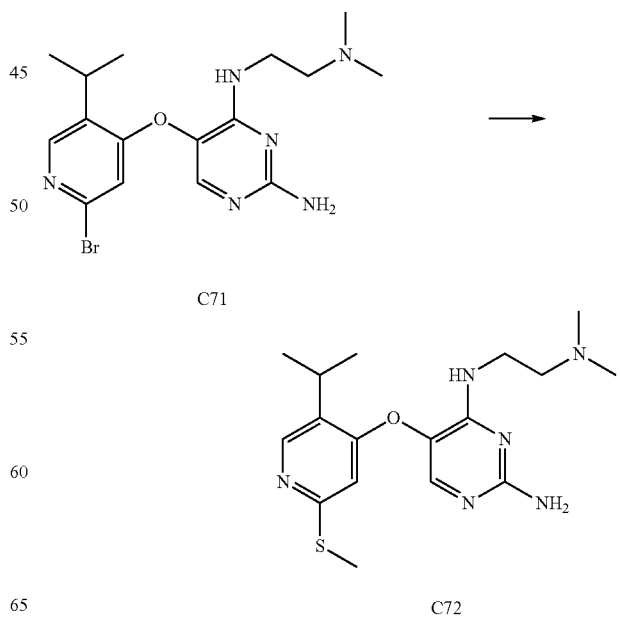

Compound C71 (12 mg, 0.031 mmol) was dissolved in 1,4-dioxane (5 mL), sodium thiomethoxide (13 mg, 0.19 mmol), DIEA (40 mg, 0.31 mmol), X-phos (5 mg) and Pd$_2$(dba)$_3$ (5 mg) were sequentially added, and the reaction was stirred at 90° C. for 16 hours. LC-MS indicated the reaction of the starting materials was substantially complete. The reaction solution was concentrated under reduced pressure to afford a crude product, which was purified by thin layer chromatography on silica gel (dichloromethane:methanol=10:1), to afford compound C72 (2 mg, white solid, yield 18%).

$^1$H NMR (400 MHz, CD$_3$OD) δ 8.26 (s, 1H), 7.60 (s, 1H), 6.54 (s, 1H), 3.81-3.78 (m, 2H), 3.36-3.35 (m, 1H), 2.95 (s, 6H), 2.48 (s, 3H), 1.37 (d, J=7.2 Hz, 6H), 0.92-0.90 (m, 2H). MS m/z (ESI): 362.9 [M+H]$^+$.

Example 29: preparation of N-(4-((2,4-diaminopyrimidin-5-yl)oxy)-5-isopropylpyridin-2-yl)acetamide (C122, compound 122)

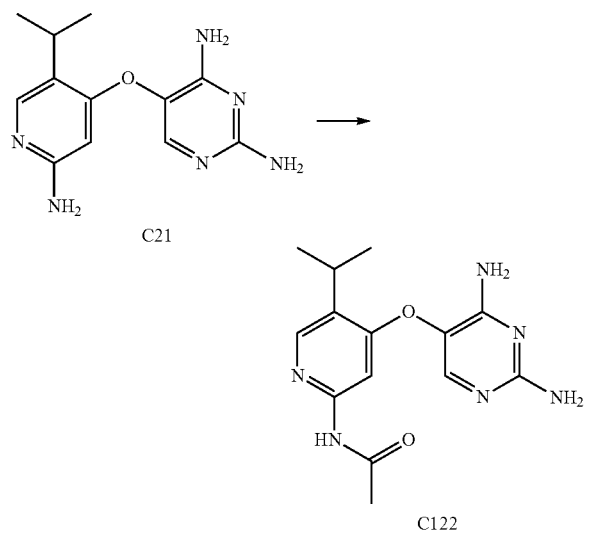

Compound C21 (25 mg, 0.096 mmol) was dissolved in dichloromethane (5 mL), acetic anhydride (29 mg, 0.29 mmol) and triethylamine (29 mg, 0.29 mmol) were sequentially added, and the reaction solution was stirred at 25° C. for 16 hours. LC-MS indicated the reaction of the starting materials was substantially complete. The reaction solution was concentrated under reduced pressure to afford a crude product, which was purified by thin layer chromatography on silica gel (dichloromethane:methanol=10:1), to afford compound C122 (10 mg, white solid, yield 34%).

$^1$H NMR (400 MHz, DMSO-d$_6$) δ 10.34 (s, 1H), 8.06 (s, 1H), 7.52 (s, 1H), 7.41 (s, 1H), 6.31 (s, 2H), 5.95 (s, 2H), 2.60 (s, 1H), 1.91 (s, 3H), 1.27 (d, J=6.8 Hz, 6H). MS m/z (ESI): 302.9 [M+H]$^+$.

Example 30: preparation of 4-((2,4-diaminopyrimidin-5-yl)oxy)-5-isopropylpicolinic acid (C128, compound 128)

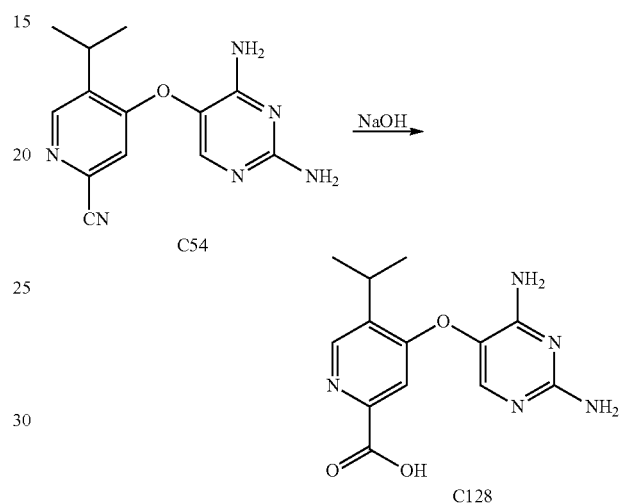

C54 (10 mg, 0.037 mmol) was dissolved in ethanol (5 mL) and water (1 mL), and sodium hydroxide (3 mg, 0.074 mmol) was added. The reaction was stirred at 80° C. for 3 hours. LC-MS indicated the reaction was complete. Then, the reaction was adjusted to pH 7 with 0.5N hydrochloric acid, concentrated to dryness, and the residue was purified by thin layer chromatography on silica gel (dichloromethane:methanol=10:1), to afford C128 (3 mg, white solid, yield 28.0%).

$^1$H NMR (400 MHz, DMSO-d$_6$) δ 8.59 (s, 1H), 8.19 (s, 2H), 7.98 (s, 1H), 7.68 (s, 2H), 7.34 (s, 1H), 3.60-3.56 (m, 1H), 1.33 (d, J=6.8 Hz, 6H). MS m/z (ESI): 289.9 [M+H]$^+$.

The compounds in the following table were prepared according to methods similar to that described in Example 30.

| No. | Compound Structure | Compound Name | Starting material or regent different from that in Example 30 | Characterization Data |
|---|---|---|---|---|
| C197 (compound 197) | 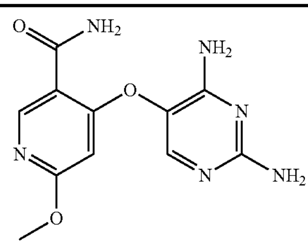 | 4-((2,4-diaminopyrimidin-5-yl)oxy)-6-methoxynicotinamide | C54 was replaced with C177. | $^1$H NMR (400 MHz, CD$_3$OD) δ 8.53 (s, 1H), 8.51 (s, 1H), 7.54 (s, 1H), 3.99 (s, 3H). MS m/z (ESI): 277.0 [M + H]$^+$. |

| No. | Compound Structure | Compound Name | Starting material or regent different from that in Example 30 | Characterization Data |
|---|---|---|---|---|
| C198 (compound 198) | 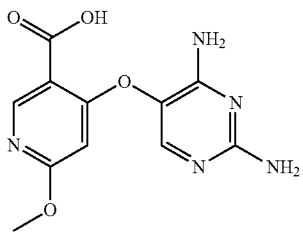 [SMILES: COc1cc(Oc2cnc(N)nc2N)c(C(=O)O)cn1] | 4-((2,4-diaminopyrimidin-5-yl)oxy)-6-methoxynicotinic acid | C54 was replaced with C177; and the duration of stirring was extended to 15 hours. | $^1$H NMR (400 MHz, CD$_3$OD) δ 8.46 (s, 1H), 7.73 (s, 1H), 6.23 (s, 1H), 3.92 (s, 3H). MS m/z (ESI): 278.1 [M + H]$^+$. |

Example 31: preparation of 4-((2,4-diaminopyrimidin-5-yl)oxy)-5-isopropylpicolinimidamide (C131, compound 131)

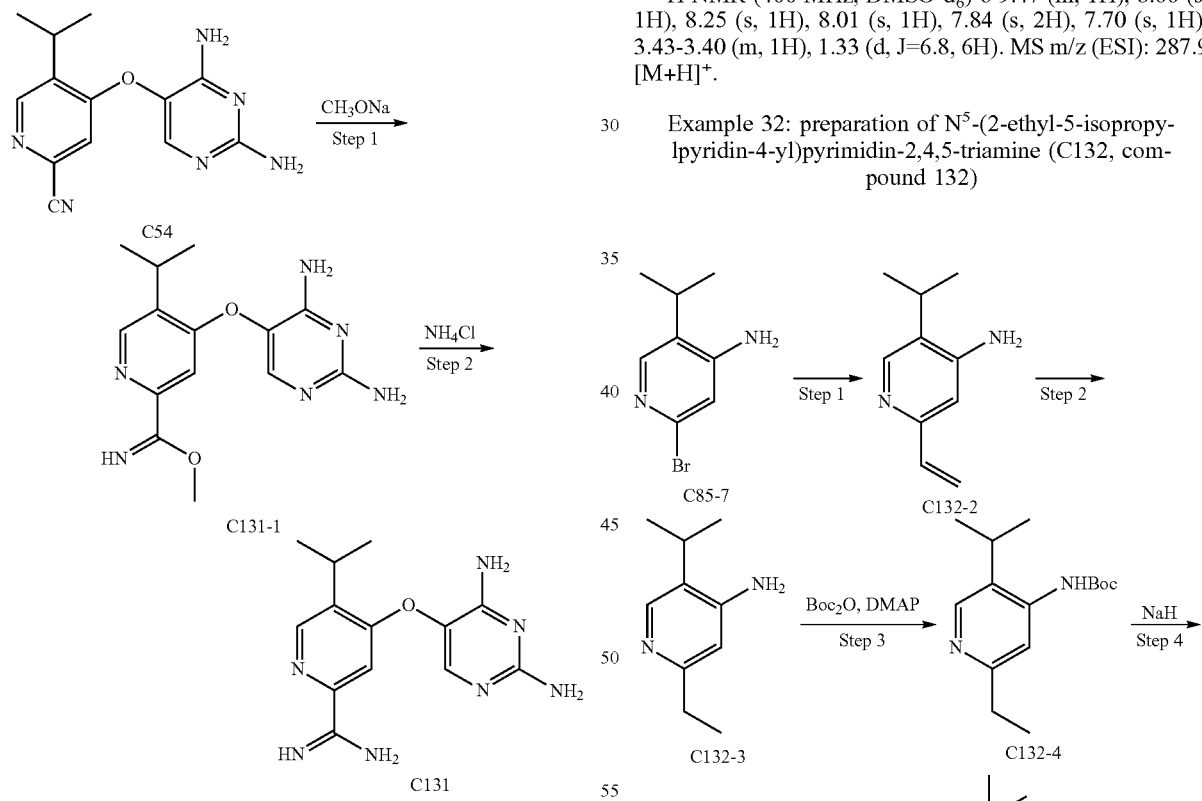

Step 1:
C54 (20 mg, 0.074 mmol) was dissolved in methanol (5 mL), and sodium methoxide (8 mg, 0.15 mmol) was added. The reaction was stirred at room temperature overnight. LC-MS indicated the reaction was complete. Then, the reaction was concentrated to dryness to give C131-1 (20 mg, oil, yield 89.3%). MS m/z (ESI): 302.9 [M+H]$^+$.

Step 2
C131-1 (10 mg, 0.033 mmol) was dissolved in ethanol (5 mL) and water (2 mL), and ammonium chloride (2 mg, 0.039 mmol) was added. The reaction was stirred at 80° C. for 2 hours. LC-MS indicated the reaction was complete. Then, the reaction was concentrated to dryness, and the residue was purified by preparative thin layer chromatography on silica gel (dichloromethane:methanol=10:1) to afford C131 (6 mg, white solid, yield 63.1%).

$^1$H NMR (400 MHz, DMSO-d$_6$) δ 9.47 (m, 1H), 8.66 (s, 1H), 8.25 (s, 1H), 8.01 (s, 1H), 7.84 (s, 2H), 7.70 (s, 1H), 3.43-3.40 (m, 1H), 1.33 (d, J=6.8, 6H). MS m/z (ESI): 287.9 [M+H]$^+$.

Example 32: preparation of N$^5$-(2-ethyl-5-isopropylpyridin-4-yl)pyrimidin-2,4,5-triamine (C132, compound 132)

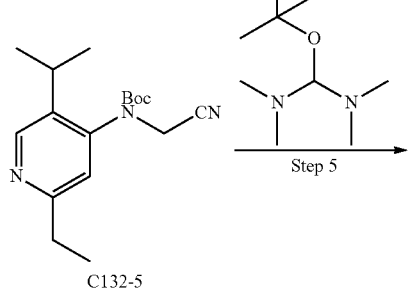

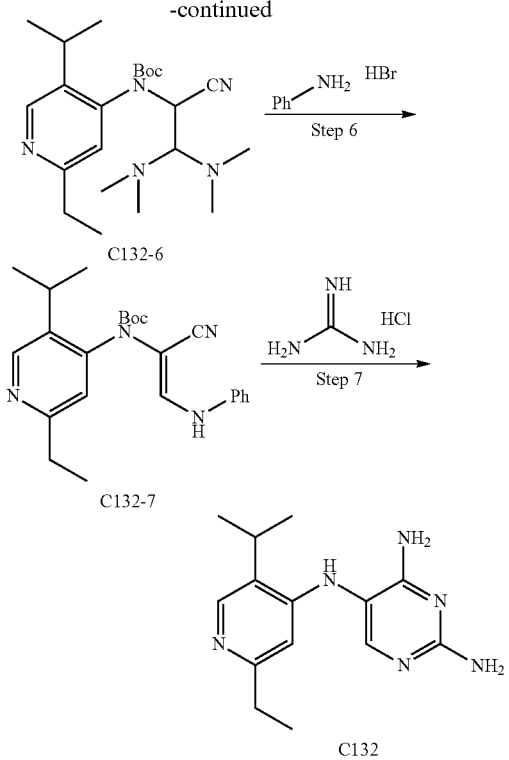

Step 1:

C85-7 (10 g, 0.0467 mol) was dissolved in 1,4-dioxane (100 mL), vinylpinacol borate (14.4 g, 0.093 mmol), potassium carbonate (19 g, 0.14 mol) and Pd(PPh$_3$)$_4$ (1 g, 0.865 mmol) were sequentially added. Purge with nitrogen was performed for 3 times, and the reaction was performed at 90° C. overnight. LC-MS indicated the reaction was complete. Then, the reaction solution was poured into water (200 mL), and extracted with ethyl acetate (200 mL×3). The organic phases were combined, washed once with saturated brine (200 mL), then dried over anhydrous sodium sulfate (50 g) for half an hour, filtered, and concentrated.

The crude product was purified by column chromatography on silica gel (petroleum ether:ethyl acetate=1:1) to afford compound C132-2 (6 g, yellow oil, yield 79.2%). MS m/z (ESI): 163.0 [M+H]$^+$.

Step 2:

C132-2 (6 g, 0.037 mol) was dissolved in ethanol (100 mL), 10% wet palladium/carbon (2 g) was added, and the reaction was performed under hydrogen at room temperature for 2 hours. LC-MS indicated the reaction was complete. Then, the reaction was filtered, and concentrated to give C132-3 (4.5 g, yellow oil, yield 74.1%). MS m/z (ESI): 165.1 [M+H]$^+$.

Step 3:

C132-3 (4.5 g, 0.03 mol) was dissolved in acetonitrile (50 mL), Boc$_2$O (7.3 g, 0.033 mol), DMAP (4 g, 0.033 mol) and triethylamine (6 g, 0.06 mol) were sequentially added. The reaction was stirred at room temperature for 6 hours. LC-MS indicated the reaction was complete. Then, the reaction was quenched by adding water, and extracted with ethyl acetate (50 mL×3). The organic phases were combined, washed once with saturated brine (50 mL), then dried over anhydrous sodium sulfate (20 g) for an hour, filtered, and concentrated. The crude product was purified by column chromatography on silica gel (petroleum ether:ethyl acetate=1:1) to afford compound C132-4 (1.4 g, white solid, yield 19.4%). MS m/z (ESI): 265.0 [M+H]$^+$.

Step 4:

C132-4 (1.4 g, 5.28 mmol) was dissolved in DMF (10 mL), sodium hydride (0.38 g, 15.8 mmol) and bromoacetonitrile (1.26 g, 10.6 mmol) were sequentially added, and the reaction was stirred at room temperature overnight. LC-MS indicated the reaction was complete. Then, the reaction was quenched by adding water, and extracted with ethyl acetate (100 mL×3). The organic phases were combined, washed with saturated brine (40 mL×3), then dried over anhydrous sodium sulfate (50 g) for half an hour, filtered, and concentrated. The crude product was purified by column chromatography on silica gel (petroleum ether:ethyl acetate=10:1) to afford compound C132-5 (1 g, oil, yield 62.5%). MS m/z (ESI): 304.0 [M+H]$^+$.

Step 5:

C132-5 (1 g, 3.3 mmol) was dissolved in DMF (10 mL), and tert-butoxy bis(dimethylamino)methane (1.7 g, 9.9 mmol) was added to the reaction solution. The reaction was stirred at 100° C. for 1 hour. LC-MS indicated the reaction was complete. Then, the reaction was quenched by adding water, and extracted with ethyl acetate (30 mL×3). The organic phase was concentrated, and the residue was purified by column chromatography on silica gel (petroleum ether:ethyl acetate=5:1) to afford C132-6 (0.5 g, yield 37.6%). MS m/z (ESI): 359.0 [M–45+H]*.

Step 6:

C132-6 (200 mg, 0.56 mmol) was dissolved in DMF (1 mL), and aniline hydrobromide (110 mg, 0.62 mmol) was added to the reaction solution. The reaction was stirred at 100° C. for 6 hours. LC-MS indicated the reaction was complete. Then, the reaction was quenched by adding water, extracted with ethyl acetate, concentrated, and the residue was purified by column chromatography on silica gel (petroleum ether:ethyl acetate=5:1) to afford compound C132-7 (80 mg, yield 39.8%). MS m/z (ESI): 407.0 [M+H]$^+$.

Step 7:

C132-7 (20 mg, 0.049 mmol) was dissolved in ethanol (2 mL), and guanidine hydrochloride (100 mg, 1.05 mmol) and sodium methoxide (30 mg, 0.55 mmol) were added to the reaction solution. The reaction was stirred at 90° C. for 6 hours. LC-MS indicated the reaction was complete. Then, the reaction was concentrated to dryness, and the residue was purified by Prep-HPLC to afford C132 (5 mg, yield 37.3%).

$^1$H NMR (400 MHz, CD$_3$OD) δ 8.06 (s, 1H), 7.92 (s, 1H), 6.73 (s, 1H), 3.21-3.18 (m, 1H), 2.83-2.79 (m, 2H), 1.39 (d, J=6.8 Hz, 6H), 1.32-1.28 (m, 3H). MS m/z (ESI): 273.0 [M+H]$^+$.

Example 33: preparation of 5-((5-isopropyl-2-(trimethylsilyl)pyridin-4-yl)oxy)pyrimidine-2,4-diamine (C133, compound 133)

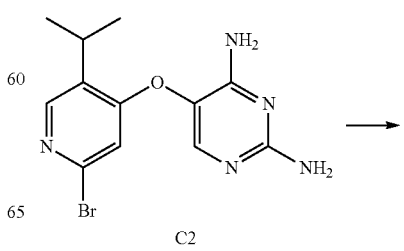

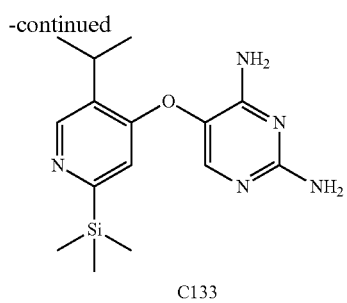

C133

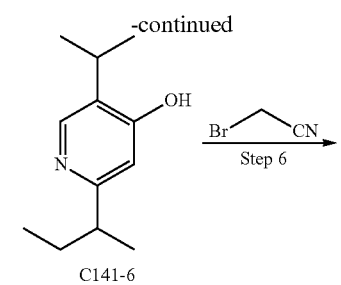

C141-6

Compound C2 (200 mg, 0.62 mmol) was dissolved in tetrahydrofuran (10 mL), and n-butyl lithium (1 mL, 2.4 mmol) was dropwise added under the protection of nitrogen at −78° C. The reaction solution was stirred at −78° C. for half an hour, and then bromotrimethylsilane (1 mL) was dropwise added. The reaction solution was stirred at −78° C. for 2 hours. LC-MS indicated the reaction of the starting materials was substantially complete. The reaction solution was quenched by adding water, adjusted to pH 7 with sodium carbonate, extracted with ethyl acetate (25 mL×3), dried over sodium sulfate, and concentrated under reduced pressure to afford a crude product. The crude product was rinsed with ethyl acetate (2 mL), filtered and dried to afford compound C133 (5 mg, yellow solid, yield 2.5%).

$^1$H NMR (400 MHz, CDCl$_3$) δ 8.69 (s, 1H), 7.76 (s, 1H), 6.88 (s, 1H), 3.44-3.40 (m, 1H), 1.39 (d, J=7.2 Hz, 6H), 0.35 (s, 9H). MS m/z (ESI): 317.9 [M+H]$^+$.

Example 34: preparation of 5-((2-(sec-butyl)-5-isopropylpyridin-4-yl)oxy)pyrimidine-2,4-diamine (C141, compound 141)

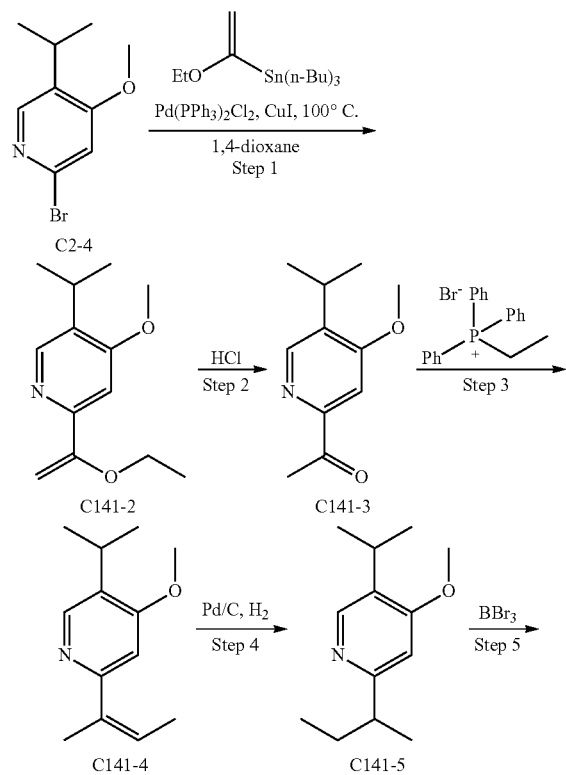

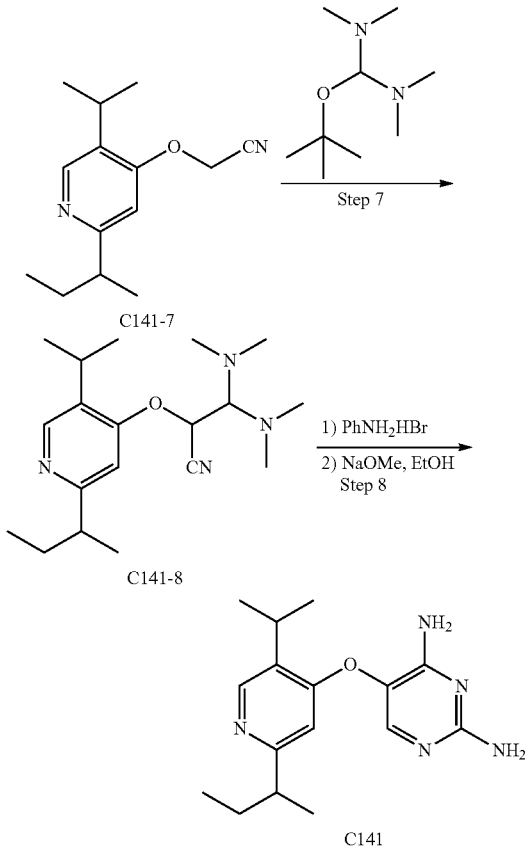

Step 1:

C2-4 (5.0 g, 22 mmol), tributyl(1-ethoxyvinyl)tin (8.7 g, 24 mmol) and dioxane (40 mL) were added to a 500 mL single-neck flask, Pd(PPh$_3$)$_2$Cl$_2$ (1.5 g, 2.2 mmol) and cuprous iodide (420 mg, 2.2 mmol) were added, purge with argon was performed for 3 times, and the reaction was placed in an oil bath at 100° C. and allowed to proceed for 1.5 h. After the reaction was complete, the reaction was cooled to room temperature, filtered with suction, and the filtrate was concentrated under reduced pressure. The residue was purified by column chromatography on silica gel (petroleum ether:ethyl acetate=10:1), to afford C141-2 (4.64 g, light yellow oil, yield 96.6%/o).

$^1$H NMR (400 MHz, CDCl$_3$) δ 8.28 (s, 1H), 7.17 (s, 1H), 5.35 (d, J=2.0 Hz, 1H), 4.33 (d, J=2.0 Hz, 1H), 3.98 (q, J=7.0 Hz, 2H), 3.90 (s, 3H), 3.25-3.18 (m, 1H), 1.44 (t, J=7.0 Hz, 3H), 1.24 (d, J=7.0 Hz, 6H). MS m/z (ESI): 222.0 [M+H]$^+$.

Step 2:

C141-2 (4.64 g, 21 mmol) was dissolved in dichloromethane (40 mL), a 4 mol/L solution of hydrochloric acid in dioxane (15.6 mL, 63 mmol) was added at room temperature, and the reaction was performed at room temperature for 20 h. After the reaction was complete, the reaction was concentrated under reduced pressure, adjusted to pH 6~7 with a 2 mol/L aqueous solution of sodium hydroxide, and extracted with ethyl acetate (100 mL×3). The organic phases were combined, then washed with a saturated aqueous solution of sodium chloride (100 mL×2), dried over anhydrous sodium sulfate, filtered, and the filtrate was concentrated to afford C141-3 (4.0 g, yellow oil, yield 99.6%).

$^1$H NMR (400 MHz, CDCl$_3$) δ 8.39 (s, 1H), 7.54 (s, 1H), 3.93 (s, 3H), 3.33-3.23 (m, 1H), 2.70 (s, 3H), 1.27 (d, J=6.8 Hz, 6H). MS m/z (ESI): 194.0 [M+H]$^+$.

Step 3:

At 0° C., to a suspension of ethyltriphenylphosphonium bromide (10.7 g, 29 mmol) in anhydrous tetrahydrofuran (80 mL), a 2.4 mol/L solution of butyllithium in n-hexane (12.1 mL, 29 mmol) was dropwise added, and the reaction was performed at 0° C. for 1 h. A solution of C141-3 (3.7 g, 19 mmol) in tetrahydrofuran (20 mL) was dropwise added at 0° C. to the above suspension, and after the dropwise addition, the reaction was warmed to room temperature and performed for 18 hours. After the reaction was complete, the reaction system was quenched by dropwise addition of a saturated aqueous solution of ammonium chloride (100 mL), and extracted with ethyl acetate (100 mL×2). The organic phases were combined, then washed with a saturated aqueous solution of sodium chloride (100 mL×2), dried over anhydrous sodium sulfate, and filtered. The filtrate was concentrated, and the residue was purified by column chromatography on silica gel (petroleum ether:ethyl acetate=6:1) to afford C141-4 (2.02 g, colorless oil, yield 51.5%).

$^1$H NMR (400 MHz, CDCl$_3$) δ 8.26 (s, 1H), 6.82 (s, 1H), 6.38-6.33 (m, 1H), 3.88 (s, 3H), 3.24-3.14 (m, 1H), 2.09 (s, 3H), 1.84 (dd, J=6.8, 0.8 Hz, 3H), 1.24 (d, J=6.8 Hz, 6H). MS m/z (ESI): 206.0 [M+H]$^+$.

Step 4:

C141-4 (1.9 g, 9.25 mmol) was dissolved in ethanol (100 mL), 10% palladium/carbon (1.9 g, 100% wt) was added, purge with hydrogen was performed for 3 times with a hydrogen balloon, and the reaction was performed at room temperature for 18 h. After the reaction was complete, the reaction was filtered with suction, and the filtrate was concentrated to afford C141-5 (1.3 g, colorless oil, crude product, yield 67.8%). MS m/z (ESI): 208.1 [M+H]$^+$.

Step 5:

C141-5 (1.3 g, 6.3 mmol) was dissolved in dichloromethane (39 mL), and boron tribromide (5 mL) was dropwise added at room temperature. After the dropwise addition, the reaction was placed in an oil bath at 45° C. and allowed to proceed for 18 h. After the reaction was complete, the reaction solution was poured into ice water, adjusted to pH 7 with a 2 mol/L aqueous solution of sodium hydroxide, and extracted with ethyl acetate (50 mL×4). The organic phases were combined, then washed with a saturated aqueous solution of sodium chloride (100 mL×2), dried over anhydrous sodium sulfate, filtered, and the filtrate was concentrated under reduced pressure to afford C141-6 (1.3 g, off-white solid, crude product, yield 100%). MS m/z (ESI): 194.0 [M+H]$^+$.

Step 6:

C141-6 (500 mg, 2.59 mmol) was dissolved in anhydrous DMF (5 mL), anhydrous potassium carbonate (716 mg, 5.18 mmol) and 2-bromoacetonitrile (372 mg, 3.1 mmol) were sequentially added to the solution, and the reaction was performed at room temperature for 8 h. The reaction solution was filtered, the filtrate was diluted with ethyl acetate (100 mL), then washed with a saturated aqueous solution of sodium chloride (100 mL×2), dried over anhydrous sodium sulfate, and filtered. The filtrate was concentrated under reduced pressure, and the residue was purified by column chromatography on silica gel (petroleum ether:ethyl acetate=3:1) to afford C141-7 (380 mg, light yellow oil, yield 63.2%).

$^1$H NMR (400 MHz, CDCl$_3$) δ 8.35 (s, 1H), 6.61 (s, 1H), 4.85 (s, 2H), 3.24-3.14 (m, 1H), 2.82-2.74 (m, 1H), 1.81-1.70 (m, 1H), 1.68-1.57 (m, 1H), 1.28 (d, J=7.6 Hz, 3H), 1.27 (d, J=6.8 Hz, 6H), 0.86 (t, J=7.4 Hz, 3H). MS m/z (ESI): 233.1 [M+H]$^+$.

Step 7:

C141-7 (600 mg, 2.6 mmol) and tert-butoxy bis(dimethylamino)methane (1.36 g, 7.8 mmol) was dissolved in anhydrous DMF (10 mL), and the reaction was placed in an oil bath at 100° C. and allowed to proceed for 2 h. After the reaction was complete, the reaction was cooled to room temperature, diluted with ethyl acetate (40 mL), then washed with a saturated aqueous solution of sodium chloride (50 mL×2), dried over anhydrous sodium sulfate, and filtered. The filtrate was concentrated, and then the residue was purified by column chromatography on silica gel (petroleum ether:ethyl acetate=2:1) to afford C141-8 (320 mg, yellow oil, crude product, yield 37.2%). MS m/z (ESI): 287.9 [M−45+H]*.

Step 8:

C141-6 (21 mg, 0.073 mmol) and aniline hydrobromide (38 mg, 0.22 mmol) were dissolved in anhydrous ethanol (5 mL), and the reaction was placed in an oil bath at 80° C. and allowed to proceed for 2 h. After the reaction was complete, the reaction was cooled to room temperature, the reaction system was added with sodium methoxide (60 mg, 1.11 mmol) and guanidine hydrochloride (60 mg, 0.62 mmol), and the reaction was again placed in an oil bath at 80° C. and allowed to proceed for 16 h. After the reaction was complete, the reaction was cooled to room temperature, filtered with suction, the filtrate was concentrated, and the residue was purified by preparative high-performance liquid chromatography to afford compound C141 (3.25 mg, off-white solid, yield 17.0%).

$^1$H NMR (300 MHz, DMSO-d$_6$) δ 8.29 (s, 1H), 7.52 (s, 1H), 6.35 (s, 2H), 6.29 (s, 1H), 5.97 (s, 2H), 3.38 (m, 1H), 2.61 (m, 1H), 1.63-1.53 (m, 1H), 1.49-1.40 (m, 1H), 1.29 (d, J=6.9 Hz, 6H), 1.10 (d, J=6.9 Hz, 3H), 0.73 (t, J=7.2 Hz, 3H). MS m/z (ESI): 302.1 [M+H]$^+$.

Example 35: preparation of 2,2'-((5-((2-bromo-5-isopropylpyridin-4-yl)oxy)pyrimidin-2,4-diyl)bis(azanediyl))diethanol (C226, compound 226)

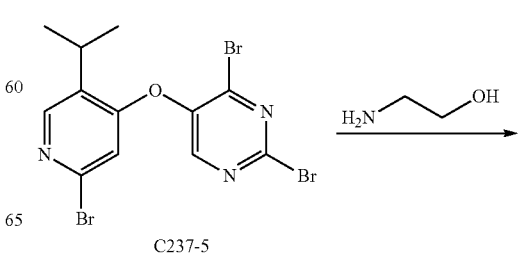

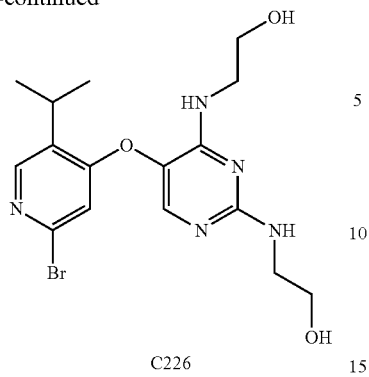

C226

Compound C237-5 (50 mg, 0.11 mmol) was dissolved in N-methylpyrrolidone (5 mL), ethanolamine (0.1 g) was added, the reaction solution was stirred under microwave radiation at 150° C. for 1 hour. LC-MS indicated the reaction of the starting materials was substantially complete. The reaction solution was concentrated under reduced pressure to afford a crude product, which was purified by preparative liquid chromatography to afford compound C226 (3 mg, white solid, yield 7%).

$^1$H NMR (400 MHz, CD$_3$OD) δ 8.22 (s, 1H), 7.68 (s, 1H), 7.01 (s, 1H), 3.77-3.72 (m, 4H), 3.66-3.65 (m, 2H), 3.64-3.58 (m, 2H), 3.43-3.40 (m, 1H), 1.37 (d, J=6.8 Hz, 6H). MS m/z (ESI): 411.7 [M+H]$^+$.

The compound in the following table was prepared according to a method similar to that described in Example 35.

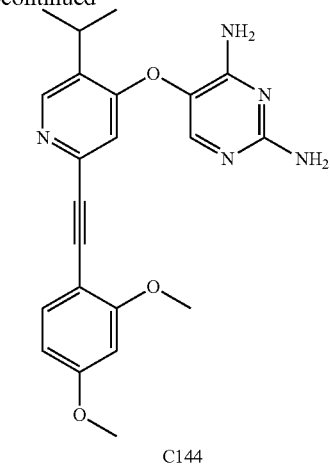

C144

Step 1:

Compound C66 (20 mg, 0.074 mmol) was dissolved in DMF (5 mL), 2,4-dimethoxybromobenzene (48 mg, 0.22 mmol), TEA (38 mg, 0.37 mmol), CuI (10 mg) and Pd(PPh$_3$)$_2$Cl$_2$ (10 mg) were sequentially added, purge with nitrogen was performed for 3 times, and the reaction was performed at 50° C. for 16 hours. LC-MS indicated the reaction of the starting materials was substantially complete. The reaction solution was cooled to room temperature,

| No. | Compound Structure | Compound Name | Starting material or regent different from that in Example 35 | Characterization Data |
|---|---|---|---|---|
| C227 (compound 227) | 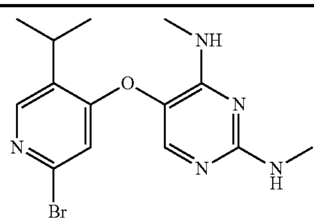 | 5-((2-bromo-5-isopropylpyridin-4-yl)oxy)-N$^2$,N$^4$-dimethylpyrimidine-2,4-diamine | Ethanolamine in Step 1 was replaced with methylamine. | $^1$H NMR (400 MHz, CD$_3$OD) δ 8.25 (s, 1H), 7.72 (s, 1H), 7.13 (s, 1H), 3.41-3.38 (m, 1H), 3.08-3.06 (m, 6H), 1.37 (d, J = 7.2 Hz, 6H). MS m/z (ESI): 351.7 [M + H]$^+$. |

Example 36: preparation of 5-((2-((2,4-dimethoxyphenyl)ethynyl)-5-isopropylpyridin-4-yl)oxy)pyrimidine-2,4-diamine (C144, compound 144)

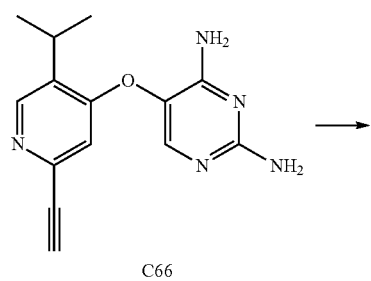

C66 filtered, the filtrate was added with purified water (50 mL), and extracted with ethyl acetate (50 mL×3). The organic phases were combined, added with anhydrous sodium sulfate (10 g), dried for 30 min, filtered, and concentrated under reduced pressure to afford a crude product, which was purified by Prep-HPLC to afford compound C144 (0.9 mg, yield 3.0%).

$^1$H NMR (400 MHz, CD$_3$OD) δ 8.45 (s, 1H), 7.84 (s, 1H), 7.47 (d, J=8.4 Hz, 1H), 7.25 (s, 1H), 6.62-6.58 (m, 2H), 3.90 (s, 3H), 3.86 (s, 3H), 3.47-3.33 (m, 1H), 1.41 (d, J=6.8 Hz, 6H). MS m/z (ESI): 405.9 [M+H]$^+$.

The compounds in the following table were prepared according to methods similar to that described in Example 36.

| No. | Compound Structure | Compound Name | Starting material or regent different from that in Example 36 | Characterization Data |
|---|---|---|---|---|
| C145 (compound 145) | 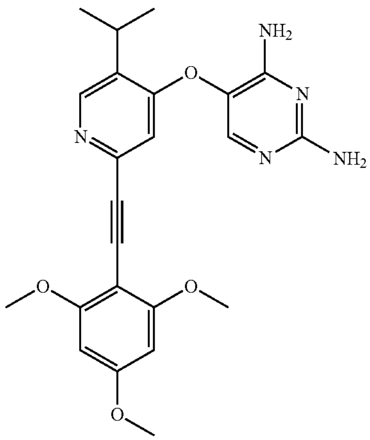 [SMILES: COc1cc(OC)c(C#Cc2cc(Oc3cnc(N)nc3N)c(C(C)C)cn2)c(OC)c1] | 5-((5-isopropyl-2-((2,4,6-trimethoxyphenyl)ethynyl)pyridin-4-yl)oxy)pyrimidine-2,4-diamine | 2,4-dimethoxybromobenzene was replaced with 2,4,6-trimethoxybromobenzene. | $^1$H NMR (400 MHz, CD$_3$OD) δ 8.36 (s, 1H), 7.72 (s, 1H), 6.93 (s, 1H), 6.25 (s, 2H), 3.86 (s, 9H), 3.50-3.33 (m, 1H), 1.40 (d, J = 6.8 Hz, 6H). MS m/z (ESI): 435.8 [M + H]$^+$. |
| C149 (compound 149) | 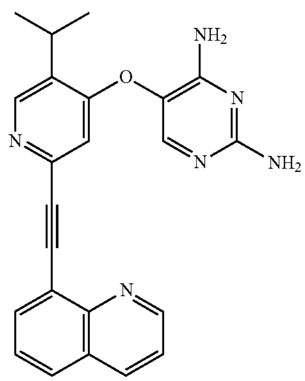 [SMILES: CC(C)c1cnc(C#Cc2cccc3cccnc23)cc1Oc1cnc(N)nc1N] | 5-((5-isopropyl-2-(quinolin-8-ylethynyl)pyridin-4-yl)oxy)pyrimidine-2,4-diamine | 2,4-dimethoxybromobenzene was replaced with 8-bromoquinoline. | $^1$H NMR (400 MHz, CD$_3$OD) δ 8.95 (d, J = 4.4 Hz, 1H), 8.50-8.40 (m, 2H), 8.12 (d, J = 7.2 Hz, 1H), 8.04 (d, J = 8.4 Hz, 1H), 7.70-7.60 (m, 3H), 7.33 (s, 1H), 3.54-3.50 (m, 1H), 1.44 (d, J = 6.8 Hz, 6H). MS m/z (ESI): 396.8 [M + H]$^+$. |
| C150 (compound 150) | 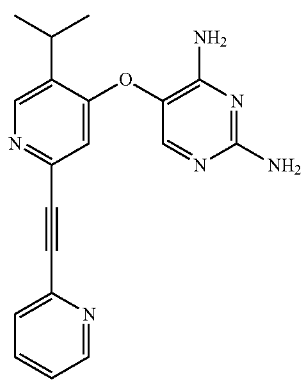 [SMILES: CC(C)c1cnc(C#Cc2ccccn2)cc1Oc1cnc(N)nc1N] | 5-((5-isopropyl-2-(pyridin-2-ylethynyl)pyridin-4-yl)oxy)pyrimidine-2,4-diamine | 2,4-dimethoxybromobenzene was replaced with 2-bromopyridine. | $^1$H NMR (400 MHz, CD$_3$OD) δ 8.73-8.70 (m, 2H), 8.10-8.03 (m, 2H), 7.91-7.89 (m, 1H), 7.82 (s, 1H), 7.68-7.65 (m, 1H), 3.59-3.55 (m, 1H), 1.45 (d, J = 6.8 Hz, 6H). MS m/z (ESI): 346.9 [M + H]$^+$. |

| No. | Compound Structure | Compound Name | Starting material or regent different from that in Example 36 | Characterization Data |
|---|---|---|---|---|
| C151 (compound 151) | 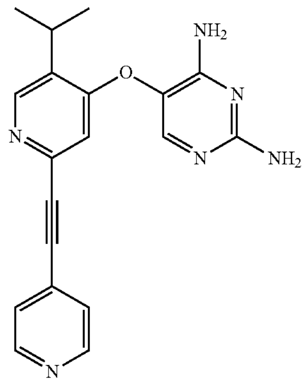 [SMILES: CC(C)c1cnc(C#Cc2ccncc2)cc1Oc1cnc(N)nc1N] | 5-((5-isopropyl-2-(pyridin-4-ylethynyl)pyridin-4-yl)oxy)pyrimidine-2,4-diamine | 2,4-dimethoxybromo-benzene was replaced with 4-bromopyridine. | $^1$H NMR (400 MHz, CDCl$_3$) δ 8.65 (d, J = 5.2 Hz, 2H), 8.52 (s, 1H), 7.71 (s, 1H), 7.45 (d, J = 5.2 Hz, 2H), 6.91 (s, 1H), 5.60 (s, 2H), 5.10 (s, 2H), 3.43-3.39 (m, 1H), 1.41 (d, J = 6.8 Hz, 6H). MS m/z (ESI): 346.9 [M + H]$^+$. |
| C195 (compound 195) | 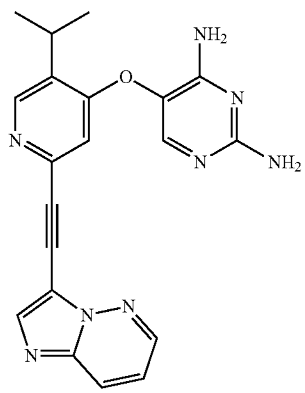 [SMILES: CC(C)c1cnc(C#Cc2cnc3cccnn23)cc1Oc1cnc(N)nc1N] | 5-((2-(imidazo[1,2-b]pyridazin-3-ylethynyl)-5-isopropylpyridin-4-yl)oxy)pyrimidine-2,4-diamine | 2,4-dimethoxybromo-benzene was replaced with 3-bromoimidazo[1,2-b]pyridazine. | $^1$H NMR (400 MHz, CD$_3$OD) δ 8.63 (s, 1H), 8.42 (s, 1H), 8.13-8.10 (m, 2H), 7.66 (s, 1H), 7.39-7.37 (m, 1H), 6.95 (s, 1H), 3.53-3.48 (m, 1H), 1.43 (d, J = 6.8 Hz, 6H). MS m/z (ESI): 386.9 [M + H]$^+$. |

Example 37: preparation of 5-((2-(aminomethyl)-5-isopropylpyridin-4-yl)oxy)pyrimidine-2,4-diamine (C157, compound 157) and 5-((2-((dimethylamino)methyl)-5-isopropylpyridin-4-yl)oxy)pyrimidine-2,4-diamine (C219, compound 219)

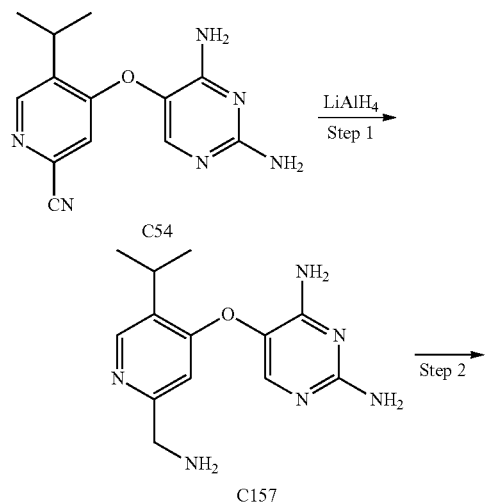

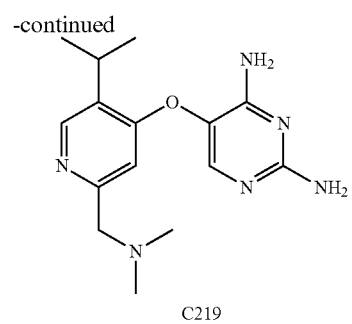

Step 1:

C54 (100 mg, 0.37 mmol) was dissolved in tetrahydrofuran (10 mL), and lithium aluminum hydride (84 mg, 2.22 mmol) was added at 0° C. The reaction was stirred at 0° C. for 30 minutes. LC-MS indicated the reaction was complete. Then, the reaction was quenched by adding water (1 mL), and filtered. The filtrate was concentrated to dryness, and the residue was purified by the Prep-HPLC method to afford compound C157 (100 mg, yellow solid, yield 98.5%).

$^1$H NMR (400 MHz, CD$_3$OD) δ 8.55 (s, 1H), 7.73 (s, 1H), 7.03 (s, 1H), 4.20 (s, 2H), 3.48-3.45 (m, 1H), 1.39 (d, J=7.2 Hz, 6H). MS m/z (ESI): 274.9 [M+H]$^+$.

Step 2:

C157 (60 mg, 0.22 mmol) was dissolved in ethanol (10 mL), and an aqueous solution of formaldehyde (17.7 mg, 0.22 mmol) and benzotriazole (26 mg, 0.22 mmol) were sequentially added. The reaction was stirred at room temperature for 6 hours, followed by addition of sodium borohydride (41.5 mg, 1.10 mmol), and then the reaction was stirred at room temperature for 1 hour. LC-MS detected the product was formed. The reaction was filtered, the filtrate was concentrated to dryness, and the residue was purified by the Prep-HPLC method to afford C219 (1 mg, white solid, yield 1.5%).

$^1$H NMR (400 MHz, CD$_3$OD) δ 8.59 (s, 1H), 7.77 (s, 1H), 7.05 (s, 1H), 4.37 (s, 2H), 3.49-3.46 (m, 1H), 2.92 (s, 6H), 1.40 (d, J=6.8 Hz, 6H). MS m/z (ESI): 302.8 [M+H]$^+$.

Example 38: preparation of 5-((2-(ethylamino)-5-(prop-1-en-2-yl)pyridin-4-yl)oxy)pyrimidine-2,4-diamine (C214, compound 214)

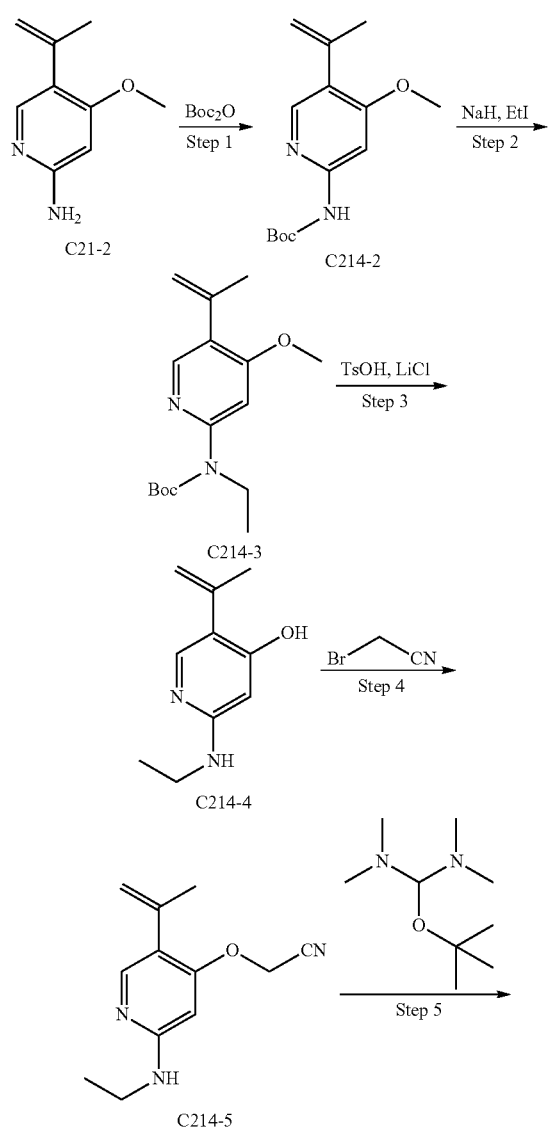

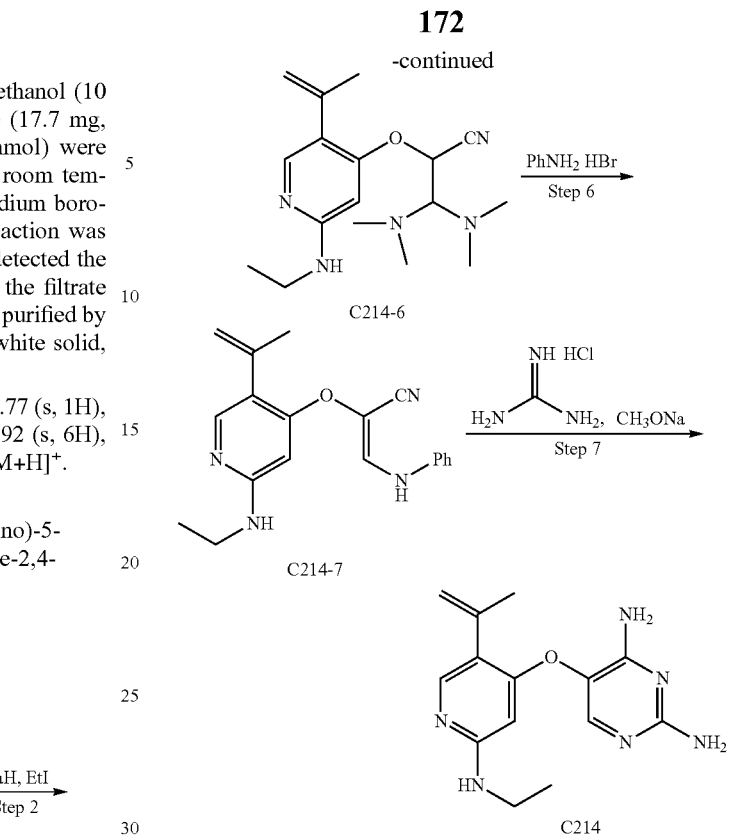

Step 1:

Compound C21-2 (10 g, 0.061 mol) was dissolved in tert-butanol (30 mL), di-tert-butyl dicarbonate (13 g, 0.073 mol) was added, and the reaction solution was stirred at 30° C. for 16 hours. LC-MS indicated the reaction of the starting materials was substantially complete. Then, the reaction was added with purified water (150 mL), and extracted with ethyl acetate (200 mL×3). The organic phases were combined, washed with an aqueous solution of NaCl (100 mL), added with anhydrous sodium sulfate (20 g), dried for 30 min, filtered, and concentrated under reduced pressure to afford a crude product, which was purified by column chromatography on silica gel (petroleum ether:ethyl acetate=10:1~5:1) to afford compound C214-2 (10 g, yellow oily liquid, yield 62%). MS m/z (ESI): 265.1 [M+H]$^+$.

Step 2:

Compound C214-2 (10 g, 0.038 mol) was dissolved in DMF (30 mL), sodium hydride (1.8 g, 0.076 mol) was added, and the reaction solution was stirred at 0° C. for 15 minutes. Then, iodoethane (8.9 g, 0.057 mmol) was added, and the reaction solution was stirred at 0° C. for 1 hour. LC-MS indicated the reaction of the starting materials was substantially complete. Then, then reaction was added with purified water (150 mL), and extracted with ethyl acetate (200 mL×3). The organic phases were combined, washed with an aqueous solution of NaCl (100 mL), added with anhydrous sodium sulfate (20 g), dried for 30 min, filtered, and concentrated under reduced pressure to afford a crude product, which was purified by column chromatography on silica gel (petroleum ether:ethyl acetate=10:1~5:1) to afford compound C214-3 (5.5 g, light yellow oily liquid, yield 55%). MS m/z (ESI): 292.9 [M+H]$^+$.

Step 3:

Compound C214-3 (5 g, 0.026 mol) was dissolved in N-methylpyrrolidone (20 mL), p-toluenesulfonic acid (22.5 g, 0.13 mol) and lithium chloride (5.5 g, 0.13 mol) were sequentially added, and the reaction solution was stirred at 180° C. for 1 hour. LC-MS indicated the reaction of the starting materials was complete. The reaction solution was directly used in the next step. MS m/z (ESI): 179.0 [M+H]⁺.

Step 4:

DMF (10 mL) was added to the reaction solution of compound C214-4, then bromoacetonitrile (6.9 g, 0.056 mol) and potassium carbonate (39 g, 0.28 mol) were sequentially added, and the reaction solution was stirred at room temperature for 16 hours. LC-MS indicated the reaction of the starting materials was complete. The reaction was quenched by adding water (100 mL), and extracted with ethyl acetate (100 mL×3). The organic phases were combined, washed once with saturated brine (100 mL), then dried over anhydrous sodium sulfate (30 g) for half an hour, filtered, and concentrated under reduced pressure to afford a crude product, which was purified by column chromatography on silica gel (petroleum ether:ethyl acetate=5:1~1:1) to afford compound C214-5 (4 g, brown oily liquid, yield 67%). MS m/z (ESI): 218.0 [M+H]⁺.

Step 5:

Compound C214-5 (3.5 g, 0.016 mol) was dissolved in DMF (20 mL), tert-butoxy bis(dimethylamino)methane (8.4 g, 0.048 mol) was added, and the reaction solution was stirred at 100° C. for 1 hour. LC-MS indicated the reaction of the starting materials was complete. The reaction solution was quenched by adding water (100 mL), and extracted with ethyl acetate (100 mL×3). The organic phases were combined, washed with saturated brine (50 mL×3), then dried over anhydrous sodium sulfate (20 g) for half an hour, filtered, and concentrated under reduced pressure to afford a crude product, which was purified by column chromatography on silica gel (petroleum ether:ethyl acetate=5:1~1:1) to afford compound C214-6 (2.3 g, brown oily liquid, yield 45%). MS m/z (ESI): 273.1 [M+H]⁺.

Step 6:

Compound C214-6 (2.3 g, 7.32 mmol) was dissolved in ethanol (10 mL), aniline hydrobromide (1.9 g, 0.011 mol) was added, and the reaction solution was stirred at 100° C. for 16 hours. LC-MS indicated the reaction of the starting materials was complete. The reaction solution was cooled to room temperature, quenched by adding water (50 mL), and extracted with ethyl acetate (50 mL×3). The organic phases were combined, then washed with saturated brine (50 mL), added with anhydrous sodium sulfate (10 g), dried for half an hour, and filtered. The filtrate was concentrated under reduced pressure to afford a crude product, which was purified by column chromatography on silica gel (petroleum ether:ethyl acetate=1:1), to afford compound C214-7 (800 mg, red solid, yield 35%). MS m/z (ESI): 321.1 [M+H]⁺.

Step 7:

Compound C214-7 (100 mg, 0.31 mmol) was dissolved in ethanol (5 mL), guanidine hydrochloride (89 mg, 0.93 mmol) and sodium methoxide (50 mg, 0.93 mmol) were sequentially added, and the reaction was stirred at 90° C. for 16 hours. LC-MS indicated the reaction of the starting materials was complete. The reaction solution was cooled to room temperature, and concentrated under reduced pressure to afford a crude product, which was purified by column chromatography on silica gel (ethyl acetate) to afford compound C214 (24 mg, light yellow solid, yield 24%).

¹H NMR (400 MHz, CD₃OD) δ 7.80 (s, 1H), 7.57 (s, 1H), 5.83 (s, 1H), 5.17 (s, 1H), 5.13 (s, 1H), 3.22 (q, J=6.8 Hz, 2H), 2.17 (s, 3H), 1.18 (t, J=7.2 Hz, 3H). MS m/z (ESI): 286.8 [M+H]⁺.

The compound in the following table was prepared according to methods similar to that described in Example 38.

| No. | Compound Structure | Compound Name | Starting material or regent different from that in Example 38 | Characterization Data |
|---|---|---|---|---|
| C192 (compound 192) | 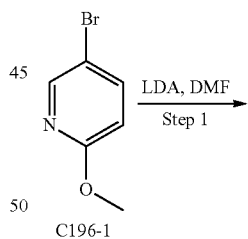 | 5-((2-(methylamino)-5-(prop-1-en-2-yl)pyridin-4-yl)oxy)pyrimidine-2,4-diamine | Iodoethane in Step 2 was replaced with iodomethane. | ¹H NMR (400 MHz, CD₃OD) δ 7.82 (s, 1H), 7.58 (s, 1H), 5.86 (s, 1H), 5.18 (s, 1H), 5.15 (s, 1H), 2.82 (s, 3H), 2.17 (s, 3H). MS m/z (ESI): 272.8 [M + H]⁺. |

Example 39: preparation of 5-((2-methoxy-5-(prop-1-en-2-yl)pyridin-4-yl)methyl)pyrimidine-2,4-diamine (C196, compound 196)

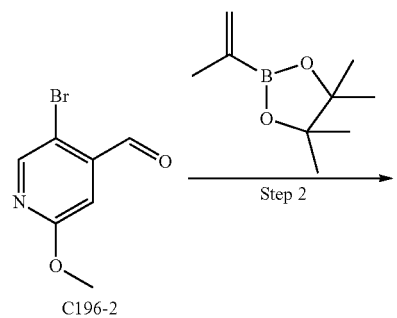

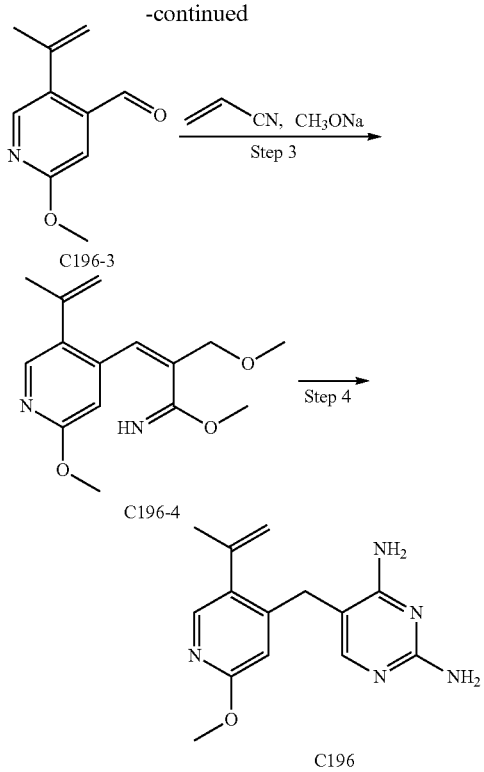

Step 1:

Compound C196-1 (10 g, 0.053 mol) was dissolved in anhydrous tetrahydrofuran (50 mL), lithium diisopropylamide (32 mL, 0.064 mol) was added at −65° C., and the reaction solution was stirred at −65° C. for 15 minutes. Then, DMF (5.8 g, 0.080 mol) was dropwise added, and the reaction solution was stirred at −65° C. for 30 minutes. LC-MS indicated the reaction of the starting materials was substantially complete.

The reaction solution was poured into water (100 mL), and extracted with ethyl acetate (200 mL×3). The organic phases were combined, washed with saturated brine (100 mL), dried over anhydrous sodium sulfate (20 g) for half an hour, filtered, and concentrated under reduced pressure to afford a crude product, which was purified by column chromatography on silica gel (petroleum ether:ethyl acetate=100:1), to afford compound C196-2 (4 g, yellow oily liquid, yield 36%). MS m/z (ESI): 215.8 [M+H]⁺.

Step 2:

Compound C196-2 (4 g, 0.019 mol) was dissolved in 1,4-dioxane (50 mL), and isopropenylpinacol borate (6.25 g, 0.072 mol), potassium carbonate (7.7 g, 0.056 mol), Pd(PPh₃)₄ (0.1 g) and water (5 mL) were sequentially added. Purge with nitrogen was performed for 3 times, and the reaction solution was stirred at 100° C. for 18 hours. LC-MS indicated the reaction of the starting materials was complete. The reaction solution was cooled to room temperature, and filtered. The filtrate was concentrated under reduced pressure to afford a crude product, which was purified by column chromatography on silica gel (petroleum ether:ethyl acetate=10:1), to afford compound C196-3 (2.4 g, yellow oily liquid, yield 73%). MS m/z (ESI): 178.0 [M+H]⁺.

Step 3

Compound C196-3 (354 mg, 0.0020 mol) was dissolved in methanol (10 mL), acrylonitrile (212 mg, 0.0040 mol), sodium methoxide (212 mg, 0.0030 mol) were sequentially added, and the reaction solution was stirred at room temperature for 16 hours. LC-MS indicated the reaction of the starting materials was substantially complete. The reaction was filtered, and concentrated under reduced pressure to afford a crude product C196-4, and the crude product was directly used in the next step (350 mg, light yellow oily liquid, yield 64%). MS m/z (ESI): 205.9 [M+H]⁺.

Step 4:

Compound C196-4 (300 mg, 1.09 mmol) was dissolved in methanol (20 mL), guanidine carbonate (1.3 g, 10.9 mmol) was added, and the reaction solution was stirred at 80° C. for 16 hours. LC-MS indicated the reaction of the starting materials was complete. The reaction solution was filtered, and the filtrate was concentrated under reduced pressure to afford a crude product, which was purified by column chromatography on silica gel (petroleum ether:ethyl acetate=5:1) to afford compound C196 (150 mg, white solid, yield 51%).

¹H NMR (400 MHz, DMSO-d) δ 7.96 (s, 1H), 7.23 (s, 1H), 6.50 (s, 1H), 5.26 (s, 1H), 4.91 (s, 1H), 3.82 (s, 3H), 3.61 (s, 2H), 1.99 (s, 3H). MS m/z (ESI): 272.0 [M+H]⁺.

Example 40: preparation of N⁴-(2-aminoethyl)-5-((2-bromo-5-isopropylpyridin-4-yl)oxy)pyrimidine-2,4-diamine (C199, compound 199)

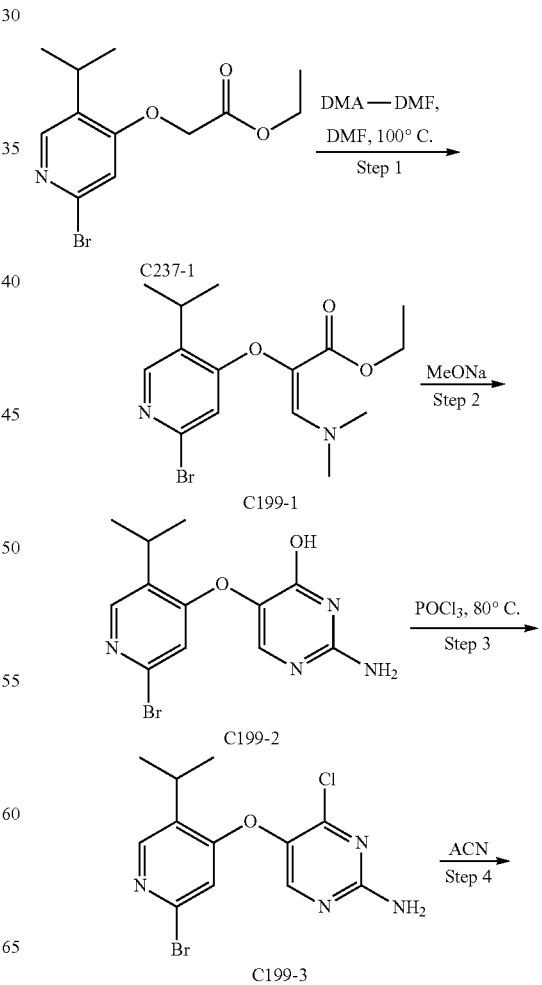

-continued

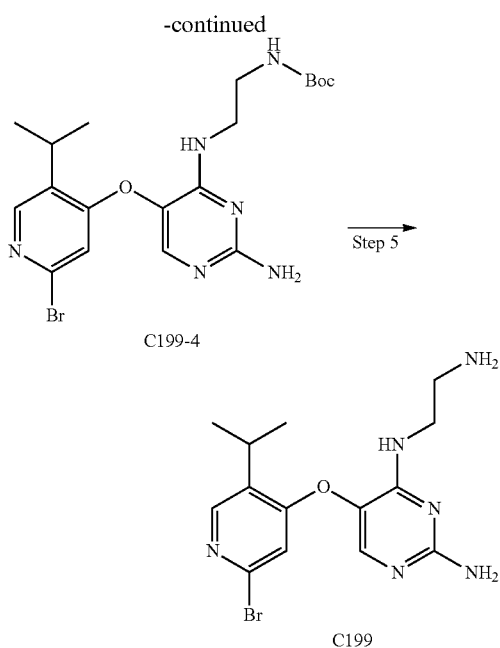

Step 1:

Compound C237-1 (4.5 g, 0.015 mol) was dissolved in DMF (30 mL), DMF-DMA (5.6 g, 0.047 mol) was added, and the reaction solution was stirred at 130° C. for 16 hours. LC-MS indicated the reaction of the starting materials was complete. The reaction was quenched by adding water (100 mL), and extracted with ethyl acetate (100 mL×3). The organic phases were combined, washed once with saturated brine (100 mL), then dried over anhydrous sodium sulfate (10 g) for half an hour, filtered, and concentrated under reduced pressure to afford a crude product, which was purified by column chromatography on silica gel (petroleum ether:ethyl acetate=10:1~5:1) to afford compound C199-1 (2 g, yellow oily liquid, yield 40%). MS m/z (ESI): 342.8 [M+H]$^+$.

Step 2:

Compound C199-1 (2 g, 0.0056 mol) was dissolved in ethanol (20 mL), guanidine hydrochloride (3.2 g, 0.034 mol) and sodium methoxide (1.82 g, 0.034 mol) were sequentially added, and the reaction solution was stirred at 90° C. for 16 hours. LC-MS indicated the reaction of the starting materials was complete. The reaction solution was filtered, the filtrate was concentrated under reduced pressure, added with purified water (50 mL), then adjusted to a pH value of 7 with 1M HCl, and extracted with ethyl acetate (100 mL×3). The organic phases were combined, washed once with saturated brine (100 mL), then dried over anhydrous sodium sulfate (10 g) for half an hour, filtered, and concentrated to afford a crude product, which was purified by column chromatography on silica gel (petroleum ether:ethyl acetate=20:1~5:1) to afford compound C199-2 (0.7 g, light yellow solid, yield 38%).

$^1$H NMR (400 MHz, DMSO-d$_6$) δ 8.19 (s, 1H), 7.88 (s, 1H), 7.67 (s, 2H), 7.16 (s, 1H), 3.25-3.18 (m, 1H), 1.27 (d, J=6.8 Hz, 6H). MS m/z (ESI): 324.8 [M+H]$^+$.

Step 3:

Compound C199-2 (200 mg, 0.617 mmol) was dissolved in phosphorus oxychloride (1 mL), the reaction was heated to 80° C., and stirred for 16 hours. LC-MS indicated the reaction of the starting materials was complete. The reaction solution was cooled to room temperature, quenched by adding water (30 mL), then adjusted to a pH value of 7-8 with sodium bicarbonate, and extracted with dichloromethane (50 mL×3). The organic phases were combined, then washed with saturated brine (50 mL), added with anhydrous sodium sulfate, dried for half an hour, and filtered. The filtrate was concentrated under reduced pressure, and the crude product was purified by column chromatography on silica gel (petroleum ether:ethyl acetate=10:1~1:1), to afford compound C199-3 (90 mg, light yellow solid, yield 42%).

$^1$H NMR (400 MHz, CDCl$_3$) δ 8.24 (s, 1H), 8.16 (s, 1H), 6.58 (s, 1H), 5.35 (s, 2H), 3.38-3.35 (m, 1H), 1.38 (d, J=6.8 Hz, 6H). MS m/z (ESI): 342.7 [M+H]$^+$.

Step 4:

Compound C199-3 (15 mg, 0.044 mmol) was dissolved in acetonitrile (5 mL), tert-butyl (2-aminoethyl)carbamate (0.5 mL) was added, and the reaction solution was stirred at 90° C. for 16 hours. LC-MS indicated the reaction of the starting materials was substantially complete. The reaction solution was concentrated under reduced pressure to afford a crude product C199-4, and this crude product was directly used in the next step. (10 mg, light yellow oily liquid, yield 47%). MS m/z (ESI): 467.0 [M+H]$^+$.

Step 5:

Compound C199-4 (10 mg, 0.021 mmol) was dissolved in dichloromethane (5 mL), trifluoroacetic acid (1 mL) was added, and the reaction solution was stirred at room temperature for 30 minutes. LC-MS indicated the reaction of the starting materials was substantially complete. The reaction solution was concentrated under reduced pressure to afford a crude product, which was purified by preparative high-performance liquid chromatography to afford compound C199 (4 mg, white solid, yield 50%).

$^1$H NMR (400 MHz, CD$_3$OD) δ 8.26 (s, 1H), 7.80 (s, 1H), 7.21 (s, 1H), 3.84 (t, J=5.6 Hz, 6H), 3.42-3.37 (m, 1H), 3.25 (t, J=5.6 Hz, 2H), 1.37 (d, J=7.2 Hz, 6H). MS m/z (ESI): 366.7 [M+H]$^+$.

The compound in the following table was prepared according to a method similar to that described in Example 40.

| No. | Compound Structure | Compound Name | Starting material or regent different from that in Example 40 | Characterization Data |
|---|---|---|---|---|
| C217 (compound 217) | 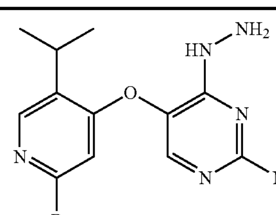 | 5-((2-bromo-5-isopropylpyridin-4-yl)oxy)-4-hydrazineylpyrimidin-2-amine | Tert-butyl (2-aminoethyl)carbamate in Step 4 was replaced with tert-butyl hydrazinecarboxylate. | $^1$H NMR (400 MHz, CD$_3$OD) δ 8.50 (s, 1H), 7.72 (s, 1H), 7.38 (s, 1H), 2.98-2.92 (m, 1H), 1.32 (d, J = 6.8 Hz, 6H). MS m/z (ESI): 338.8 [M + H]$^+$. |

Example 41: preparation of 5-((2-ethynyl-5-isopropylpyridin-4-yl)oxy)-N⁴-isopropylpyrimidine-2,4-diamine (C212, compound 212)

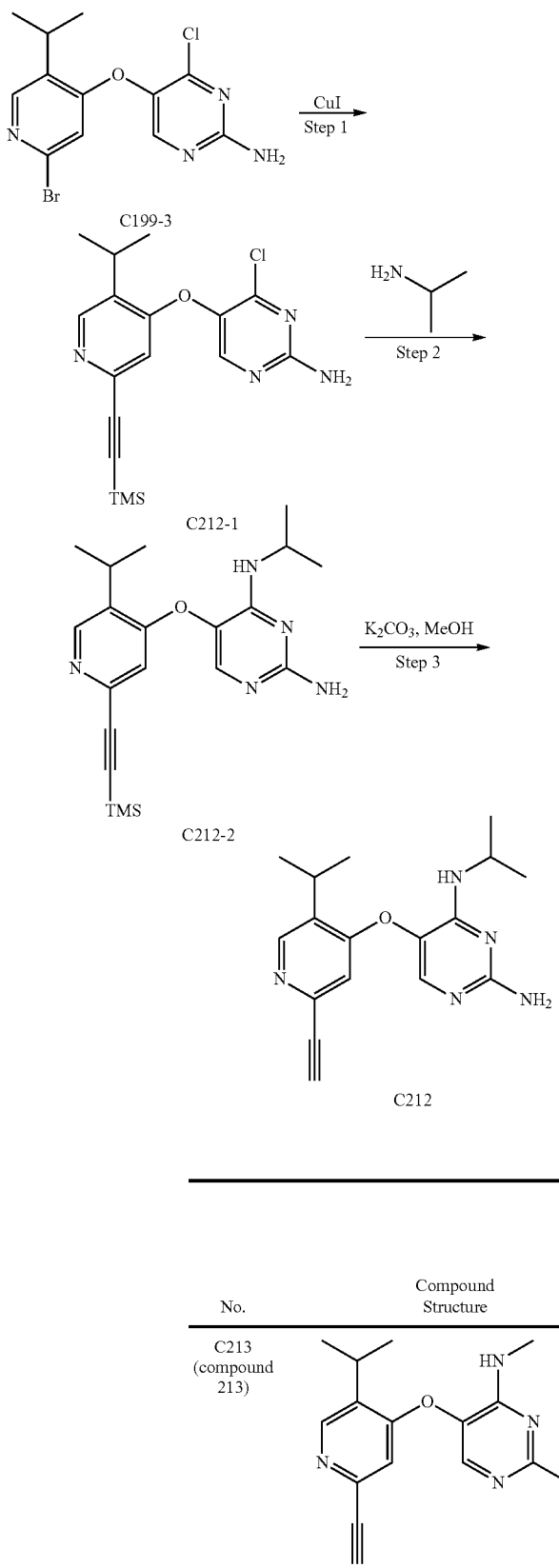

Step 1:

Compound C199-3 (700 mg, 0.020 mol) was dissolved in anhydrous tetrahydrofuran (20 mL), trimethylsilylacetylene (200 mg, 0.020 mol), N,N-diisopropylethylamine (1.2 g, 0.0095 mol), cuprous iodide (40 mg, 0.21 mmol) and Pd(PPh$_3$)$_2$Cl$_2$ (143 mg, 0.21 mmol) were sequentially added, and the reaction solution was stirred under the protection of nitrogen at 50° C. for 2 hours. LC-MS indicated the reaction of the starting materials was substantially complete. The reaction solution was concentrated under reduced pressure to afford a crude product, which was purified by column chromatography on silica gel (petroleum ether:ethyl acetate=10:1~5:1), to afford compound C212-1 (400 mg, yellow solid, yield 55%). MS m/z (ESI): 361.1 [M+H]⁺.

Step 2:

Compound C212-1 (20 mg, 0.056 mmol) was dissolved in acetonitrile (5 mL), isopropylamine was added, and the reaction solution was stirred at 90° C. for 16 hours. LC-MS indicated the reaction of the starting materials was substantially complete. The reaction solution was concentrated under reduced pressure to afford a crude product, which was purified by preparative thin layer chromatography on silica gel (dichloromethane:methanol=10:1), to afford compound C212-2 (15 mg, yellow oily liquid, yield 71%). MS m/z (ESI): 383.8 [M+H]⁺.

Step 3:

Compound C212-2 (15 mg, 0.039 mmol) was dissolved in methanol (5 mL), potassium carbonate (5 mg) was added, and the reaction solution was stirred at room temperature for 20 minutes. LC-MS indicated the reaction of the starting materials was complete. The reaction solution was filtered, and the filtrate was concentrated under reduced pressure to give a crude product, which was purified by preparative thin layer chromatography on silica gel (dichloromethane:methanol=10:1), to afford compound C212 (3 mg, white solid, yield 25%).

¹H NMR (400 MHz, CD$_3$OD) δ 8.36 (s, 1H), 7.52 (s, 1H), 6.75 (s, 1H), 4.42-4.39 (m, 1H), 3.70 (s, 1H), 3.50-3.45 (m, 1H), 1.38 (d, J=7.2 Hz, 6H), 1.21 (d, J=6.4 Hz, 6H). MS m/z (ESI): 311.8 [M+H]⁺.

The compounds in the following table were prepared according to methods similar to that described in Example 41.

| No. | Compound Structure | Compound Name | Starting material or regent different from that in Example 41 | Characterization Data |
|---|---|---|---|---|
| C213 (compound 213) | 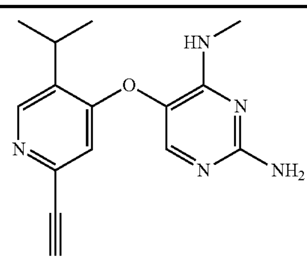 | 5-((2-ethynyl-5-isopropylpyridin-4-yl)oxy)-N⁴-methylpyrimidine-2,4-diamine | Isopropylamine in Step 2 was replaced with methylamine. | ¹H NMR (400 MHz, CD$_3$OD) δ 8.36 (s, 1H), 7.54 (s, 1H), 6.76 (s, 1H), 3.70 (s, 1H), 3.45 (m, 1H), 2.94 (s, 3H), 1.39 (d, J = 6.8 Hz, 6H). MS m/z (ESI): 283.8 [M + H]⁺. |

| No. | Compound Structure | Compound Name | Starting material or regent different from that in Example 41 | Characterization Data |
|---|---|---|---|---|
| C211 (compound 211) | 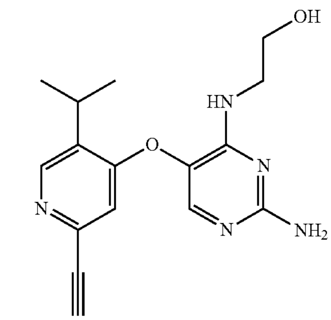 [SMILES: C#Cc1cc(Oc2cnc(N)nc2NCCO)c(C(C)C)cn1] | 2-((2-amino-5-((2-ethynyl-5-isopropylpyridin-4-yl)oxy)pyrimidin-4-yl)amino)ethanol | Isopropylamine in Step 2 was replaced with ethanolamine. | $^1$H NMR (400 MHz, CD$_3$OD) δ 8.34 (s, 1H), 7.54 (s, 1H), 6.78 (s, 1H), 3.69-3.67 (m, 3H), 3.57-3.54 (m, 2H), 3.49-3.46 (m, 1H), 1.39 (d, J = 6.8 Hz, 6H). MS m/z (ESI): 313.9 [M + H]$^+$. |
| C216 (compound 216) | 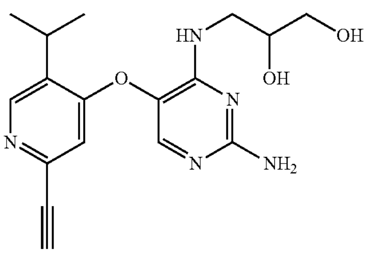 [SMILES: C#Cc1cc(Oc2cnc(N)nc2NCC(O)CO)c(C(C)C)cn1] | 3-((2-amino-5-((2-ethynyl-5-isopropylpyridin-4-yl)oxy)pyrimidin-4-yl)amino)propane-1,2-diol | Isopropylamine in Step 2 was replaced with 3-aminopropane-1,2-diol. | $^1$H NMR (400 MHz, CD$_3$OD) δ 8.35 (s, 1H), 7.57 (s, 1H), 6.80 (s, 1H), 3.81-3.79 (m, 1H), 3.70 (s, 1H), 3.53-3.44 (m, 5H), 1.39 (d, J = 6.8 Hz, 6H). MS m/z (ESI): 343.8 [M + H]$^+$. |

Reference Example: preparation of 5-((5-chloro-2-isopropylpyridin-3-yl)oxy)pyrimidine-2,4-diamine (00, compound 10)

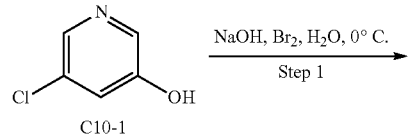
C10-1 → (NaOH, Br$_2$, H$_2$O, 0° C., Step 1)

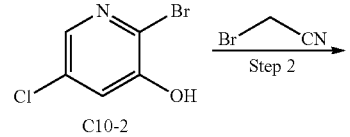
C10-2 → (BrCH$_2$CN, Step 2)

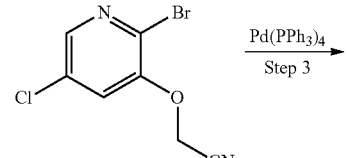
C10-3 → (Pd(PPh$_3$)$_4$, Step 3)

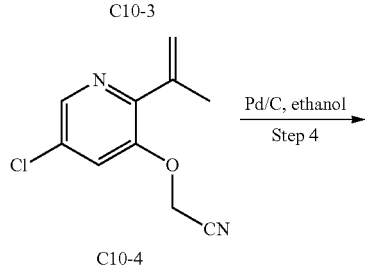
C10-4 → (Pd/C, ethanol, Step 4)

-continued

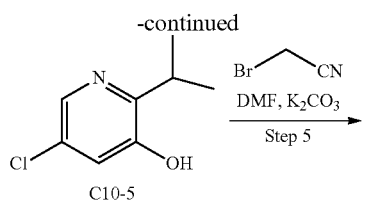
C10-5 → (BrCH$_2$CN, DMF, K$_2$CO$_3$, Step 5)

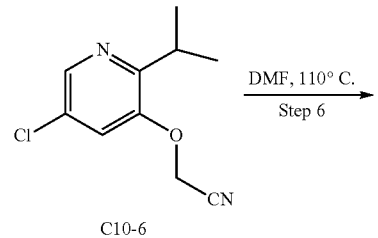
C10-6 → (DMF, 110° C., Step 6)

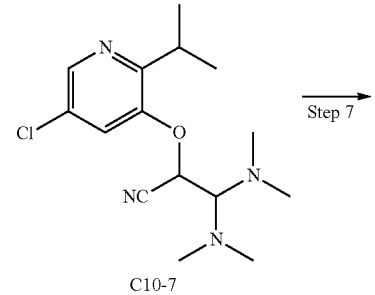
C10-7 → Step 7

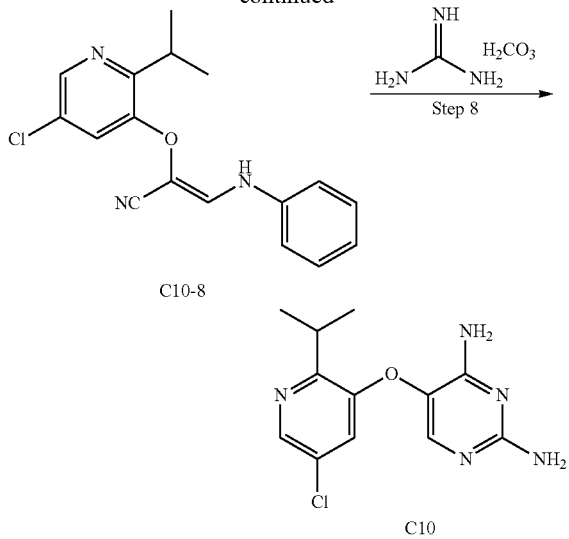

Step 1:

At 20° C., to compound C10-1 (20 g, 0.155 mol) in a 10% aqueous solution of NaOH (140 mL), Br$_2$ (24.5 g, 0.153 mol) in a 10% aqueous solution of NaOH (144 mL) was slowly dropwise added. The reaction was stirred at this temperature for 30 min, and then the reaction solution was slowly poured into water (300 mL). The large amount of white solid thus obtained was filtered to afford compound C10-2 (15 g, crude product), and the crude product was directly used in the next step. MS m/z (ESI): 207.8 [M+H]$^+$.

Step 2:

At 25° C., compound C10-2 (17 g, 0.07 mol), bromoacetonitrile (17.5 g, 0.1 mol) were dissolved in DMF (100 mL), and then K$_2$CO$_3$ (19.3 g, 0.14 mol) was slowly added. The reaction mixture was stirred at this temperature overnight. The reaction solution was slowly poured into water (500 mL). The aqueous phase was extracted with ethyl acetate, the organic phase was washed with saturated brine, dried over anhydrous sodium sulfate, filtered, and concentrated under reduced pressure to give a crude product. The crude product was purified by column chromatography on silica gel (petroleum ether:ethyl acetate=10:1, 100~200 mesh silica gel) to afford compound C10-3 (8.5 g, light yellow solid, yield: 49.36%).

$^1$H NMR (400 MHz, DMSO-d$_6$) δ 8.23 (s, 1H), 7.94 (s, 1H), 5.38 (s, 2H); MS m/z (ESI): 246.7 [M+H]$^+$.

Step 3:

At 25° C. and under the protection of nitrogen, tetrakis(triphenylphosphine)palladium(0.8 g) was added to a mixed system of compound C10-3 (8.5 g, 0.034 mol), isopropenylpinacol borate (11.6 g, 0.069 mol), water (10 mL), potassium carbonate (9.6 g, 0.069 mol) and 1,4-dioxane (200 mL). The reaction was stirred at 90° C. overnight. The reaction solution was poured into water (300 mL). The aqueous phase was extracted with ethyl acetate, the organic phase was washed with saturated brine, dried over anhydrous sodium sulfate, filtered, concentrated under reduced pressure to give a crude product. The crude product was purified by column chromatography on silica gel (petroleum ether:ethyl acetate=10:1, 100~200 mesh silica gel) to afford compound C10-4 (5.5 g, crude product, light yellow oil). MS m/z (ESI): 208.9 [M+H]$^+$.

Step 4:

At 20° C., wet Pd/C (0.5 g) was added to a solution of compound C10-4 (5.5 g, 0.0259 mol) in ethanol (50 mL). Purge with hydrogen was performed 3 times, the reaction was performed under hydrogen (0.4 Mpa), and then the reaction mixture was filtered. The filtrate was concentrated to dryness to afford compound C10-5 (5.2 g, light brown oil, crude product). The crude product was directly used in the next step. MS m/z (ESI): 171.9 [M+H]$^+$.

Step 5:

At 25° C., K$_2$CO$_3$ (8.4 g, 0.06 mol) was slowly added to a solution of compound C10-5 (5.2 g, 0.03 mol) and bromoacetonitrile (5.5 g, 0.046 mol) in DMF (50 mL). The reaction was stirred at this temperature for 16 hours. The reaction solution was poured into water (300 mL). The aqueous phase was extracted with ethyl acetate, separated, the organic phase was washed with saturated brine, dried over anhydrous sodium sulfate, filtered, and concentrated under reduced pressure to give a crude product. The crude product was purified by column chromatography on silica gel (petroleum ether:ethyl acetate=30:1, 100~200 mesh silica gel) to afford compound C10-6 (2.7 g, oil product, crude product). MS m/z (ESI): 210.9 [M+H]$^+$.

Step 6:

At 25° C., tert-butoxy bis(dimethylamino)methane (1 mL) was added to a solution of compound C10-6 (1 g, 4.76 mmol) in DMF (5 mL). The reaction was stirred at 100° C. for 1 h. The reaction solution was poured into water (50 mL). The aqueous phase was extracted with ethyl acetate, the organic phase was washed with saturated brine, dried over anhydrous sodium sulfate, filtered, and concentrated under reduced pressure to give a crude product. The crude product was purified by column chromatography on silica gel (petroleum ether:ethyl acetate=5:1, 100~200 mesh silica gel) to afford compound C10-7 (0.84 g, oil, crude product). MS m/z (ESI): 265.9 [M+H]$^+$.

Step 7:

At 25° C., aniline hydrochloride (0.2 g, 1.5 mmol) was added to a solution of compound C10-7 (0.4 g, 1.3 mmol) in DMF (2 mL). The reaction was stirred at 100° C. for 5 hours. TLC (petroleum ether:ethyl acetate=5:1, UV) indicated the reaction was complete. The reaction solution was poured into water (20 mL). The aqueous phase was extracted with ethyl acetate, the organic phase was washed with saturated brine, dried over anhydrous sodium sulfate, filtered, and concentrated under reduced pressure to give a crude product. The crude product was purified by column chromatography on silica gel (petroleum ether:ethyl acetate=20:1, 100~200 mesh silica gel) to afford C10-8 (0.26 g, light yellow solid, yield: 64.00%).

Step 8:

At 25° C., guanidine carbonate (155 mg, 1.27 mmol) was added to a solution of compound C10-8 (200 mg, 0.64 mmol) in ethanol (10 mL). The reaction was stirred under microwave radiation at 100° C. for 1 h. The reaction solution was concentrated under reduced pressure to give a crude product. The crude product was added to a solution of petroleum ether:ethyl acetate=1:30, stirred for 1 h, and filtered to afford compound C10 (20 mg, light yellow solid, yield: 11.2%, compound 10).

$^1$H NMR (400 MHz, DMSO-d$_6$) δ 8.23 (s, 1H), 7.58 (s, 1H), 6.90 (s, 1H), 6.48 (s, 2H), 6.00 (s, 2H), 3.53-3.49 (m, 1H), 1.26 (d, J=6.8 Hz, 6H); MS m/z (ESI): 279.9 [M+H]$^+$.

The following compounds were prepared according to methods similar to those described in the above Examples.

| No. | Structure | MS Data |
|---|---|---|
| C24 | 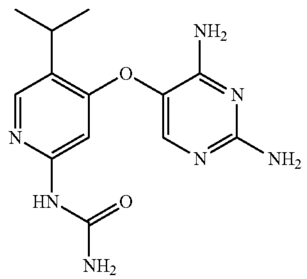 [SMILES: CC(C)c1cnc(NC(N)=O)cc1Oc1cnc(N)nc1N] | 303.9 |
| C25 | 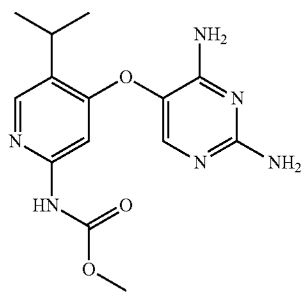 [SMILES: COC(=O)Nc1cc(Oc2cnc(N)nc2N)c(C(C)C)cn1] | 318.9 |
| C28 | 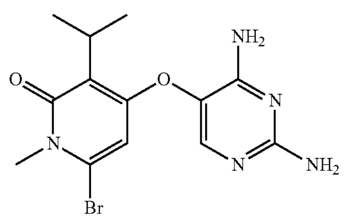 [SMILES: CC(C)c1c(Oc2cnc(N)nc2N)cc(Br)n(C)c1=O] | 353.8 |
| C29 | 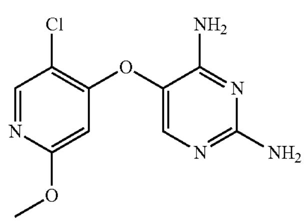 [SMILES: COc1cc(Oc2cnc(N)nc2N)c(Cl)cn1] | 267.8 |
| C32 | 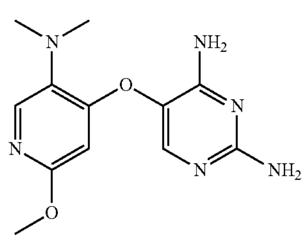 [SMILES: COc1cc(Oc2cnc(N)nc2N)c(N(C)C)cn1] | 276.9 |
| C36 | 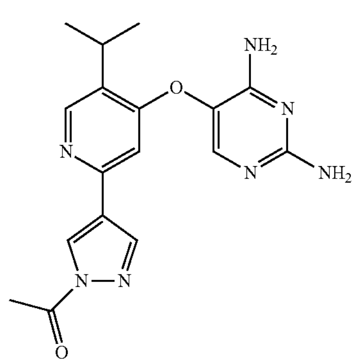 [SMILES: CC(=O)n1cc(-c2cc(Oc3cnc(N)nc3N)c(C(C)C)cn2)cn1] | 353.9 |
| C37 | | 328.9 |
| C50 | | 301.9 |
| C51 | | 301.9 |
| C53 | | 313.9 |
| C55 | | 303.9 |
| C56 | | 289.9 |

| No. | Structure | MS Data |
|---|---|---|
| C57 | 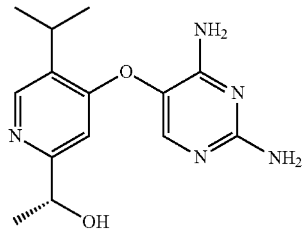 [SMILES: CC(C)c1cnc([C@@H](C)O)cc1Oc1cnc(N)nc1N] | 289.9 |
| C58 | 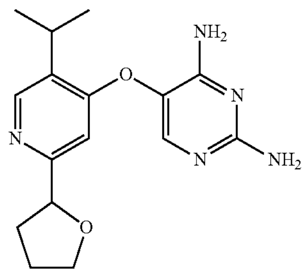 [SMILES: CC(C)c1cnc(C2CCCO2)cc1Oc1cnc(N)nc1N] | 315.9 |
| C59 | 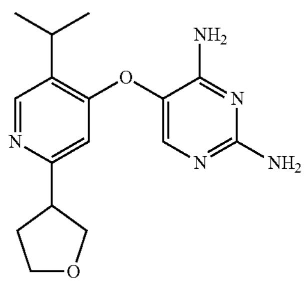 [SMILES: CC(C)c1cnc(C2CCOC2)cc1Oc1cnc(N)nc1N] | 315.9 |
| C60 | 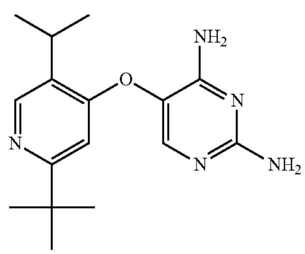 [SMILES: CC(C)c1cnc(C(C)(C)C)cc1Oc1cnc(N)nc1N] | 301.9 |
| C62 | 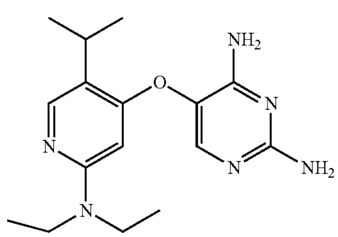 [SMILES: CCN(CC)c1cc(Oc2cnc(N)nc2N)c(C(C)C)cn1] | 316.9 |
| C64 | 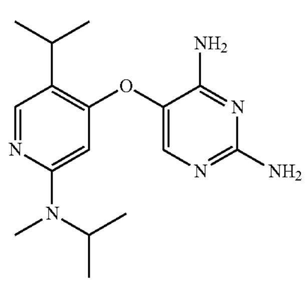 [SMILES: CC(C)c1cnc(N(C)C(C)C)cc1Oc1cnc(N)nc1N] | 316.9 |
| C68 | | 313.9 |
| C69 | | 394.0 |
| C70 | | 350.0 |
| C73 | | 278.9 |
| C74 | | 322.8 |
| C75 | | 370.8 |

-continued

| No. | Structure | MS Data |
|---|---|---|
| C76 | 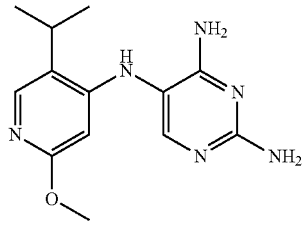 | 274.9 |
| C77 | 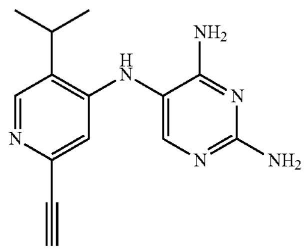 [SMILES: C#Cc1cc(Nc2cnc(N)nc2N)c(C(C)C)cn1] | 268.9 |
| C78 | 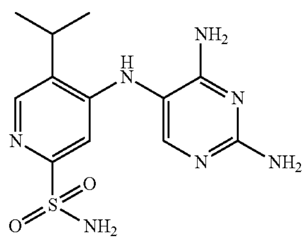 [SMILES: CC(C)c1cnc(S(N)(=O)=O)cc1Nc1cnc(N)nc1N] | 323.9 |
| C79 | 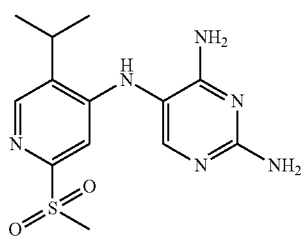 [SMILES: CC(C)c1cnc(S(C)(=O)=O)cc1Nc1cnc(N)nc1N] | 322.9 |
| C80 | 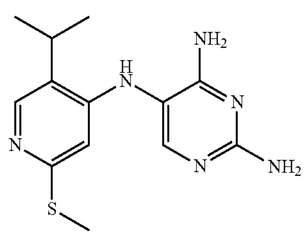 [SMILES: CSc1cc(Nc2cnc(N)nc2N)c(C(C)C)cn1] | 290.9 |
| C81 | 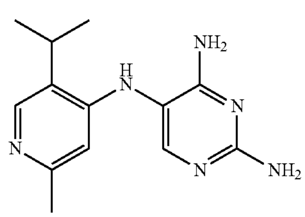 [SMILES: Cc1cc(Nc2cnc(N)nc2N)c(C(C)C)cn1] | 258.9 |

-continued

| No. | Structure | MS Data |
|---|---|---|
| C82 | 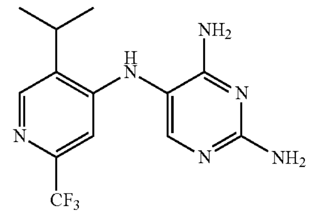 [SMILES: CC(C)c1cnc(C(F)(F)F)cc1Nc1cnc(N)nc1N] | 312.9 |
| C83 | 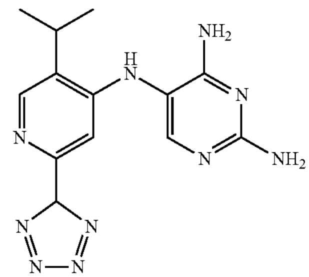 [SMILES: CC(C)c1cnc(C2N=NN=N2)cc1Nc1cnc(N)nc1N] | 312.9 |
| C86 | 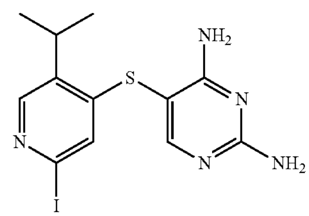 [SMILES: CC(C)c1cnc(I)cc1Sc1cnc(N)nc1N] | 387.8 |
| C87 | 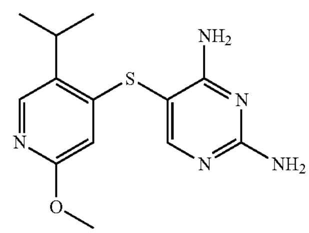 [SMILES: COc1cc(Sc2cnc(N)nc2N)c(C(C)C)cn1] | 291.9 |
| C89 | 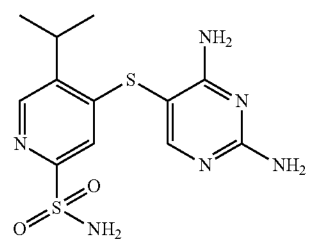 [SMILES: CC(C)c1cnc(S(N)(=O)=O)cc1Sc1cnc(N)nc1N] | 340.8 |
| C90 | 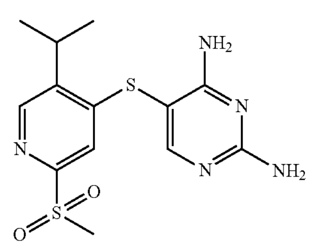 [SMILES: CC(C)c1cnc(S(C)(=O)=O)cc1Sc1cnc(N)nc1N] | 339.9 |

| No. | Structure | MS Data |
|---|---|---|
| C93 | 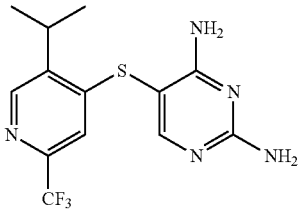 | 329.9 |
| C94 | 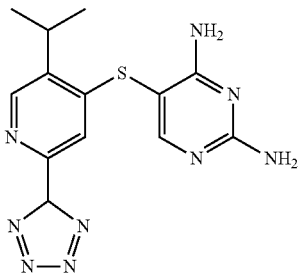 | 329.9 |
| C96 | 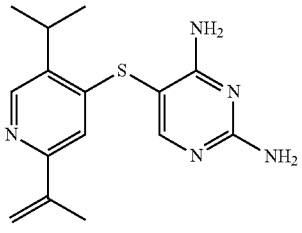 [SMILES: C=C(C)c1cc(Sc2cnc(N)nc2N)c(C(C)C)cn1] | 301.9 |
| C97 | 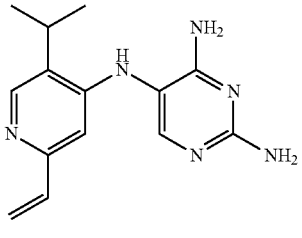 [SMILES: C=Cc1cc(Nc2cnc(N)nc2N)c(C(C)C)cn1] | 270.9 |
| C98 | 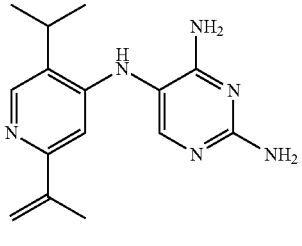 [SMILES: C=C(C)c1cc(Nc2cnc(N)nc2N)c(C(C)C)cn1] | 284.9 |
| C99 | 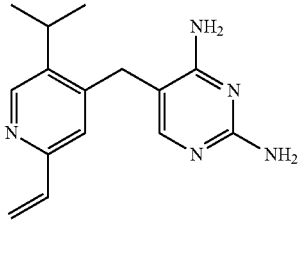 [SMILES: C=Cc1cc(Cc2cnc(N)nc2N)c(C(C)C)cn1] | 269.9 |
| C100 | 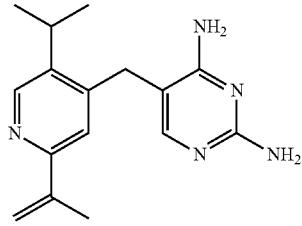 [SMILES: C=C(C)c1cc(Cc2cnc(N)nc2N)c(C(C)C)cn1] | 283.9 |
| C101 | 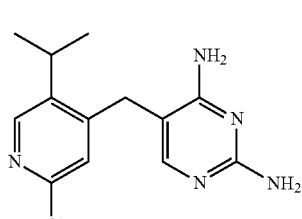 | 277.9 |
| C102 | 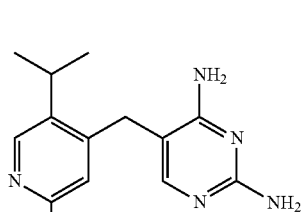 | 321.8 |
| C103 | 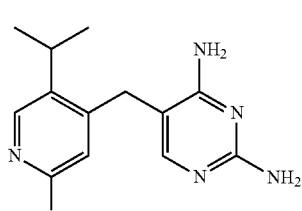 | 369.8 |
| C104 | 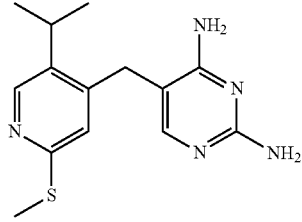 [SMILES: CSc1cc(Cc2cnc(N)nc2N)c(C(C)C)cn1] | 289.9 |
| C105 | 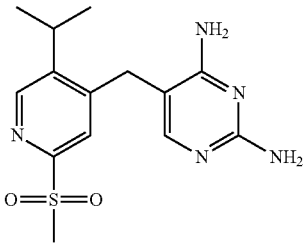 [SMILES: CC(C)c1cnc(S(C)(=O)=O)cc1Cc1cnc(N)nc1N] | 321.9 |

-continued

| No. | Structure | MS Data |
|---|---|---|
| C106 | 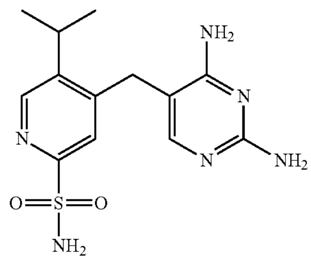 [SMILES: CC(C)c1cnc(S(N)(=O)=O)cc1Cc1cnc(N)nc1N] | 322.9 |
| C107 | 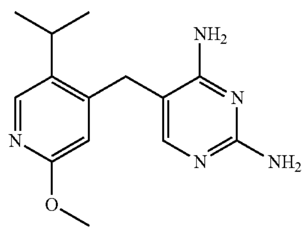 [SMILES: COc1cc(Cc2cnc(N)nc2N)c(C(C)C)cn1] | 273.9 |
| C108 | 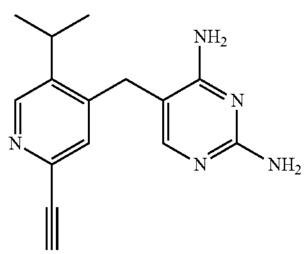 [SMILES: C#Cc1cc(Cc2cnc(N)nc2N)c(C(C)C)cn1] | 267.9 |
| C110 | 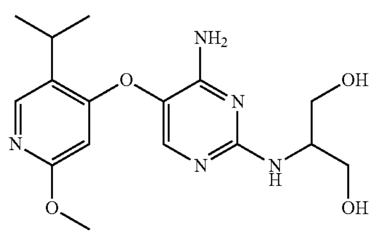 [SMILES: COc1cc(Oc2cnc(NC(CO)CO)nc2N)c(C(C)C)cn1] | 349.9 |
| C112 | 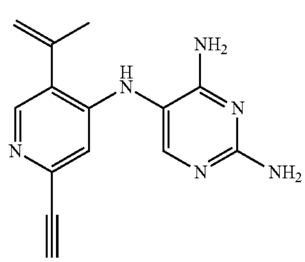 [SMILES: C#Cc1cc(Nc2cnc(N)nc2N)c(C(=C)C)cn1] | 266.9 |
| C113 | 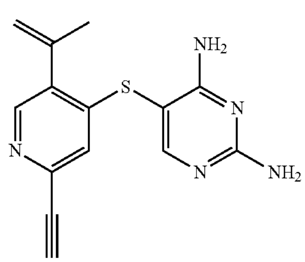 [SMILES: C#Cc1cc(Sc2cnc(N)nc2N)c(C(=C)C)cn1] | 283.8 |

-continued

| No. | Structure | MS Data |
|---|---|---|
| C114 | 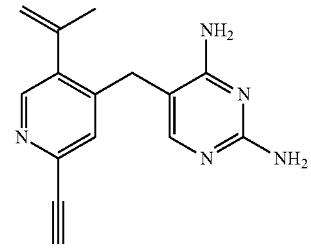 [SMILES: C#Cc1cc(Cc2cnc(N)nc2N)c(C(=C)C)cn1] | 265.9 |
| C123 | 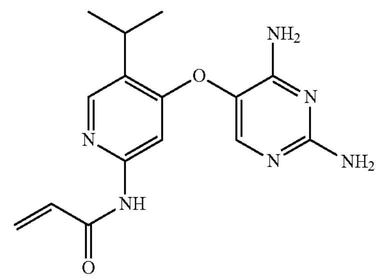 [SMILES: C=CC(=O)Nc1cc(Oc2cnc(N)nc2N)c(C(C)C)cn1] | 314.9 |
| C130 | 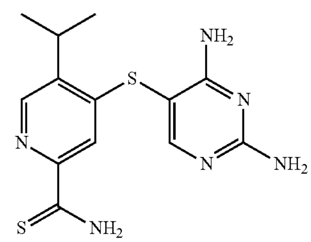 [SMILES: CC(C)c1cnc(C(N)=S)cc1Sc1cnc(N)nc1N] | 320.8 |
| C139 | 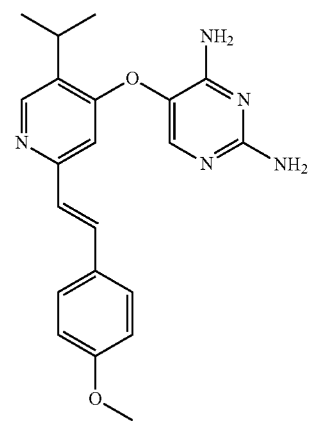 [SMILES: COc1ccc(/C=C/c2cc(Oc3cnc(N)nc3N)c(C(C)C)cn2)cc1] | 377.9 |
| C140 | 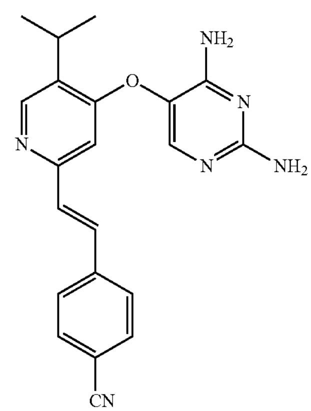 [SMILES: CC(C)c1cnc(/C=C/c2ccc(C#N)cc2)cc1Oc1cnc(N)nc1N] | 372.9 |

| No. | Structure | MS Data |
|---|---|---|
| C146 | 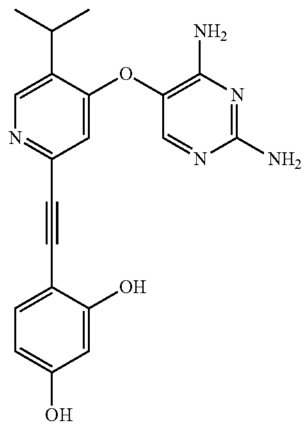 [SMILES: CC(C)c1cnc(C#Cc2ccc(O)cc2O)cc1Oc1cnc(N)nc1N] | 377.9 |
| C147 | 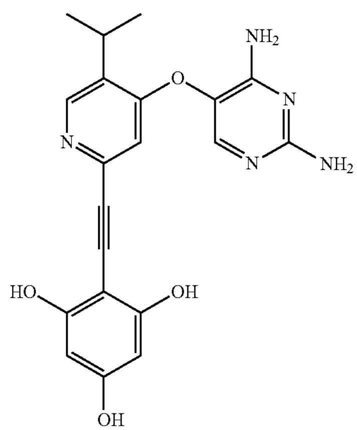 [SMILES: CC(C)c1cnc(C#Cc2c(O)cc(O)cc2O)cc1Oc1cnc(N)nc1N] | 393.9 |
| C156 | 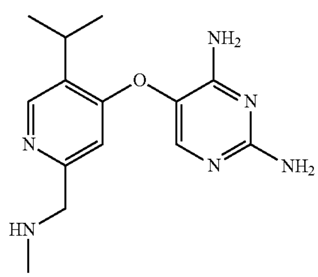 [SMILES: CNCc1cc(Oc2cnc(N)nc2N)c(C(C)C)cn1] | 288.9 |
| C158 | 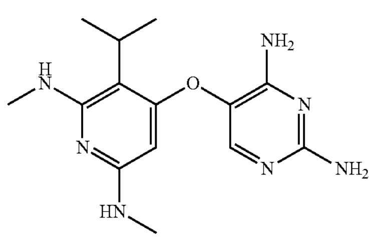 [SMILES: CNc1cc(Oc2cnc(N)nc2N)c(C(C)C)c(NC)n1] | 303.9 |
| C159 | 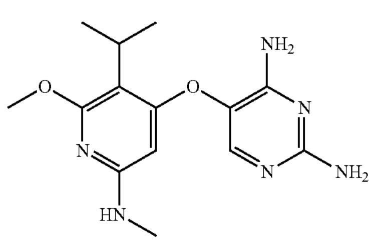 [SMILES: CNc1cc(Oc2cnc(N)nc2N)c(C(C)C)c(OC)n1] | 304.9 |
| C160 | | 292.9 |
| C161 | | 305.9 |
| C166 | | 333.9 |
| C167 | | 405.8 |
| C168 | | 413.8 |

-continued

| No. | Structure | MS Data |
|---|---|---|
| C169 | 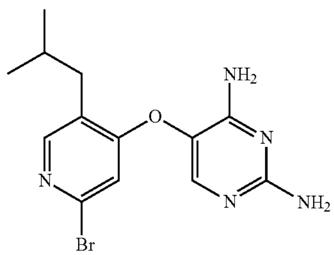 [SMILES: CC(C)Cc1cnc(Br)cc1Oc1cnc(N)nc1N] | 337.8 |
| C178 | 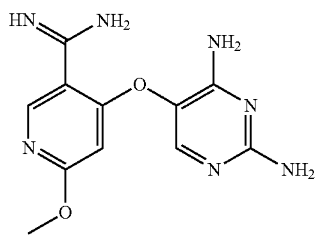 [SMILES: COc1cc(Oc2cnc(N)nc2N)c(C(=N)N)cn1] | 275.9 |
| C184 | 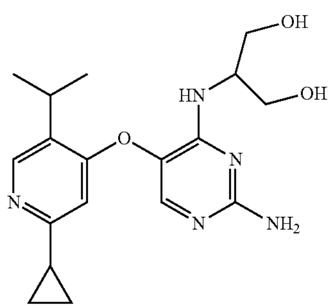 [SMILES: CC(C)c1cnc(C2CC2)cc1Oc1cnc(N)nc1NC(CO)CO] | 359.9 |
| C185 | 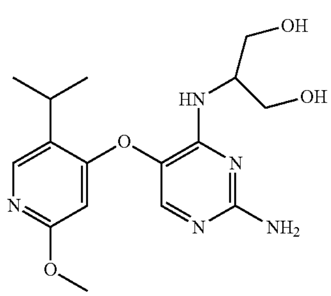 [SMILES: COc1cc(Oc2cnc(N)nc2NC(CO)CO)c(C(C)C)cn1] | 349.9 |
| C186 | 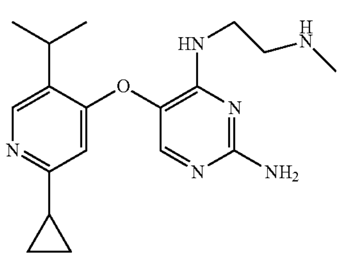 [SMILES: CNCCNc1nc(N)ncc1Oc1cc(C2CC2)ncc1C(C)C] | 343.0 |

-continued

| No. | Structure | MS Data |
|---|---|---|
| C187 | 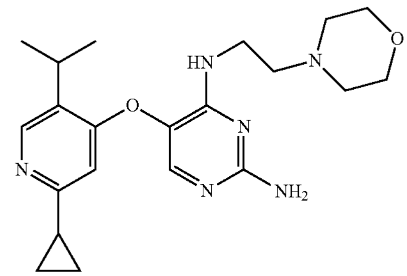 [SMILES: CC(C)c1cnc(C2CC2)cc1Oc1cnc(N)nc1NCCN1CCOCC1] | 399.0 |
| C188 | 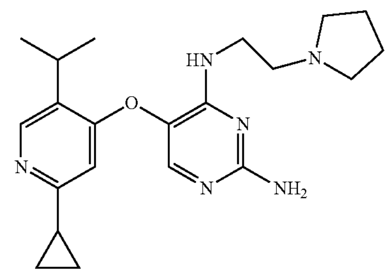 [SMILES: CC(C)c1cnc(C2CC2)cc1Oc1cnc(N)nc1NCCN1CCCC1] | 383.1 |
| C189 | 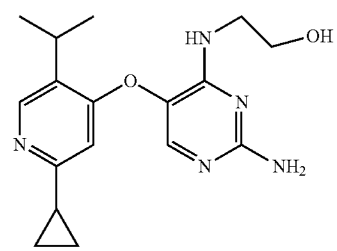 [SMILES: CC(C)c1cnc(C2CC2)cc1Oc1cnc(N)nc1NCCO] | 329.9 |
| C190 | 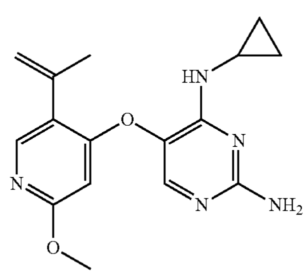 [SMILES: C=C(C)c1cnc(OC)cc1Oc1cnc(N)nc1NC1CC1] | 313.9 |
| C191 | 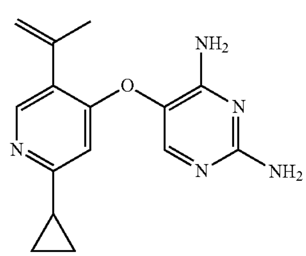 [SMILES: C=C(C)c1cnc(C2CC2)cc1Oc1cnc(N)nc1N] | 283.9 |

| No. | Structure | MS Data |
|-----|-----------|---------|
| C193 |  | 325.9 |
| C200 | 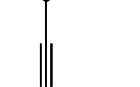 | 299.9 |
| C206 |  | 301.9 |
| C220 | 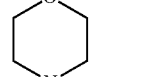 | 318.9 |
| C221 |  | 287.9 |
| No. | Structure | MS Data |
|-----|-----------|---------|
| C223 | 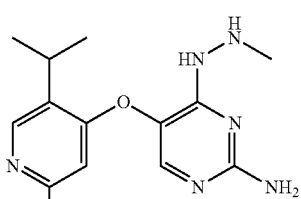 | 298.9 |
| C224 | | 360.9 |
| C225 | | 326.9 |
| C232 | | 309.9 |
| C234 | | 384.9 |

-continued

| No. | Structure | MS Data |
|---|---|---|
| C240 | 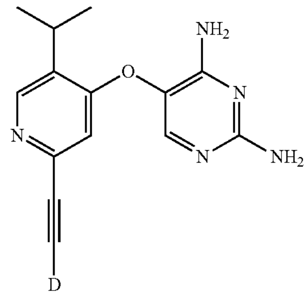 [SMILES: [2H]C#Cc1cc(Oc2cnc(N)nc2N)c(C(C)C)cn1] | 270.9 |
| C244 | 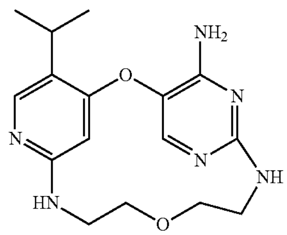 [SMILES: CC(C)c1cnc2cc1Oc1cnc(nc1N)NCCOCCN2] | 330.9 |
| C245 | 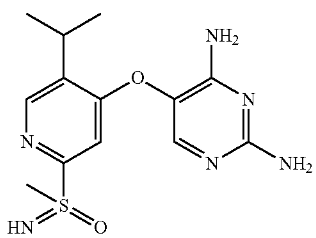 [SMILES: CC(C)c1cnc(S(C)(=N)=O)cc1Oc1cnc(N)nc1N] | 322.9 |
| C247 | 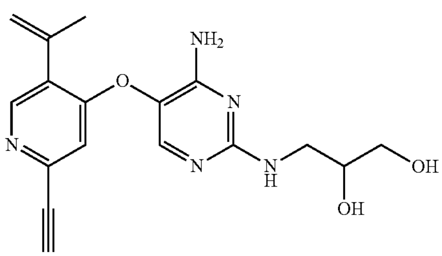 [SMILES: C#Cc1cc(Oc2cnc(NCC(O)CO)nc2N)c(C(=C)C)cn1] | 341.9 |
| C248 | 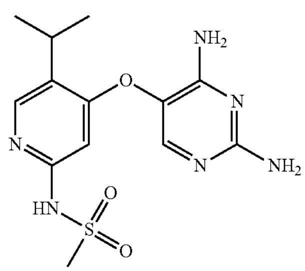 [SMILES: CC(C)c1cnc(NS(C)(=O)=O)cc1Oc1cnc(N)nc1N] | 338.9 |

Biological Assay: Determination of the Inhibitory Activity of the Compounds on Human P2X3 and P2X2/3 Receptors Cells were seeded into a poly-D-lysine-coated 384-well cell culture plate (Corning) at a density of 11,000 cells/well/ 25 µL of cell inoculation medium, and were cultured in a cell incubator overnight. On the day of the test, the calcium 6 dye was diluted to a 2× concentration with a assay buffer, 25 µL of the 2× calcium 6 dye was added to the 384-well cell culture plate, which was incubated at 37° C. for 2 hours, and then placed at room temperature for further use. The test compound and the agonist, α,β-MeATP were diluted to a 7× concentration with the assay buffer, 10 µL of the 7× test compound was added to the 384-well cell culture plate, which was incubated at room temperature for 15 minutes, and 10 µL of the 7× α,β-MeATP was transferred into the 384-well cell culture plate. The data were measured and analyzed using FLIPR Tetra, and the half inhibitory concentration ($IC_{50}$) of the test compound on P2X3 and P2X2/3 receptors was calculated with the GraphPad Prism four-parameter equation.

Cell lines: human embryonic kidney cells HEK293-P2X3 and HEK293-P2X2/3 stably expressing cell lines;

Complete cell culture medium: DMEM High Glucose (Life Technology), which contained 10% fetal bovine serum, 4 mM GlutaMAX, 1% penicillin-streptomycin, and 350 µg/mL G418;

Cell inoculation medium: DMEM High Glucose (Life Technology), which contained 2% fetal bovine serum, and 4 mM GlutaMAX;

Cell culture conditions: 37° C., 5% $CO_2$;

Assay buffer: HBSS (containing calcium and magnesium ions), which contained 20 mM HEPES;

Detection equipment: FLIPR Tetra (Molecular Devices);

Detection parameters: excitation wavelength 470-495 nm, emission wavelength 515-575 nm; fluorescence signal was measured once every second for 260 seconds in total.

The experimental data obtained from the above biological assay are shown in the table below.

| Compound No. | P2X3 $IC_{50}$ (µM) |
|---|---|
| C1 | 0.7460 |
| C2 | 0.0881 |
| C3 | 0.2047 |
| C4 | 0.1022 |
| C6 | 0.348 |
| C9 | 0.2543 |
| Reference Compound C10 | 2.5070 |
| C12 | 0.0736 |
| C13 | 0.3552 |
| C15 | 0.3070 |
| C16 | 0.8015 |
| C20 | 0.0444 |
| C21 | 0.131 |
| C22 | 0.037 |
| C23 | 0.3650 |
| C33 | 0.238 |
| C35 | 1.1670 |
| C38 | 0.787 |
| C39 | 0.166 |
| C41 | 1.8540 |
| C43 | 0.0550 |
| C44 | 0.1156 |
| C45 | 0.4350 |
| C52 | 0.147 |
| C61 | 0.274 |
| C65 | 0.334 |
| C66 | 0.085 |
| C67 | 0.490 |
| C71 | 0.072 |
| C72 | 0.127 |
| C84 | 0.536 |
| C85 | 0.078 |
| C88 | 0.133 |
| C91 | 0.227 |
| C92 | 0.109 |
| C95 | 0.138 |
| C111 | 0.104 |
| C117 | 0.151 |
| C118 | 0.142 |
| C119 | 0.540 |
| C120 | 0.492 |
| C124 | 1.243 |
| C125 | 0.731 |

-continued

| Compound No. | IC50 (μM) |
|---|---|
| C127 | 0.147 |
| C129 | 0.377 |
| C133 | 1.441 |
| C134 | 0.391 |
| C135 | 0.303 |
| C136 | 0.270 |
| C137 | 0.503 |
| C138 | 0.635 |
| C142 | 0.302 |
| C145 | 0.809 |
| C148 | 0.215 |
| C149 | 0.130 |
| C150 | 0.211 |
| C151 | 0.59 |
| C152 | 0.211 |
| C153 | 0.083 |
| C154 | 0.072 |
| C155 | 0.926 |
| C157 | 0.736 |
| C162 | 0.296 |
| C164 | 0.046 |
| C165 | 0.163 |
| C172 | 0.116 |
| C173 | 0.188 |
| C174 | 0.100 |
| C175 | 0.108 |
| C176 | 0.611 |
| C179 | 0.051 |
| C180 | 0.207 |
| C181 | 0.084 |
| C182 | 0.67 |
| C192 | 0.053 |
| C194 | 0.322 |
| C195 | 0.316 |
| C196 | 0.208 |
| C199 | 0.186 |
| C201 | 0.316 |
| C202 | 0.103 |
| C203 | 0.157 |
| C204 | 0.044 |
| C207 | 0.113 |
| C208 | 0.07528 |
| C209 | 0.144 |
| C210 | 0.269 |
| C211 | 0.064 |
| C212 | 0.081 |
| C213 | 0.112 |
| C214 | 0.044 |
| C215 | 0.08818 |
| C216 | 0.062 |
| C218 | 0.186 |
| C222 | 0.048 |
| C226 | 0.1146 |
| C227 | 0.948 |
| C228 | 0.119 |
| C229 | 0.065 |
| C230 | 0.060 |
| C233 | 0.072 |
| C235 | 0.090 |
| C236 | 0.088 |
| C237 | 0.363 |
| C238 | 0.104 |
| C239 | 0.107 |
| C242 | 0.744 |

| Compound No. | P2X2/3 IC50 (μM) |
|---|---|
| C2 | 0.2490 |
| C3 | 0.3411 |
| C4 | 0.1583 |
| C9 | 0.3788 |
| Reference Compound C10 | 1.8200 |
| C12 | 0.0567 |
| C13 | 0.5992 |
| C15 | 0.7930 |
| C20 | 0.0757 |
| C21 | 0.200 |
| C22 | 0.057 |
| C23 | 0.6440 |
| C33 | 0.262 |
| C39 | 0.243 |
| C43 | 0.1800 |
| C44 | 0.4228 |
| C52 | 0.589 |
| C61 | 0.592 |
| C65 | 0.506 |
| C66 | 0.154 |
| C71 | 0.067 |
| C72 | 0.089 |
| C84 | 0.742 |
| C85 | 0.205 |
| C88 | 0.122 |
| C91 | 0.271 |
| C92 | 0.222 |
| C95 | 0.163 |
| C111 | 0.129 |
| C117 | 0.487 |
| C118 | 0.366 |
| C119 | 0.505 |
| C127 | 0.234 |
| C133 | 0.770 |
| C134 | 0.685 |
| C135 | 0.488 |
| C136 | 0.416 |
| C137 | 0.567 |
| C142 | 0.549 |
| C145 | 0.623 |
| C148 | 0.113 |
| C149 | 0.266 |
| C150 | 0.232 |
| C151 | 0.961 |
| C152 | 0.375 |
| C153 | 0.096 |
| C154 | 0.046 |
| C157 | 0.978 |
| C162 | 0.429 |
| C164 | 0.071 |
| C165 | 0.338 |
| C172 | 0.209 |
| C173 | 0.259 |
| C174 | 0.145 |
| C175 | 0.141 |
| C176 | 0.984 |
| C179 | 0.043 |
| C180 | 0.220 |
| C181 | 0.078 |
| C192 | 0.069 |
| C194 | 0.446 |
| C196 | 0.652 |
| C199 | 0.333 |
| C201 | 0.498 |
| C202 | 0.166 |
| C203 | 0.275 |
| C204 | 0.056 |
| C207 | 0.163 |
| C208 | 0.1055 |
| C209 | 0.209 |
| C210 | 0.399 |
| C211 | 0.121 |
| C212 | 0.123 |
| C213 | 0.295 |
| C214 | 0.072 |
| C215 | 0.1942 |
| C216 | 0.065 |
| C218 | 0.383 |
| C222 | 0.040 |
| C226 | 0.1547 |
| C228 | 0.125 |
| C229 | 0.113 |
| C230 | 0.106 |
| C233 | 0.125 |
| C235 | 0.145 |
| C236 | 0.134 |
| C237 | 0.781 |
| C238 | 0.206 |
| C239 | 0.131 |

According to the experimental data in the above table, compared with reference compound 10 (the group corresponding to $V^1$ in Formula (I) of the present invention is a carbon-containing group, and the group corresponding to $V^2$ is a nitrogen atom), the test compounds (the groups corresponding to $V^1$ in Formula (I) are all nitrogen-containing groups and the groups corresponding to $V^2$ are all carbon-containing groups) have significantly increased inhibitory activity on the P2X3 and P2X2/3 receptors. The remaining compounds of the present invention also have significantly increased inhibitory activity on the P2X3 and P2X2/3 receptors.

Various modifications of the invention in addition to those described herein will become apparent to those skilled in the art from the foregoing description. Such modifications are intended to fall within the scope of the appended claims. Each reference, including all patents, applications, journal articles, books and any other disclosure, referred to herein is hereby incorporated by reference in its entirety.

What is claimed is:

1. A method for the treatment of a disease mediated by the P2X3 and/or P2X2/3 receptor antagonist, wherein the method comprises administering to a subject in need thereof an effective amount of a compound having the structure of Formula (I) or a pharmaceutically acceptable salt, ester, stereoisomer, polymorph, solvate, N-oxide, isotopically labeled compound or prodrug thereof:

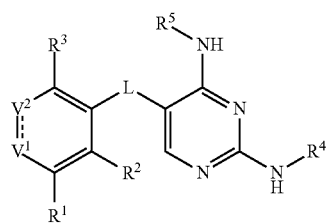

Formula (I)

wherein:
L is O;
$V^1$ is selected from the group consisting of N,

and NR;

$V^2$ is selected from the group consisting of $CR^6$ and $C(=O)$;

$=$ represents either a single bond or a double bond, provided that when $=$ is a single bond, $V^1$ is NR and $V^2$ is $C(=O)$;

R is selected from the group consisting of H, halogen, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl, and at most 2 ring members in the cyclic hydrocarbyl and heterocyclyl are $C(=O)$;

$R^1$, $R^2$, $R^3$ and $R^6$ are each independently selected from the group consisting of H, halogen, —CN, —$NH_2$, —OH, —SH, —Se—R, —$Si(R)_3$, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl, $C_{6-12}$ aralkyl, $C_{1-6}$ haloalkyl, —$C(=O)R^a$, —$OC(=O)R^a$, —$C(=O)OR^a$, —$OR^a$, —$SR^a$, —$S(=O)R^a$, —$S(=O)_2R^a$, —$S(=O)_2NR^aR^b$, —$S(=O)(=NR)R^a$, —$NR^aR^b$, —$C(=O)NR^aR^b$, —$C(=S)NR^aR^b$, —$C(=NR)NR^aR^b$, —$NR^a$—$C(=O)R^b$, —$NR^a$—$C(=O)OR^b$, —$NR^a$—$S(=O)_2$—$R^b$, —$NR^a$—$C(=O)$—$NR^aR^b$, —$C_{1-6}$ alkylene-$NR^aR^b$, —$C_{1-6}$ alkylene-$OR^a$, —$C_{1-6}$ alkylene-$C(=O)R$, —$C_{1-6}$ alkenylene-$OR^a$, —O—$C_{1-6}$ alkylene-$NRaR^b$ and —$P(=O)RaR^b$;

$R^4$ and $R^5$ are each independently selected from the group consisting of H, —$C(=O)OR^a$, —$NRaR^b$, —$NR^a$—$C(=O)R^b$, —$NR^a$—$C(=O)OR^b$, —$C_{1-6}$ alkylene-$NRaR^b$, —$C_{1-6}$ alkylene-$OR^a$, —$C_{1-6}$ alkylene-$O$—$C_{1-6}$ alkylene-$OR^a$, $C_{1-6}$ alkyl, $C_{1-6}$ haloalkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl;

alternatively, $R^1$ and $R^4$ together form —NH—($C_{1-6}$ alkylene)-L-($C_{1-6}$ alkylene)-;

the above alkyl, alkylene, alkenyl, alkynyl, cyclic hydrocarbyl, heterocyclyl, aryl, heteroaryl and aralkyl, at each occurrence, are each optionally substituted with one or more substituents independently selected from the group consisting of halogen, hydroxyl, oxo, amino, cyano, nitro, —$Si(R)_3$, $C_{1-6}$ alkyl, saturated or partially unsaturated $C_{3-6}$ cyclic hydrocarbyl, saturated or partially unsaturated 3- to 10-membered heterocyclyl, $C_{6-10}$ aryl, 5- to 14-membered heteroaryl, $C_{6-12}$ aralkyl, —$C(=O)R^a$, —$OC(=O)R^a$, —$C(=O)OR^a$, —$OR^a$, —$SR^a$, —$S(=O)R^a$, —$S(=O)_2R^a$, —$S(=O)_2NR^aR^b$, —$NR^aR^b$, —$C(=O)NR^aR^b$, —$NR^a$—$C(=O)R^b$, —$NR^a$—$C(=O)OR^b$, —$NR^a$—$S(=O)_2$—$R^b$, —$NR^a$—$C(=O)$—$NR^aR^b$, —$C_{1-6}$ alkylene-$NR^aR^b$, —$C_{1-6}$ alkylene-$OR^a$, —$C_{1-6}$ alkenylene-$OR^a$ and —O—$C_{1-6}$ alkylene-$NR^aR^b$, the alkyl, cyclic hydrocarbyl, heterocyclyl, aryl, heteroaryl and aralkyl are further optionally substituted with one or more substituents independently selected from the group consisting of halogen, hydroxyl, oxo, amino, cyano, nitro, —$NR^aR^b$, $C_{1-6}$ alkyl, —O—$C_{1-6}$ alkyl, saturated or partially unsaturated $C_{3-6}$ cyclic hydrocarbyl, saturated or partially unsaturated 3- to 10-membered heterocyclyl, $C_{6-10}$ aryl, 5- to 14-membered heteroaryl and $C_{6-12}$ aralkyl; and $R^1$ and $R^b$, at each occurrence, are each independently selected from the group consisting of H, —OH, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl; alternatively, $R^1$ and $R^b$ together with the atom to which they are attached form a 3- to 12-membered heterocycle or heteroaromatic ring, the above groups are further optionally substituted with one or more substituents independently selected from the group consisting of halogen, hydroxyl, oxo, amino, cyano, nitro, $C_{1-6}$ alkyl, —O—$C_{1-6}$ alkyl, saturated or partially unsaturated $C_{3-6}$ cyclic hydrocarbyl, saturated or partially unsaturated 3- to 10-membered heterocyclyl, $C_{6-10}$ aryl, 5- to 14-membered heteroaryl and $C_{6-12}$ aralkyl.

2. A method for the treatment of a disease mediated by the P2X3 and/or P2X2/3 receptor antagonist, wherein the method comprises administering to a subject in need thereof an effective amount of a compound having the structure of Formula (I) or a pharmaceutically acceptable salt, ester, stereoisomer, polymorph, solvate, N-oxide, isotopically labeled compound or prodrug thereof:

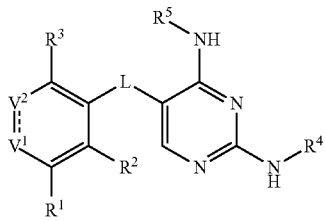

wherein:
L is O;
$V^1$ is selected from the group consisting of N,

and NR;
$=$ represents either a single bond or a double bond, provided that when $=$ is a single bond, $V^1$ is NR and $V^2$ is C(=O);
R is selected from the group consisting of H, halogen, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl, and at most 2 ring members in the cyclic hydrocarbyl and heterocyclyl are C(=O);
$R^1$, $R^2$, $R^3$ and $R^6$ are each independently selected from the group consisting of H, halogen, —CN, —NH$_2$, —OH, —SH, —Se—R, —Si(R)$_3$, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl, $C_{6-12}$ aralkyl, $C_{1-6}$ haloalkyl, —C(=O)R$^a$, —OC(=O)R$^a$, —C(=O)OR$^a$, —OR$^a$, —SR$^a$, —S(=O)R$^a$, —S(=O)$_2$R$^a$, —S(=O)$_2$NR$^a$R$^b$, —S(=O)(=NR)R$^a$, —NR$^a$R$^b$, —C(=O)NR$^a$R$^b$, —C(=S)NR$^a$R$^b$, —C(=NR)NR$^a$R$^b$, —NR$^a$—C(=O)R$^b$, —NR$^a$—C(=O)OR$^b$, —NR$^a$—S(=O)$_2$—R$^b$, —NR$^a$—C(=O)—NR$^a$R$^b$, —C$_{1-6}$ alkylene-NR$^a$R$^b$, —C$_{1-6}$ alkylene-OR$^a$, —C$_{1-6}$ alkylene- C(=O)R, —C$_{1-6}$ alkenylene-OR$^a$, —O—C$_{1-6}$ alkylene-NR$^a$R$^b$ and —P(=O)R$^a$R$^b$;
$R^4$ and $R^5$ are each independently selected from the group consisting of H, —C(=O)OR$^a$, —NR$^a$R$^b$, —NR$^a$—C(=O)R$^b$, —NR$^a$—C(=O)OR$^b$, —C$_{1-6}$ alkylene-NR$^a$R$^b$, —C$_{1-6}$ alkylene-OR$^a$, —C$_{1-6}$ alkylene-O—C$_{1-6}$ alkylene-OR$^a$, $C_{1-6}$ alkyl, $C_{1-6}$ haloalkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl;
alternatively, $R^1$ and $R^4$ together form —NH—(C$_{1-6}$ alkylene)-L-(C$_{1-6}$ alkylene)-;
the above alkyl, alkylene, alkenyl, alkynyl, cyclic hydrocarbyl, heterocyclyl, aryl, heteroaryl and aralkyl, at each occurrence, are each optionally substituted with one or more substituents independently selected from the group consisting of halogen, hydroxyl, oxo, amino, cyano, nitro, —Si(R)$_3$, $C_{1-6}$ alkyl, saturated or partially unsaturated $C_{3-6}$ cyclic hydrocarbyl, saturated or partially unsaturated 3- to 10-membered heterocyclyl, $C_{6-10}$ aryl, 5- to 14-membered heteroaryl, $C_{6-12}$ aralkyl, —C(=O)R$^a$, —OC(=O)R$^a$, —C(=O)OR$^a$, —OR$^a$, —SR$^a$, —S(=O)R$^a$, —S(=O)$_2$R$^a$, —S(=O)$_2$NR$^a$R$^b$, —NR$^a$R$^b$, —C(=O)NR$^a$R$^b$, —NR$^a$—C(=O)R$^b$, —NR$^a$—C(=O)OR$^b$, —NR$^a$—S(=O)$_2$—R$^b$, —NR$^a$—C(=O)—NR$^a$R$^b$, —C$_{1-6}$ alkylene-NR$^a$R$^b$, —C$_{1-6}$ alkylene-OR$^a$, —C$_{1-6}$ alkenylene-OR$^a$ and —O—C$_{1-6}$ alkylene-NR$^a$R$^b$, the alkyl, cyclic hydrocarbyl, heterocyclyl, aryl, heteroaryl and aralkyl are further optionally substituted with one or more substituents independently selected from the group consisting of halogen, hydroxyl, oxo, amino, cyano, nitro, —NR$^a$R$^b$, $C_{1-6}$ alkyl, —O—C$_{1-6}$ alkyl, saturated or partially unsaturated $C_{3-6}$ cyclic hydrocarbyl, saturated or partially unsaturated 3- to 10-membered heterocyclyl, $C_{6-10}$ aryl, 5- to 14-membered heteroaryl and $C_{6-12}$ aralkyl; and
R$^a$ and R$^b$, at each occurrence, are each independently selected from the group consisting of H, —OH, methyl, ethyl, n-propyl, isopropyl, cyclopropyl, phenyl, benzyl, methoxy and ethoxy; or, R$^1$ and R$^b$ together with the atom to which they are attached form a 5- to 8-membered heterocycle or heteroaromatic ring.

3. The method according to claim 1, wherein $R^1$, $R^2$, $R^3$ and $R^6$ are each independently selected from the group consisting of H, F, Cl, Br, I, —CN, —NH$_2$, —OH, —SH, —Se—CH$_3$, —Si(CH$_3$)$_3$, —CH$_2$NH$_2$, —CH$_2$NHCH$_3$, —CH$_2$N(CH$_3$)$_2$, methyl, ethyl, n-propyl, isopropyl, n-butyl, isobutyl, tert-butyl, cyclopropyl, cyclobutyl, cyclopentyl, cyclohexyl, vinyl, propenyl, allyl, ethynyl, propynyl, trifluoromethyl, acetyl, —C(=O)OH, —C(=O)NH$_2$, —C(=S)NH$_2$, —C(=NH)NH$_2$, —NHCH$_3$, —NHCH$_2$CH$_3$, —NHCH$_2$CF$_3$, —N(CH$_3$)$_2$, —N(CH$_3$)(C$_2$H$_5$), —N(C$_2$H$_5$)$_2$, —NHCH$_2$CH$_2$OH, —NH—C(=O)CH$_3$, —NH—C(=O)CH=CH$_2$, methoxy, ethoxy, propoxy, phenyl, —NH—C(=O)—NH$_2$, —NH—C(=O)OCH$_3$, —SCH$_3$, —SCH$_2$CH$_3$, —SC(CH$_3$)$_3$, —SBn, —S(=O)CH$_3$, —S(=O)Bn, —S(=O)$_2$CH$_3$, —S(=O)$_2$Bn, —S(=O)$_2$NH$_2$, —S(=O)$_2$NHCH$_3$, —S(=O)$_2$N(CH$_3$)$_2$, —S(=O)(=NH)CH$_3$, —P(=O)(CH$_3$)$_2$, —P(=O)(C$_2$H$_5$)$_2$,

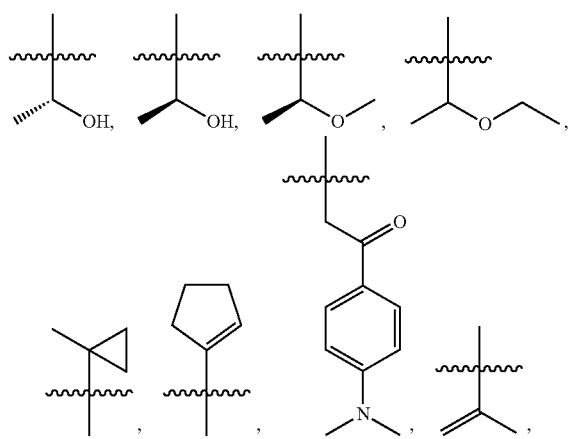

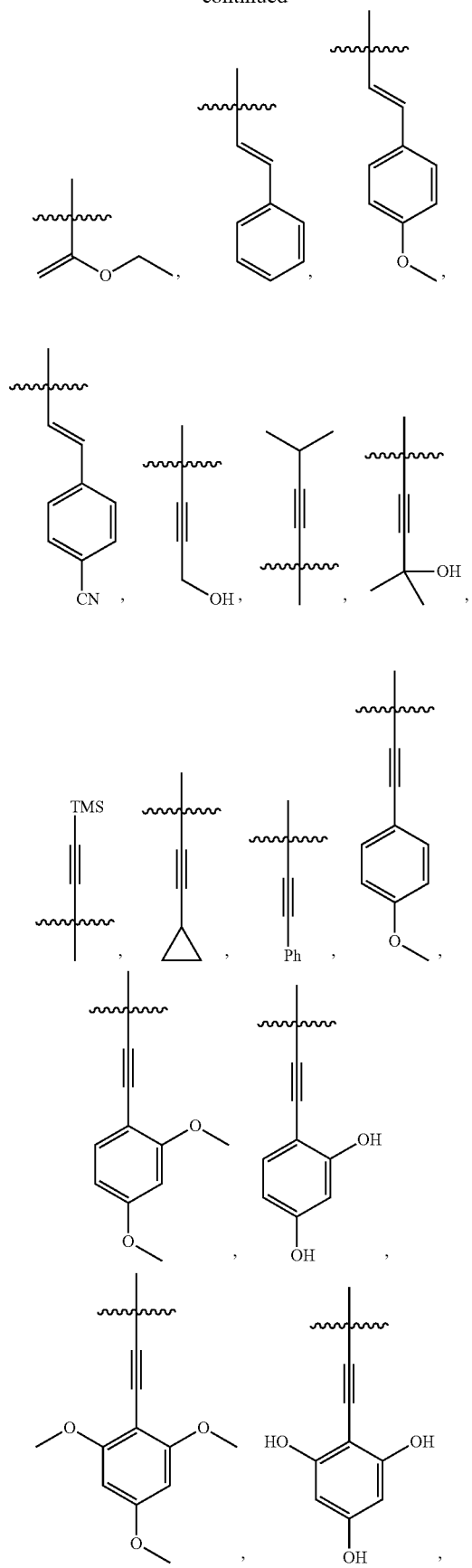
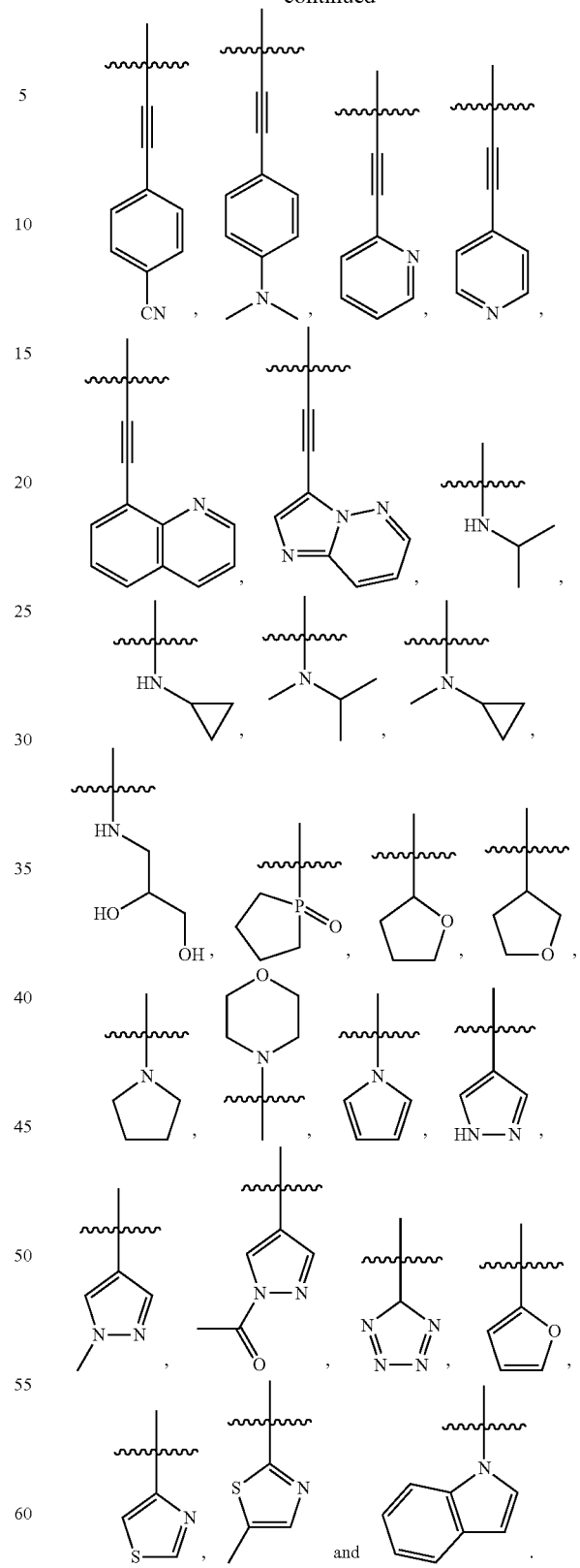
4. The method according to claim 1, wherein $R^4$ and $R^5$ are each independently selected from the group consisting of H, —C(═O)OC(CH$_3$)$_3$, —NH$_2$, —NHCH$_3$, —NHPh, —NHC(═O)CH$_3$, —NHBoc, methyl, ethyl, —CH$_2$CF$_3$, n-propyl, isopropyl, n-butyl, isobutyl, tert-butyl, cyclopropyl, cyclobutyl, cyclopentyl, cyclohexyl, phenyl, benzyl,

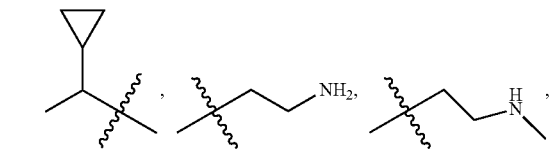

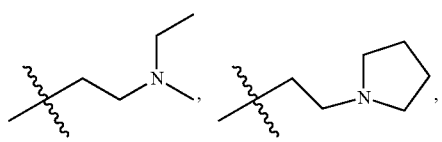

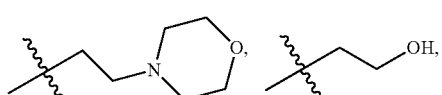

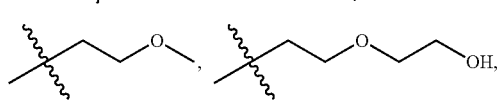

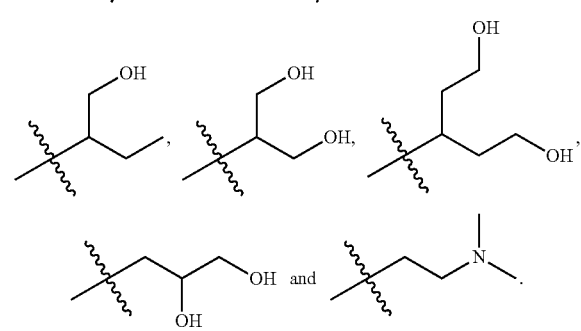

5. The method according to claim 1, wherein the method comprises administering to a subject in need thereof an effective amount of the compound has the structure of any of the following formulae, or a pharmaceutically acceptable salt, ester, stereoisomer, polymorph, solvate, or prodrug thereof:

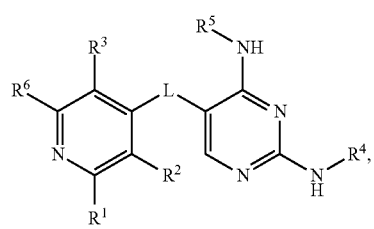
(II')

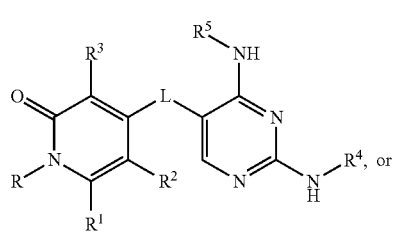
(III'), or

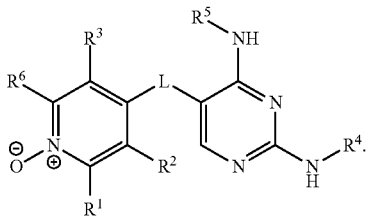
(IV')

6. The method according to claim 1, wherein the compound has the following structure:

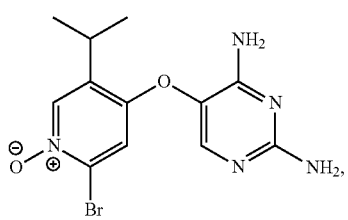
1

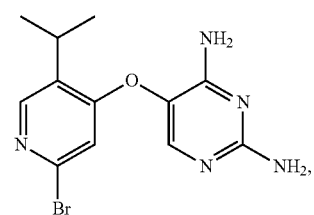
2

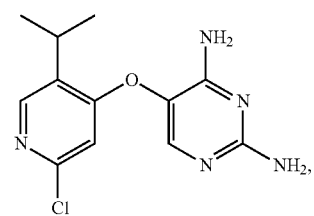
3

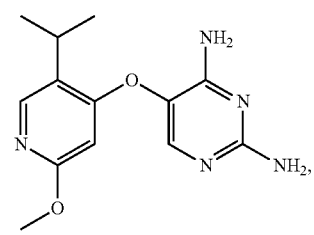
4

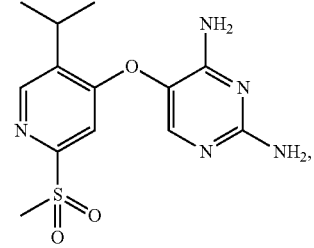
5

213
-continued
6
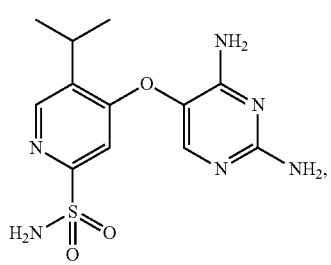
7
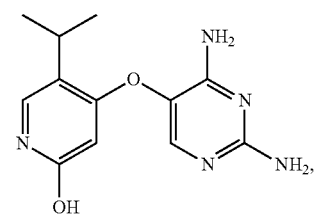
8
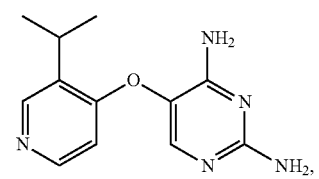
9
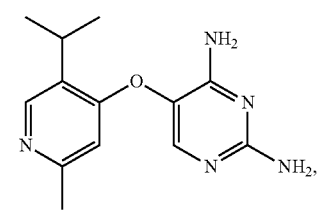
10
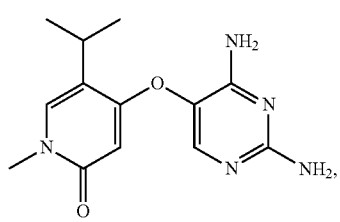
12
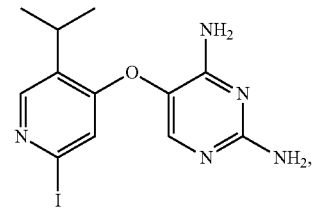
13
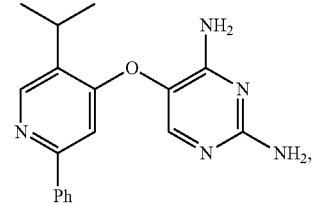
214
-continued
14
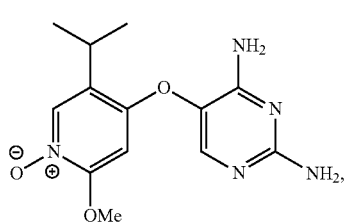
15
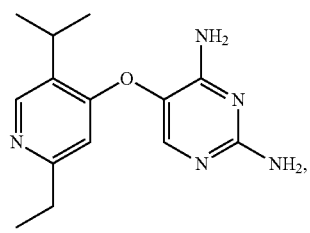
16
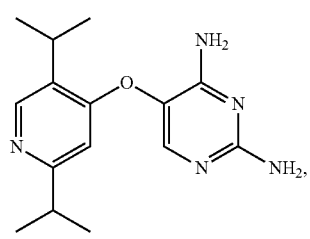
17
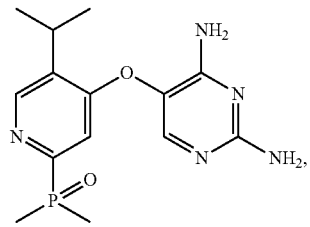
18
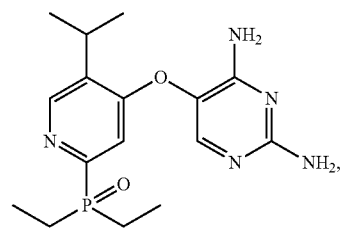
19
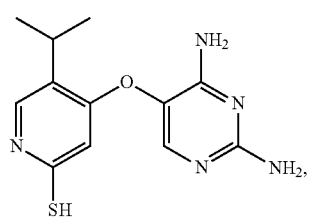
20
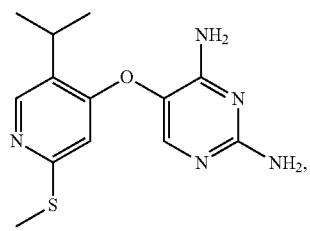

21
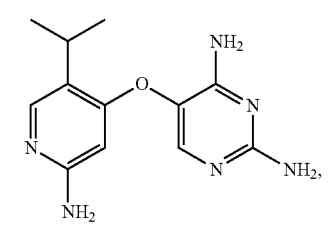
22
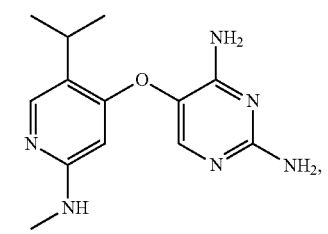
23
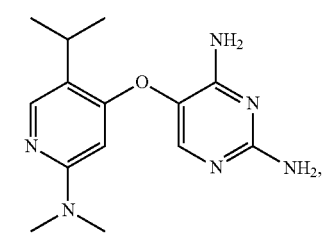
24
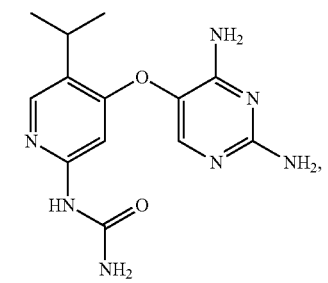
25
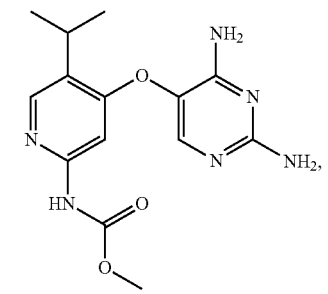
26
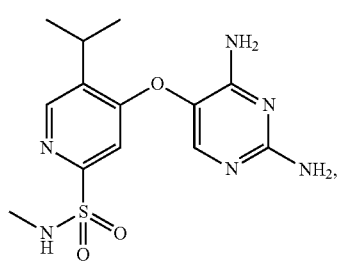
27
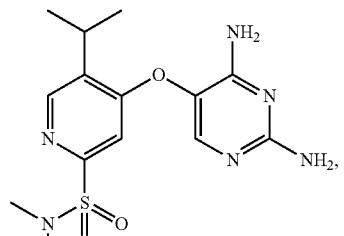
28
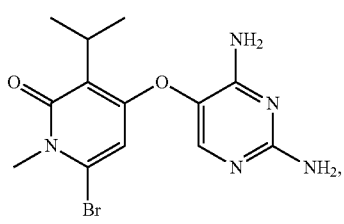
29
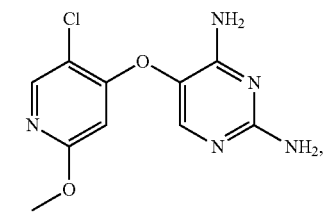
30
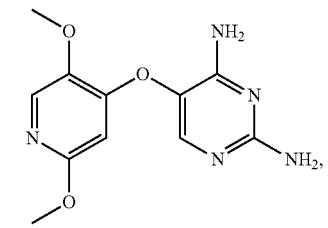
31
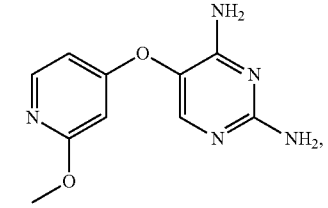
32
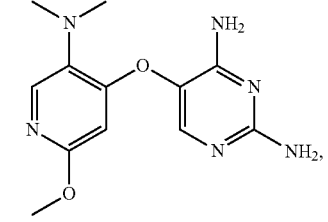
33

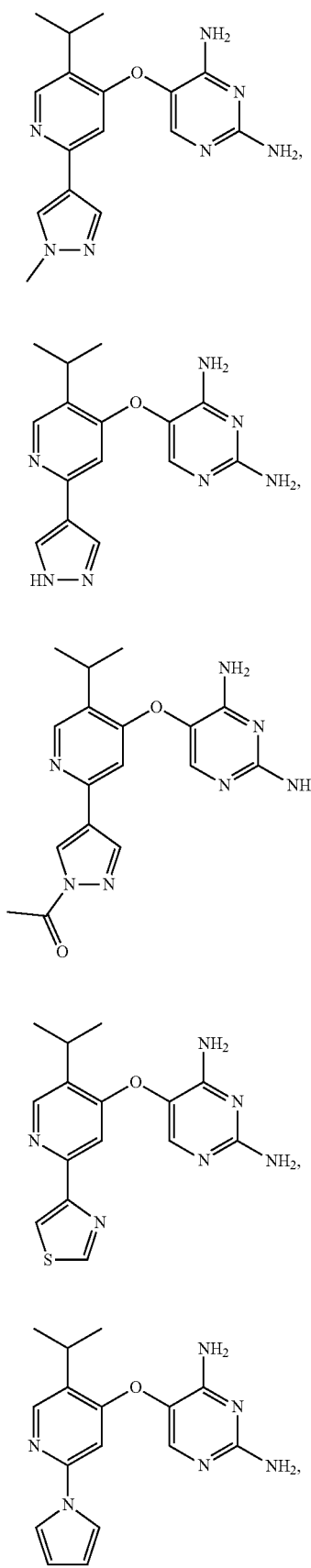
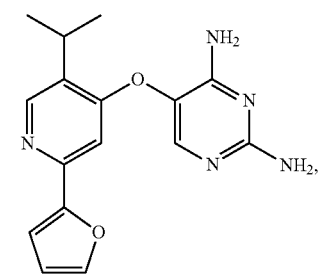
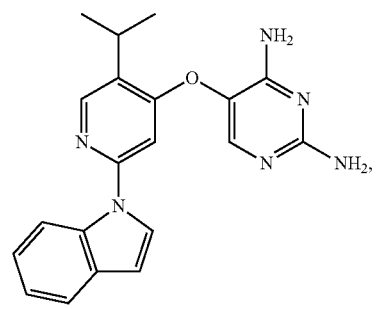
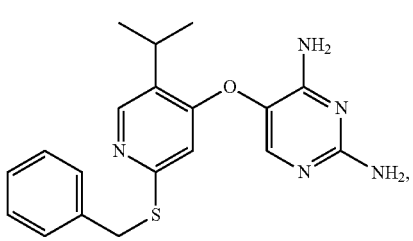
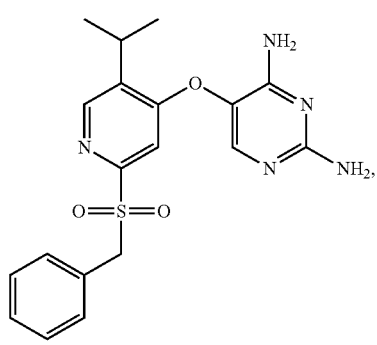
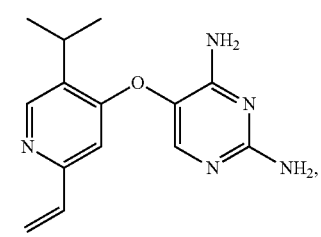
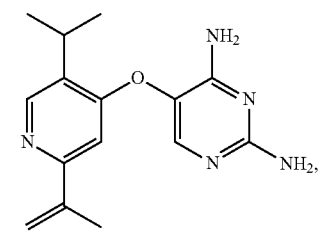

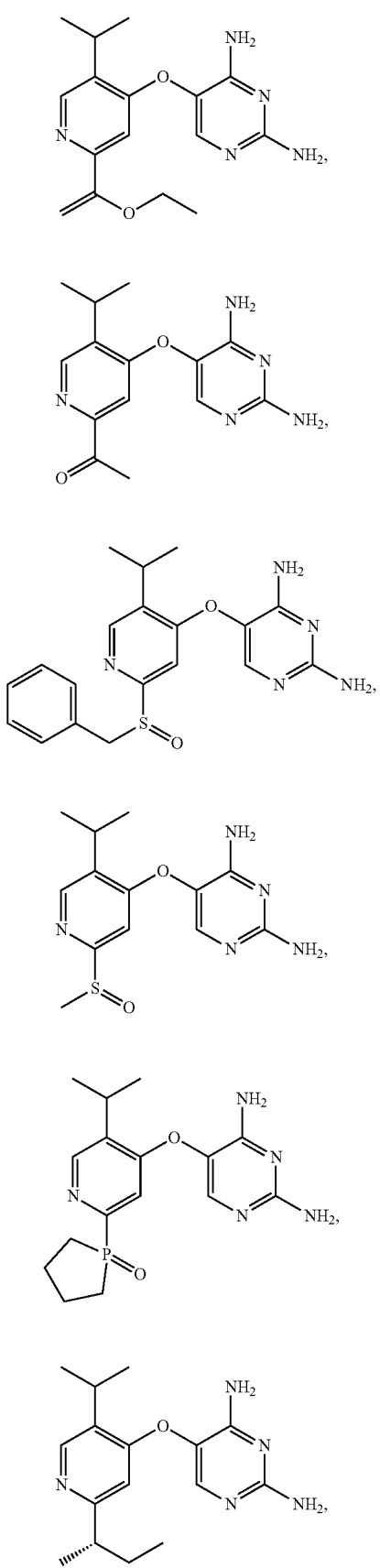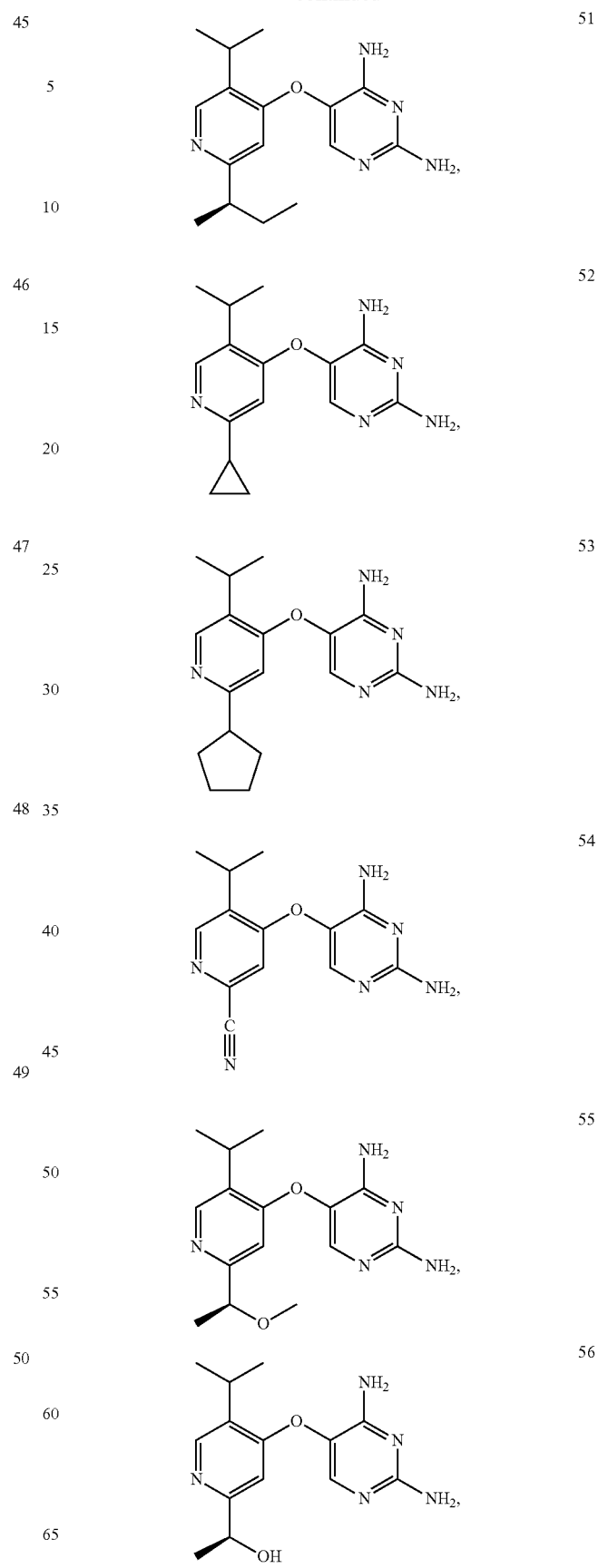

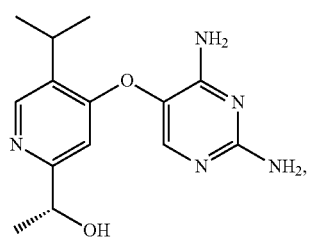
57
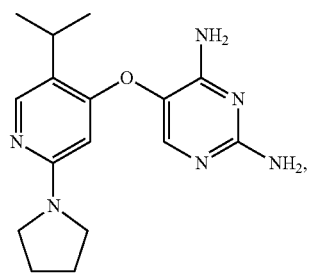
63
58
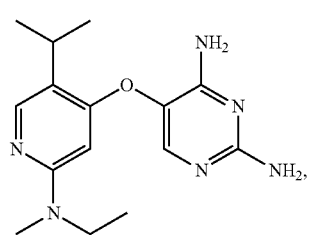
64
59
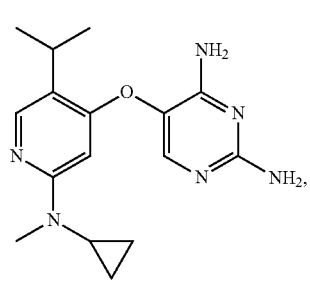
65
60
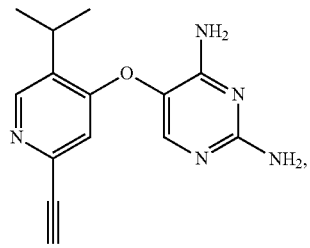
66
61
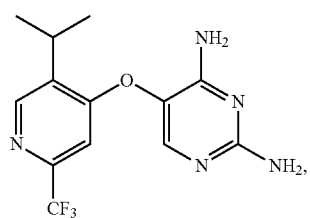
67
62
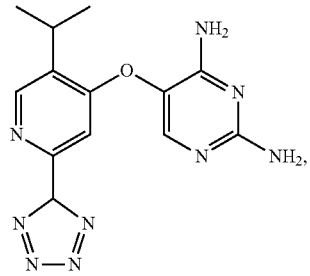
68

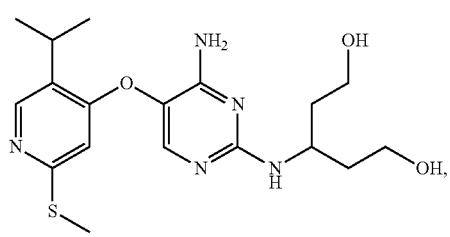
69
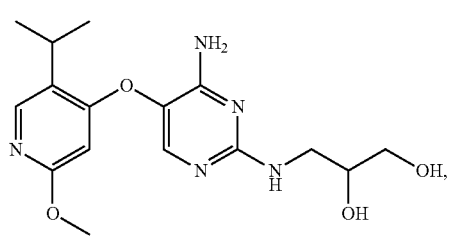
70
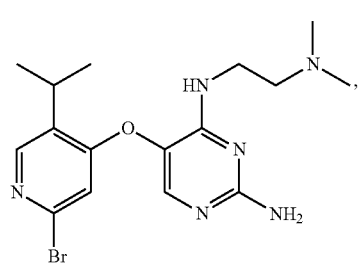
71
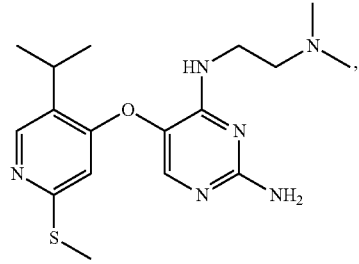
72
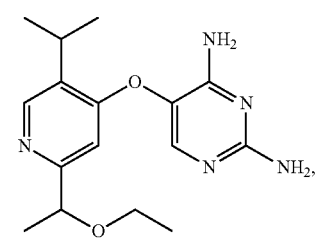
109
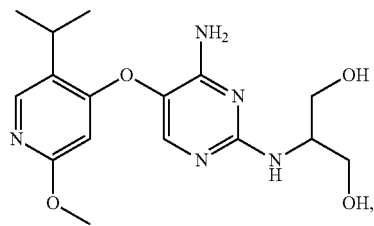
110
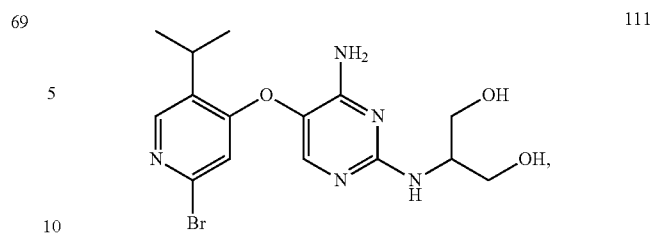
111
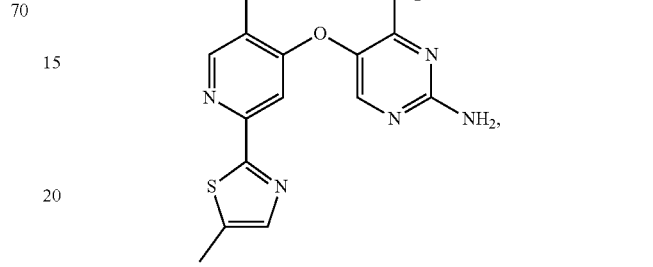
115
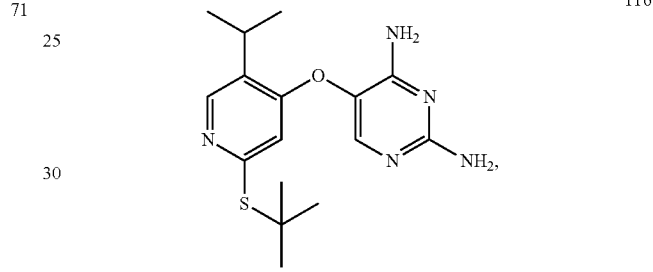
116
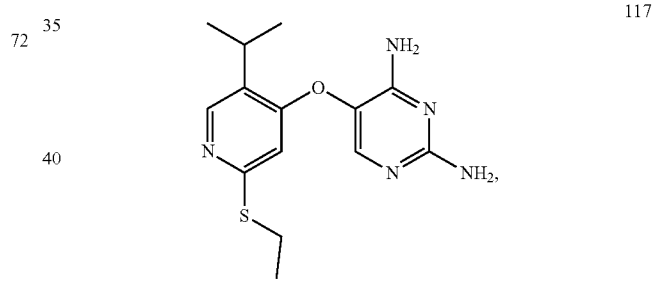
117
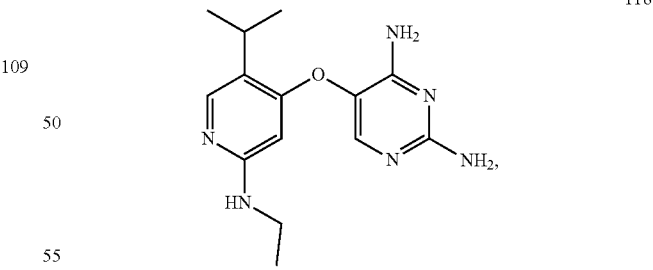
118
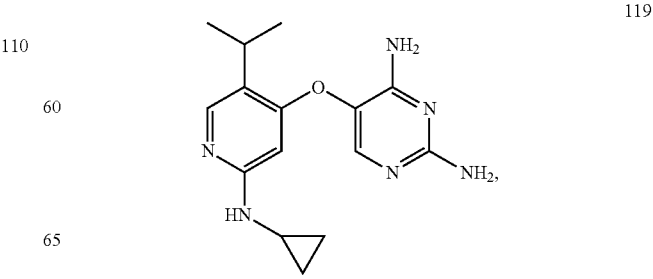
119

| 120 | 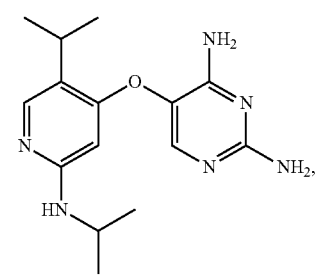 | 126 | 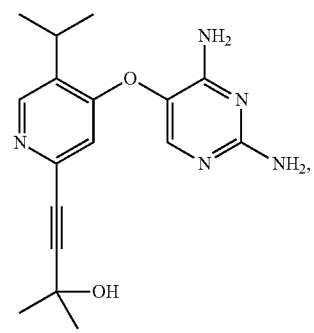 |
| 121 | 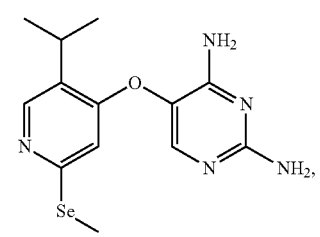 | 128 | 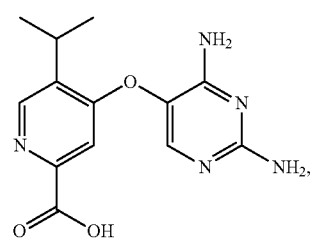 |
| 122 | 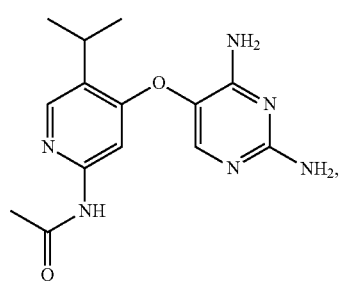 | 129 | 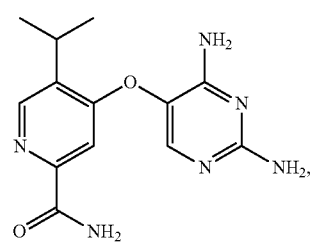 |
| 123 | 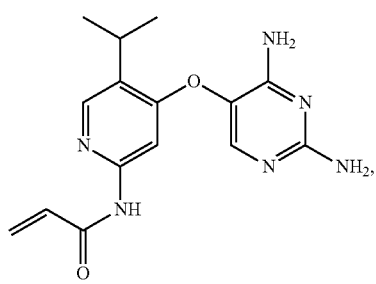 | 131 | 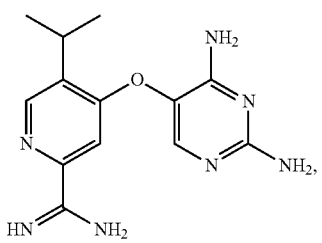 |
| | | 133 | 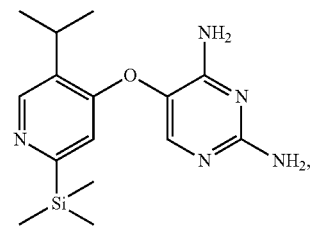 |
| 124 | 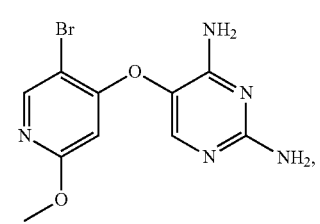 | 134 | 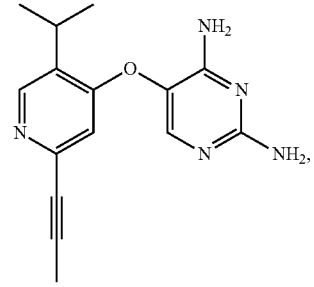 |

| 135 | 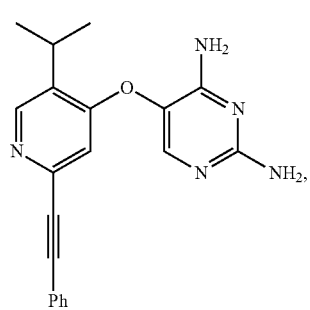 | 139 | 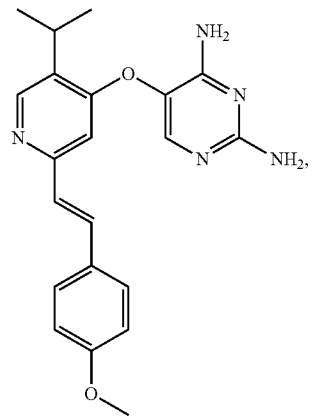 |
| 136 | 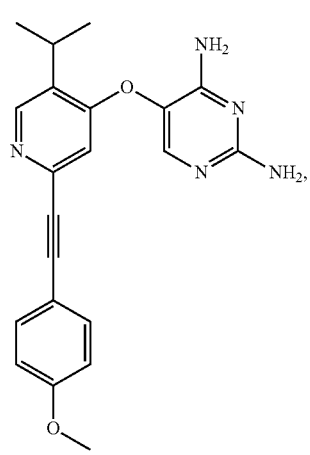 | 140 | 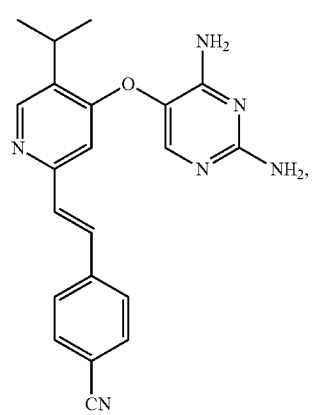 |
| 137 | 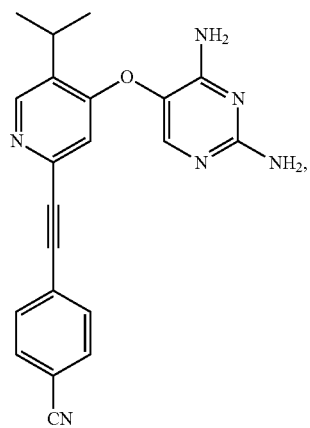 | 141 | 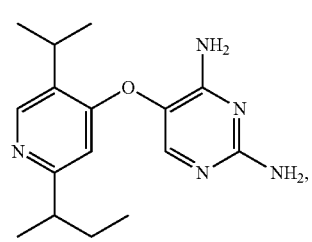 |
| 138 | 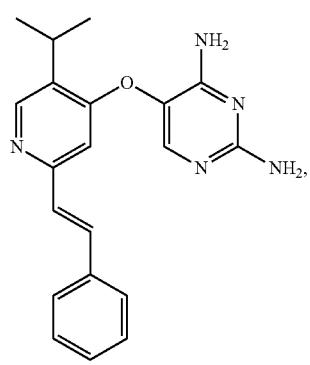 | 142 | 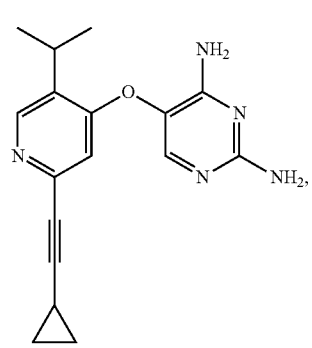 |

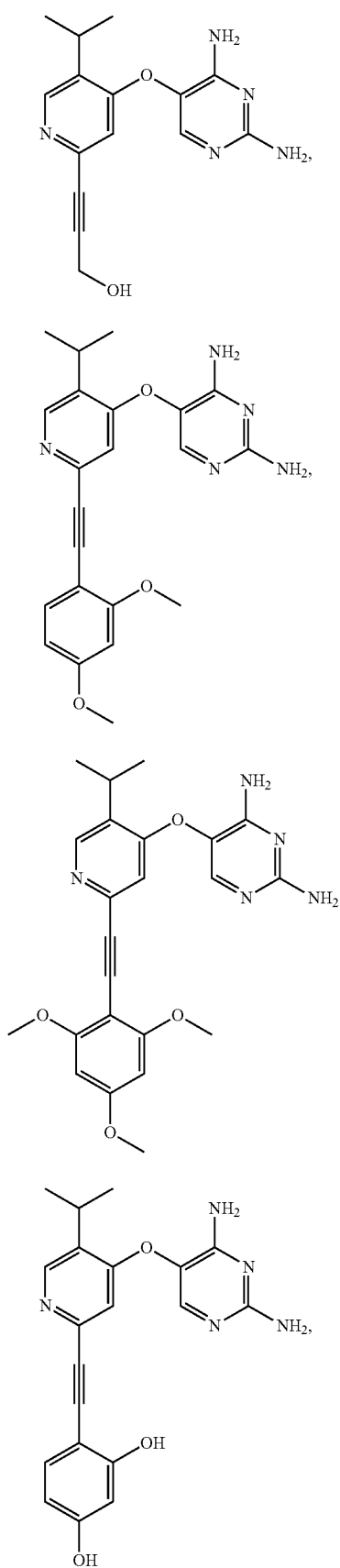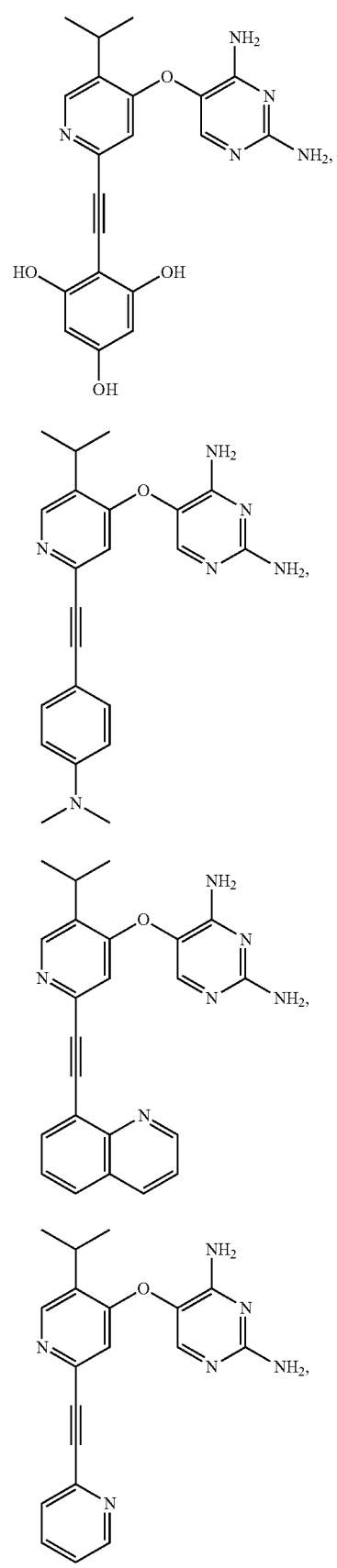

-continued
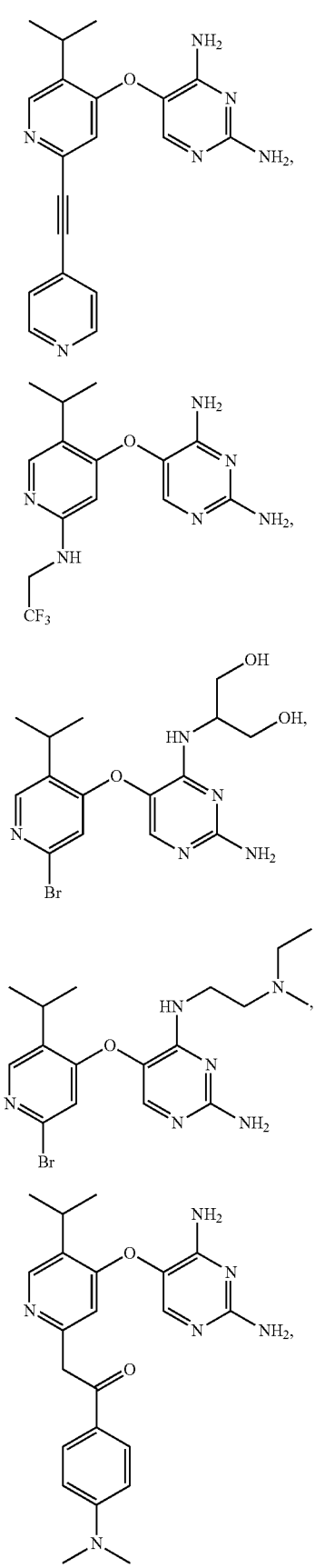
-continued
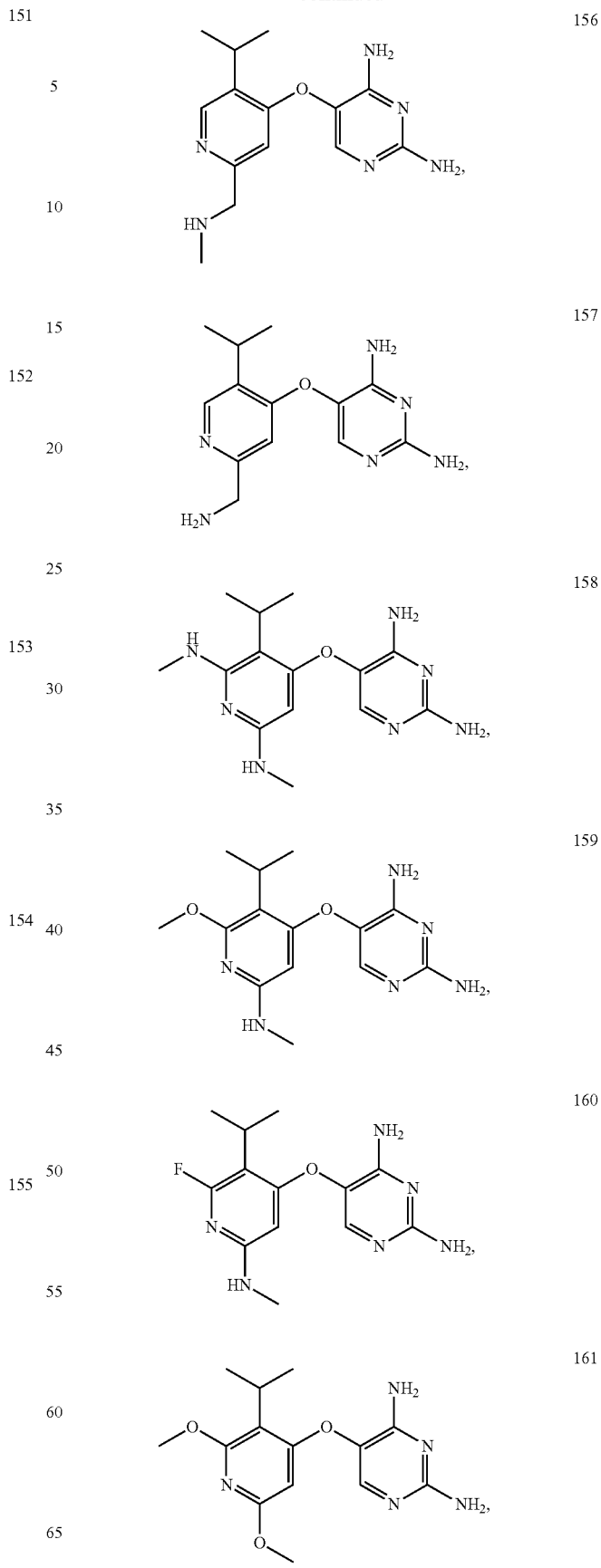

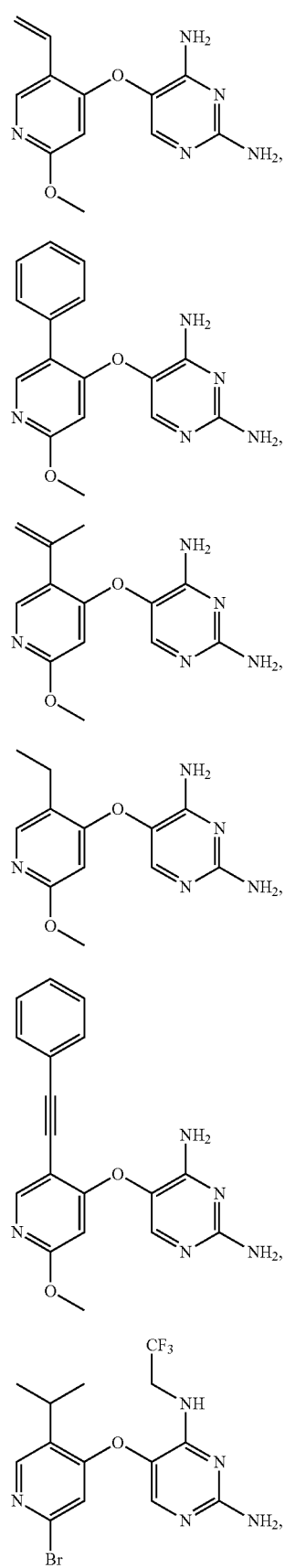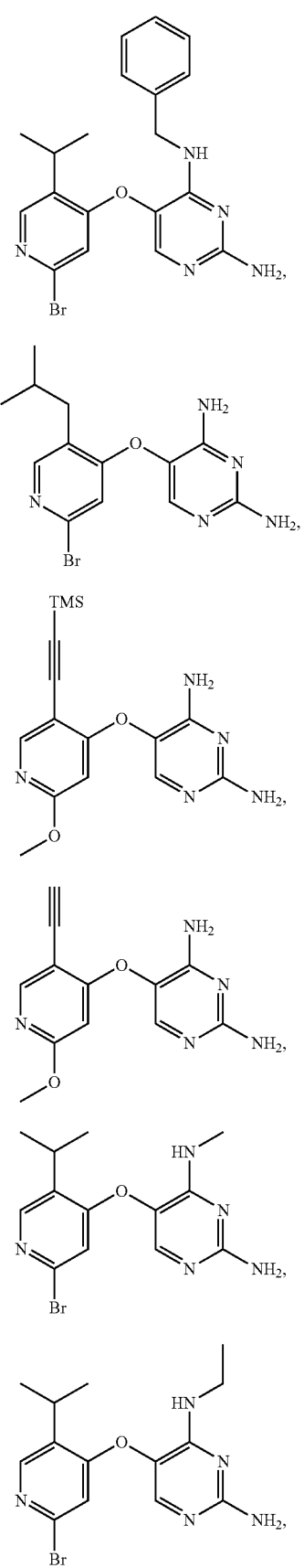

| | |
|---|---|
| 174 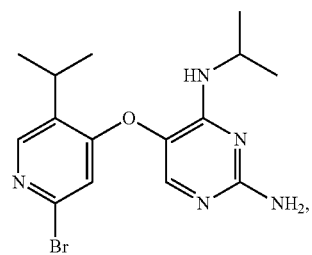 | 180 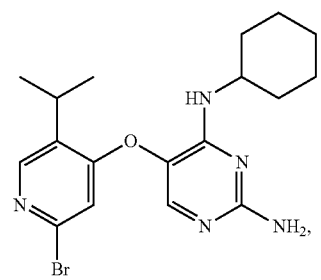 |
| 175 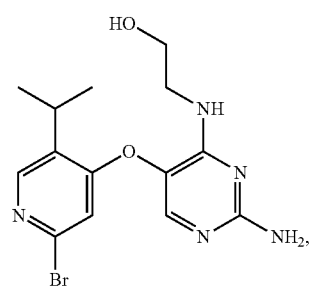 | 181 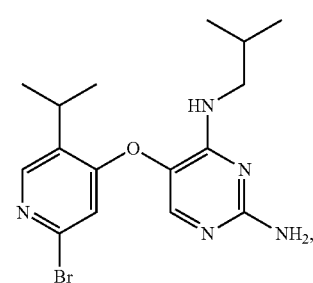 |
| 176 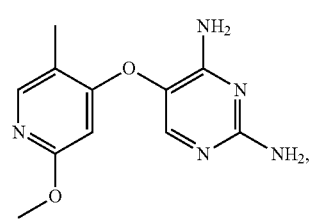 | 182 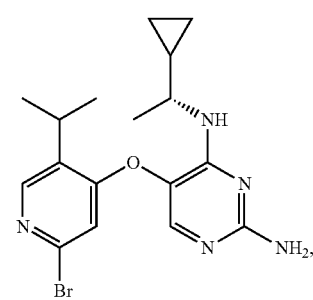 |
| 177 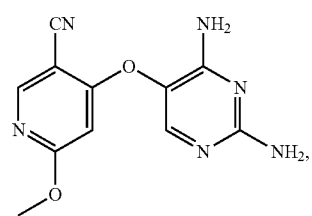 | 183 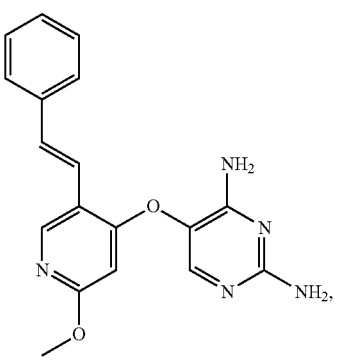 |
| 178 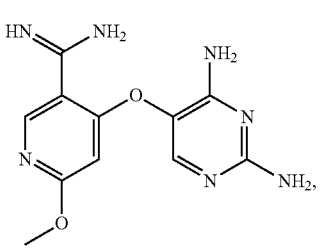 | 184 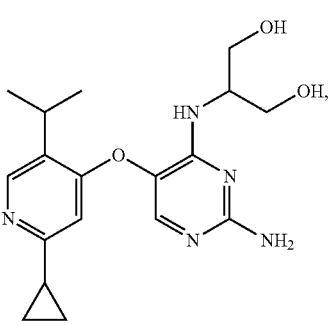 |
| 179 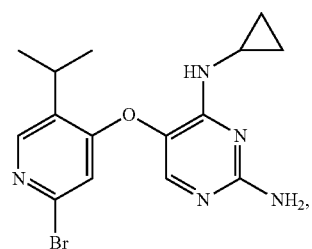 | |

| | | | |
|---|---|---|---|
| 185 | 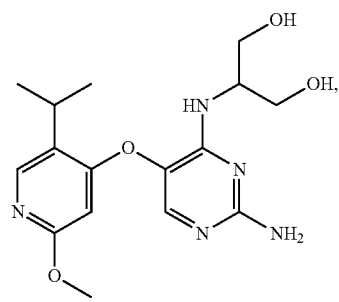 | 190 | 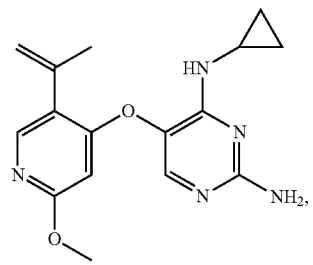 |
| 186 | 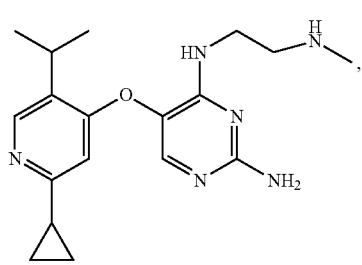 | 191 | 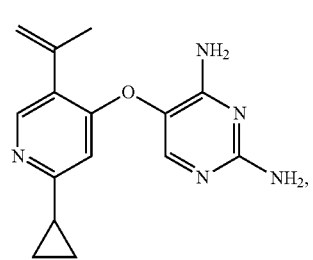 |
| 187 | 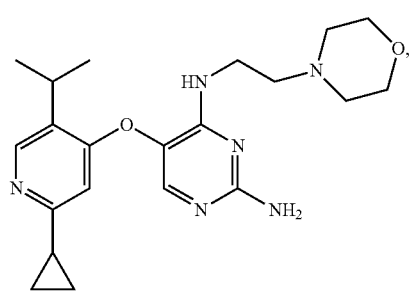 | 192 | 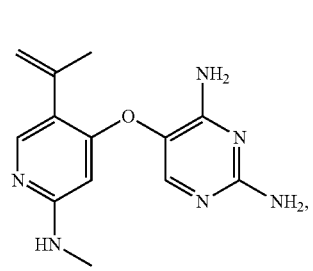 |
| 188 | 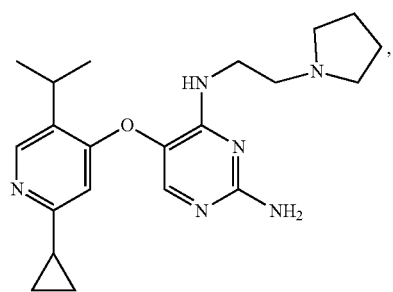 | 193 | 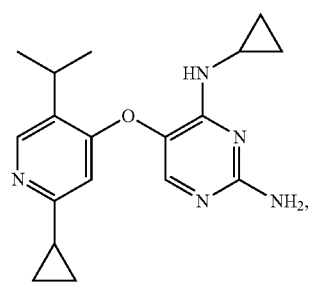 |
| 189 | 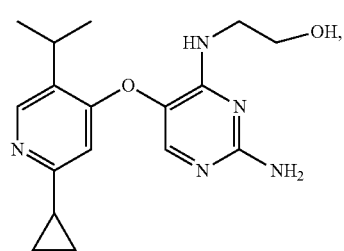 | 194 | 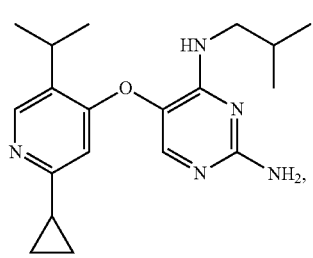 |

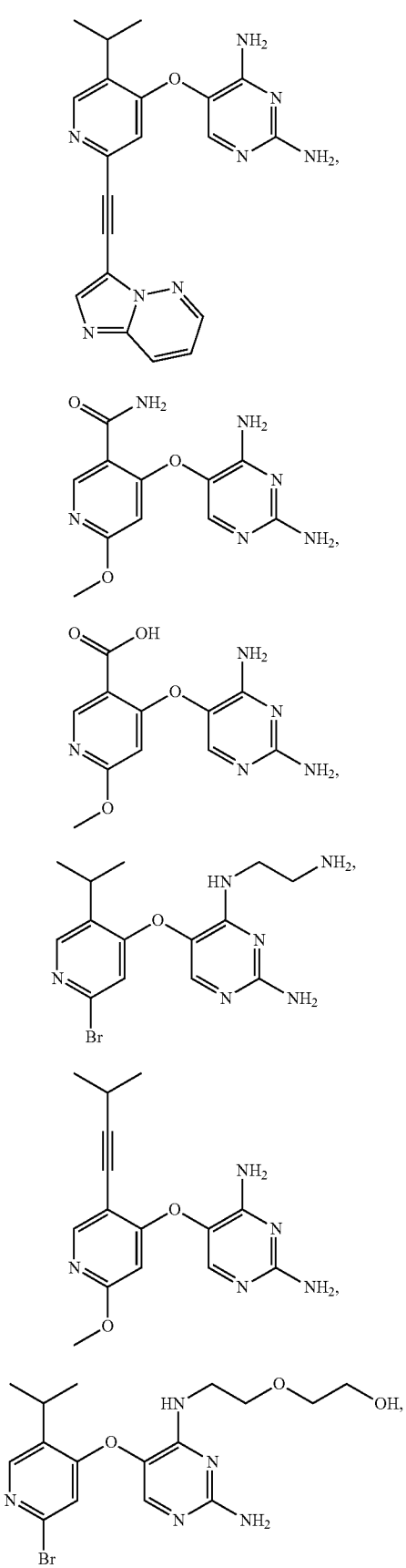

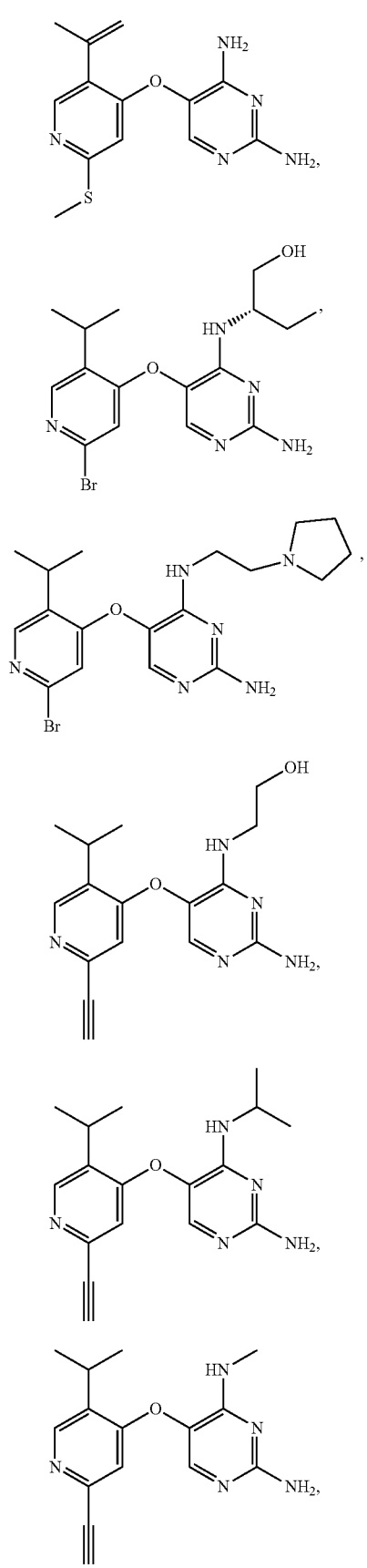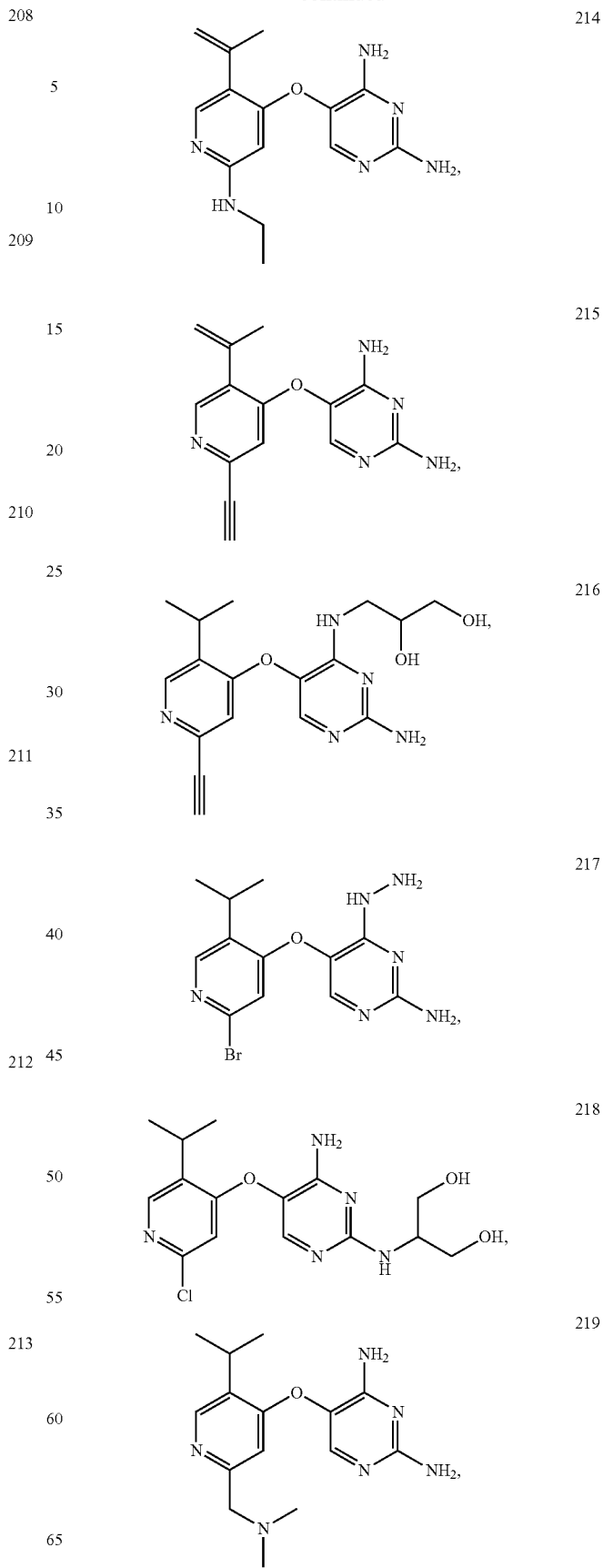

220 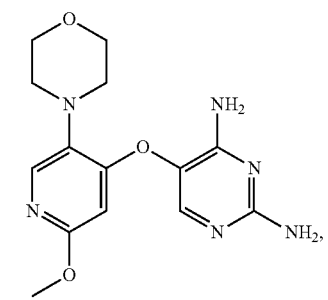
221 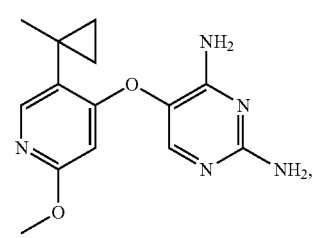
222 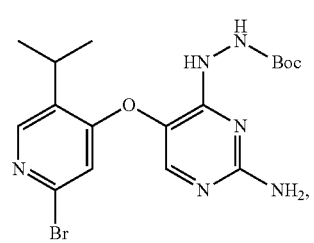
223 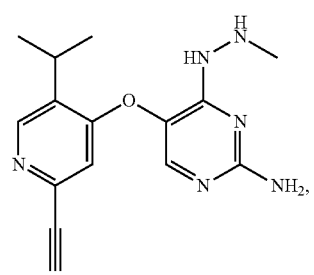
224 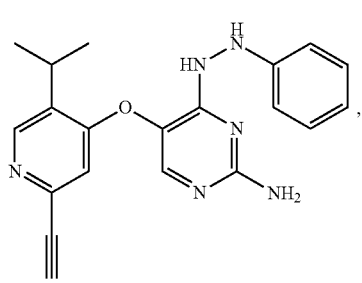
225 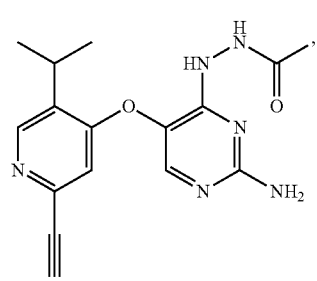
226 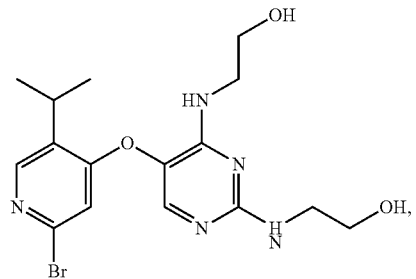
227 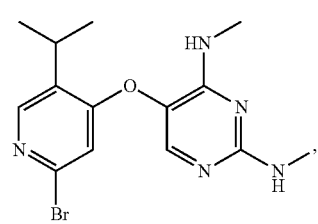
228 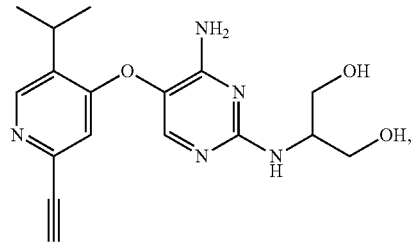
229 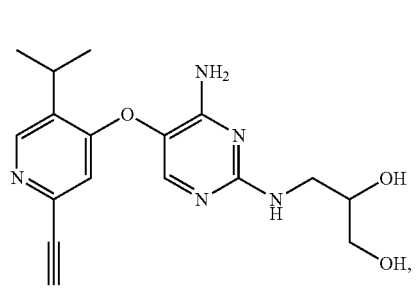
230 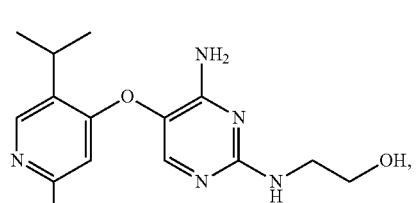
231 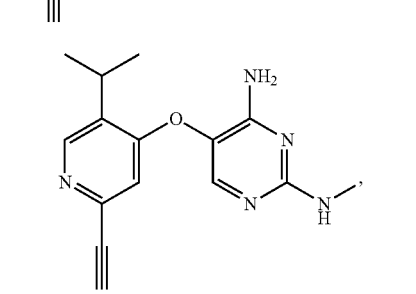

232 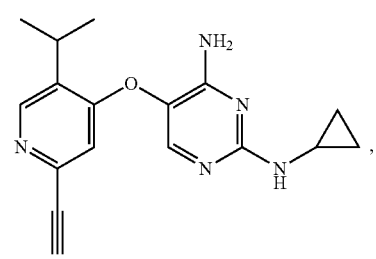
233 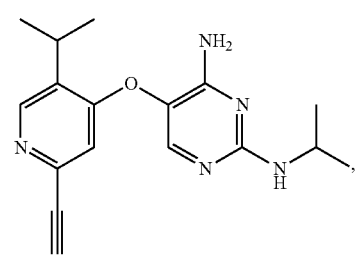
234 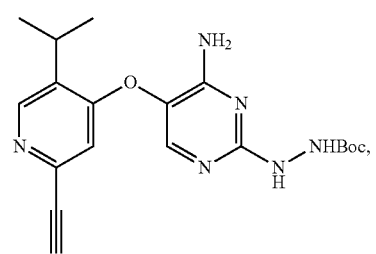
235 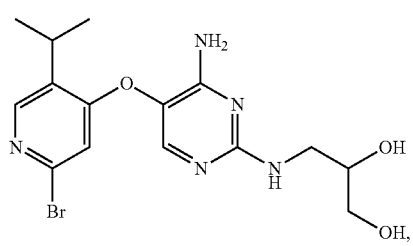
236 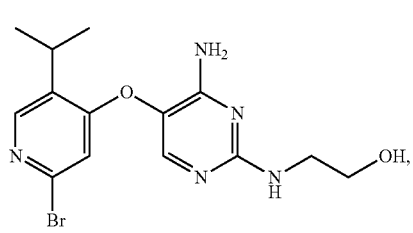
237 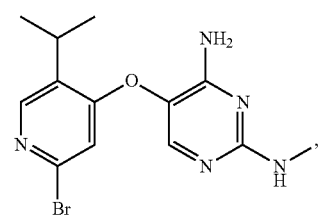
238 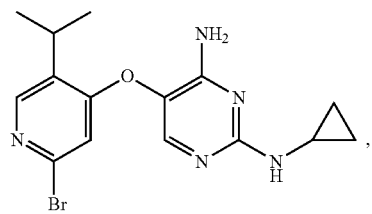
239 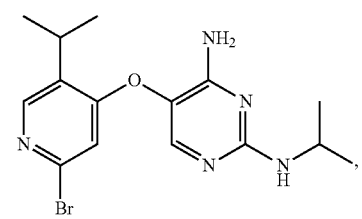
240 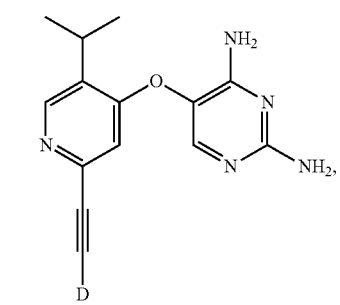
241 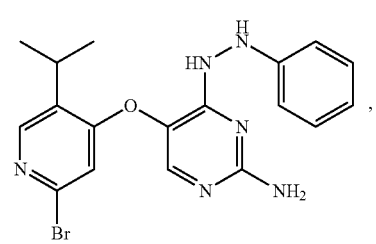
242 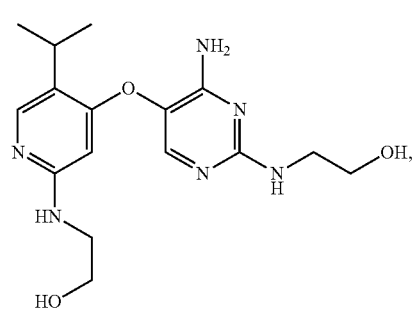
243 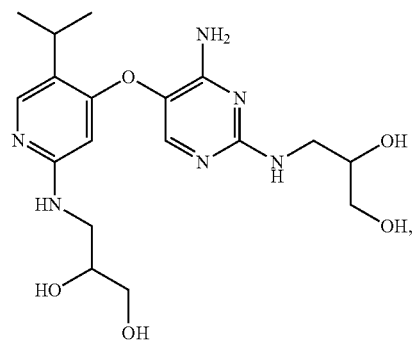

-continued

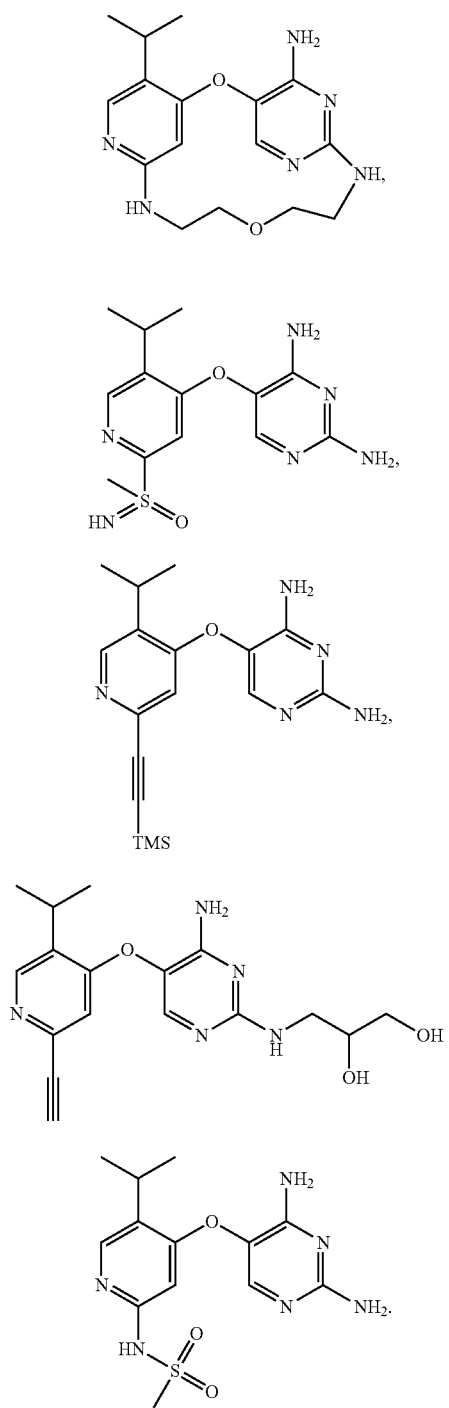

7. A method for the treatment of a disease mediated by the P2X3 and/or P2X2/3 receptor antagonist, wherein the method comprises administering to a subject in need thereof a pharmaceutical composition, the pharmaceutical composition comprises a prophylactically or therapeutically effective amount of a compound having the structure of Formula (I), or a pharmaceutically acceptable salt, ester, stereoisomer, polymorph, solvate, N-oxide, isotopically labeled compound or prodrug thereof, and a pharmaceutically acceptable carrier:

Formula (I)

wherein:
L is O;
$V^1$ is selected from the group consisting of N, $\overset{\oplus}{N}\text{—}\overset{\ominus}{O}$ and NR;
$V^2$ is selected from the group consisting of $CR^6$ and $C(=O)$;
$=$ represents either a single bond or a double bond, provided that when $=$ is a single bond, $V^1$ is NR and $V^2$ is $C(=O)$;
R is selected from the group consisting of H, halogen, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl, and at most 2 ring members in the cyclic hydrocarbyl and heterocyclyl are $C(=O)$;
$R^1$, $R^2$, $R^3$ and $R^6$ are each independently selected from the group consisting of H, halogen, —CN, —NH$_2$, —OH, —SH, —Se—R, —Si(R)$_3$, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl, $C_{6-12}$ aralkyl, $C_{1-6}$ haloalkyl, —C(=O)R$^a$, —OC(=O)R$^a$, —C(=O)OR$^a$, —OR$^a$, —SR$^a$, —S(=O)R$^a$, —S(=O)$_2$R$^a$, —S(=O)$_2$NR$^a$R$^b$, —S(=O)(=NR)R$^a$, —NR$^a$R$^b$, —C(=O)NR$^a$R$^b$, —C(=S)NR$^a$R$^b$, —C(=NR)NR$^a$R$^b$, —NR$^a$—C(=O)R$^b$, —NR$^a$—C(=O)OR$^b$, —NR$^a$—S(=O)$_2$—R$^b$, —NR$^a$—C(=O)—NR$^a$R$^b$, —C$_{1-6}$ alkylene-NR$^a$R$^b$, —C$_{1-6}$ alkylene-OR$^a$, —C$_{1-6}$ alkylene- C(=O)R, —C$_{1-6}$ alkenylene-OR$^a$, —O—C$_{1-6}$ alkylene-NRaR$^b$ and —P(=O)RaR$^b$;
$R^4$ and $R^5$ are each independently selected from the group consisting of H, —C(=O)OR$^a$, —NR$^a$R$^b$, —NR$^a$—C(=O)R$^b$, —NR$^a$—C(=O)OR$^b$, —C$_{1-6}$ alkylene-NR$^a$R$^b$, —C$_{1-6}$ alkylene-OR$^a$, —C$_{1-6}$ alkylene-O—C$_{1-6}$ alkylene-OR$^a$, $C_{1-6}$ alkyl, $C_{1-6}$ haloalkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12\ aralkyl}$;
alternatively, $R^1$ and $R^4$ together form —NH—($C_{1-6}$ alkylene)-L-($C_{1-6}$ alkylene)-;
the above alkyl, alkylene, alkenyl, alkynyl, cyclic hydrocarbyl, heterocyclyl, aryl, heteroaryl and aralkyl, at each occurrence, are each optionally substituted with one or more substituents independently selected from the group consisting of halogen, hydroxyl, oxo, amino, cyano, nitro, —Si(R)$_3$, $C_{1-6}$ alkyl, saturated or partially unsaturated $C_{3-6}$ cyclic hydrocarbyl, saturated or partially unsaturated 3- to 10-membered heterocyclyl, $C_{6-10}$ aryl, 5- to 14-membered heteroaryl, $C_{6-12}$ aralkyl, —C(=O)R$^a$, —OC(=O)R$^a$, —C(=O)OR$^a$, —OR$^a$, —SR—, —S(=O)R$^a$, —S(=O)$_2$R$^a$, —S(=O)$_2$NR$^a$R$^b$, —NR$^a$R$^b$, —C(=O)NR$^a$R$^b$, —NR$^a$—C(=O)R$^b$, —NR$^a$—C(=O)OR$^b$, —NR$^a$—S(=O)$_2$—R$^b$, —NR$^a$—C(=O)—NR$^a$R$^b$, —C$_{1-6}$ alkylene-NR$^a$R$^b$, —C$_{1-6}$ alkylene-OR$^a$, —C$_{1-6}$ alkenylene-OR$^a$ and —O—C$_{1-6}$ alkylene-NR$^a$R$^b$, the alkyl, cyclic hydrocarbyl, heterocyclyl, aryl, heteroaryl and aralkyl are further optionally substituted with one or more substituents independently selected from the group consisting of halogen, hydroxyl, oxo, amino, cyano, nitro, —NR$^a$R$^b$, C$_{1-6}$ alkyl, —O—C$_{1-6}$ alkyl, saturated or partially unsaturated C$_{3-6}$ cyclic hydrocarbyl, saturated or partially unsaturated 3- to 10-membered heterocyclyl, C$_{6-10}$ aryl, 5- to 14-membered heteroaryl and C$_{6-12}$ aralkyl; and R$^a$ and R$^b$, at each occurrence, are each independently selected from the group consisting of H, —OH, C$_{1-6}$ alkyl, C$_{2-6}$ alkenyl, C$_{2-6}$ alkynyl, saturated or partially unsaturated C$_{3-10}$ cyclic hydrocarbyl, saturated or partially unsaturated 3- to 10-membered heterocyclyl, C$_{6-10}$ aryl, 5- to 14-membered heteroaryl and C$_{6-12}$ aralkyl; alternatively, R$^1$ and R$^b$ together with the atom to which they are attached form a 3- to 12-membered heterocycle or heteroaromatic ring, the above groups are further optionally substituted with one or more substituents independently selected from the group consisting of halogen, hydroxyl, oxo, amino, cyano, nitro, C$_{1-6}$ alkyl, —O—C$_{1-6}$ alkyl, saturated or partially unsaturated C$_{3-6}$ cyclic hydrocarbyl, saturated or partially unsaturated 3- to 10-membered heterocyclyl, C$_{6-10}$ aryl, 5- to 14-membered heteroaryl and C$_{6-12}$ aralkyl.

8. The method according to claim 1, wherein the disease is selected from the group consisting of a urinary tract disease selected from reduced bladder capacity, frequent micturition, urge incontinence, stress incontinence, bladder hyperreactivity, benign prostatic hypertrophy, prostatitis, detrusor hyperreflexia, nocturia, urinary urgency, pelvic hypersensitivity, urethritis, pelvic pain syndrome, prostatodynia, cystitis, and idiopathic bladder hypersensitivity; pain disease selected from inflammatory pain, surgical pain, visceral pain, dental pain, premenstrual pain, central pain, pain due to burns, migraine and cluster headaches, nerve injury, neuritis, neuralgia, poisoning, ischemic injury, interstitial cystitis, cancer pain, viral, parasitic or bacterial infection, post-traumatic injury and pain associated with irritable bowel syndrome; cardiovascular system disease; respiratory disease selected from chronic obstructive pulmonary disease, asthma and bronchospasm; gastrointestinal disease selected from irritable bowel syndrome, inflammatory bowel disease, biliary colic, renal colic, and pain associated with gastrointestinal distension.

9. The method according to claim 7, wherein the disease is selected from the group consisting of a urinary tract disease selected from reduced bladder capacity, frequent micturition, urge incontinence, stress incontinence, bladder hyperreactivity, benign prostatic hypertrophy, prostatitis, detrusor hyperreflexia, nocturia, urinary urgency, pelvic hypersensitivity, urethritis, pelvic pain syndrome, prostatodynia, cystitis, and idiopathic bladder hypersensitivity; pain disease selected from inflammatory pain, surgical pain, visceral pain, dental pain, premenstrual pain, central pain, pain due to burns, migraine and cluster headaches, nerve injury, neuritis, neuralgia, poisoning, ischemic injury, interstitial cystitis, cancer pain, viral, parasitic or bacterial infection, post-traumatic injury and pain associated with irritable bowel syndrome; cardiovascular system disease; respiratory disease selected from chronic obstructive pulmonary disease, asthma and bronchospasm; gastrointestinal disease selected from irritable bowel syndrome, inflammatory bowel disease, biliary colic, renal colic, and pain associated with gastrointestinal distension.

10. A method for the treatment of a disease mediated by the P2X3 and/or P2X2/3 receptor antagonist, wherein the method comprises administering to a subject in need thereof a pharmaceutical composition, the pharmaceutical composition comprises a prophylactically or therapeutically effective amount of a compound, or a pharmaceutically acceptable salt, ester, stereoisomer, polymorph, solvate, N-oxide, isotopically labeled compound or prodrug thereof, and a pharmaceutically acceptable carrier, wherein the compound has the following structure:

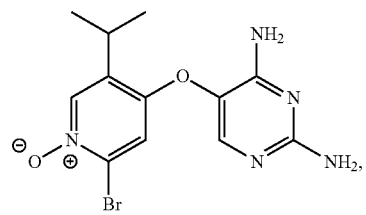

1

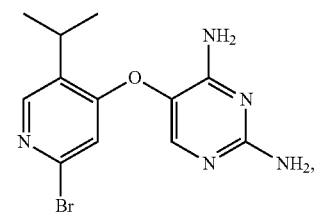

2

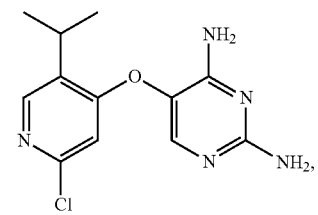

3

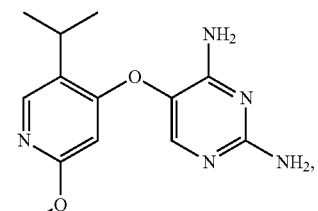

4

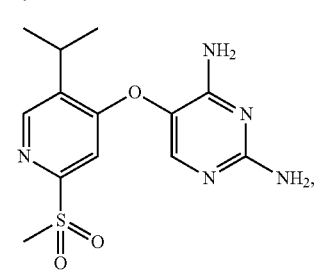

5

6
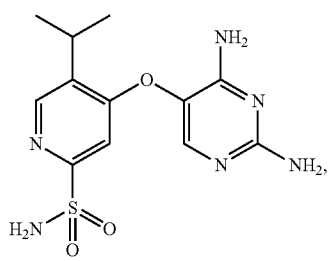
7
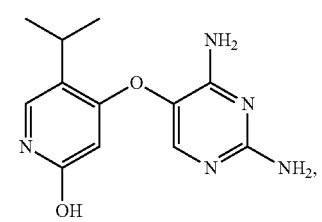
8
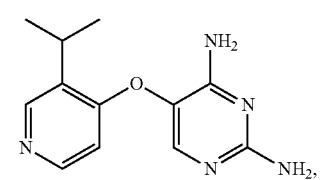
9
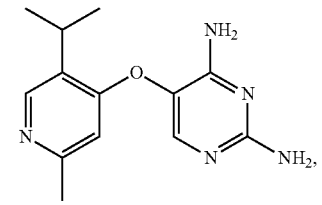
11
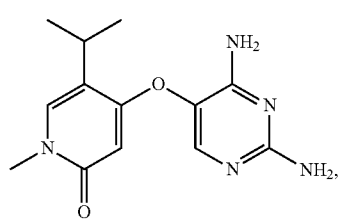
12
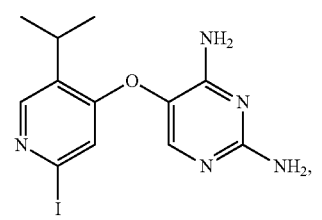
13
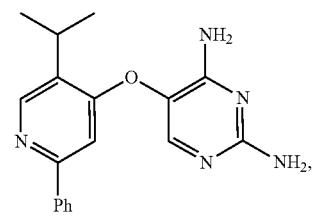
14
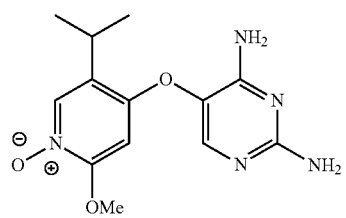
15
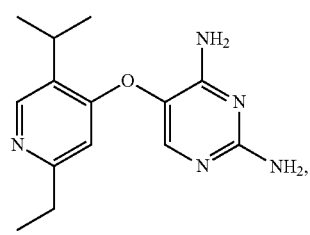
16
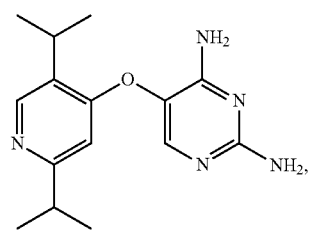
17
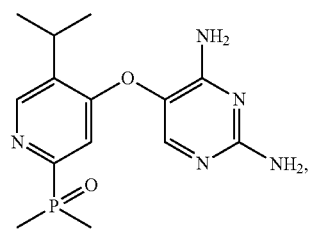
18
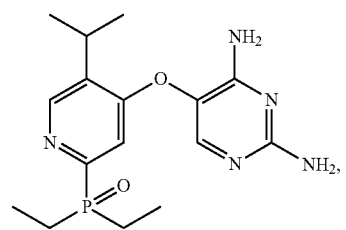
19
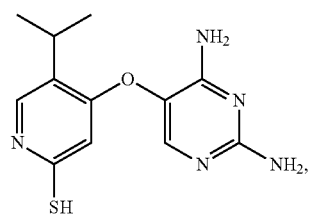
20
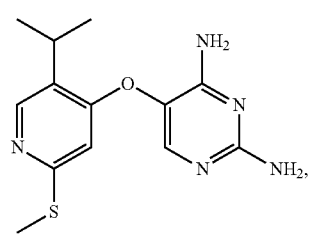

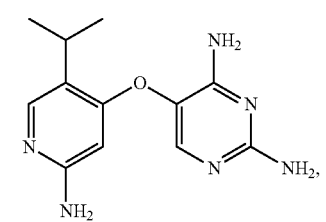
21
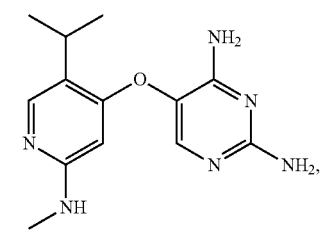
22
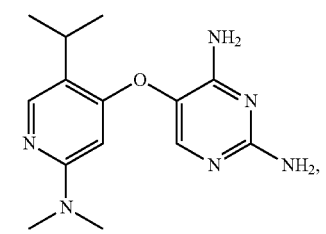
23
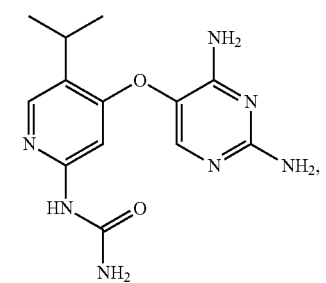
24
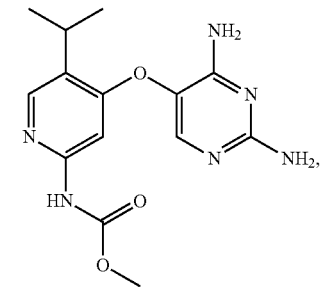
25
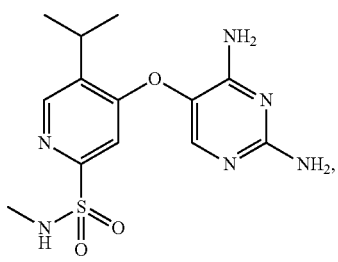
26
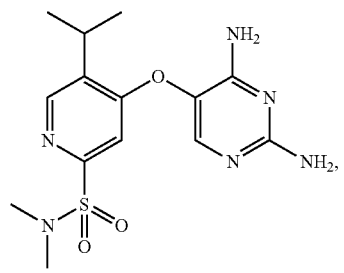
27
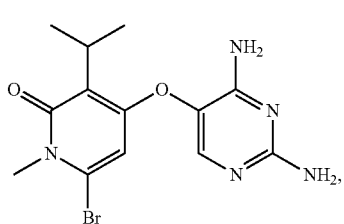
28
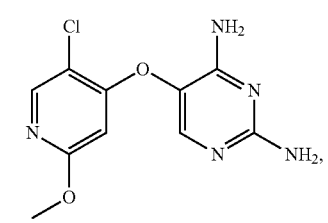
29
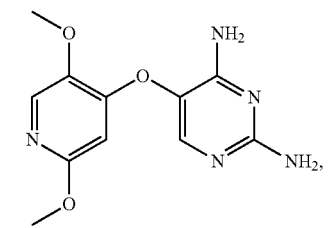
30
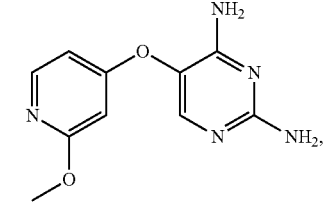
31
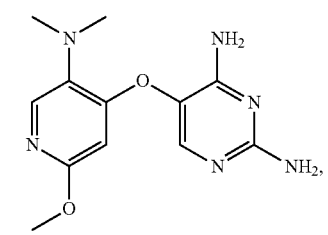
32
33

34
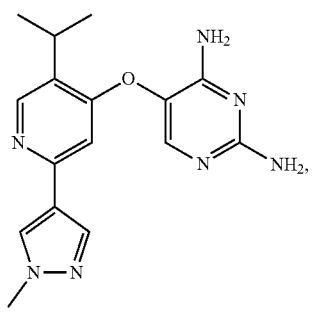
35
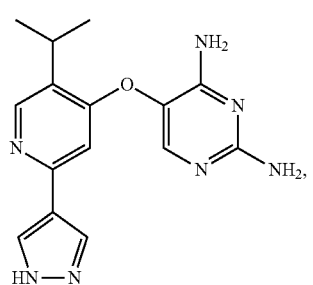
36
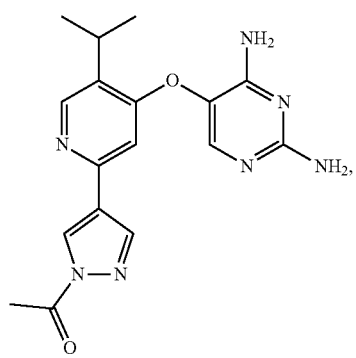
37
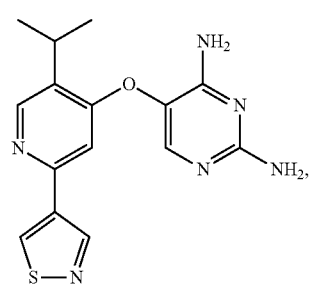
38
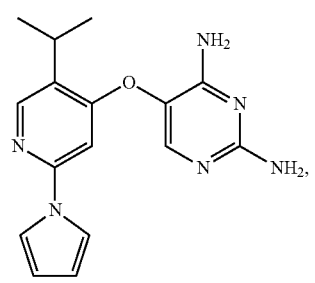
39
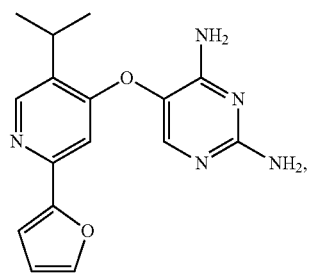
40
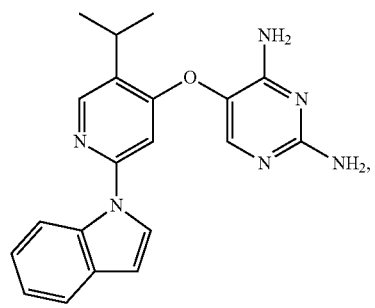
41
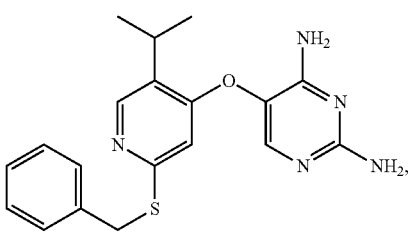
42
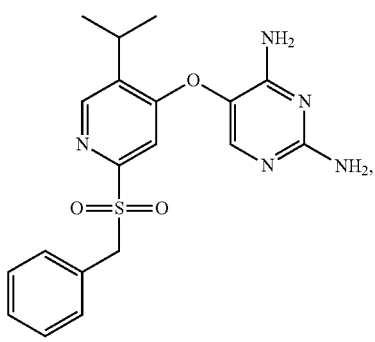
43
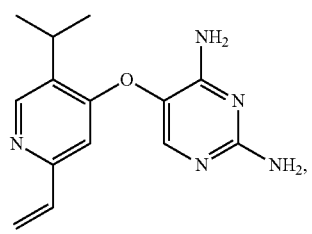
44
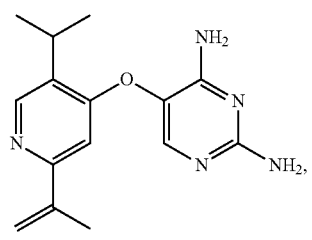

-continued

| | |
|---|---|
| 57 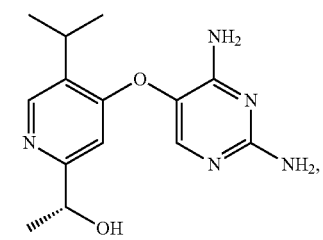 | 63 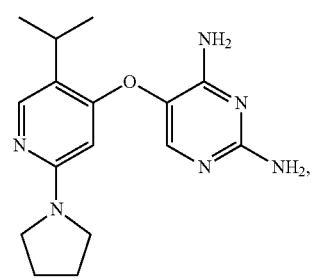 |
| 58 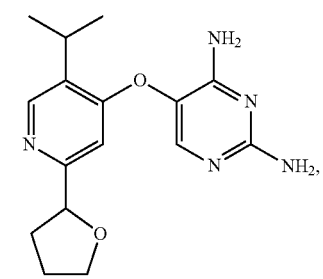 | 64 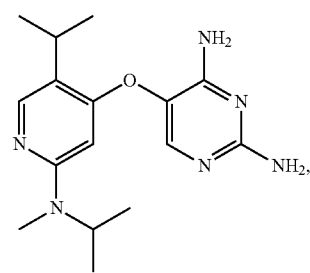 |
| 59 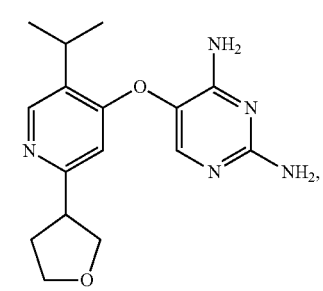 | 65 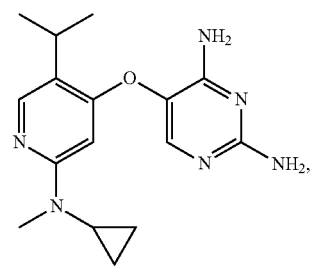 |
| 60 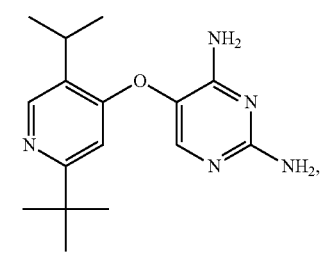 | 66 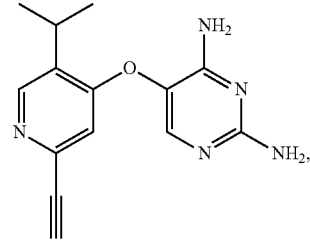 |
| 61 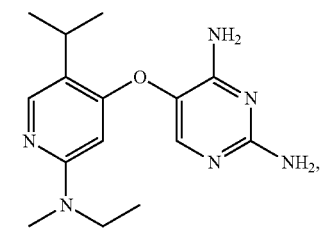 | 67 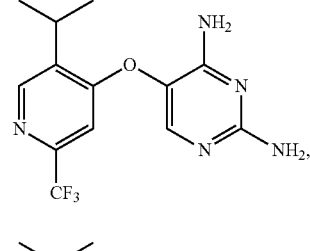 |
| 62 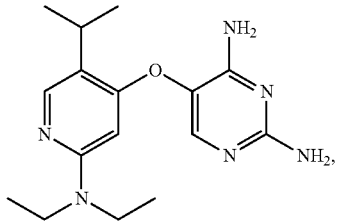 | 68 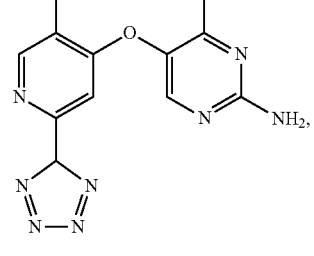 |

69 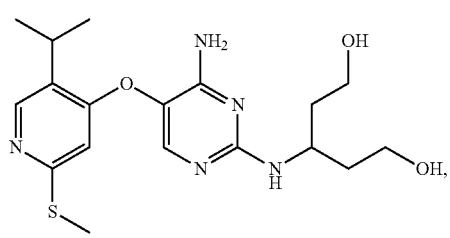
70 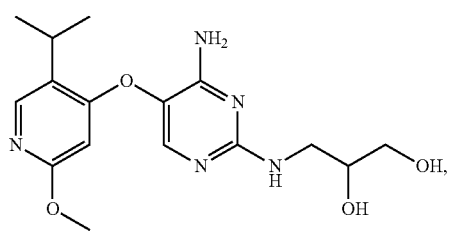
71 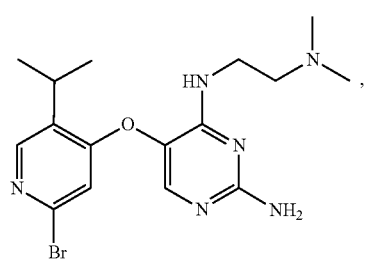
72 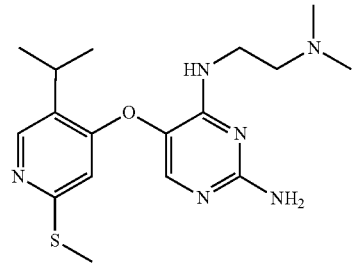
109 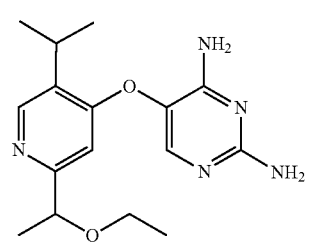
110 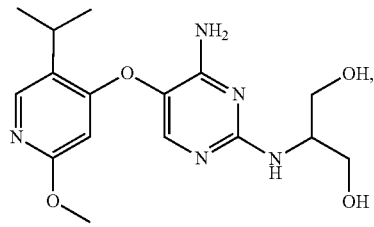
111 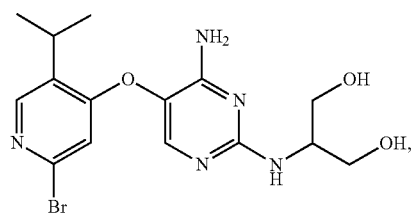
115 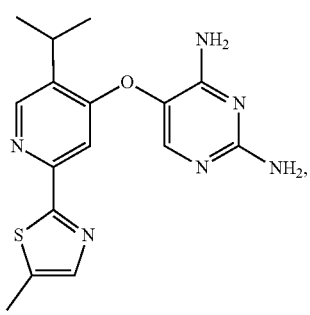
116 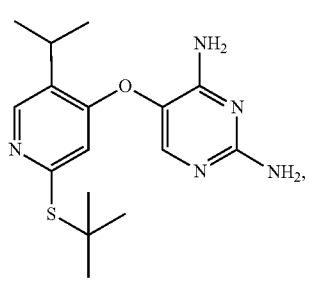
117 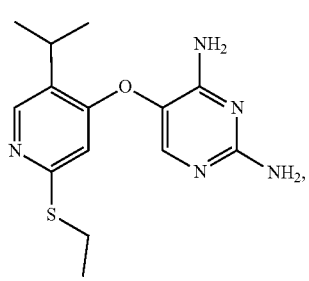
118 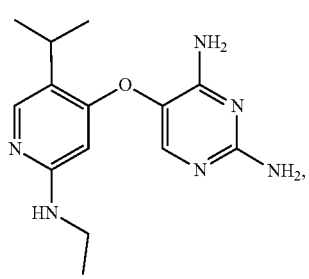
119 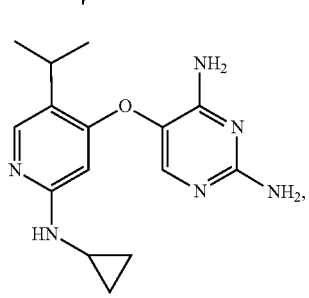

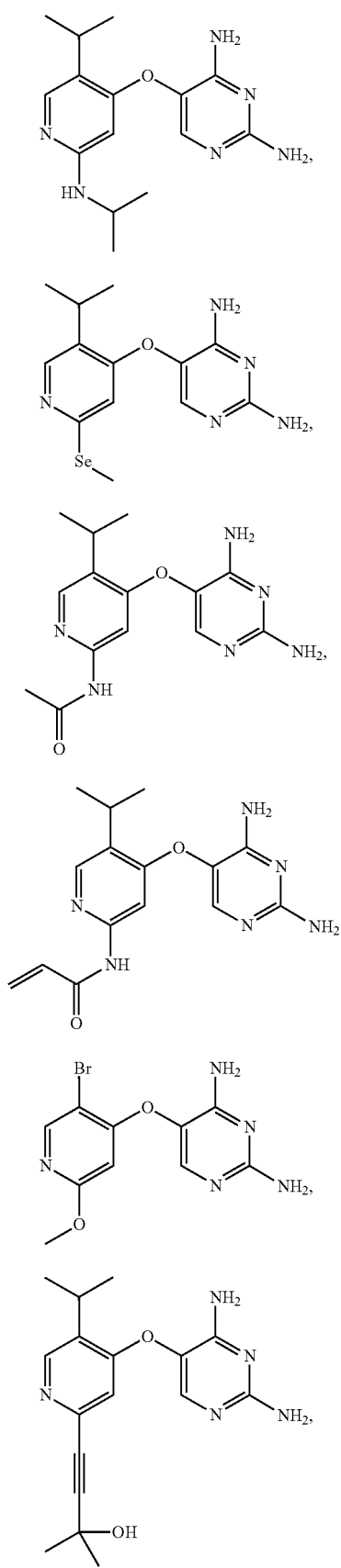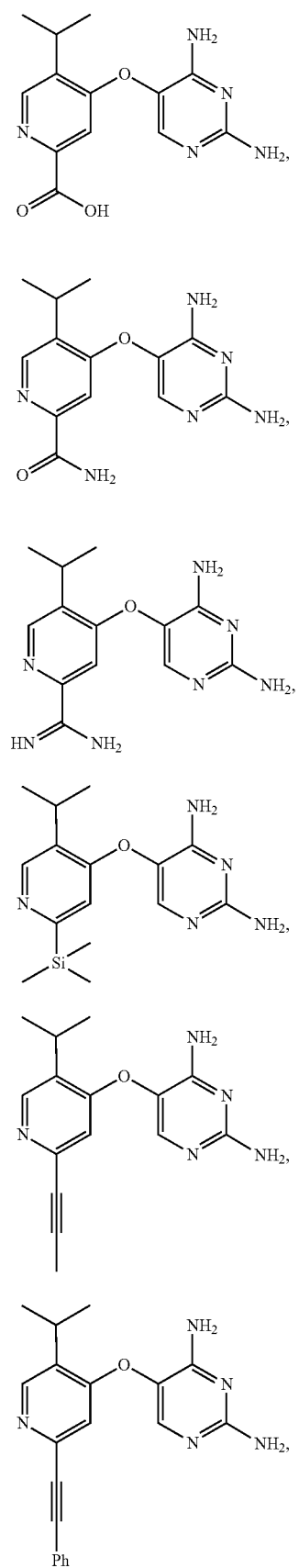

136 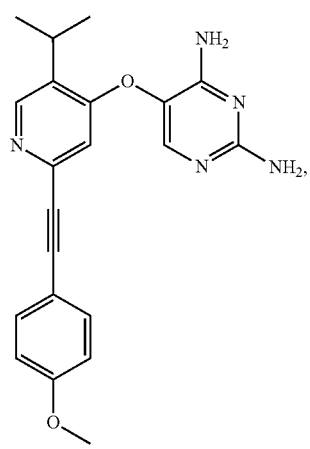
137 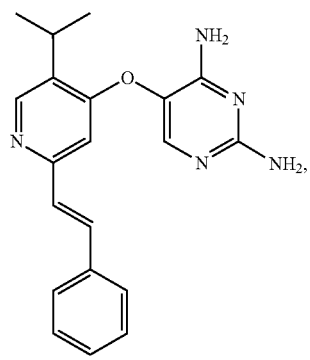
138 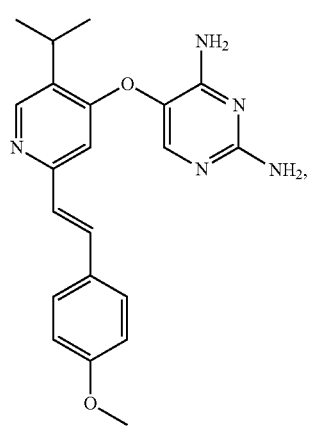
139
140 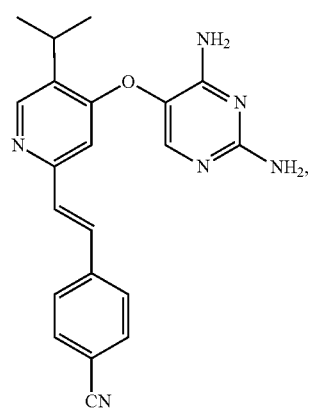
141 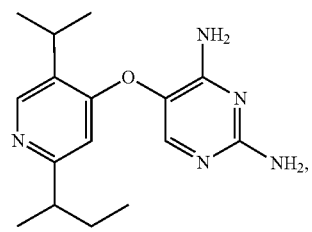
142 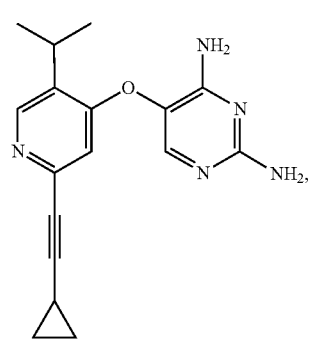
143 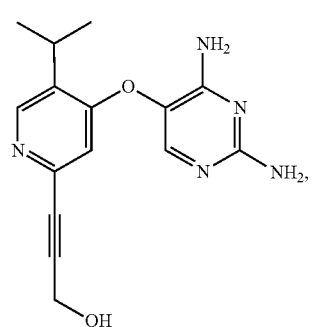

144
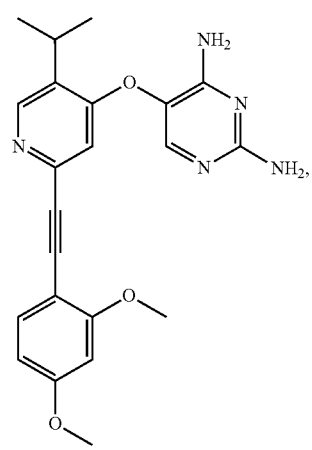
145
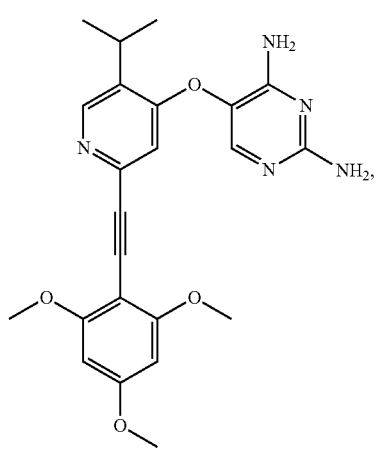
146
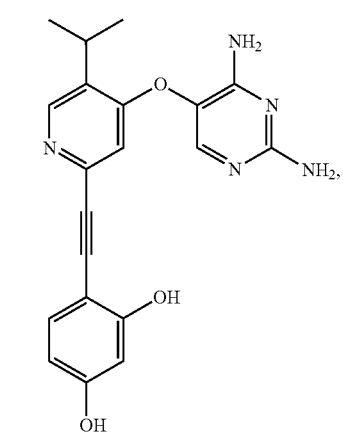
147
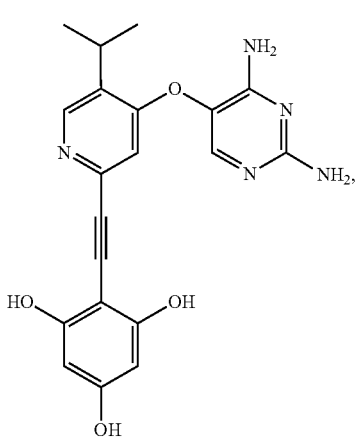
148
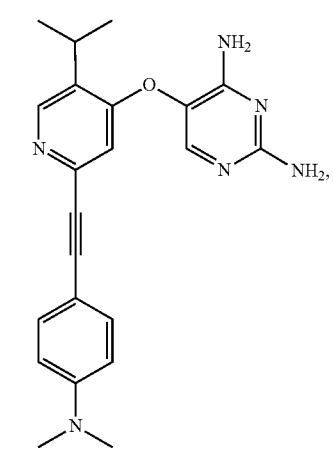
149
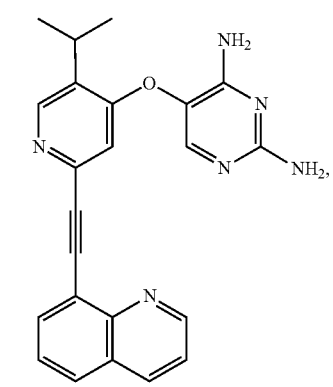
150
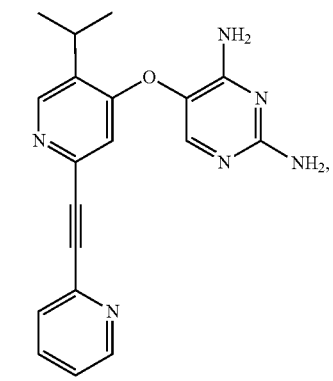

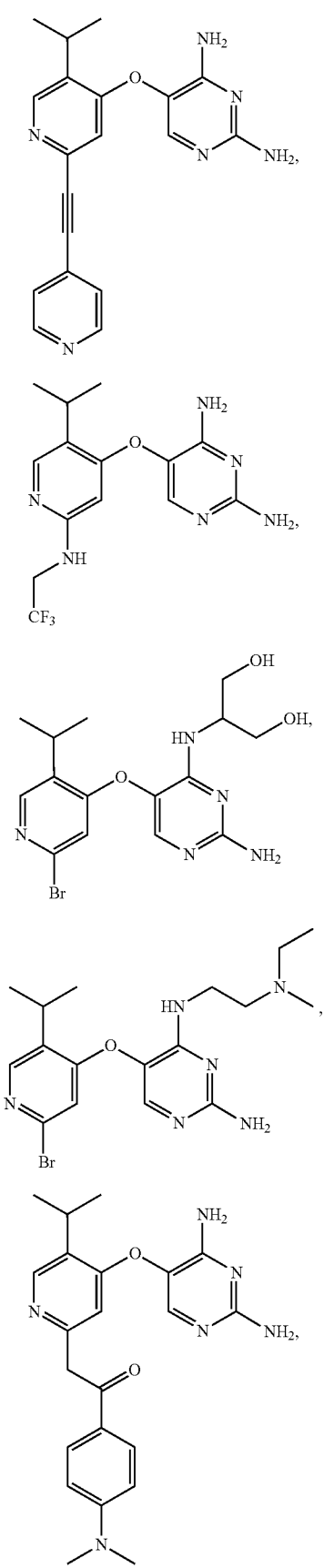
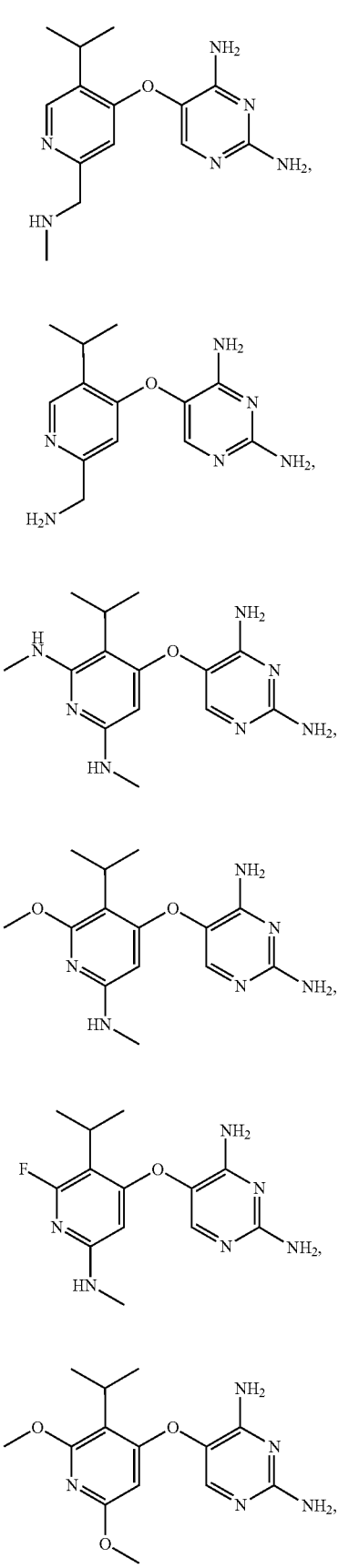

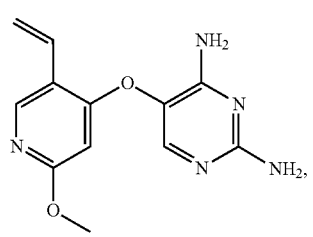
162
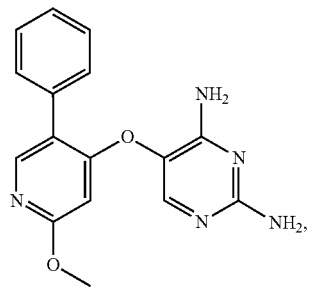
163
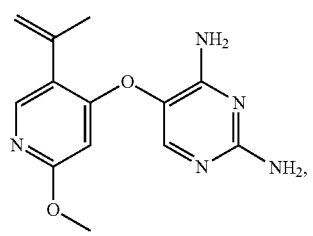
164
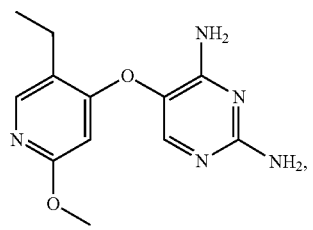
165
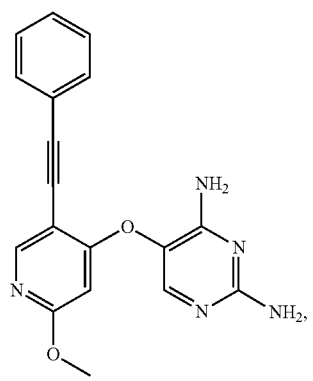
166
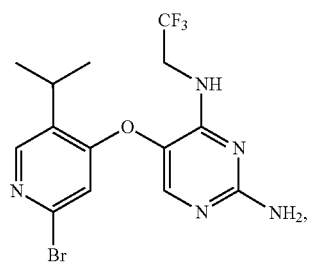
167
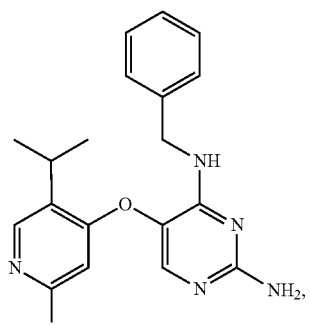
168
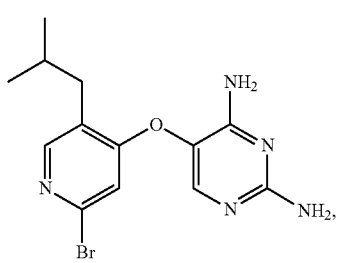
169
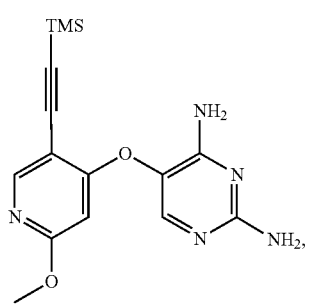
170
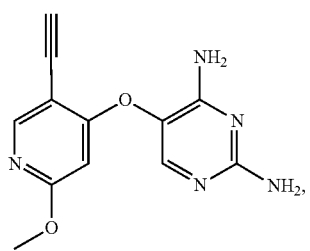
171
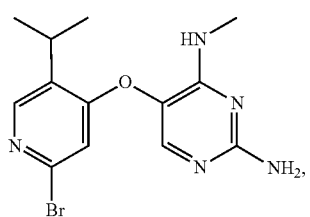
172

-continued
| | |
|---|---|
| 173 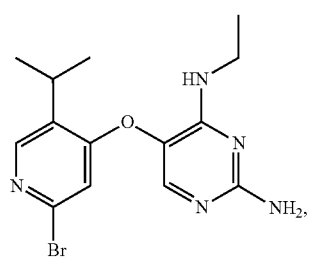 | 179 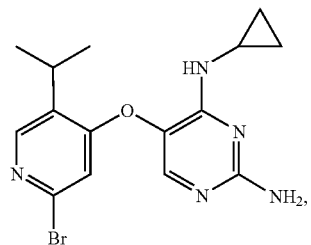 |
| 174 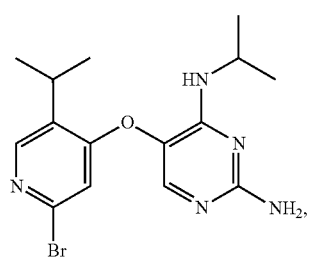 | 180 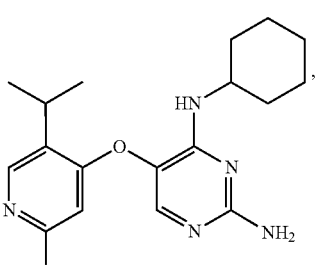 |
| 175 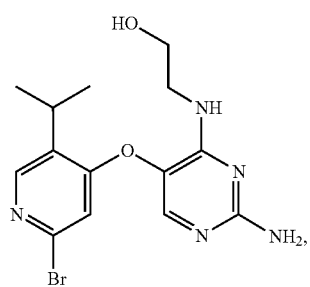 | 181 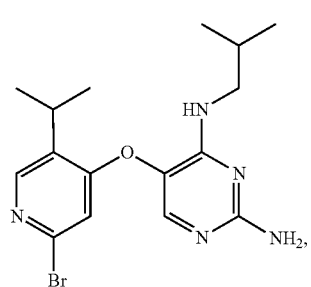 |
| 176 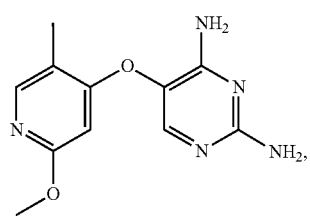 | 182 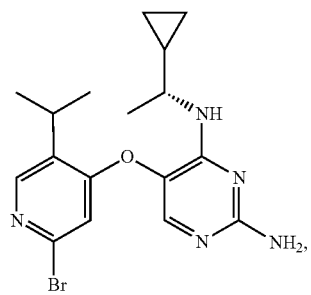 |
| 177 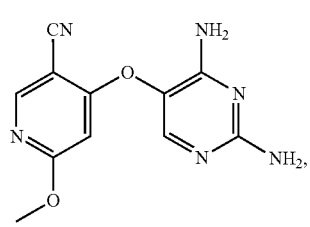 | 183 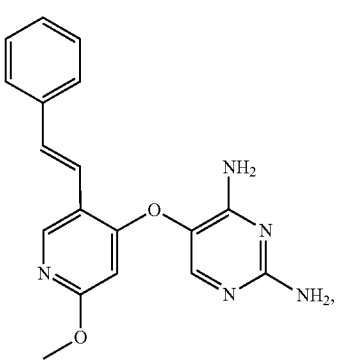 |
| 178 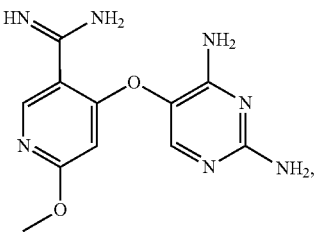 | |

-continued
184
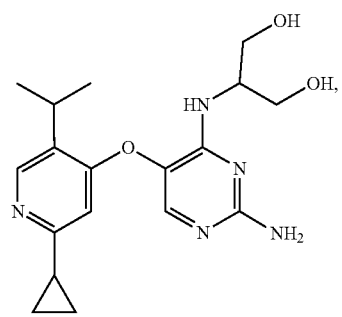
185
186
187
188
-continued
189
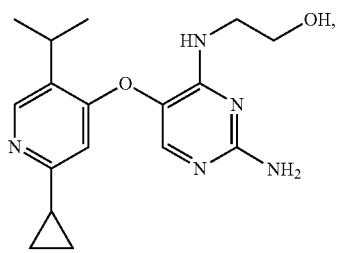
190
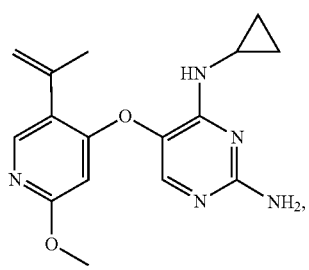
191
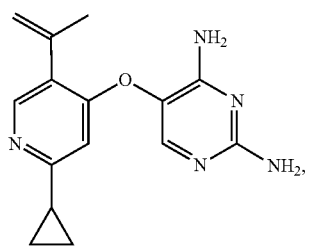
192
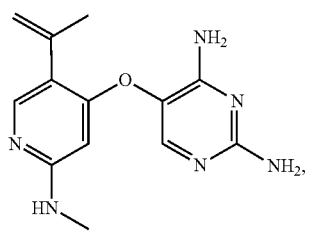
193
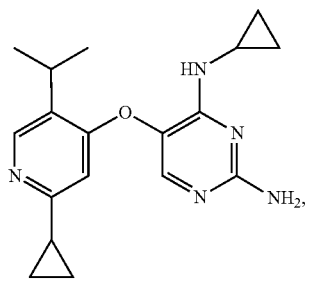
194
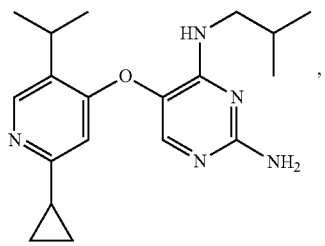

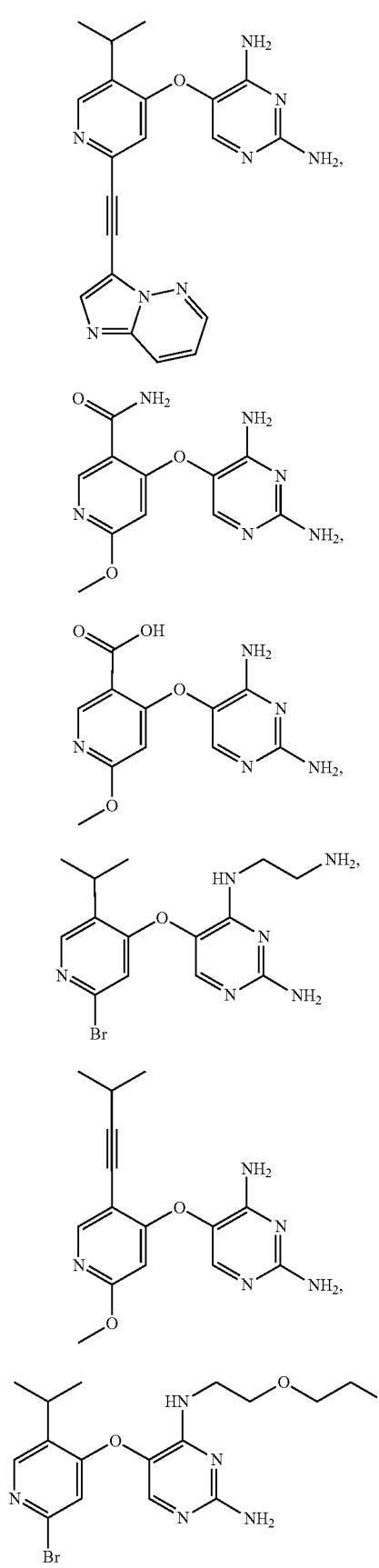
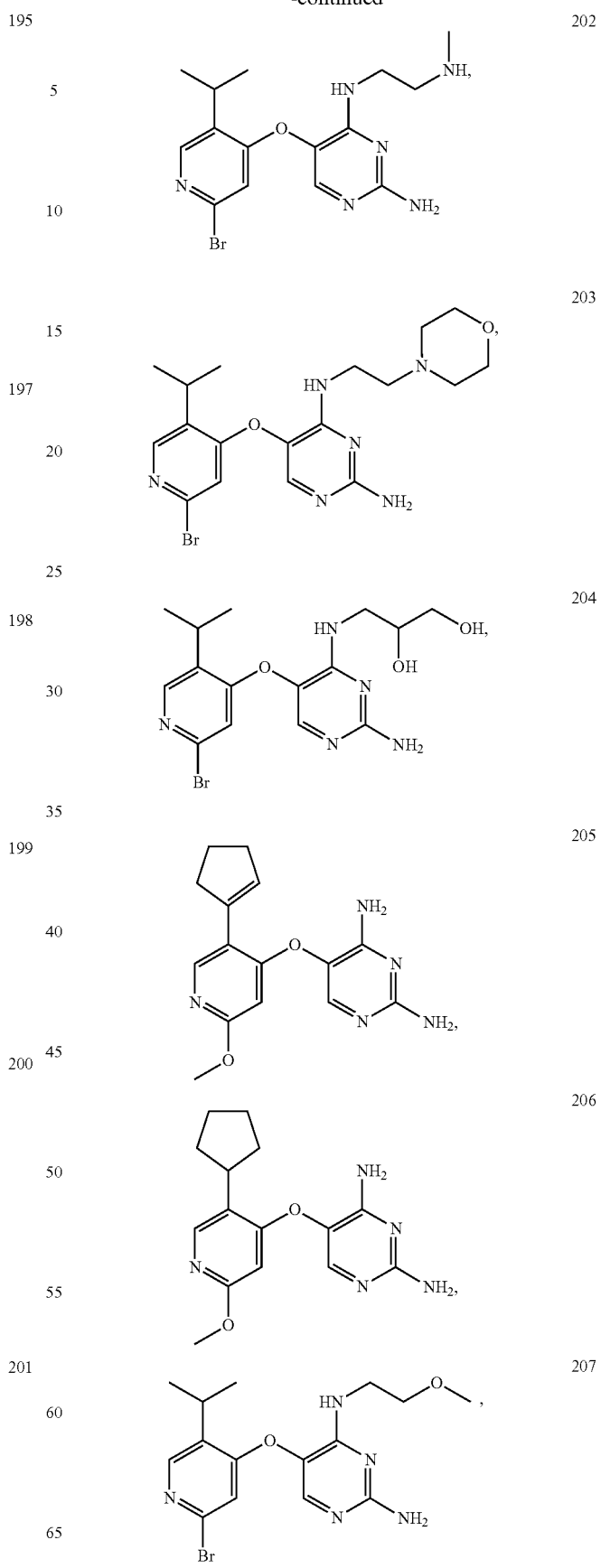

| | | | |
|---|---|---|---|
| 208 | 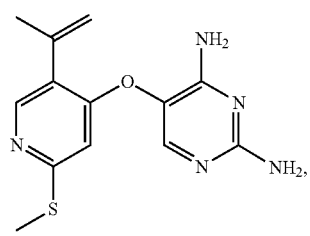 | 213 | 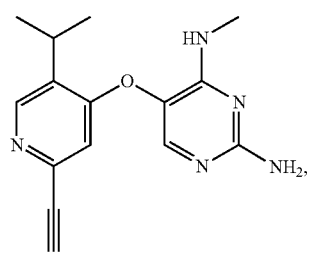 |
| 209 | 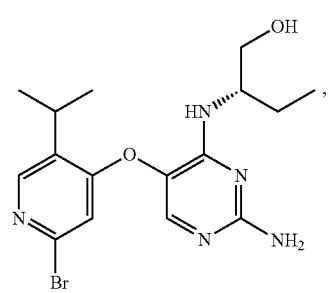 | 214 | 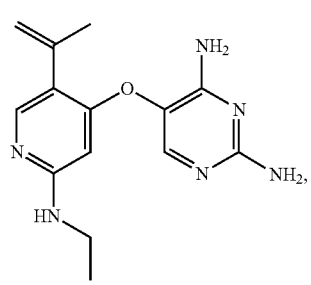 |
| 210 | 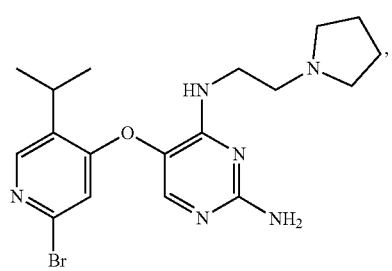 | 215 | 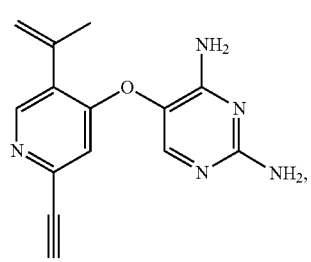 |
| 211 | 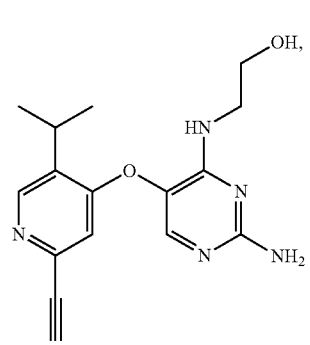 | 216 | 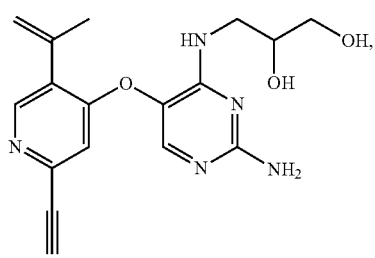 |
| | | 217 | 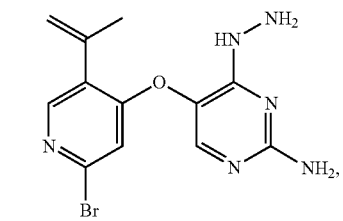 |
| 212 | 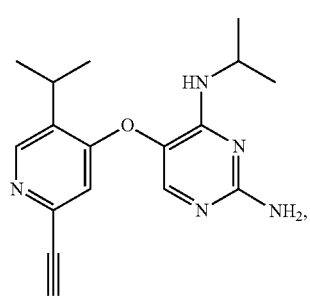 | 218 | 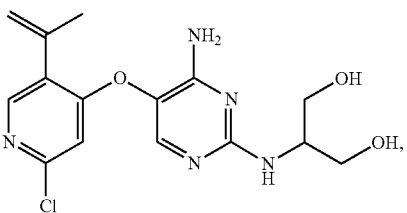 |

219 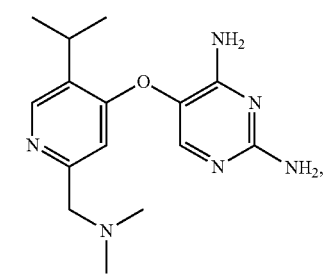
220 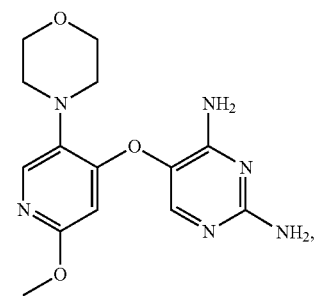
221 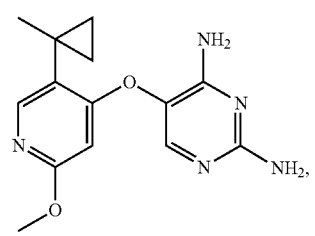
222 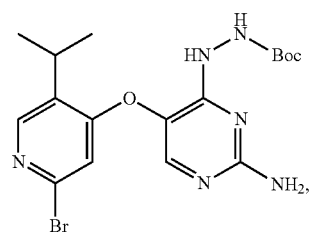
223 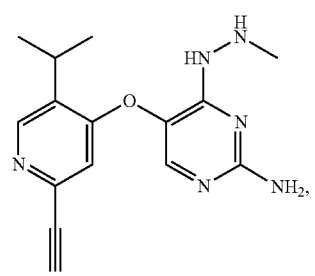
224 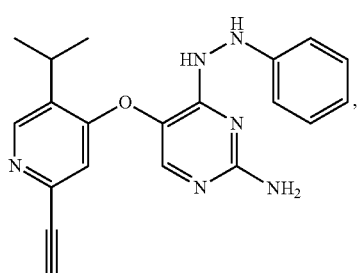
225 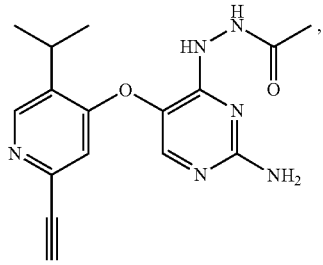
226 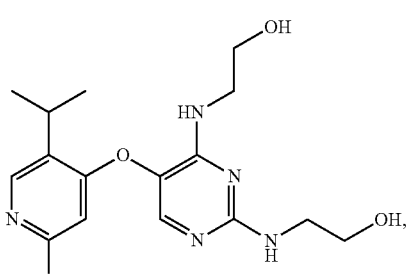
227 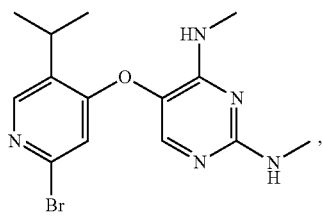
228 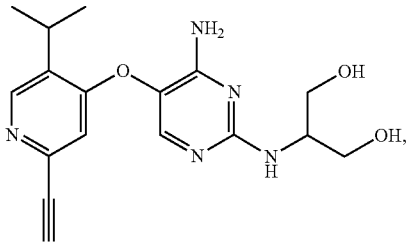
229 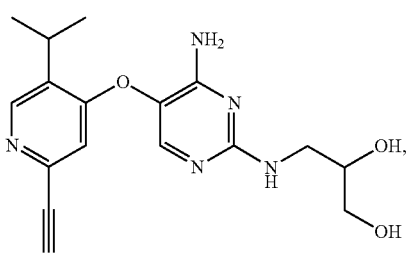
230 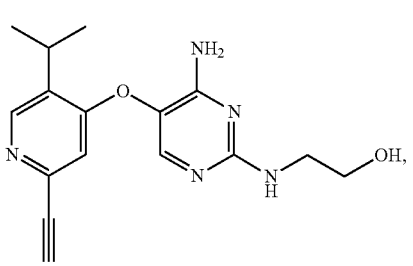

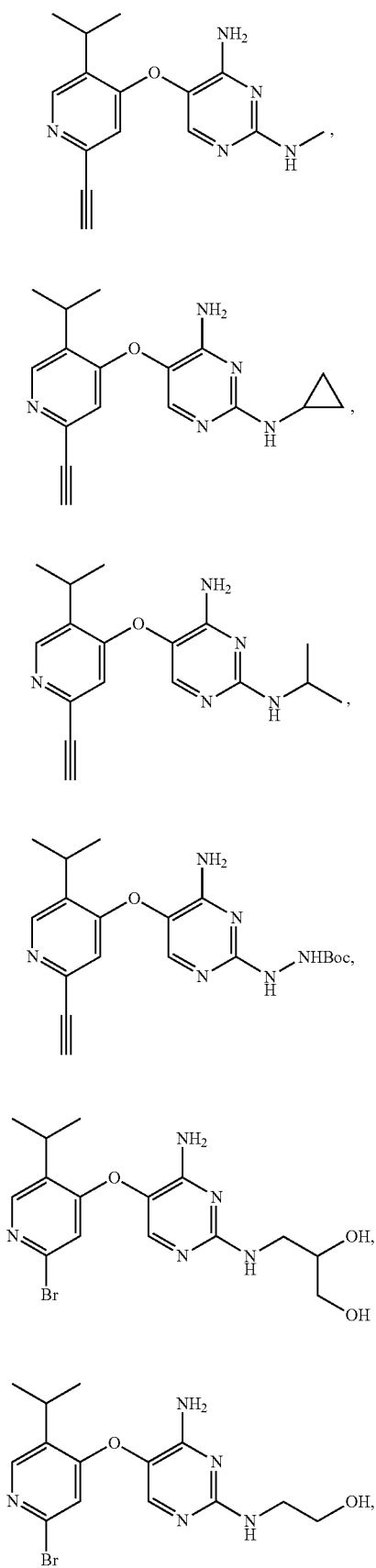
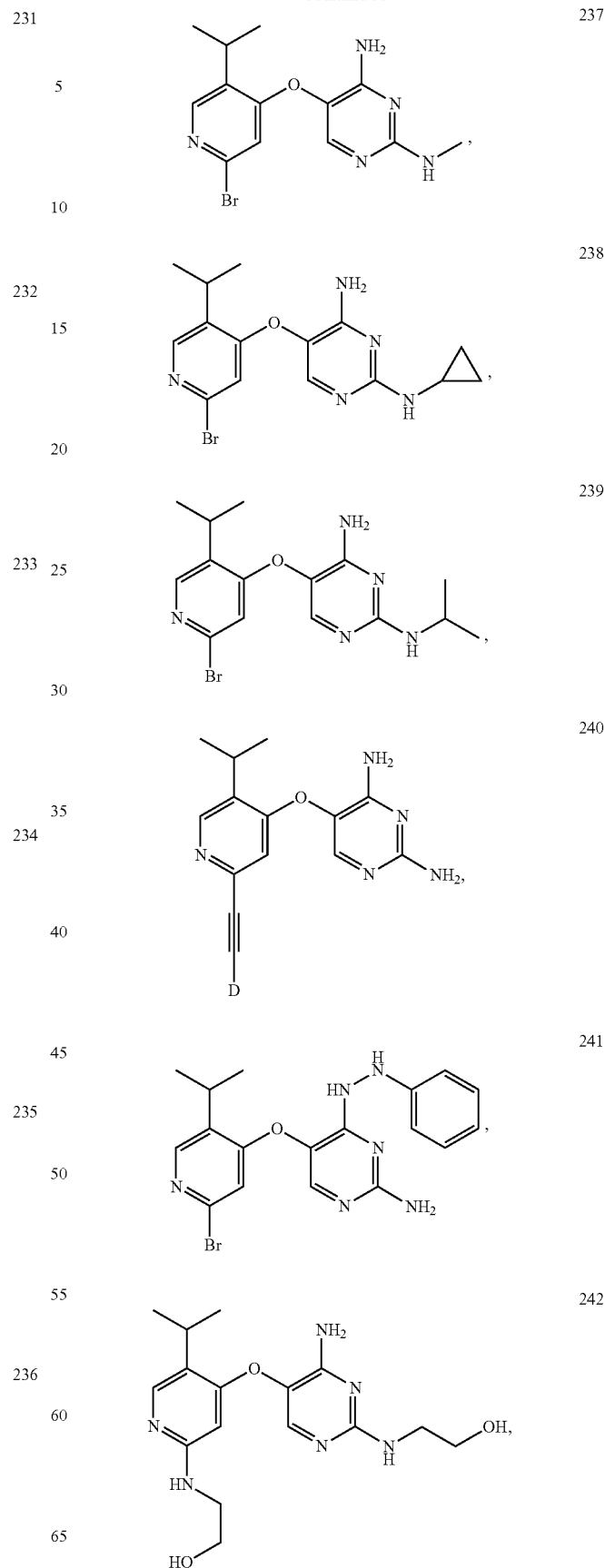

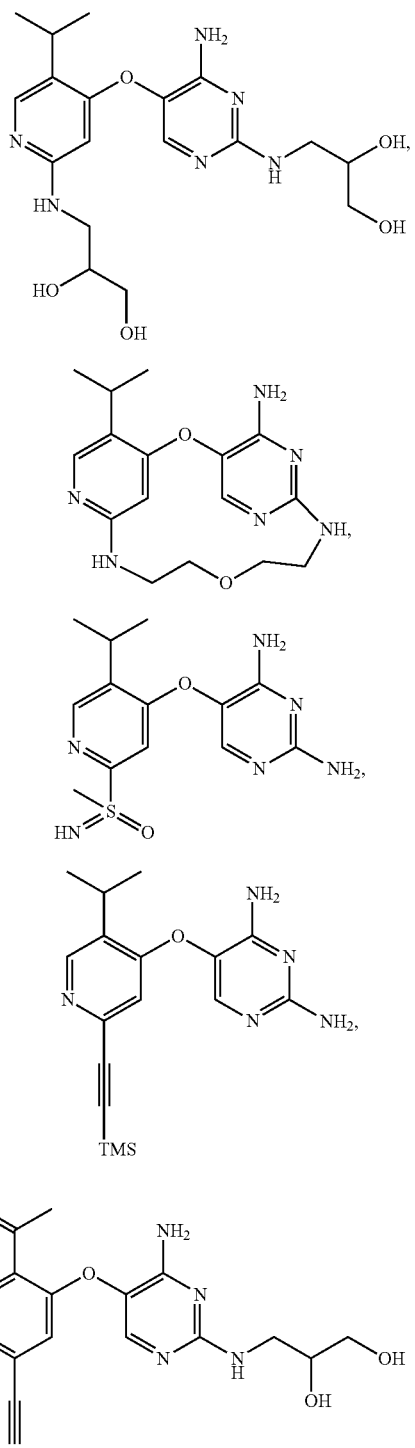

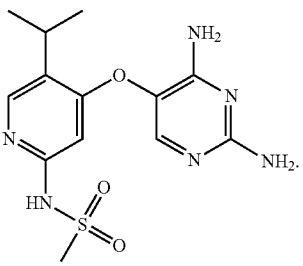

11. The method according to claim 10, wherein the disease is selected from the group consisting of a urinary tract disease selected from reduced bladder capacity, frequent micturition, urge incontinence, stress incontinence, bladder hyperreactivity, benign prostatic hypertrophy, prostatitis, detrusor hyperreflexia, nocturia, urinary urgency, pelvic hypersensitivity, urethritis, pelvic pain syndrome, prostatodynia, cystitis, and idiopathic bladder hypersensitivity; pain disease selected from inflammatory pain, surgical pain, visceral pain, dental pain, premenstrual pain, central pain, pain due to burns, migraine and cluster headaches, nerve injury, neuritis, neuralgia, poisoning, ischemic injury, interstitial cystitis, cancer pain, viral, parasitic or bacterial infection, post-traumatic injury and pain associated with irritable bowel syndrome; cardiovascular system disease; respiratory disease selected from chronic obstructive pulmonary disease, asthma and bronchospasm; gastrointestinal disease selected from irritable bowel syndrome, inflammatory bowel disease, biliary colic, renal colic, and pain associated with gastrointestinal distension.

12. The method according to claim 1, wherein $R^1$ and $R^4$ together form —NHCH$_2$CH$_2$—O—CH$_2$CH$_2$—.

13. The method according to claim 7, wherein the pharmaceutical composition is in the form of a solid, semi-solid, liquid, or gas preparation.

14. The method according to claim 8, wherein the cardiovascular system disease is hypertension.

15. The method according to claim 8, wherein the irritable bowel syndrome is diarrhea-dominant irritable bowel syndrome.

16. The method according to claim 9, wherein the cardiovascular system disease is hypertension.

17. The method according to claim 9, wherein the irritable bowel syndrome is diarrhea-dominant irritable bowel syndrome.

18. The method according to claim 10, wherein the pharmaceutical composition is in the form of a solid, semi-solid, liquid, or gas preparation.

19. The method according to claim 11, wherein the cardiovascular system disease is hypertension.

20. The method according to claim 11, wherein the irritable bowel syndrome is diarrhea-dominant irritable bowel syndrome.

* * * * *